(12) United States Patent
Balog et al.

(10) Patent No.: US 9,598,436 B2
(45) Date of Patent: Mar. 21, 2017

(54) SUBSTITUTED BICYCLIC HETEROARYL COMPOUNDS

(71) Applicant: BRISTOL-MYERS SQUIBB COMPANY, Princeton, NJ (US)

(72) Inventors: James Aaron Balog, Lambertville, NJ (US); Audris Huang, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 58 days.

(21) Appl. No.: 14/968,259

(22) Filed: Dec. 14, 2015

(65) Prior Publication Data
US 2016/0096847 A1 Apr. 7, 2016

Related U.S. Application Data

(62) Division of application No. 14/598,721, filed on Jan. 16, 2015, now Pat. No. 9,242,967, which is a division of application No. 14/347,893, filed as application No. PCT/US2012/057406 on Sep. 27, 2012, now Pat. No. 8,969,586.

(51) Int. Cl.

| | | |
|---|---|---|
| C07D 413/00 | (2006.01) | |
| C07D 498/04 | (2006.01) | |
| C07D 413/14 | (2006.01) | |
| C07D 409/04 | (2006.01) | |
| C07D 413/04 | (2006.01) | |
| C07D 487/04 | (2006.01) | |
| C07D 409/14 | (2006.01) | |
| C07D 417/14 | (2006.01) | |
| C07D 471/04 | (2006.01) | |
| C07D 495/04 | (2006.01) | |
| C07D 519/00 | (2006.01) | |
| C07D 413/06 | (2006.01) | |

(52) U.S. Cl.
CPC ......... *C07D 498/04* (2013.01); *C07D 409/04* (2013.01); *C07D 409/14* (2013.01); *C07D 413/04* (2013.01); *C07D 413/06* (2013.01); *C07D 413/14* (2013.01); *C07D 417/14* (2013.01); *C07D 471/04* (2013.01); *C07D 487/04* (2013.01); *C07D 495/04* (2013.01); *C07D 519/00* (2013.01)

(58) Field of Classification Search
CPC .................................................. C07D 498/04
USPC ........................................................ 548/241
See application file for complete search history.

(56) References Cited

U.S. PATENT DOCUMENTS

| | | |
|---|---|---|
| 6,124,463 A | 9/2000 | Beck et al. |
| 6,362,180 B1 | 3/2002 | Wilde et al. |
| 2008/0255085 A1 | 10/2008 | Arvidsson et al. |
| 2010/0331326 A1 | 12/2010 | Bock et al. |
| 2012/0108589 A1 | 5/2012 | Kitade et al. |
| 2013/0045980 A1 | 2/2013 | Velaparthi et al. |

FOREIGN PATENT DOCUMENTS

| | | |
|---|---|---|
| WO | WO98/08847 | 3/1998 |
| WO | WO00/01675 | 1/2000 |
| WO | WO03/027094 | 4/2003 |
| WO | WO2005/051906 | 6/2005 |
| WO | WO2006/004188 | 1/2006 |
| WO | WO 2006/020049 | 2/2006 |
| WO | WO2007/038314 | 4/2007 |
| WO | WO2008/030579 | 3/2008 |
| WO | WO2008/070354 | 6/2008 |
| WO | WO2008/075109 | 6/2008 |
| WO | WO2009/017954 | 2/2009 |
| WO | WO2010/059788 | 5/2010 |
| WO | WO2010/129668 | 11/2010 |
| WO | WO2011/137155 | 11/2011 |
| WO | WO2012/009510 | 1/2012 |
| WO | WO2012/015723 | 2/2012 |
| WO | WO2012/044537 | 4/2012 |
| WO | WO2012/064815 | 5/2012 |

OTHER PUBLICATIONS

International Preliminary Report on Patentability for PCT/US2012/057406 issued Apr. 1, 2014.
Moreira et al.,"Synthesis and evaluation of novem 17-indazole androstene derivatives designed as CYP17 inhibitors," Steroids 72 (2007) pp. 939-948.
CAS Structures for Example 116 in WO 2006/020049 (Feb. 23, 2006).
CAS Structures for Example 67 (Reaction Schemes) in WO 2006/020049 (Feb. 23, 2006).
CAS 877263-59-7 entered STN: Mar. 20, 2006.
Third Party Observation for Application No. EP20120783408 issued by European Patent Office; transmittal to applicant on Jun. 10, 2015.

*Primary Examiner* — Nizal Chandrakumar
(74) *Attorney, Agent, or Firm* — Gary D. Greenblatt

(57) ABSTRACT

Disclosed are azaindazole compounds of Formula (I):

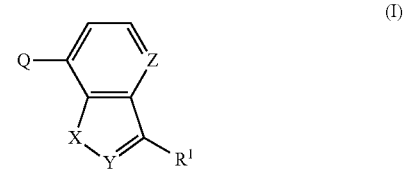

or a pharmaceutically acceptable salt thereof, wherein: X is O and Y is N; or X is S and Y is CH; Z is $CR^2$ or N; Q is a heteroaryl; and $R_1$ is defined herein. Also disclosed are methods of using such compounds in the treatment of at least one CYP17 associated condition, such as, for example, cancer, and pharmaceutical compositions comprising such compounds.

8 Claims, No Drawings

SUBSTITUTED BICYCLIC HETEROARYL COMPOUNDS

This application is a divisional application, which claims priority to U.S. patent application Ser. No. 14/598,721, filed Jan. 16, 2015, which is a divisional application of U.S. patent application Ser. No. 14/347,893, filed Mar. 27, 2014, which claims priority to national phase application under 35 U.S.C. §371 of International Patent Application No. PCT/US2012/057406, filed Sep. 27, 2012, which claims priority to provisional application U.S. 61/539,570, filed Sep. 27, 2011, the contents of which are herein incorporated by reference.

The present invention generally relates to substituted bicyclic heteroaryl compounds useful as CYP17 inhibitors. Provided herein are substituted bicyclic heteroaryl compounds, compositions comprising such compounds, and methods of their use. The invention further pertains to pharmaceutical compositions comprising at least one compound according to the invention that is useful for the treatment of conditions related to the CYP17 enzyme, such as cancer and other proliferative diseases.

Prostate cancer is the second leading cause of cancer related mortality in American men. In 2007, there were 218,890 new cases with 27,000 deaths associated with prostate cancer. It is well known that androgens, such as testosterone and dihydrotestosterone, drive the growth of the prostate as well as prostate cancer at the level of the androgen receptor. The standard of care for advanced hormone sensitive prostate cancer involves surgical or chemical castration with a leutenizing releasing hormone agonist/antagonist to remove the androgens produced in the gonads from circulation. However, approximately 90% of androgens are produced in the testes with the remaining 10% being produced through the action of the adrenal gland. Thus, castration does not alleviate the action of all androgens. Further once a patient progresses to castration resistant prostate cancer, androgens are also produced at the level of the tumor, making treatment with antiandrogens more difficult.

The cytochrome P450 CYP17 is responsible for the biosynthesis of both dihydroepiandrostenedione and androstenedione which are precursors of both androgens and estrogen. Thus the production of all androgens and estrogens produced in the human body is mediated by CYP17. Blocking this enzyme would inhibit the production of gonadal, adrenal and tumoral androgens and could offer a new treatment option for prostate cancer and estrogen receptor-positive breast cancer patients.

Clinical proof-of-concept for CYP17 as a target for prostate cancer has been achieved with the antifungal ketoconazole and the steroidal CYP17 inhibitor abiraterone, which has progressed to Phase III clinical trials for prostate cancer.

There remains a need for compounds that are useful as inhibitors of CYP17 enzymes.

Applicants have found potent compounds that have activity as CYP17 inhibitors. These compounds are provided to be useful as pharmaceuticals with desired stability, bioavailability, therapeutic index, and toxicity values that are important to their drugability.

SUMMARY OF THE INVENTION

The present invention fills the foregoing need by providing substituted bicyclic heteroaryl compounds, which are useful as inhibitors of CYP17 enzymes, including salts and prodrugs thereof.

The present invention also provides pharmaceutical compositions comprising a pharmaceutically acceptable carrier; and at least one compound of Formula (I), or salts or prodrugs thereof.

The present invention also provides a method of treating a disease or disorder associated with the activity of the CYP17 enzyme, the method comprising administering to a mammalian patient a compound of Formula (I) or pharmaceutically acceptable salts or prodrugs thereof.

The present invention also provides processes and intermediates for making the compounds of Formula (I) or salts or prodrugs thereof.

The present invention also provides the compounds of Formula (I), or pharmaceutically acceptable salts or prodrugs thereof, for use in therapy.

The present invention also provides use of a compound of Formula (I) or pharmaceutically acceptable salts or prodrugs thereof, for the manufacture of a medicament for the treatment of cancer.

The compounds of Formula (I) and compositions comprising the compounds are inhibitors of CYP17 enzymes, and may be used in treating, prevention, or curing various CYP17 enzyme related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

DETAILED DESCRIPTION

The first aspect of the invention provides compounds of Formula (I):

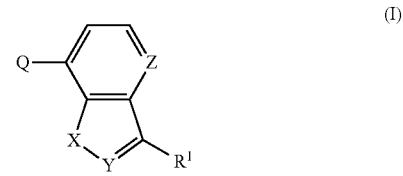

or pharmaceutically acceptable salts or prodrugs thereof, wherein:
X is O and Y is N; or X is S and Y is CH;
Z is $CR^2$ or N;
Q is:
(i)

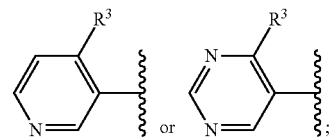

or
(ii) 9- to 10-membered bicyclic heteroaryl selected from

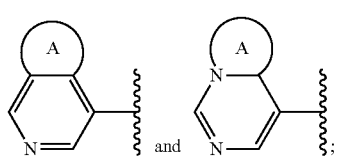

wherein Ring A is a 5- to 6-membered aryl or heteroaryl fused ring;

$R^1$ is:

(i) H, halo, $C_{1-4}$fluoroalkyl, $C_{1-6}$alkoxy, $C_{1-4}$fluoroalkoxy, —S($C_{1-4}$fluoroalkyl), —O($C_{1-4}$alkylenyl)O($C_{1-3}$alkyl), —O($CH_2$)$_{1-4}$N($C_{1-3}$alkyl)$_2$, —O($C_{3-6}$alkynyl), or —O(methylpiperidinyl);

(ii) phenyl substituted with zero to 2 substituents independently selected from F, Cl, —$CF_3$, and/or —$OCH_3$;

(iii) $C_{3-6}$cycloalkyl, morpholinyl, thiazolyl, pyridinyl, pyridazinyl, or pyrazinyl; or (iv) —O($CH_2$)$_{1-4}R^x$ wherein $R^x$ is imidazolyl, thiazolyl, phenyl, fluorophenyl, chlorophenyl, methoxyphenyl, naphthalenyl, or pyrazinyl;

$R^2$ is H or —NHS(O)$_2$($C_{1-4}$alkyl); and $R^3$ is:

(i) F, Cl, $C_{1-4}$alkyl, $C_{1-4}$alkoxy, or $C_{1-4}$fluoroalkoxy;

(ii) $C_{3-6}$cyclopropyl, morpholinyl, pyrazolyl, imidazolyl, or triazolyl;

(iii) —O($CH_2$)$_{1-4}R^y$ wherein $R^y$ is phenyl, morpholinyl, or pyridazinyl;

(iv) pyrrolidinyl substituted with zero to 2 substituents independently selected from —$CH_3$ and/or —OH; or (v) —$NH_2$, —NH($C_{1-4}$alkyl), —NH($C_{2-3}$fluoroalkyl), or —NH($C_{3-6}$cycloalkyl).

One embodiment provides compounds of Formula (I) or pharmaceutically acceptable salts or prodrugs thereof, wherein X is O and Y is N; and Z, $R^1$, and Q are defined in the first aspect. Compounds of this embodiment have the structure of Formula (II):

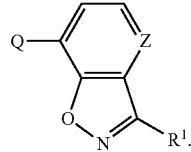

(II)

Included in this embodiment are compounds in which Z is $CR^2$ and $R^1$ is: (i) Cl, —$NH_2$, —$CH_2CH_2CF_3$, $C_{1-6}$alkoxy, fluoroethoxy, —$SCH_2CF_3$, —$OCH_2CH_2OCH_3$, —$OCH_2CH_2N(CH_3)_2$, —O($CH_2C\equiv H$), or —O(methylpiperidinyl); (ii) phenyl substituted with zero to 2 substituents independently selected from F, Cl, and/or —$OCH_3$; (iii) cyclopropyl, thiazolyl, pyridinyl, pyridazinyl, or pyrazinyl; or (iv) —O($CH_2$)$_{1-4}R^x$ wherein $R^x$ is imidazolyl, thiazolyl, phenyl, chlorophenyl, methoxyphenyl, naphthalenyl, or pyrazinyl.

One embodiment provides compounds of Formula (I) or pharmaceutically acceptable salts or prodrugs thereof, wherein X is S and Y is CH; and Z, $R^1$, and Q are defined in the first aspect. Compounds of this embodiment have the structure of Formula (III):

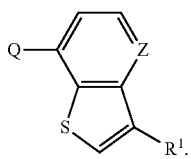

(III)

Included in this embodiment are compounds in which Z is $CR^2$ and $R^1$ is H, pyridinyl, or phenyl substituted with 1 to 2 substituents independently selected from F and/or Cl.

One embodiment provides compounds of Formula (I) or pharmaceutically acceptable salts or prodrugs thereof, wherein Z is $CR^2$; and X, Y, $R^1$, $R^2$, and Q are defined in the first aspect. Compounds of this embodiment have the structure of Formula (IV):

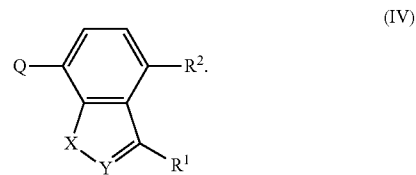

(IV)

One embodiment provides compounds of Formula (I) or pharmaceutically acceptable salts or prodrugs thereof, wherein Z is N; and X, Y, $R^1$, and Q are defined in the first aspect. Compounds of this embodiment have the structure of Formula (V):

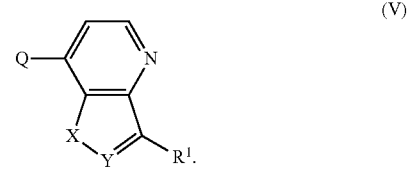

(V)

Included in this embodiment are compounds of Formula (V) in which Q is:

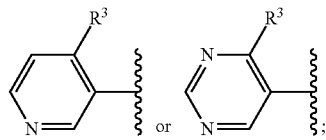

and $R^3$ is defined in the first aspect.

One embodiment provides compounds of Formula (I) or pharmaceutically acceptable salts or prodrugs thereof, wherein X is O, Y is N; Z is $CR^2$; and $R^1$ and Q are defined in the first aspect. Compounds of this embodiment have the structure of Formula (VI):

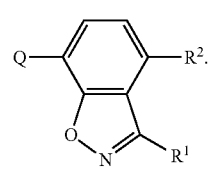

(VI)

Included in this embodiment are compounds of Formula (VI) in which Q is:

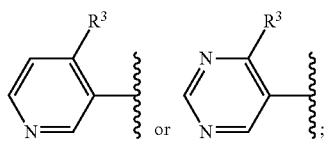

and R³ is defined in the first aspect. Also included in this embodiment are compounds in which R³ is (i) Cl, —CH₃, C₁₋₃alkoxy, or fluoroethoxy; (ii) cyclopropyl, morpholinyl, pyrazolyl, imidazolyl, or triazolyl; (iii) —O(CH₂)₁₋₂R^y wherein R^y is phenyl, morpholinyl, or pyridazinyl; (iv) pyrrolidinyl substituted with —CH₃ and —OH; or (v) —NH₂, —NH(CH₂—CF₃), or —NH(cyclopropyl).

One embodiment provides compounds of Formula (I) or pharmaceutically acceptable salts or prodrugs thereof, wherein X is O, Y is N; Z is N; and R¹, R², and Q are defined in the first aspect. Compounds of this embodiment have the structure of Formula (VII):

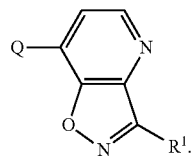

(VII)

Included in this embodiment are compounds of Formula (VII) in which Q is:

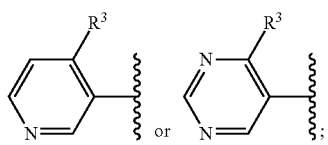

and R³ is defined in the first aspect. Examples of suitable R³ groups include —CH₃ and —NH₂.

One embodiment provides compounds of Formula (I) or pharmaceutically acceptable salts or prodrugs thereof, wherein X is S, Y is CH; Z is CR²; and R¹, R², and Q are defined in the first aspect. Compounds of this embodiment have the structure of Formula (VIII):

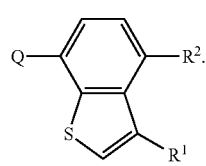

(VIII)

Included in this embodiment are compounds of Formula (VIII) in which Q is:

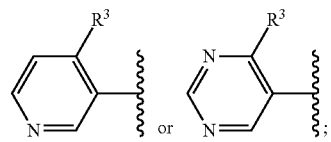

and R³ is defined in the first aspect. Examples of suitable R3 groups include —CH₃ and cyclopropyl.

One embodiment provides compounds of Formula (I) or pharmaceutically acceptable salts or prodrugs thereof, wherein X is S, Y is CH; Z is N; and R¹ and Q are defined in the first aspect. Compounds of this embodiment have the structure of Formula (IX):

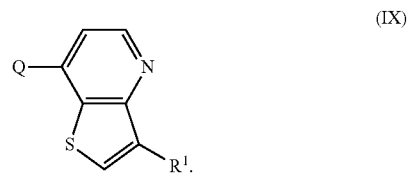

(IX)

Included in this embodiment are compounds of Formula (IX) in which Q is:

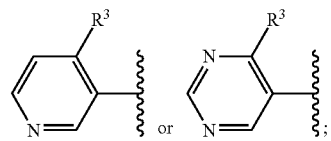

and R³ is defined in the first aspect.

One embodiment provides compounds of Formula (I) or pharmaceutically acceptable salts or prodrugs thereof, wherein Q is:

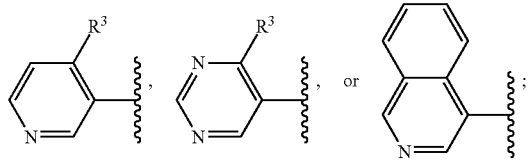

and X, Y, Z, R¹, and R³ are defined in the first aspect. Included in this embodiment are compounds in which Q is:

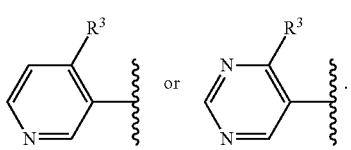

One embodiment provides compounds of Formula (I) or pharmaceutically acceptable salts or prodrugs thereof, wherein Q is a 9- to 10-membered bicyclic heteroaryl selected from:

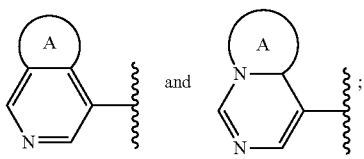

wherein Ring A is a 5- to 6-membered aryl or heteroaryl fused ring; and X, Y, Z, $R^1$, and $R^3$ are defined in the first aspect. Included in this embodiment are compounds in which Q is:

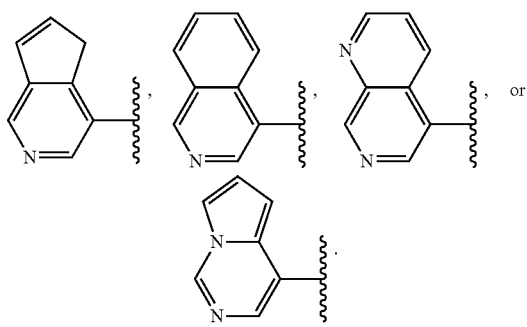

One embodiment provides compounds of Formula (I) or pharmaceutically acceptable salts or prodrugs thereof, wherein Q is:

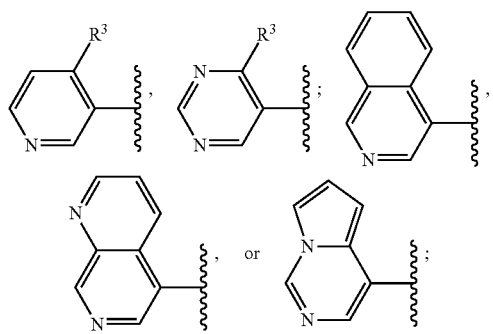

and X, Y, Z, $R^1$, and $R^3$ are defined in the first aspect.

One embodiment provides compounds of Formula (I) or pharmaceutically acceptable salts or prodrugs thereof, wherein $R^1$ is H, halo, $C_{1-4}$fluoroalkyl, $C_{1-6}$alkoxy, $C_{1-4}$fluoroalkoxy, —S($C_{1-4}$fluoroalkyl), —O($C_{1-4}$alkylenyl)O($C_{1-3}$alkyl), —O(CH$_2$)$_{1-4}$N($C_{1-3}$alkyl)$_2$, —O($C_{3-6}$alkynyl), or —O(methylpiperidinyl); and X, Y, Z, and Q are defined in the first aspect.

One embodiment provides compounds of Formula (I) or pharmaceutically acceptable salts or prodrugs thereof, wherein $R^1$ is phenyl substituted with zero to 2 substituents independently selected from F, Cl, —CF$_3$, and/or —OCH$_3$; and X, Y, Z, and Q are defined in the first aspect.

One embodiment provides compounds of Formula (I) or pharmaceutically acceptable salts or prodrugs thereof, wherein $R^1$ is $C_{3-6}$cycloalkyl, morpholinyl, thiazolyl, pyridinyl, pyridazinyl, or pyrazinyl; and X, Y, Z, and Q are defined in the first aspect.

One embodiment provides compounds of Formula (I) or pharmaceutically acceptable salts or prodrugs thereof, wherein $R^1$ is —O(CH$_2$)$_{1-4}R^x$ wherein $R^x$ is imidazolyl, thiazolyl, phenyl, fluorophenyl, chlorophenyl, methoxyphenyl, naphthalenyl, or pyrazinyl; and X, Y, Z, and Q are defined in the first aspect.

One embodiment provides compounds of Formula (I) or pharmaceutically acceptable salts or prodrugs thereof, wherein Z is $CR^2$; $R^2$ is H; and X, Y, and Q are defined in the first aspect.

One embodiment provides compounds of Formula (I) or pharmaceutically acceptable salts or prodrugs thereof, wherein Z is $CR^2$; $R^2$ is —NHS(O)$_2$($C_{1-4}$alkyl); and X, Y, and Q are defined in the first aspect.

One embodiment provides compounds of Formula (I) or pharmaceutically acceptable salts or prodrugs thereof, wherein:

Q is

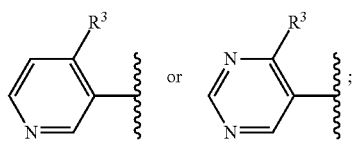

$R^3$ is F, Cl, $C_{1-4}$alkyl, $C_{1-4}$alkoxy, or $C_{1-4}$fluoroalkoxy;

and X, Y, and Z are defined in the first aspect.

One embodiment provides compounds of Formula (I) or pharmaceutically acceptable salts or prodrugs thereof, wherein:

Q is

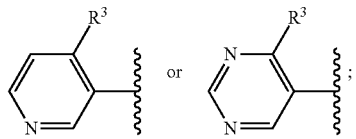

$R^3$ is $C_{3-6}$cyclopropyl, morpholinyl, pyrazolyl, imidazolyl, or triazolyl;

and X, Y, and Z are defined in the first aspect.

One embodiment provides compounds of Formula (I) or pharmaceutically acceptable salts or prodrugs thereof, wherein:

Q is

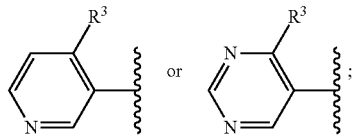

$R^3$ is —O(CH$_2$)$_{1-4}R^y$ wherein $R^y$ is phenyl, morpholinyl, or pyridazinyl;

and X, Y, and Z are defined in the first aspect.

One embodiment provides compounds of Formula (I) or pharmaceutically acceptable salts or prodrugs thereof, wherein:

Q is

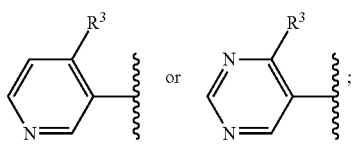

R³ is pyrrolidinyl substituted with zero to 2 substituents independently selected from —CH₃ and/or —OH;
and X, Y, and Z are defined in the first aspect.

One embodiment provides compounds of Formula (I) or pharmaceutically acceptable salts or prodrugs thereof, wherein:

Q is

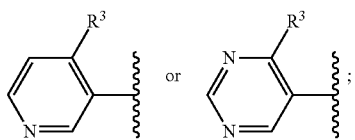

R³ is —NH₂, —NH(C₁₋₄alkyl), —NH(C₂₋₃fluoroalkyl), or —NH(C₃₋₆cycloalkyl);
and X, Y, and Z are defined in the first aspect.

One embodiment provides compounds of Formula (I) or pharmaceutically acceptable salts or prodrugs thereof, wherein:
R¹ is:
(i) H, Cl, —CH₂CH₂CF₃, C₁₋₆alkoxy, fluoroethoxy, —SCH₂CF₃, —OCH₂CH₂OCH₃, —OCH₂CH₂N(CH₃)₂, —O(CH₂C≡H), or —O(methylpiperidinyl);
(ii) phenyl substituted with zero to 2 substituents independently selected from F, Cl, —CF₃, and/or —OCH₃;
(iii) cyclopropyl, morpholinyl, thiazolyl, pyridinyl, pyridazinyl, or pyrazinyl; or
(iv) —O(CH₂)₁₋₄Rˣ wherein Rˣ is imidazolyl, thiazolyl, phenyl, chlorophenyl, methoxyphenyl, naphthalenyl, or pyrazinyl;
R² is H or —NHS(O)₂CH₃; and
R³ is:
(i) Cl, —CH₃, C₁₋₃alkoxy, or fluoroethoxy;
(ii) cyclopropyl, morpholinyl, pyrazolyl, imidazolyl, or triazolyl;
(iii) —O(CH₂)₁₋₂Rʸ wherein Rʸ is phenyl, morpholinyl, or pyridazinyl;
(iv) pyrrolidinyl substituted with —CH₃ and —OH; or
(v) —NH₂, —NH(CH₂CF₃), or —NH(cyclopropyl).

One embodiment provides compounds of Formula (I) or pharmaceutically acceptable salts or prodrugs thereof, wherein:
X is O;
Y is N;
Z is CR²;
R¹ is:
(i) Cl, —NH₂, —CH₂CH₂CF₃, C₁₋₆alkoxy, fluoroethoxy, —SCH₂CF₃, —OCH₂CH₂OCH₃, —OCH₂CH₂N(CH₃)₂, —O(CH₂C≡H), or —O(methylpiperidinyl);
(ii) phenyl substituted with zero to 2 substituents independently selected from F, Cl, and/or —OCH₃;
(iii) cyclopropyl, thiazolyl, pyridinyl, pyridazinyl, or pyrazinyl; or
(iv) —O(CH₂)₁₋₄Rˣ wherein Rˣ is imidazolyl, thiazolyl, phenyl, chlorophenyl, methoxyphenyl, naphthalenyl, or pyrazinyl;
R² is H or —NHS(O)₂CH₃; and
R³ is:
(i) Cl, —CH₃, C₁₋₃alkoxy, or fluoroethoxy;
(ii) cyclopropyl, morpholinyl, pyrazolyl, imidazolyl, or triazolyl;
(iii) —O(CH₂)₁₋₂Rʸ wherein Rʸ is phenyl, morpholinyl, or pyridazinyl;
(iv) pyrrolidinyl substituted with —CH₃ and —OH; or
(v) —NH₂, —NH(CH₂CF₃), or —NH(cyclopropyl).

One embodiment provides compounds of Formula (I) or pharmaceutically acceptable salts or prodrugs thereof, wherein:
X is O;
Y is N;
Z is N;
Q is

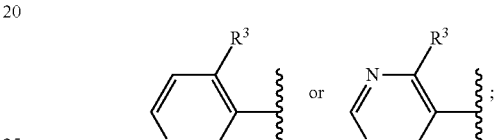

R¹ is Cl, morpholinyl, or phenyl substituted with zero to 2 substituents independently selected from F, Cl, and/or —OCH₃; and
R³ is —CH₃ or —NH₂.

One embodiment provides compounds of Formula (I) or pharmaceutically acceptable salts or prodrugs thereof, wherein:
X is S;
Y is CH;
Z is CR²;
Q is

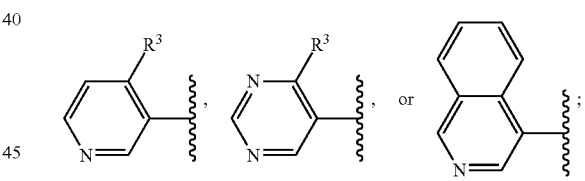

R¹ is H, pyridinyl, or phenyl substituted with 1 to 2 substituents independently selected from F and/or Cl;
R² is H or —NHS(O)₂CH₃; and
R³ is —CH₃ or cyclopropyl.

One embodiment provides compounds of Formula (I) or pharmaceutically acceptable salts or prodrugs thereof, wherein:
X is S;
Y is CH;
Z is N;
Q is

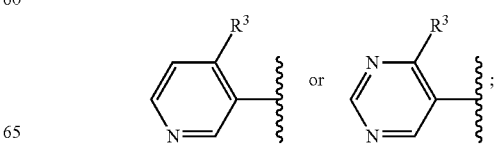

R¹ is thiazolyl, pyridinyl, pyrazinyl, or phenyl substituted with zero to 2 substituents independently selected from F, Cl, and/or —CF₃; and R³ is —CH₃, cyclopropyl, or —NH₂.

One embodiment provides a compound of Formula (I) wherein said compound is selected from 7-(4-methylpyridin-3-yl)-3-phenylbenzo[d]isoxazole (1); 7-(4-methoxypyridin-3-yl)-3-phenylbenzo[d]isoxazole (2); 7-(4-chloropyridin-3-yl)-3-phenylbenzo[d]isoxazole (3); 7-(4-methylpyrimidin-5-yl)-3-phenylbenzo[d]isoxazole (4); 7-(isoquinolin-4-yl)-3-phenylbenzo[d]isoxazole (5); 3-(4-fluorophenyl)-7-(4-methylpyridin-3-yl)benzo[d]isoxazole (6); 7-(4-chloropyridin-3-yl)-3-(4-fluorophenyl)benzo[d]isoxazole (7); 3-(4-fluorophenyl)-7-(4-methoxypyridin-3-yl)benzo[d]isoxazole (8); 3-(4-fluorophenyl)-7-(4-methylpyrimidin-5-yl)benzo[d]isoxazole (9); 3-(4-fluorophenyl)-7-(isoquinolin-4-yl)benzo[d]isoxazole (10); 7-(4-cyclopropylpyrimidin-5-yl)-3-(4-fluorophenyl)benzo[d]isoxazole (11); 3-(4-fluorophenyl)-7-(4-(2,2,2-trifluoroethoxy)pyrimidin-5-yl)benzo[d]isoxazole (12); 3-(4-fluorophenyl)-7-(1,7-naphthyridin-5-yl)benzo[d]isoxazole (13); 3-(4-fluorophenyl)-7-(pyrrolo[1,2-c]pyrimidin-4-yl)benzo[d]isoxazole (14); 5-(3-(4-fluorophenyl)benzo[d]isoxazol-7-yl)-N-(2,2,2-trifluoroethyl)pyrimidin-4-amine (15); 3-(4-fluorophenyl)-7-(4-morpholinopyrimidin-5-yl)benzo[d]isoxazole (16); 7-(4-methylpyridin-3-yl)-3-(pyridin-2-yl)benzo[d]isoxazole (17); 7-(4-chloropyridin-3-yl)-3-(pyridin-2-yl)benzo[d]isoxazole (18); 7-(isoquinolin-4-yl)-3-(pyridin-2-yl)benzo[d]isoxazole (19); 7-(4-methylpyridin-3-yl)-3-(thiazol-2-yl)benzo[d]isoxazole (20); 7-(4-chloropyridin-3-yl)-3-(pyrazin-2-yl)benzo[d]isoxazole (21); 7-(4-methylpyridin-3-yl)-3-(pyrazin-2-yl)benzo[d]isoxazole (22); 7-(isoquinolin-4-yl)-3-(pyrazin-2-yl)benzo[d]isoxazole (23); 7-(4-methoxypyridin-3-yl)-3-(pyrazin-2-yl)benzo[d]isoxazole (24); 7-(4-cyclopropylpyrimidin-5-yl)-3-(pyrazin-2-yl)benzo[d]isoxazole (25); 3-(pyrazin-2-yl)-7-(4-(2,2,2-trifluoroethoxy)pyrimidin-5-yl)benzo[d]isoxazole (26); 7-(4-methylpyrimidin-5-yl)-3-(pyrazin-2-yl)benzo[d]isoxazole (27); 3-cyclopropyl-7-(4-methylpyridin-3-yl)benzo[d]isoxazole (28); 3-cyclopropyl-7-(4-methoxypyridin-3-yl)benzo[d]isoxazole (29); 7-(4-chloropyridin-3-yl)-3-cyclopropylbenzo[d]isoxazole (30); 3-cyclopropyl-7-(4-cyclopropylpyrimidin-5-yl)benzo[d]isoxazole (31); 3-cyclopropyl-7-(4-methylpyrimidin-5-yl)benzo[d]isoxazole (32); 7-(4-methylpyridin-3-yl)-3-(pyridazin-3-yl)benzo[d]isoxazole (33); 7-(4-chloropyridin-3-yl)-3-(pyridazin-3-yl)benzo[d]isoxazole (34); 3-(5-fluoro-2-methoxyphenyl)-7-(4-methylpyridin-3-yl)benzo[d]isoxazole (35); 3-(5-fluoro-2-methoxyphenyl)-7-(4-morpholinopyrimidin-5-yl)benzo[d]isoxazole (36); 3-(5-fluoro-2-methoxyphenyl)-7-(4-methylpyrimidin-5-yl)benzo[d]isoxazole (37); 7-(4-chloropyridin-3-yl)-3-(5-fluoro-2-methoxyphenyl)benzo[d]isoxazole (38); 7-(4-cyclopropylpyrimidin-5-yl)-3-(5-fluoro-2-methoxyphenyl)benzo[d]isoxazole (39); 3-(5-fluoro-2-methoxyphenyl)-7-(4-(2,2,2-trifluoroethoxy)pyrimidin-5-yl)benzo[d]isoxazole (40); 3-(5-fluoro-2-methoxyphenyl)-7-(isoquinolin-4-yl)benzo[d]isoxazole (41); 5-(3-(5-fluoro-2-methoxyphenyl)benzo[d]isoxazol-7-yl)pyrimidin-4-amine (42); 3-(4-fluoro-2-methoxyphenyl)-7-(4-methylpyridin-3-yl)benzo[d]isoxazole (43); 7-(4-chloropyridin-3-yl)-3-(4-fluoro-2-methoxyphenyl)benzo[d]isoxazole (44); 3-(4-fluoro-2-methoxyphenyl)-7-(4-morpholinopyrimidin-5-yl)benzo[d]isoxazole (45); 3-(4-fluoro-2-methoxyphenyl)-7-(4-(2,2,2-trifluoroethoxy)pyrimidin-5-yl)benzo[d]isoxazole (46); 3-(4-fluoro-2-methoxyphenyl)-7-(4-methylpyrimidin-5-yl)benzo[d]isoxazole (47); 7-(4-cyclopropylpyrimidin-5-yl)-3-(4-fluoro-2-methoxyphenyl)benzo[d]isoxazole (48); 3-(4-fluoro-2-methoxyphenyl)-7-(isoquinolin-4-yl)benzo[d]isoxazole (49); 3-chloro-7-(4-methylpyridin-3-yl)benzo[d]isoxazole (50); 7-(4-(1H-pyrazol-1-yl)pyrimidin-5-yl)-3-(2-chlorophenyl)benzo[d]isoxazole (51); 7-(4-(1H-1,2,4-triazol-1-yl)pyrimidin-5-yl)-3-(2-chlorophenyl)benzo[d]isoxazole (52); (R)-1-(5-(3-(2-chlorophenyl)benzo[d]isoxazol-7-yl)pyrimidin-4-yl)-3-methylpyrrolidin-3-ol (53); 5-(3-(2-chlorophenyl)benzo[d]isoxazol-7-yl)-N-cyclopropylpyrimidin-4-amine (54); 3-(2-chlorophenyl)-7-(4-methylpyrimidin-5-yl)benzo[d]isoxazole (55); 3-(2-chlorophenyl)-7-(4-ethoxypyrimidin-5-yl)benzo[d]isoxazole (56); 7-(4-(2H-1,2,3-triazol-2-yl)pyrimidin-5-yl)-3-(2-chlorophenyl)benzo[d]isoxazole (57); 3-(2-chlorophenyl)-7-(4-methylpyridin-3-yl)benzo[d]isoxazole (58); 3-(2-chlorophenyl)-7-(isoquinolin-4-yl)benzo[d]isoxazole (59); 7-(4-(1H-imidazol-1-yl)pyrimidin-5-yl)-3-(2-chlorophenyl)benzo[d]isoxazole (60); 7-(isoquinolin-4-yl)-3-(2,2,2-trifluoroethoxy)benzo[d]isoxazole (61); 7-(4-methylpyridin-3-yl)-3-(2,2,2-trifluoroethoxy)benzo[d]isoxazole (62); 3-isopropoxy-7-(isoquinolin-4-yl)benzo[d]isoxazole (63); 3-isobutoxy-7-(isoquinolin-4-yl)benzo[d]isoxazole (64); 7-(isoquinolin-4-yl)-3-(2,2,2-trifluoroethylthio)benzo[d]isoxazole (65); 7-(isoquinolin-4-yl)-3-(2,2,2-trifluoroethylthio)benzo[d]isoxazole (66); 3-(2-methoxyethoxy)-7-(4-methylpyridin-3-yl)benzo[d]isoxazole (67); 3-(2-methoxyethoxy)-7-(4-methylpyridin-3-yl)benzo[d]isoxazole (68); 3-isopropoxy-7-(4-methylpyridin-3-yl)benzo[d]isoxazole (69); 7-(4-methylpyridin-3-yl)-3-(2,2,2-trifluoroethylthio)benzo[d]isoxazole (70); 3-isobutoxy-7-(4-methylpyridin-3-yl)benzo[d]isoxazole (71); 3-(2-methoxyphenyl)-7-(4-methylpyridin-3-yl)benzo[d]isoxazole (72); 7-(4-(benzyloxy)pyrimidin-5-yl)-3-(2-methoxyphenyl)benzo[d]isoxazole (73); 7-(4-(2-fluoroethoxy)pyrimidin-5-yl)-3-(2-methoxyphenyl)benzo[d]isoxazole (74); 7-(4-isopropoxypyrimidin-5-yl)-3-(2,2,2-trifluoroethoxy)benzo[d]isoxazole (75); 3-(2-methoxyphenyl)-7-(4-(2-morpholinoethoxy)pyrimidin-5-yl)benzo[d]isoxazole (76); 3-(2-methoxyphenyl)-7-(4-(pyridazin-3-ylmethoxy)pyrimidin-5-yl)benzo[d]isoxazole (77); 3-(2-methoxyphenyl)-7-(4-(pyridazin-3-ylmethoxy)pyrimidin-5-yl)benzo[d]isoxazole (78); 7-(4-chloropyridin-3-yl)-3-(2-methoxyphenyl)benzo[d]isoxazole (79); 7-(isoquinolin-4-yl)-3-(2-methoxyphenyl)benzo[d]isoxazole (80); 7-(4-(2,2-difluoroethoxy)pyrimidin-5-yl)-3-(2-methoxyphenyl)benzo[d]isoxazole (81); 3-(2-methoxyphenyl)-7-(4-methylpyrimidin-5-yl)benzo[d]isoxazole (82); 3-(2-methoxyphenyl)-7-(4-morpholinopyrimidin-5-yl)benzo[d]isoxazole (83); 3-(2-methoxyphenyl)-7-(pyrrolo[1,2-c]pyrimidin-4-yl)benzo[d]isoxazole (84); 7-(4-methylpyridin-3-yl)-3-(3,3,3-trifluoropropyl)benzo[d]isoxazole (85); N-(3-amino-7-(4-methylpyridin-3-yl)benzo[d]isoxazol-4-yl)methanesulfonamide (104); 7-(4-methylpyridin-3-yl)-3-phenethoxybenzo[d]isoxazole (115); 3-(4-chlorophenethoxy)-7-(4-methylpyridin-3-yl)benzo[d]isoxazole (116); 7-(4-methylpyridin-3-yl)-3-(prop-2-ynyloxy)benzo[d]isoxazole (117); 3-(3,3-dimethylbutoxy)-7-(4-methylpyridin-3-yl)benzo[d]isoxazole (118); 3-(isopentyloxy)-7-(4-methylpyridin-3-yl)benzo[d]isoxazole (119); 7-(4-methylpyridin-3-yl)-3-propoxybenzo[d]isoxazole (120); 7-(4-methylpyridin-3-yl)-3-(3-phenylpropoxy)benzo[d]isoxazole (121); 7-(4-methylpyridin-3-yl)-3-(4-phenylbutoxy)benzo[d]isoxazole (122); 3-ethoxy-7-(4-methylpyridin-3-yl)benzo[d]isoxazole (123); 7-(4-methylpyridin-3-yl)-3-(naphthalen-2-ylmethoxy)benzo[d]isoxazole (124); 3-tert-butoxy-7-(4-methylpyridin-3-yl)benzo[d]isoxazole (125); 3-methoxy-7-(4-methylpyridin-3- yl)benzo[d]isoxazole (126); 3-(benzyloxy)-7-(4-methylpyridin-3-yl)benzo[d]isoxazole (127); 3-(4-chlorobenzyloxy)-7-(4-methylpyridin-3-yl)benzo[d]isoxazole (128); 3-(4-methoxybenzyloxy)-7-(4-methylpyridin-3-yl)benzo[d]isoxazole (129); 3-(1-methylpiperidin-4-yloxy)-7-(4-methylpyridin-3-yl)benzo[d]isoxazole (130); 3-isopropoxy-7-(4-methylpyridin-3-yl)benzo[d]isoxazole (131); 3-(2-(1H-imidazol-1-yl)ethoxy)-7-(4-methylpyridin-3-yl)benzo[d]isoxazole (132); 7-(4-methylpyridin-3-yl)-3-(pyrazin-2-ylmethoxy)benzo[d]isoxazole (133); 7-(4-methylpyridin-3-yl)-3-(thiazol-2-ylmethoxy)benzo[d]isoxazole (134); and pharmaceutically acceptable salts and prodrugs thereof.

One embodiment provides a compound of Formula (I) wherein said compound is selected from 3-(4-fluorophenyl)-7-(4-methylpyridin-3-yl)isoxazolo[4,5-b]pyridine (86); 3-chloro-7-(4-methylpyridin-3-yl)isoxazolo[4,5-b]pyridine (87); 7-(4-methylpyridin-3-yl)-3-morpholinoisoxazolo[4,5-b]pyridine (88); 7-(4-methylpyridin-3-yl)-3-phenylisoxazolo[4,5-b]pyridine (89); 3-(5-fluoro-2-methoxyphenyl)-7-(4-methylpyridin-3-yl)isoxazolo[4,5-b]pyridine (90); 5-(3-(2-chloro-4-fluorophenyl)isoxazolo[4,5-b]pyridin-7-yl)pyrimidin-4-amine (91); 5-(3-(4-fluorophenyl)isoxazolo[4,5-b]pyridin-7-yl)pyrimidin-4-amine (92); and pharmaceutically acceptable salts and prodrugs thereof.

One embodiment provides a compound of Formula (I) wherein said compound is selected from 7-(4-methylpyridin-3-yl)-3-(pyridin-2-yl)thieno[3,2-b]pyridine (93); 7-(4-methylpyridin-3-yl)-3-(thiazol-2-yl)thieno[3,2-b]pyridine (94); 7-(4-methylpyridin-3-yl)-3-(pyrazin-2-yl)thieno[3,2-b]pyridine (95); 3-(4-fluorophenyl)-7-(4-methylpyridin-3-yl)thieno[3,2-b]pyridine (96); 7-(4-methylpyridin-3-yl)-3-phenylthieno[3,2-b]pyridine (97); 3-(4-fluorophenyl)-7-(4-methylpyrimidin-5-yl)thieno[3,2-b]pyridine (98); 7-(4-cyclopropylpyrimidin-5-yl)-3-(4-fluorophenyl)thieno[3,2-b]pyridine (99); 5-(3-(4-fluorophenyl)thieno[3,2-b]pyridin-7-yl)pyrimidin-4-amine (100); 5-(3-(4-fluoro-2-(trifluoromethyl)phenyl)thieno[3,2-b]pyridin-7-yl)pyrimidin-4-amine (101); 5-(3-(2,4-difluorophenyl)thieno[3,2-b]pyridin-7-yl)pyrimidin-4-amine (102); 5-(3-(2-chloro-4-fluorophenyl)thieno[3,2-b]pyridin-7-yl)pyrimidin-4-amine (103); and pharmaceutically acceptable salts and prodrugs thereof.

One embodiment provides a compound of Formula (I) wherein said compound is selected from N-(7-(4-methylpyridin-3-yl)benzo[b]thiophen-4-yl)methanesulfonamide (105); N-(7-(4-cyclopropylpyrimidin-5-yl)benzo[b]thiophen-4-yl)methanesulfonamide (106); N-(7-(4-cyclopropylpyridin-3-yl)benzo[b]thiophen-4-yl)methanesulfonamide (107); 5-(3-(4-fluorophenyl)benzo[b]thiophen-7-yl)-4-methylpyrimidine (108); 4-(3-(4-fluorophenyl)benzo[b]thiophen-7-yl)isoquinoline (109); 4-(3-(2-chloro-4-fluorophenyl)benzo[b]thiophen-7-yl)isoquinoline (110); 3-(3-(4-fluorophenyl)benzo[b]thiophen-7-yl)-4-methylpyridine (111); 4-methyl-3-(3-(pyridin-2-yl)benzo[b]thiophen-7-yl)pyridine (112); 3-(3-(2,4-difluorophenyl)benzo[b]thiophen-7-yl)-4-methylpyridine (113); 3-(3-(2-chloro-4-fluorophenyl)benzo[b]thiophen-7-yl)-4-methylpyridine (114); and pharmaceutically acceptable salts and prodrugs thereof.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

As used herein, "alkylenyl" refers to a bivalent alkyl radical having the general formula —$(CH_2)_n$—, where n is 1 to 10. Non-limiting examples include methylene, dimethylene, trimethylene, tetramethylene, pentamethylene, and hexamethylene. For example, "$C_{1-6}$alkylene" denotes straight and branched chain alkylene groups with one to six carbon atoms. Further, for example, "$C_{0-4}$alkylene" denotes a bond and straight and branched chain alkylene groups with one to four carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "cyano" refers to the group —CN.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$).

"Fluoroalkoxy" and "—O(fluoroalkyl)" represent a fluoroalkyl group as defined above attached through an oxygen linkage (—O—). For example, "$C_{1-4}$fluoroalkoxy" is intended to include $C_1$, $C_2$, $C_3$, and $C_4$ fluoroalkoxy groups.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The term "heteroatom" refers to oxygen (O), sulfur (S), and nitrogen (N).

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazolyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., p. 1418 (Mack Publishing Company, Easton, Pa., 1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate (i.e., 1,1'-methylene-bis-(2-hydroxy-3-naphthoate)) salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes amides and carbamates formed by reacting one or more amino groups of compounds of Formula (I) with alkyl, alkoxy, or aryl substituted acylating agents employing procedures known to those skilled in the art to generate amides, ureas, carbamates, and the like.

Various forms of prodrugs are well known in the art and are described in:

a) Wermuth, C. G. et al., *The Practice of Medicinal Chemistry*, Ch. 31, (Academic Press, 1996);

b) Bundgaard, H., ed., *Design of Prodrugs*, (Elsevier, 1985);

c) Krogsgaard-Larson, P. et al., eds., *A Textbook of Drug Design and Development*, Ch. 5, pp. 113-191 (Harwood Academic Publishers, 1991); and d) Testa, B. et al., *Hydrolysis in Drug and Prodrug Metabolism*, (Wiley-VCH, 2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an antagonist of CYP17 enzyme, or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention are intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg body weight, preferably between about 0.05 and about 50 mg/kg body weight and most preferably between about 0.05 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

UTILITY

The compounds of Formula (I) are useful for the treatment of cancer, for example, cancers dependent upon androgen receptor signaling. These compounds inhibit the activity of the CYP17 enzyme, which is involved in biosynthesis of androgens and estrogens. Blocking this enzyme would inhibit the production of gonadal, adrenal, and tumoral androgens and offers a new treatment option for cancers dependent upon androgen receptor and estrogen receptor signaling, such as prostate cancer and estrogen receptor-positive breast cancer patients. Thus, the treatment comprises administering to the patient a compound of Formula (I) or a pharmaceutically acceptable salt or prodrug thereof.

In one embodiment, a method is provided for treating cancer comprising administering compound of Formula (I) or a pharmaceutically acceptable salt or prodrug thereof to a mammal in need thereof. The method of this embodiment can be used to treat a variety of cancers, including, but not limited to, breast cancer, ovarian cancer, and prostate cancer. Preferably, the method of this embodiment is used to treat prostate cancer or breast cancer. In one method of this embodiment, compound of Formula (I) is administered in a therapeutically effective amount.

In one embodiment, provided are methods for treating cancer in a patient wherein the cancer is dependent upon CYP17 activation, comprising administering to the patient in need thereof a compound of Formula (I) or a pharmaceutically acceptable salt or prodrug thereof. In one method of this embodiment, a compound of Formula (I) is administered to treat prostate cancer. In another method of this embodiment, a compound of Formula (I) is administered to treat breast cancer. Preferably, a therapeutically effective amount of Compound (I) is administered.

The amount of a compound of Formula (I) which is administered and the dosage regimen for treating a particular cancer depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.05 and about 50 mg/kg body weight and most preferably between about 0.05 to 20 mg/kg body weight, may be appropriate may be appropriate. The daily dose can be administered in one to four doses per day.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, a compound of Formula (I) may be administered in combination with other anti-cancer treatments useful in the treatment of cancer or other proliferative diseases. The invention herein further comprises use of a compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of a compound of Formula (I) and one or more additional agents in kit form, e.g., where they are packaged together or placed in separate packages to be sold together as a kit, or where they are packaged to be formulated together.

The compound of Formula (I) can be formulated or co-administered with other therapeutic agents that are selected for their particular usefulness in addressing side effects associated with the aforementioned conditions. For example, the compound of Formula (I) may be formulated with agents to prevent nausea, hypersensitivity and gastric irritation, such as antiemetics, and $H_1$ and $H_2$ antihistaminics.

The phrase "anti-cancer treatment" includes but is not limited to, for example, radiation therapy and surgery.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The above other therapeutic agents, when employed in combination with a compound of Formula (I), can be used, for example, in those amounts indicated in the *Physicians' Desk Reference* (PDR) or as otherwise determined by one of ordinary skill in the art.

In one embodiment, a method is provided for treating cancer comprising administering to a mammal in need thereof a compound of Formula (I) or a pharmaceutically acceptable salt or prodrug thereof; administering a glucocorticoid; and optionally, one or more additional anticancer agent. Examples of suitable glucocorticoids include, but are not limited to, dexamethasone and prednisolone.

In one embodiment, a method is provided for treating cancer comprising administering to a mammal in need thereof a compound of Formula (I) or a pharmaceutically acceptable salt or prodrug thereof; administering a mineralocorticoid receptor antagonist; and optionally, one or more additional anticancer agent. Examples of suitable mineralocorticoid receptor antagonists include, but are not limited to, eplerenone.

In another embodiment, a compound of Formula (I) or a pharmaceutically acceptable salt thereof is used to treat prostate cancer.

In one embodiment, the patient is an animal.

In another embodiment, the patient is a mammalian species including, but not limited to, for example, humans and domestic animals, such as, for example, dogs, cats, and horses.

In one embodiment, the present invention provides a compound of Formula (I) or a pharmaceutically acceptable salt thereof for use in therapy.

In one embodiment, the use of a compound of Formula (I) or a pharmaceutically acceptable salt thereof in the manufacture of a medicament for the treatment of cancer, including prostate cancer, is provided.

In one embodiment, the use of a compound of Formula (I) or a pharmaceutically acceptable salt thereof in the manufacture of a medicament for the treatment of cancer, including breast cancer, is provided.

Methods of Preparation

The compounds of the present invention may be prepared by synthetic routes that include processes analogous to those well-known in the chemical arts, particularly in light of the description provided herein. For illustrative purposes, general Schemes 1 to 20 below show general methods for preparing the compounds of the present invention, as well as key intermediates. For a more detailed description of the individual reaction steps, see the Example section below. Those skilled in the art will appreciate that other synthetic routes may be used to synthesize the inventive compounds. Although specific starting materials and reagents are depicted in the Schemes and discussed below, other starting materials and reagents can easily be substituted to provide a variety of compounds of the present invention. In addition, many of the compounds prepared by the methods below can be further modified in light of this disclosure using conventional chemistry well known to those skilled in the art.

As shown in Scheme 1, for instance, C1-aryl or alkyl substituted benzoisoxazoles of type IA can be prepared from 3-bromo-2-fluorobenzaldehyde II via a Grignard addition into the aldehyde. The resultant alcohol III can be oxidized, by Dess-Martin periodinane for example, to afford the ketone of general structure IV. Treatment of the ketone with hydroxylamine can afford oxime V. Subsequently, cyclization to provide the corresponding benzoisoxazole VI will occur in the presence of a base, such as NaH. Under standard Suzuki coupling conditions, benzoisoxazole VI can be coupled with a boronic ester or acid VII to furnish compounds of general structure IA.

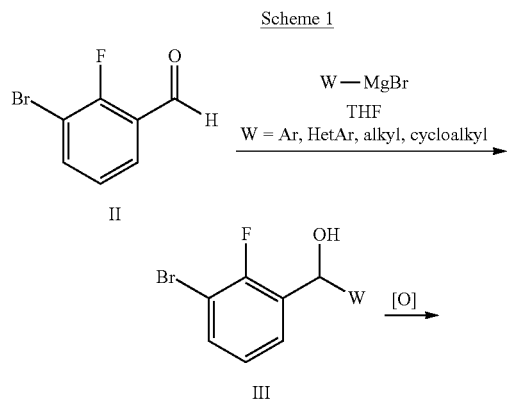

Scheme 1

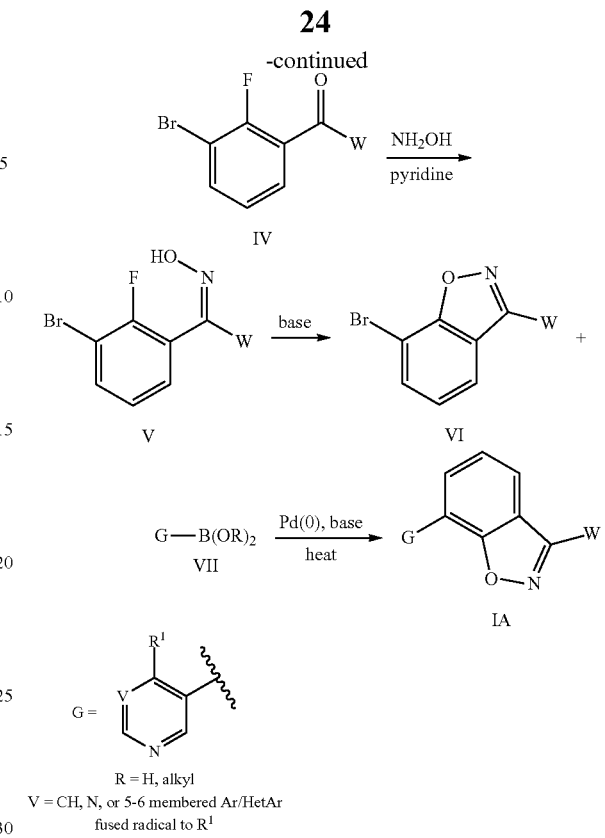

The general structure of the aryl boronic ester or acid of type VII shown in Scheme 1 can be synthesized from the corresponding halide VIII by a palladium-mediated reaction with a source of boron, such as bis(pinacolato)diboron (Scheme 2). Alternatively halogen-metal exchange with aryl halide VIII and a subsequent reaction with triisopropyl borate will also afford boronic esters or acids of type VII.

Scheme 2

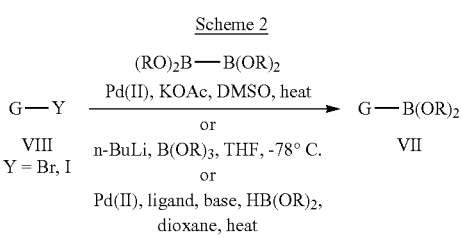

The general halides of type VIII used in the synthesis of aryl boronic ester or acid VII can originate from pyrimidyl ethers X (Scheme 3), pyrimidyl amines XI (Scheme 4), 4-alkyl or 4-aryl pyrimidines XIII (Scheme 5), 4-aryl pyridines XV (Scheme 6), and 4-cycloalkyl XVII or 4-alkyl pyridines XVII, XVIII (Scheme 7 and 8). Each of these halides can be synthesized in the following manner. The pyrimidyl ethers X can be generated from displacement of the corresponding pyrimidyl chloride IX with an alcohol and base. The pyrimidyl amines XI can be synthesized under the same reaction conditions from the pyrimidyl chloride IX and ammonia or a primary or secondary amine. 4-Alkyl and 4-aryl substituted pyrimidines XIII can be prepared by many methods well known to those skilled in the art. Scheme 5 depicts one such method where 5-bromopyrimidine XII can be treated with an alkyl or aryl lithium or a Grignard reagent to give the 4-substituted dihydropyrimidine. Subsequent oxidation by, for example, DDQ, then gives the desired 4-substituted pyrimidine XIII In contrast, 4-aryl pyridines of general structure XV can be prepared by Suzuki coupling of boronic ester XIV with an aryl iodide under palladium catalysis. Substituted pyridines of type XVII and XVIII can be synthesized by deprotonation of 3-bromopyridine with a strong base such as LDA to generate an anion, and then a subsequent reaction with an alkyl or cycloalkyl ketone to give substituted pyridines of type XVII or treatment with an alkyl iodide to afford 4-alkyl pyridines of type XVIII. Finally, the pyrrolopyrimidine XX depicted in Scheme 9 can be prepared from 5-bromopyrimidine XII. Addition of an alkyllithium reagent to this commercially available starting material will give the corresponding 4-substituted dihydropyrimidine XIX. Subsequent oxidation by, for example, DDQ then gives the desired 4-substituted pyrimidine. Treatment of this intermediate XIX with an organic acid, such as formic acid, will generate the corresponding aldehyde. Further reaction of the aldehyde with Burgess reagent will promote cyclization to the desired pyrrolopyrimidine XX.

Scheme 3

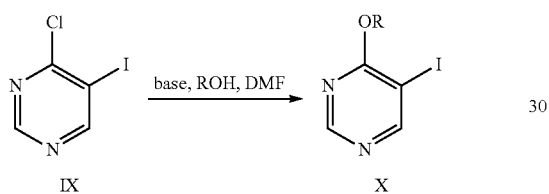

Scheme 4

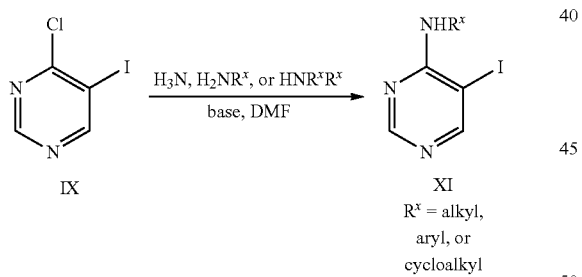

Scheme 5

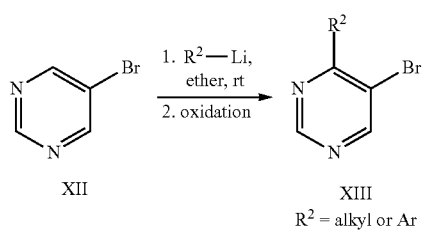

Scheme 6

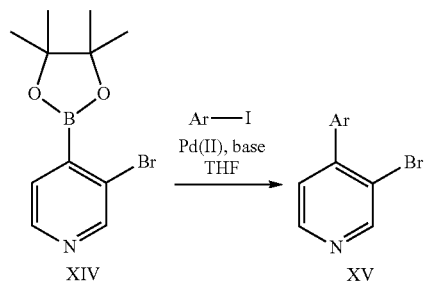

Scheme 7

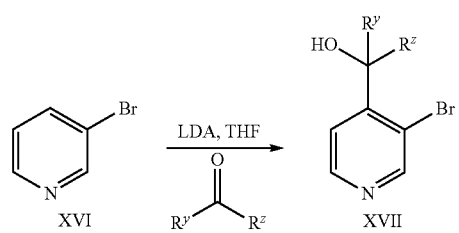

Scheme 8

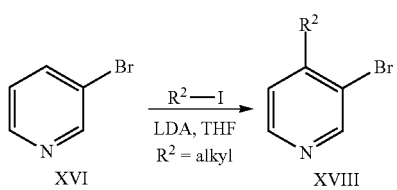

Scheme 9

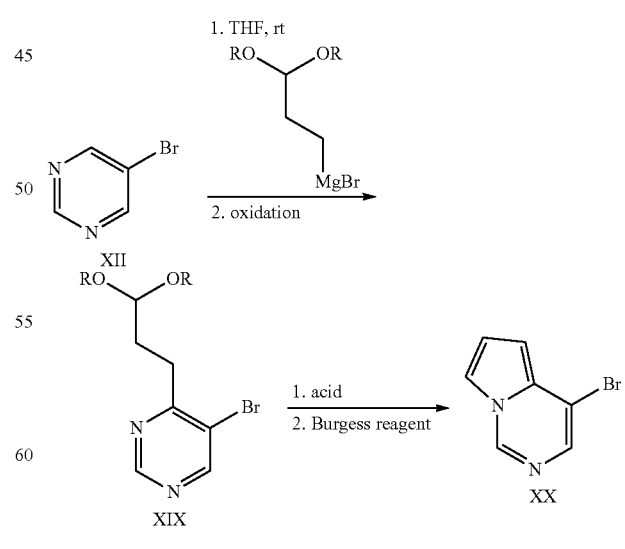

The compounds of type IA depicted in Scheme 1 can alternatively be synthesized by a Pd (II) mediated coupling of benzoisoxazole VI with a boron source XXI, such as 4,4,5,5,-tetramethyl-1,3,2-dioxaborolane, to form benzoisoxazole ester or acid XXII (Scheme 10). Reaction of intermediate XXII with a heteroaryl halide VIII under standard Suzuki conditions can afford analogs of general structure IA.

induces cyclization and formation of benzoisoxazole amine XXV. Treatment of the primary amine with sodium nitrite and hydrochloric acid can provide the corresponding benzoisoxazole chloride XXVI. Finally, displacement of the aryl chloride with an alcohol, thiol or amine in the presence of a base will afford analogs of general structure IB.

Scheme 11

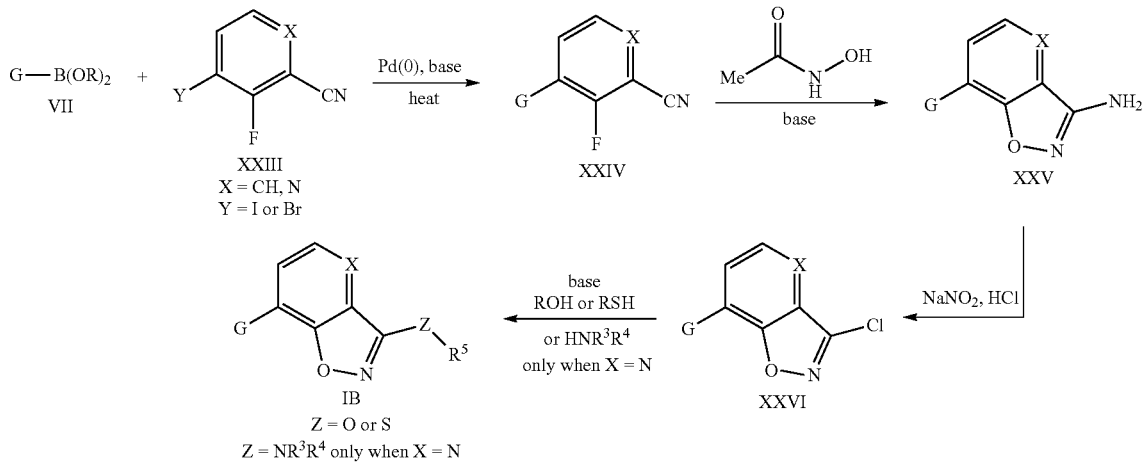

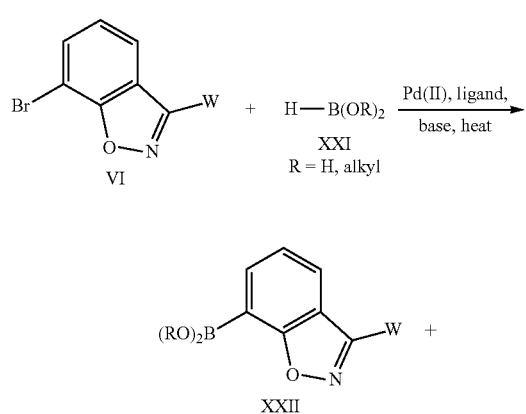

Scheme 10

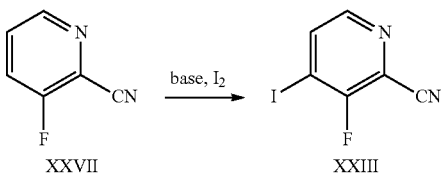

Scheme 12

Preparation of benzoisoxazoles linked to a heteroatom at C3 can be accomplished by literature methods that are well known to those skilled in the art. Scheme 11 depicts a commonly used method for the preparation of benzoisoxazole IB from commercially available 3-bromo-2-fluorobenzonitrile or from 3-fluoro-4-iodopicolinonitrile XXIII, which is available in one step from the iodination of 3-fluoropicolinonitrile XXVII (Scheme 12). A standard Suzuki coupling of the general aryl halide XXIII with boronic ester or acid VII can afford biaryls of type XXIV. Subsequently, reaction of this intermediate with N-hydroxyacetamide Another method of generating benzonitrile XXIV utilized in Scheme 11, when X=C, can be achieved by a standard Suzuki reaction between heteroaryl halide VIII and commercially available boronic ester or acid XXVIII (Scheme 13).

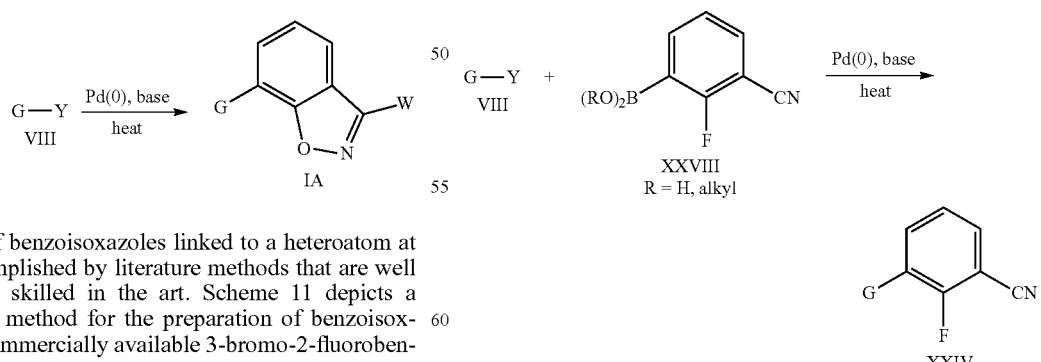

Additionally, if aryl, heteroaryl, alkyl, or cycloalkyl groups are desired at C3 of the general structure IA or IC, those skilled in the art can prepare such compounds from intermediate XXIV (Scheme 14). A Grignard addition into the nitrile and a subsequent hydrolysis of the in situ generated imine with HCl can provide ketone XXIX. Further reaction of intermediate XXIX with hydroxylamine will afford oxime XXX, which can be cyclized to the corresponding benzoisoxazole of general structure IA or IC in the presence of a base, such as NaH.

Scheme 14

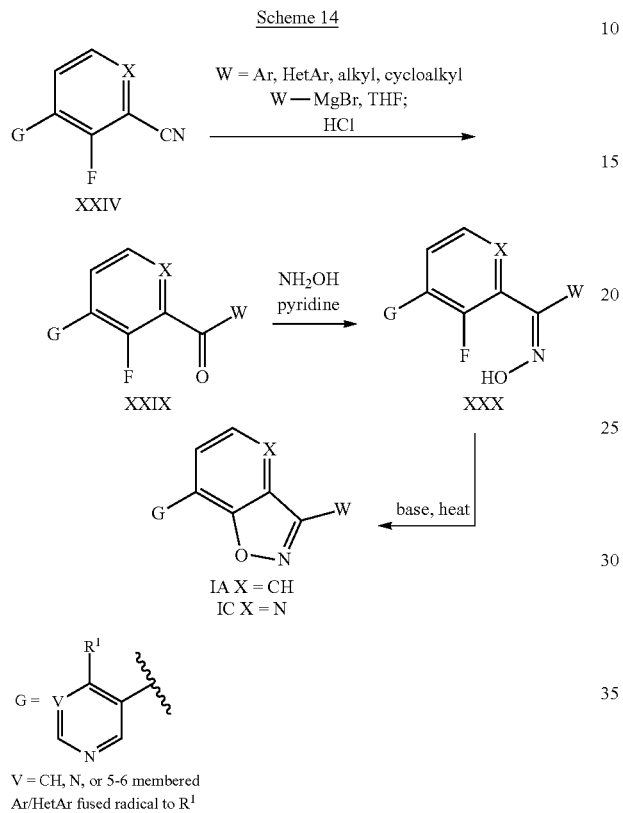

Furthermore, benzoisoxazoles linked to a variety of substituted pyrimidines of general structure IA, IB, or IC can be synthesized from compounds of general structure XXXI (Scheme 15). Treatment of compound XXXI with peroxyacetic acid and sulfuric acid can provide hydroxylated intermediate XXXII. Reaction of the pyrimidinol with phosphorus oxychloride will furnish chloropyrimidine XXXIII Finally, displacement of the chloride with an alcohol or amine can lead to compounds of general structure IA, IB, or IC.

Scheme 15

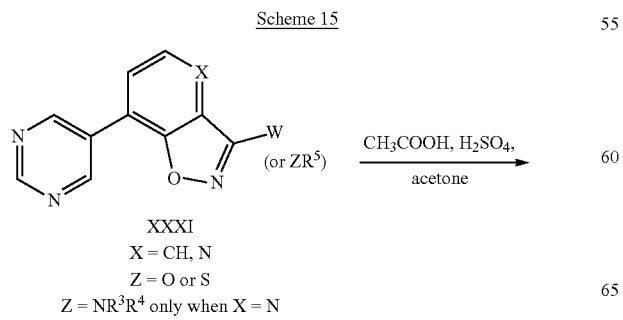

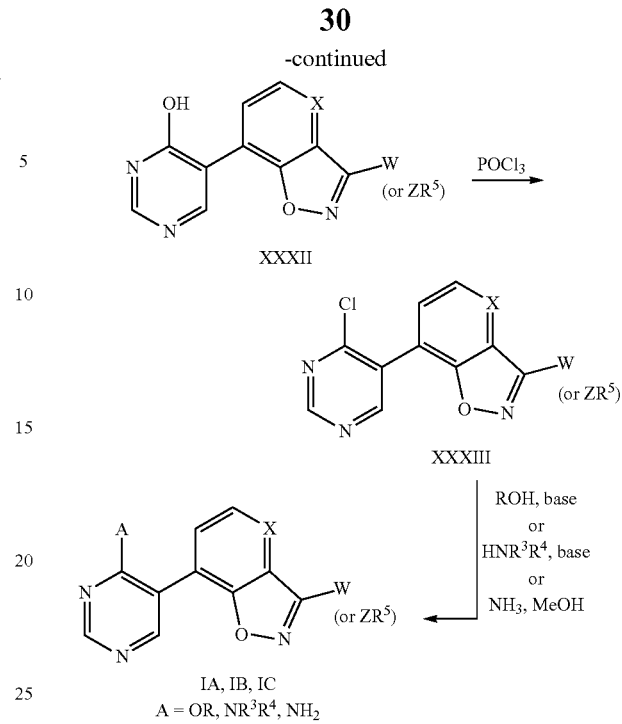

Those skilled in the art will also find that substituted pyrimidines linked to benzoisoxazoles of general structure IA or IC can be synthesized from biaryl intermediate XXXIV (Scheme 16). Similar to the reaction sequence shown in Scheme 15, treatment of the pyrimidine with peroxyacetic acid and sulfuric acid will give pyrimidinol XXXV. Subsequently, a Grignard addition into the nitrile followed by hydrolysis with hydrochloric acid can lead to a variety of substituted ketones of type XXXVI. Reaction of this ketone with hydroxylamine will furnish oxime XXXVII. As previously described, cyclization to the corresponding benzoisoxazole can be accomplished with base. Conversion of the pyrimidinol XXXII to the chloropyrimidine XXXIII can occur by reaction with phosphorus oxychloride. Lastly, displacement of the chloride with an alcohol or amine can lead to compounds of general structure IA or IC.

Scheme 16

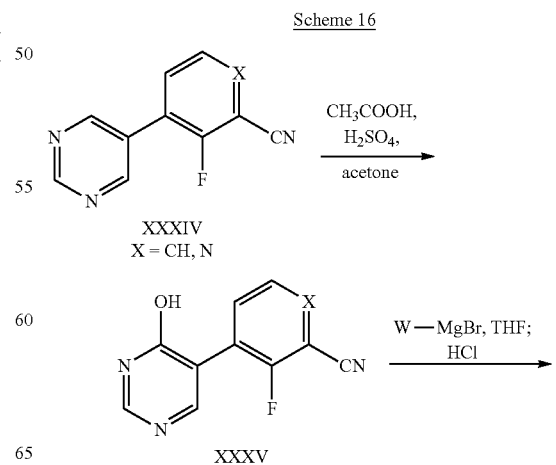

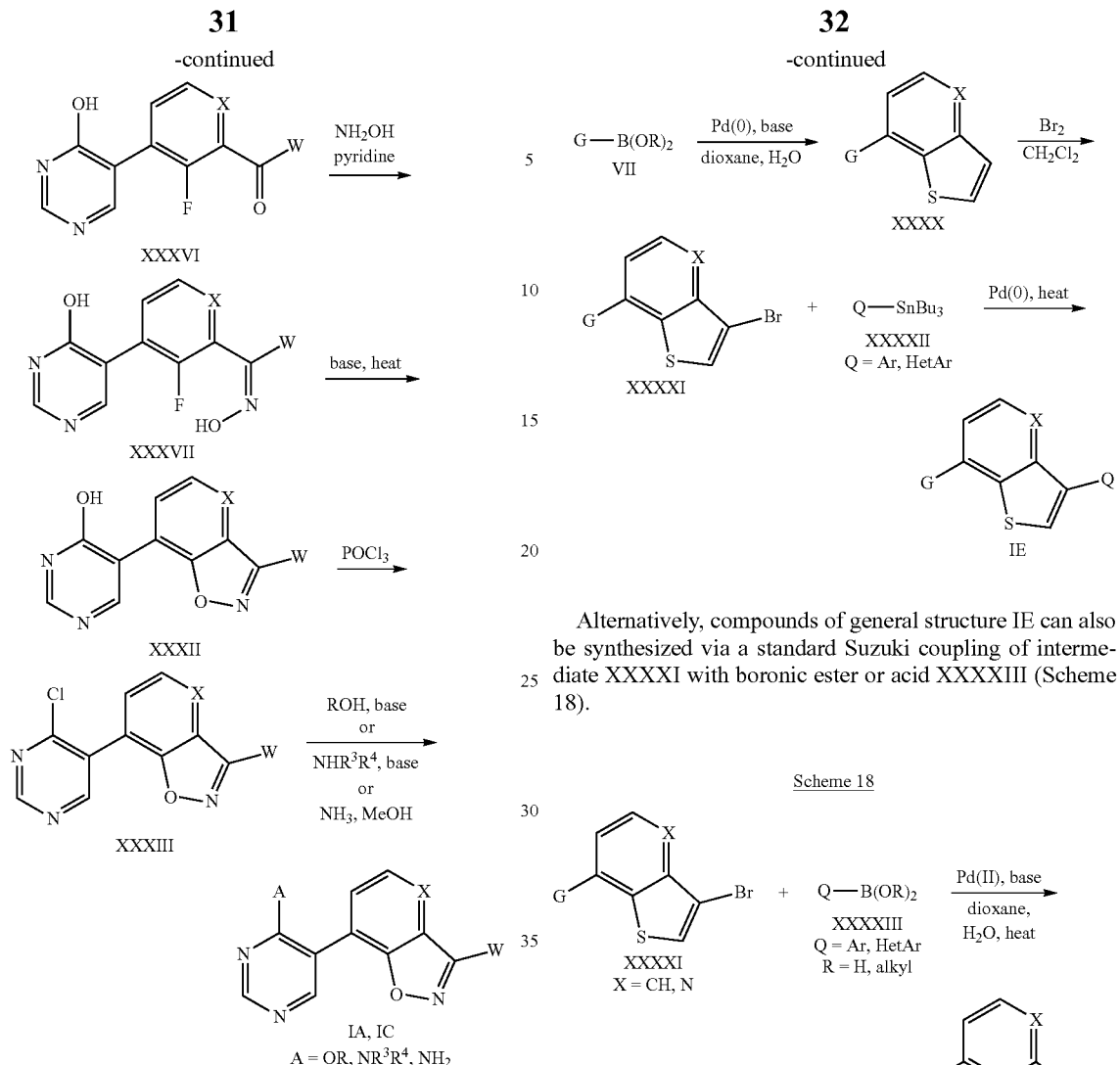

Alternatively, compounds of general structure IE can also be synthesized via a standard Suzuki coupling of intermediate XXXXI with boronic ester or acid XXXXIII (Scheme 18).

Benzothiophenes or thienopyridines of general structure IE can be synthesized from the commercially available alcohol XXXVIII (Scheme 17). Halogenation of this starting material with phosphorus oxychloride or bromide can provide an intermediate of type XXXIX. Following a standard Suzuki coupling of (hetero)aryl halide XXXIX with a general boronic ester or acid VII, an analog of type XXXX can be formed. Functionalization at C3 can be accomplished by a bromination step and then a Pd(0)-mediated Stille coupling of intermediate XXXXI with stannane XXXXII to give compounds of general structure IE.

Benzothiophenes of general structure IF can be synthesized from benzo[b]thiophen-4-amine XXXXIIII (Scheme 19). Treatment of this commercially available starting material with methanesulfonyl chloride will afford sulfonamide XXXXV. Iodination of this intermediate with I2 in pyridine will provide the aryl iodide XXXXIV. Subsequently, a standard Suzuki coupling of this compound with a boronic ester or acid VII can furnish analogs of general structure IF.

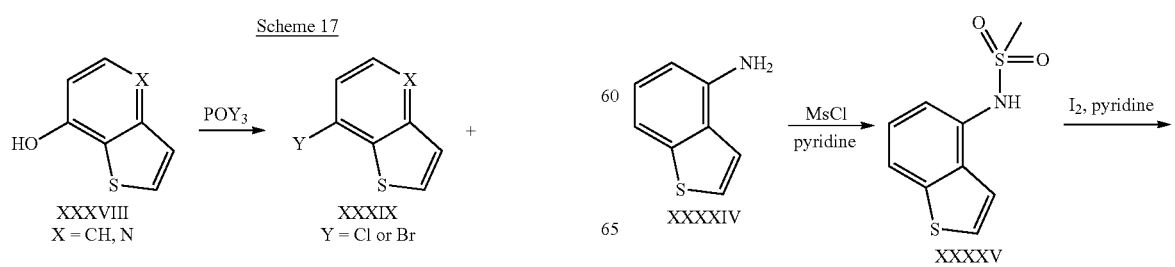

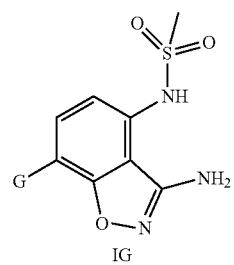

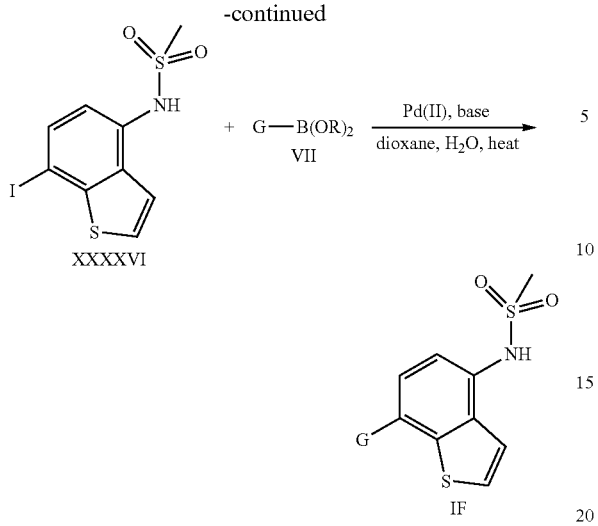

Benzoisoxazoles of general structure IG can be synthesized from 2-amino-6-fluorobenzonitrile XXXXVII (Scheme 20). Iodination of this commercially available starting material with a reagent, such as ICl, will provide aryl iodide XXXXVIII. Reaction of the primary amine with methanesulfonyl chloride and pyridine will give sulfonamide XXXXIX. Following ring closure to benzoisoxazole XXXXX by reaction of intermediate XXXXIX with N-hydroxyacetamide, a standard Suzuki coupling of benzoisoxazole XXXXX with boronic ester or acid VII can lead to compounds of general structure IG.

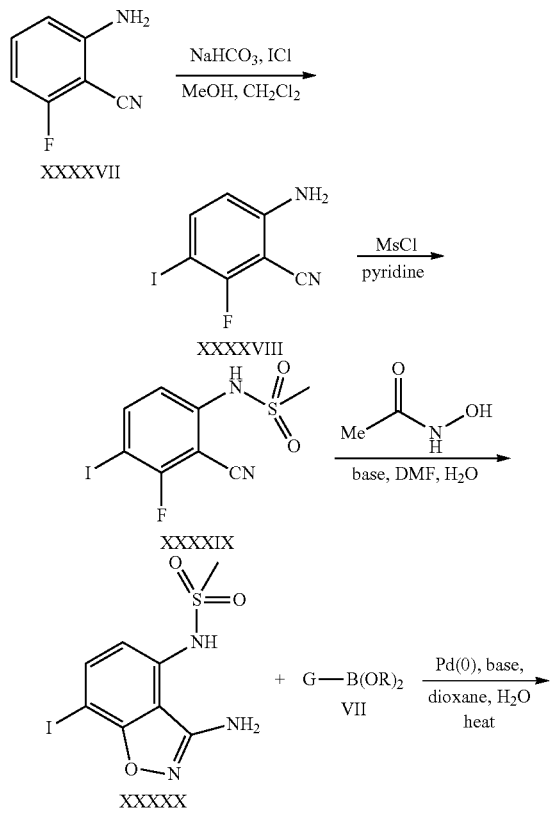

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

ABBREVIATIONS

AcOH acetic acid
Ac$_2$O acetic anhydride
aq. aqueous
CH$_2$Cl$_2$ dichloromethane
DCE dichloroethane
DCM dichloromethane
DDQ 2,3-dichloro-5,6-dicyano-p-benzoquinone
DMAP dimethylaminopyridine
DIEA diisopropylethylamine
DME dimethyl ether
DMF dimethylformamide
DMSO dimethylsulfoxide
Et ethyl
Et$_2$O diethyl ethyl
EtOAc ethyl acetate
EtOH ethanol
Et$_3$N triethyl amine
Et$_3$SiH trifluorosilane
g gram(s)
h or hr hour
HCl hydrochloric acid
HPLC high performance liquid chromatography
iPr isopropyl
iPrOH isopropanol
L liter
LC/MS liquid chromatography/mass spectrometry
LDA lithium diisopropylamine
LTMP lithium 2,2,6,6-tetramethylpiperidine
Me methyl
MeOH methanol
mg milligram(s).
min minute
mL milliliter
mmol millimole(s).
mp melting point
mol moles
MS mass spectrometry
NBS N-bromosuccinimide
n-BuLi n-butyl lithium NaOMe sodium methoxide PdCl₂(dppf)-CH₂Cl₂ dichloro[1,1'-bis(diphenylphosphino)ferrocene]palladium(II) dichloromethane adduct Pd(PPh₃)₄ tetrakis(triphenylphosphine)palladium PMe₃ trimethyl phosphine Prep HPLC preparative reverse phase HPLC ret. T HPLC retention time (minutes).

RT or rt room temperature sat or sat'd saturated

TBSCl tert-butyldimethylsilylchloride

TFA trifluoroacetic acid

Tf₂O trifluoromethylsulfonic anhydride

THF tetrahydrofuran

TLC thin layer chromatography

VCD vibrational circular dichroism

μL microliter

HPLC Conditions:

A: Column: Mac-mod Halo C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 45° C.; Gradient: 0-100% B over 4 minutes, then a 1-minute hold at 100% B; Flow: 4 mL/min.

B: SUPELCO® Ascentis Express C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 35° C.; Gradient: 0-100% B over 4 minutes, then a 1-minute hold at 100% B; Flow: 4 mL/min.

C: YMC S5 ODS column, 4.6×50 mm. 4 min gradient (0-100% B), 4 mL/min, 40° C. @ 220 nm, solvent A: 0.2% H₃PO₄ in 10% MeOH-90% H₂O, solvent B: 0.2% H₃PO₄ in 90% MeOH-10% H₂O.

D: SUPELCO® Ascentis Express C18, 4.6×50 mm, 2.7-μm particles; Mobile Phase A: 5:95 acetonitrile:water with 10 mM ammonium acetate; Mobile Phase B: 95:5 acetonitrile:water with 10 mM ammonium acetate; Temperature: 35° C.; Gradient: 0-100% B over 4 minutes, then a 1-minute hold at 100% B; Flow: 4 mL/min.

E: Waters Acquity UPLC BEH C18, 2.1×50 mm, 1.7-μm particles; Mobile Phase A: 5:95 acetonitrile:water with 10 mM ammonium acetate; Mobile Phase B: 90:10 acetonitrile:water with 10 mM ammonium acetate; Temperature: 50° C.; Gradient: 0-100% B over 3 minutes, then a 0.75-minute hold at 100% B; Flow: 1.11 mL/min.

LC/MS Conditions:

F: Column: Luna C18 4.6×30 mm 3 u A: 10:90 H₂O:ACN NH₄OAc/B: 10:90 H₂O:ACN NH₄OAc; 0%-95% B in 2 min; 4 mL/min flow G: PHENOMENEX®-Luna 4.6×30 mm S10, 4 minute gradient time, flow rate: 4.0 mL/min, Solvent A: 10% MeOH/90% water/0.1% TFA; Solvent B: 90% MeOH/10% water/0.1% TFA, wavelength 220 nm.

H: PHENOMENEX® Luna C18, 50×2, 3μ, 4 minute gradient time, flow rate: 0.8 mL/min, Solvent A: 10% MeOH/90% water/10 mM Ammonium Acetate; Solvent B: 90% MeOH/10% water/10 mM ammonium acetate, wavelength 220 nm.

Example 1

7-(4-Methylpyridin-3-yl)-3-phenylbenzo[d]isoxazole

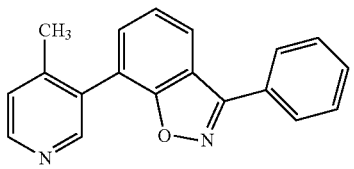

(1)

Preparation 1A:
(3-Bromo-2-fluorophenyl)(phenyl)methanol

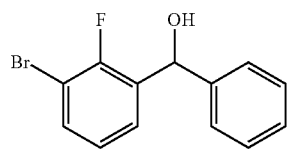

(1A)

To a solution of 3-bromo-2-fluorobenzaldehyde (0.150 g, 0.739 mmol) in THF (3.21 mL) cooled to −78° C. was added phenylmagnesium bromide (0.887 mL, 0.887 mmol). The reaction mixture was maintained at −78° C. for at least 1 hr and then allowed to warm to room temperature slowly over 3 hr. The reaction was quenched with a saturated aqueous solution of NH₄Cl. The reaction mixture was diluted with CH₂Cl₂ and the layers were separated. The aqueous phase was extracted twice with CH₂Cl₂. The organic layers were combined, dried over Na₂SO₄, filtered, and concentrated to afford the title compound as a colorless residue.

Preparation 1B:
(3-Bromo-2-fluorophenyl)(phenyl)methanone

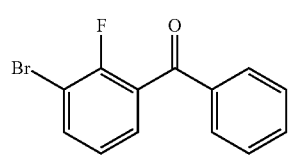

(1B)

To a solution of Preparation 1A (205 mg, 0.729 mmol) in wet CH₂Cl₂ (2917 μL) was added Dess-Martin periodinane (650 mg, 1.531 mmol) at room temperature. After 5.5 hr, the reaction was quenched with a 1:1 solution of saturated aqueous NaHCO₃:10% (w/w) aqueous Na₂S₂O₃. The reaction mixture was diluted with additional CH₂Cl₂ and the resulting mixture was stirred until both layers became clear. The layers were separated and the organic phase washed with saturated aqueous NaHCO₃. The aqueous phase was extracted twice with CH₂Cl₂. The organic phases were combined, dried over Na₂SO₄, filtered, and concentrated to afford the title compound as a colorless residue.

Preparation 1C:
(Z)-(3-Bromo-2-fluorophenyl)(phenyl)methanone oxime

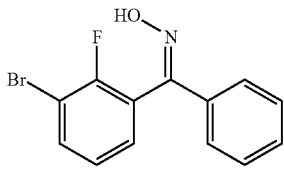
(1C)

A solution of Preparation 1B (0.204 g, 0.731 mmol) and hydroxylamine hydrochloride (0.345 g, 4.97 mmol) in pyridine (1.700 mL) was refluxed for 5 hr, allowed to cool to room temperature, and then concentrated in vacuo. The crude material was partitioned between EtOAc and 1N HCl. The layers were separated and the aqueous phase extracted with EtOAc (3×). Organics combined, dried over $Na_2SO_4$, filtered, and concentrated to afford the title compound as a yellow solid.

Preparation 1D:
7-Bromo-3-phenylbenzo[d]isoxazole

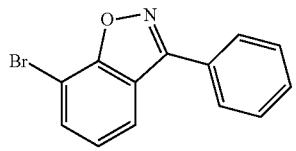
(1D)

To a suspension of sodium hydride (0.050 g, 1.243 mmol) in THF (1.880 mL) was added dropwise Preparation 1C (0.215 g, 0.731 mmol) in DMF (500 µL). The syringe was rinsed with additional DMF (500 µL) into the reaction vial. The reaction mixture was heated at 70° C. for 2.25 hr, then allowed to cool to room temperature. The reaction was quenched with $H_2O$. The reaction mixture was extracted with EtOAc (3×). The organic phases were combined, dried over $Na_2SO_4$, filtered, concentrated, and further dried under high vacuum to afford a yellow solid. The crude material was dissolved in a minimal amount of $CH_2Cl_2$. Purification of the crude material by silica gel chromatography using an ISCO machine (40 g column, 40 mL/min, 0-30% EtOAc in hexanes over 18 min, $t_r$=11 min) gave the title compound (140 mg, 0.511 mmol, 69.9% yield) as a white crystalline solid. LC/MS: Example 1D @ 1.70 (RT) (Condition F). MS (ES): m/z=276.0 $[M+H]^+$.

Example 1

A reaction flask was charged with tetrakis(triphenylphosphine)palladium(0) (3.58 mg, 3.10 µmol), Preparation 1D (17.0 mg, 0.062 mmol), sodium carbonate (26.3 mg, 0.248 mmol), and 4-methylpyridin-3-ylboronic acid (8.92 mg, 0.065 mmol). The mixture was stirred at room temperature for 10 min under $N_2$, then DME (231 µL), EtOH (116 µL), and water (116 µL) were added sequentially. The resultant mixture was heated at 90° C. overnight. After 19 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to afford the title compound (7.8 mg, 44%). ESI MS $(M+H)^+$= 287.1. HPLC Peak $t_r$=2.62 minutes. Purity=99%. HPLC Conditions: A.

Example 2

7-(4-Methoxypyridin-3-yl)-3-phenylbenzo[d]isoxazole

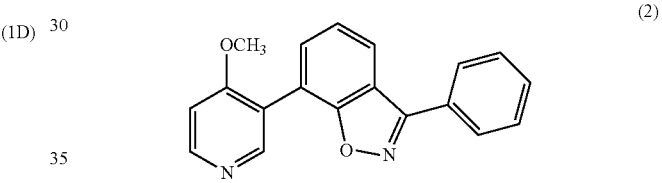
(2)

A reaction flask was charged with tetrakis(triphenylphosphine)palladium(0) (10.03 mg, 8.68 µmol), Preparation 1D (47.6 mg, 0.174 mmol), sodium carbonate (92 mg, 0.868 mmol), and 4-methoxypyridin-3-ylboronic acid, HCl (99 mg, 0.521 mmol). The mixture was stirred at room temperature for 10 min under $N_2$, then DME (648 µL), EtOH (324 µL), and water (324 µL) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a yellow residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (2.1 mg, 3.9% yield). ESI MS $(M+H)^+$=303.2. HPLC Peak $t_r$=2.39 minutes. Purity=97%. HPLC Conditions: A.

Example 3

7-(4-Chloropyridin-3-yl)-3-phenylbenzo[d]isoxazole (3)

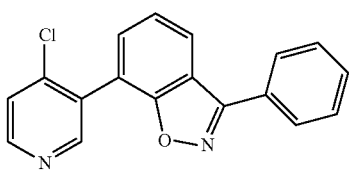

A reaction flask was charged with tetrakis(triphenylphosphine)palladium(0) (5.90 mg, 5.11 µmol), Preparation 1D (28 mg, 0.102 mmol), sodium carbonate (43.3 mg, 0.409 mmol), and 4-chloro-3-(4,4,5,5-tetramethyl-1,3,2-dioxaborolan-2-yl)pyridine (73.4 mg, 0.306 mmol). The mixture was stirred at room temperature for 10 min under $N_2$, then DME (381 µL), EtOH (191 µL), and water (191 µL) were added sequentially. The resultant mixture was heated at 90° C. overnight. After 19 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a yellow residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (7.5 mg, 24% yield). ESI MS $(M+H)^+$=306.9. HPLC Peak $t_r$=2.75 minutes. Purity=99%. HPLC Conditions: A.

Example 4

7-(4-Methylpyrimidin-5-yl)-3-phenylbenzo[d]isoxazole (4)

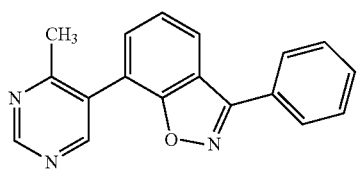

Preparation 4A: 4-Methyl-5-(4,4,5,5-tetramethyl-1,3,2-dioxaborolan-2-yl)pyrimidine

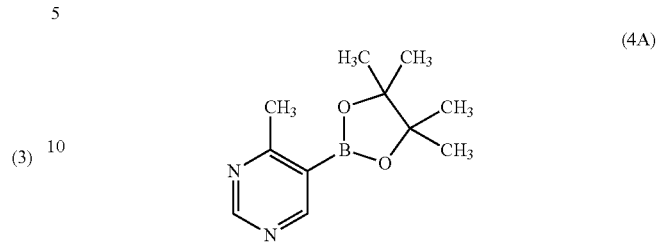

(4A)

Nitrogen was bubbled into a mixture of 5-bromo-4-methylpyrimidine (0.100 g, 0.578 mmol), 4,4,4',4',5,5,5',5'-octamethyl-2,2'-bi(1,3,2-dioxaborolane) (0.191 g, 0.751 mmol), and potassium acetate (0.129 g, 1.316 mmol) in DMSO (2.89 mL) for 10 min. Then 1,1'-bis(diphenylphosphino)ferrocene-palladium(II)dichloride dichloromethane complex (0.019 g, 0.024 mmol) was added and the reaction mixture was heated at 90° C. overnight. The reaction was quenched with $H_2O$. The reaction mixture was extracted with EtOAc (3×). The organic phases were combined, dried over $Na_2SO_4$, filtered, and concentrated to afford the title compound (127 mg, 100%) as a dark brown residue.

Example 4

A reaction flask was charged with tetrakis(triphenylphosphine)palladium(0) (5.69 mg, 4.92 µmol), Preparation 1D (27 mg, 0.098 mmol), sodium carbonate (41.8 mg, 0.394 mmol), and Preparation 4A (65.0 mg, 0.295 mmol). The mixture was stirred at room temperature for 10 min under $N_2$, then DME (368 µL), EtOH (184 µL), and water (184 µL) were added sequentially. The resultant mixture was heated at 90° C. overnight. After 19 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a dark brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compounds (2.1 mg, 7.4% yield). ESI MS $(M+H)^+$=288.0. HPLC Peak $t_r$=2.31 minutes. Purity >99%. HPLC Conditions: A.

Example 5

7-(Isoquinolin-4-yl)-3-phenylbenzo[d]isoxazole

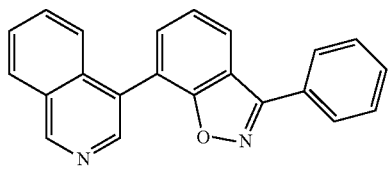

(5)

A reaction flask was charged with tetrakis(triphenylphosphine)palladium(0) (5.78 mg, 5.00 μmol), Preparation 1D (27.4 mg, 0.100 mmol), sodium carbonate (42.4 mg, 0.400 mmol), and 4-(4,4,5,5-tetramethyl-1,3,2-dioxaborolan-2-yl)isoquinoline (26.8 mg, 0.105 mmol). The mixture was stirred at room temperature for 10 min under $N_2$, then DME (373 μL), EtOH (187 μL), and water (187 μL) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford an orange residue. The crude material was dissolved in a minimal amount of $CH_2Cl_2$ to be chromatographed. Purification of the crude material by silica gel chromatography using an ISCO machine (12 g column, 30 mL/min, 0-50% EtOAc in hexanes over 18 min, tr=9 min) gave 7-(isoquinolin-4-yl)-3-phenylbenzo[d]isoxazole (9.5 mg, 0.029 mmol, 29.5% yield) as a yellow residue. The crude material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 0-60% B over 25 minutes, then a 15-minute hold at 60% B; Flow: 20 mL/min. Fractions containing the desired product were combined and dried via centrifugal evaporation to afford the title compound (9.5 mg, 30%). ESI MS $(M+H)^+=323.1$. HPLC Peak $t_r=2.88$ minutes. Purity >99%. HPLC Conditions: A.

Example 6

3-(4-Fluorophenyl)-7-(4-methylpyridin-3-yl)benzo[d]isoxazole

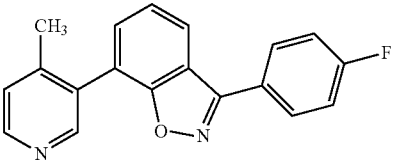

(6)

Preparation 6A: (3-Bromo-2-fluorophenyl)(4-fluorophenyl)methanol

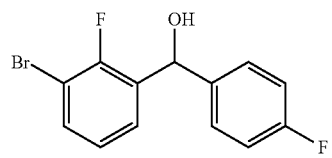

(6A)

To a solution of 3-bromo-2-fluorobenzaldehyde (0.150 g, 0.739 mmol) in THF (3.21 mL) cooled to −78° C. was added (4-fluorophenyl)magnesium bromide (0.443 mL, 0.887 mmol). The reaction mixture was maintained at −78° C. for at least 1 hr, then allowed to warm to room temperature slowly over 2 hr. The reaction was quenched with a saturated aqueous solution of $NH_4Cl$. The reaction mixture was diluted with $CH_2Cl_2$ and the layers were separated. The aqueous phase was extracted with $CH_2Cl_2$ (2×). Organics were combined, dried over $Na_2SO_4$, filtered, and concentrated to afford the title compound as a yellow residue.

Preparation 6B: (3-Bromo-2-fluorophenyl)(4-fluorophenyl)methanone

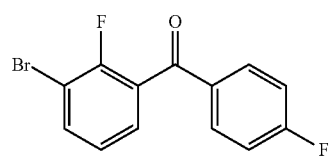

(6B)

To a solution of Preparation 6A (0.221 g, 0.739 mmol) in wet $CH_2Cl_2$ (2.96 mL) was added Dess-Martin periodinane (0.658 g, 1.552 mmol) at room temperature. After 1.75 hr, the reaction was quenched with a 1:1 solution of saturated aqueous $NaHCO_3$: 10% (w/w) aqueous $Na_2S_2O_3$. The reaction mixture was diluted with additional $CH_2Cl_2$. The mixture was stirred until both layers became clear. The layers were separated and the aqueous phase extracted with $CH_2Cl_2$ (2×). The organic phases were combined, dried over $Na_2SO_4$, filtered, and concentrated to afford the title compound as a yellow residue.

Preparation 6C: (Z)-(3-Bromo-2-fluorophenyl)(4-fluorophenyl)methanone oxime

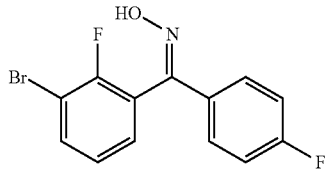

(6C)

A solution of Preparation 6B (0.220 g, 0.741 mmol) and hydroxylamine hydrochloride (0.350 g, 5.04 mmol) in pyridine (1.722 mL) was refluxed for 1.5 hr, allowed to cool to room temperature, then concentrated in vacuo. The crude material was partitioned between EtOAc and 1N HCl. The layers were separated and the aqueous phase extracted with EtOAc (3×). The organics were combined, dried over $Na_2SO_4$, filtered, and concentrated to afford (Z)-(3-bromo-2-fluorophenyl)(4-fluorophenyl)methanone oxime (231 mg, 0.740 mmol, 100% yield) as an orange residue. LC/MS: Example 5C @ 1.50 (RT) (Condition A). MS (ES): m/z=312.0 $[M+H]^+$.

Preparation 6D:
7-Bromo-3-(4-fluorophenyl)benzo[d]isoxazole

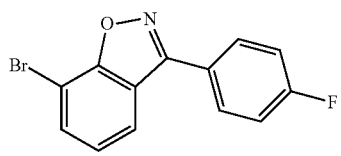

(6D)

To a suspension of sodium hydride (0.050 g, 1.258 mmol) in THF (9.52 mL) was added dropwise Preparation 6C (0.231 g, 0.740 mmol) in DMF (2.6 mL). The syringe was rinsed with additional DMF (2.6 mL) into the reaction vial. The reaction mixture was heated at 70° C. for 2.5 hr, then allowed to cool to room temperature. The reaction was quenched with $H_2O$. The reaction mixture was extracted with EtOAc (3×). The organic phases were combined, dried over $Na_2SO_4$, filtered, concentrated, and further dried under high vacuum to afford a yellow solid. The crude material was dissolved in a minimal amount of $CH_2Cl_2$. Purification of the crude material by silica gel chromatography using an ISCO machine (40 g column, 40 mL/min, 0-30% EtOAc in hexanes over 25 min, $t_r$=9 min) gave the title compound (162 mg, 0.555 mmol, 74.9% yield) as a white crystalline solid.

Example 6

3-(4-Fluorophenyl)-7-(4-methylpyridin-3-yl)benzo[d]isoxazole

A reaction flask was charged with tetrakis(triphenylphosphine)palladium(0) (6.13 mg, 5.31 µmol), Preparation 6D (31 mg, 0.106 mmol), sodium carbonate (45.0 mg, 0.425 mmol), and 4-methylpyridin-3-ylboronic acid (15.26 mg, 0.111 mmol). The mixture was stirred at room temperature for 10 min under $N_2$, then DME (396 µL), EtOH (198 µL), and water (198 µL) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (13.0 mg, 40%). ESI MS $(M+H)^+$=305.01. HPLC Peak $t_r$=2.67 minutes. Purity >99%. HPLC Conditions: A.

Example 7

7-(4-Chloropyridin-3-yl)-3-(4-fluorophenyl)benzo[d]isoxazole

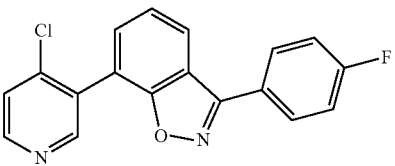

(7)

A reaction flask was charged with tetrakis(triphenylphosphine)palladium(0) (6.13 mg, 5.31 µmol), Preparation 6D (31 mg, 0.106 mmol), sodium carbonate (45.0 mg, 0.425 mmol), and 4-chloro-3-(4,4,5,5-tetramethyl-1,3,2-dioxaborolan-2-yl)pyridine (76 mg, 0.318 mmol). The mixture was stirred at room temperature for 10 min under $N_2$, then DME (396 µL), EtOH (198 µL), and water (198 µL) were added sequentially. The resultant mixture was heated at 90° C. overnight. After 26 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a yellow residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 40-100% B over 25 minutes, then a 5-minute hold at 100% B; Flow: 20 mL/min. Fractions containing the desired product were combined and dried via centrifugal evaporation to afford the title compound (6.2 mg, 18%). ESI MS $(M+H)^+$=325.0. HPLC Peak $t_r$=2.78 minutes. Purity >99%. HPLC Conditions: A.

Example 8

3-(4-Fluorophenyl)-7-(4-methoxypyridin-3-yl)benzo[d]isoxazole

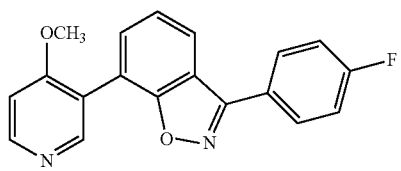

(8)

A reaction flask was charged with tetrakis(triphenylphosphine)palladium(0) (7.91 mg, 6.85 µmol), Preparation 6D (40 mg, 0.137 mmol), sodium carbonate (72.6 mg, 0.685 mmol), and 4-methoxypyridin-3-ylboronic acid, HCl (78 mg, 0.411 mmol). The mixture was stirred at room temperature for 10 min under $N_2$, then DME (511 µL), EtOH (255 µL), and water (255 µL) were added sequentially. The resultant mixture was heated at 90° C. overnight. After 24 hr, the reaction mixture was allowed to cool to room temperature. Then, the reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a yellow residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 0.05% TFA; Mobile Phase B: 95:5 acetonitrile:water with 0.05% TFA; Gradient: 5-85% B over 25 minutes, then a 5-minute hold at 85% B; Flow: 20 mL/min. Fractions containing the desired product were combined and dried via centrifugal evaporation to afford the title compound (1.7 mg, 3.9%). ESI MS $(M+H)^+=321.2$. HPLC Peak $t_r=2.45$ minutes. Purity >99%. HPLC Conditions: B.

Example 9

3-(4-Fluorophenyl)-7-(4-methylpyrimidin-5-yl)benzo[d]isoxazole

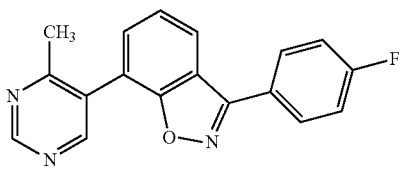

(9)

Preparation 9A: 3-(4-Fluorophenyl)-7-(4,4,5,5-tetramethyl-1,3,2-dioxaborolan-2-yl)benzo[d]isoxazole

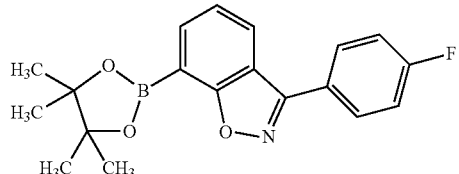

(9A)

A vial was charged with bis(acetonitrile)palladium(II) chloride (3.20 mg, 0.012 mmol), dicyclohexyl(2',6'-dimethoxybiphenyl-2-yl)phosphine (10.12 mg, 0.025 mmol), and Preparation 6D (0.180 g, 0.616 mmol). The vial was capped with a rubber septum and then evacuated and backfilled with $N_2$ (this sequence was carried out a total of 2 times). Dioxane (0.369 mL) was added via syringe, through the septum, followed by the addition of triethylamine (0.258 mL, 1.849 mmol) and 4,4,5,5-tetramethyl-1,3,2-dioxaborolane (0.134 mL, 0.924 mmol) dropwise. The septum was then replaced with a Teflon screw valve, and the vial was sealed. The reaction mixture was heated at 110° C. After 24 hr, the reaction mixture was allowed to cool to room temperature. The reaction mixture was filtered through a disposable fritted funnel and the filter cake washed with $CH_2Cl_2$. The filtrate was concentrated to afford the title compound (209 mg, 100%) as a yellow solid.

Example 9

A reaction flask was charged with tetrakis(triphenylphosphine)palladium(0) (5.78 mg, 5.00 µmol), Preparation 9A (33.9 mg, 0.100 mmol), sodium carbonate (42.4 mg, 0.400 mmol), and 5-bromo-4-methylpyrimidine (18.17 mg, 0.105 mmol). The mixture was stirred at room temperature for 10 min under $N_2$, then DME (Ratio: 2.0, Volume: 373 µl), EtOH (Ratio: 1.000, Volume: 187 µl), and water (Ratio: 1.000, Volume: 187 µl) were added sequentially. The resultant mixture was heated at 90° C. overnight. After 17.5 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (1.9 mg, 6.2%). ESI MS $(M+H)^+=306.1$. HPLC Peak $t_r=2.41$ minutes. Purity >99%. HPLC Conditions: B.

Example 10

3-(4-Fluorophenyl)-7-(isoquinolin-4-yl)benzo[d]isoxazole

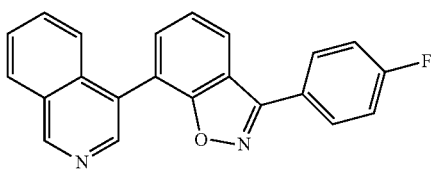

(10)

A reaction flask was charged with tetrakis(triphenylphosphine)palladium(0) (5.78 mg, 5.00 μmol), Preparation 6D (29.2 mg, 0.100 mmol), sodium carbonate (42.4 mg, 0.400 mmol), and 4-(4,4,5,5-tetramethyl-1,3,2-dioxaborolan-2-yl)isoquinoline (26.8 mg, 0.105 mmol). The mixture was stirred at room temperature for 10 min under $N_2$, then DME (373 μL), EtOH (187 μL), and water (187 μL) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 10-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 10-minute hold at 100% B; Flow: 20 mL/min. Fractions containing the desired product were combined and dried via centrifugal evaporation to afford the title compound (11.1 mg, 33%). ESI MS $(M+H)^+$=341.1. HPLC Peak $t_r$=2.91 minutes. Purity >99%. HPLC Conditions: A.

Example 11

7-(4-Cyclopropylpyrimidin-5-yl)-3-(4-fluorophenyl)benzo[d]isoxazole

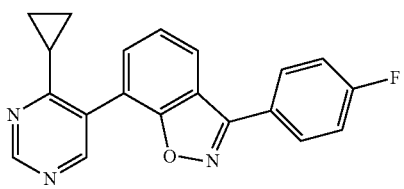

(11)

Preparation 11A: 5-Bromo-4-cyclopropylpyrimidine

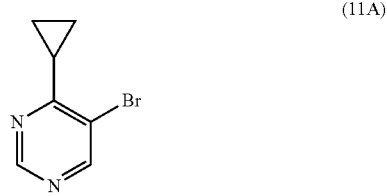

(11A)

To a solution of 5-bromopyrimidine (3 g, 18.87 mmol) in $Et_2O$ (120 mL) and THF (20 ml) was added cyclopropylmagnesium bromide (39.6 mL, 19.81 mmol) at 0° C. The resulting white suspension was stirred at room temperature for 1 h and quenched with water (0.340 mL, 18.87 mmol) followed by addition of DDQ (4.28 g, 18.87 mmol) in THF (10 ml). The resulting black mixture was stirred at room temperature overnight. The reaction mixture was extracted with EtOAc. The aqueous layer was extracted with EtOAc and the combined organic layer was washed with NaOH (1N) and brine. The crude product was purified by BIOTAGE® (0-15% EtOAc/hexanes, 1.2 L) to afford the title compound (700 mg, 20%) as a yellow solid. $^1$H NMR (500 MHz, chloroform-d) δ ppm 8.87 (1 hr, s), 8.66 (1 hr, s), 2.40-2.56 (1 hr, m), 1.13-1.32 (4 hr, m).

Example 11

A reaction flask was charged with tetrakis(triphenylphosphine)palladium(0) (5.78 mg, 5.00 μmol), Preparation 9A (33.9 mg, 0.100 mmol), sodium carbonate (42.4 mg, 0.400 mmol), and Preparation 11A (20.90 mg, 0.105 mmol). The mixture was stirred at room temperature for 10 min under $N_2$, then DME (Ratio: 2.0, Volume: 373 μl), EtOH (Ratio: 1.000, Volume: 187 μl), and water (Ratio: 1.000, Volume: 187 μl) were added sequentially. The resulting mixture was heated at 90° C. overnight. After 16 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to afford the title compound (4.0 mg, 11%). ESI MS $(M+H)^+$=332.1. HPLC Peak $t_r$=2.87 minutes. Purity=95%. HPLC Conditions: B.

Example 12

3-(4-Fluorophenyl)-7-(4-(2,2,2-trifluoroethoxy)pyrimidin-5-yl)benzo[d]isoxazole

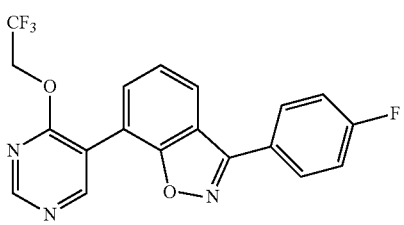

(12)

Preparation 12A:
5-Iodo-4-(2,2,2-trifluoroethoxy)pyrimidine

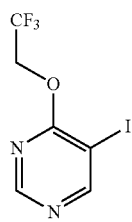

(12A)

To a solution of 2,2,2-trifluoroethanol (0.672 mL, 9.36 mmol) in THF (18.08 mL) was added, portion wise, at 0° C., NaH (0.424 g, 10.61 mmol). The reaction mixture was stirred at 0° C. for 30 min. Then 4-chloro-5-iodopyrimidine (1.5 g, 6.24 mmol) was added and the reaction mixture was refluxed for about 1 hr. The reaction mixture was allowed to cool to room temperature, then a saturated aqueous solution of NH$_4$Cl was added. The mixture was diluted with EtOAc and the layers were separated. The aqueous phase was extracted with EtOAc (2×). The combined organics were washed with brine (1×), dried over Na$_2$SO$_4$, filtered, and concentrated in vacuo to afford the title compound as a yellow solid. ESI MS (M+H)$^+$=304.7.

Example 12

A reaction flask was charged with tetrakis(triphenylphosphine)palladium(0) (5.78 mg, 5.00 μmol), Preparation 9A (33.9 mg, 0.100 mmol), sodium carbonate (42.4 mg, 0.400 mmol), and Preparation 12A (31.9 mg, 0.105 mmol). The mixture was stirred at room temperature for 10 min under N$_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 16 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to afford the title compound (4.3 mg, 11%). ESI MS (M+H)$^+$=390.0. HPLC Peak t$_r$=2.96 minutes. Purity=99%. HPLC Conditions: B.

Example 13

3-(4-Fluorophenyl)-7-(1,7-naphthyridin-5-yl)benzo[d]isoxazole

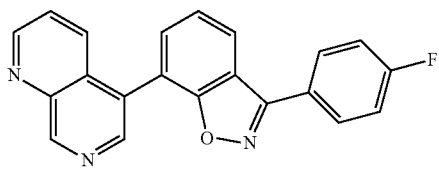

(13)

A reaction flask was charged with tetrakis(triphenylphosphine)palladium(0) (5.78 mg, 5.00 μmol), Preparation 9A (33.9 mg, 0.100 mmol), sodium carbonate (42.4 mg, 0.400 mmol), and 5-bromo-1,7-naphthyridine (21.95 mg, 0.105 mmol). The mixture was stirred at room temperature for 10 min under N$_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 16 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (1.8 mg, 4.6%). ESI MS (M+H)$^+$=342.1. HPLC Peak t$_r$=2.48 minutes. Purity=88%. HPLC Conditions: B.

Example 14

3-(4-Fluorophenyl)-7-(pyrrolo[1,2-c]pyrimidin-4-yl)benzo[d]isoxazole

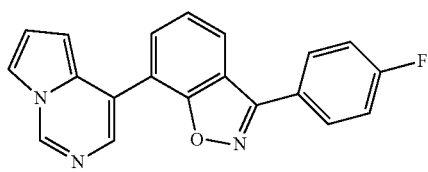

(14)

Preparation 14A: 4-(2-(1,3-Dioxan-2-yl)ethyl)-5-bromopyrimidine

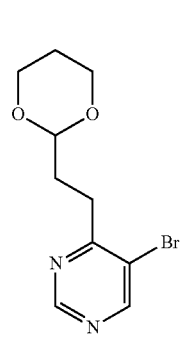

(14A)

To a solution of 5-bromopyrimidine (2 g, 12.58 mmol) in Et$_2$O (40 mL) at room temperature was slowly added (2-(1,3-dioxan-2-yl)ethylmagnesium bromide (0.5M, 27.7 mL, 13.84 mmol). After 1 hr, water (2 mL) was added followed by the careful addition of 4,5-dichloro-3,6-dioxocyclohexa-1,4-diene-1,2-dicarbonitrile (3.14 g, 13.84 mmol) as a solution in THF (15 mL). The resulting dark brown suspension was stirred at room temperature for an additional 24 hr. The resulting mixture was then diluted with EtOAc and water, the organics were separated and the remaining aqueous layer was extracted twice more. The separated organic layers were combined and washed with 1N NaOH, then washed with brine, dried over sodium sulfate, and concentrated to afford Intermediate 8A (2.62 g, 76% yield). MS (ES): m/z=274.8 [M+H]$^+$. $^1$H NMR (400 MHz, DMSO-d$_6$) δ ppm 9.05 (1 hr, s), 8.89 (1 hr, s), 4.62 (1 hr, t, J=4.95 Hz), 3.92-4.04 (2 hr, m), 3.61-3.75 (2 hr, m), 2.83-3.00 (2 hr, m), 1.77-1.98 (4 hr, m).

Preparation 14B: 3-(5-Bromopyrimidin-4-yl)propanal

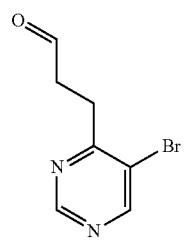

(14B)

To a solution of Preparation 14A (0.920 g, 3.37 mmol) in DCE (6.5 mL) at 0° C. was slowly added formic acid (6.46 mL, 168 mmol). The system was equipped with a reflux condenser and was heated to 50° C. for 5 hr. The resulting solution was allowed to cool to room temperature and the volatile solvents were removed in vacuo. The system was diluted with DCM and washed 1× with saturated aqueous sodium bicarbonate, then washed with brine, dried over sodium sulfate and concentrated to afford the title compound (724 mg, 100% yield). MS (ES): m/z=216.8 [M+H]$^+$. $^1$H NMR (400 MHz, DMSO-d$_6$) δ ppm 9.77 (1 hr, s), 9.03 (1 hr, s), 8.91 (1 hr, s), 3.14 (2 hr, t, J=6.60 Hz), 2.96 (3 hr, t, J=6.60 Hz).

Preparation 14C: 4-Bromopyrrolo[1,2-c]pyrimidine

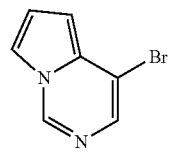

(14C)

To a solution of Preparation 14B (724 mg, 3.37 mmol) in THF (10 mL) at room temperature was added Burgess Reagent (964 mg, 4.04 mmol). The system was stirred for 10 minutes, at which time it was concluded to be complete. Volatile solvents were removed in vacuo. The crude material was diluted with DCM and washed 1× with water, then washed with brine, dried over sodium sulfate and concentrated to afford the title compound (664 mg, 100% yield). MS (ES): m/z=198.8 [M+H]$^+$. $^1$H NMR (400 MHz, DMSO-d$_6$) δ ppm 9.17 (1 hr, s), 7.81 (1 hr, dd, J=2.86, 1.32 Hz), 7.61 (1 hr, s), 6.95-7.03 (1 hr, m), 6.55 (1 hr, d, J=3.96 Hz).

Example 14

A reaction flask was charged with tetrakis(triphenylphosphine)palladium(0) (5.78 mg, 5.00 μmol), Preparation 9A (33.9 mg, 0.100 mmol), sodium carbonate (42.4 mg, 0.400 mmol), and Preparation 14C (20.69 mg, 0.105 mmol). The mixture was stirred at room temperature for 10 min under N$_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 15.5 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to afford the title compound (1.2 mg, 3.6%). ESI MS (M+H)$^+$=330.0. HPLC Peak t$_r$=2.84 minutes. Purity >99%. HPLC Conditions: B.

Example 15

5-(3-(4-Fluorophenyl)benzo[d]isoxazol-7-yl)-N-(2,2,2-trifluoroethyl)pyrimidin-4-amine

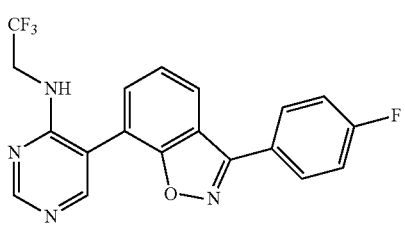

(15)

Preparation 15A:
5-Iodo-N-(2,2,2-trifluoroethyl)pyrimidin-4-amine

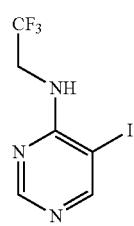

(15A)

To a solution of 4-chloro-5-iodopyrimidine (0.250 g, 1.040 mmol) and 2,2,2-trifluoroethanamine (0.216 g, 2.184 mmol) in EtOH (volume: 2.080 ml) was added Hunig's Base (0.200 ml, 1.144 mmol). The reaction mixture was heated in a microwave for 4 hr at 120° C. and then allowed to cool to room temperature. The solvent was evaporated. The crude material was dissolved in a minimal amount of $CH_2Cl_2$ to be chromatographed. Purification of the crude material by silica gel chromatography using an ISCO machine (24 g column, 35 mL/min, 0-90% EtOAc in hexanes over 25 min, $t_r$=12 min) gave the title compound (0.188 g, 0.614 mmol, 59.1% yield) as a yellow residue. ESI MS (M+H)$^+$=303.9.

Example 15

A reaction flask was charged with tetrakis(triphenylphosphine)palladium(0) (5.78 mg, 5.00 μmol), Preparation 9A (33.9 mg, 0.100 mmol), sodium carbonate (42.4 mg, 0.400 mmol), and Preparation 15A (26.9 mg, 0.105 mmol). The mixture was stirred at room temperature for 10 min under $N_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 17.5 hr, the reaction mixture was allowed to cool to room temperature. The reaction was quenched with water. The reaction mixture was diluted with EtOAc. The layers were separated and the aqueous phase was extracted with EtOAc (3x). The organic phases were combined, dried over $Na_2SO_4$, filtered, and concentrated to afford a residue. The crude material was purified via preparative LC/MS with the following conditions: Column: Waters XBridge C18, 19x250 mm, 5-μm particles; Guard Column: Waters XBridge C18, 19x10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (2.0 mg, 4.7%). ESI MS (M+H)$^+$=389.1. HPLC Peak $t_r$=2.59 minutes. Purity=92%. HPLC Conditions: B.

Example 16

3-(4-Fluorophenyl)-7-(4-morpholinopyrimidin-5-yl)benzo[d]isoxazole

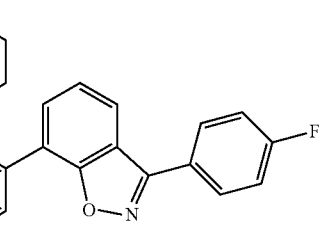

(16)

Preparation 16A:
4-(5-Iodopyrimidin-4-yl)morpholine (16A)

To a vial containing a solution of 4-chloro-5-iodopyrimidine (0.200 g, 0.832 mmol) in DMF (1.333 mL) was added morpholine (0.291 mL, 3.33 mmol) followed by cesium carbonate (0.542 g, 1.664 mmol). The vial was sealed with a Teflon cap and heated at 90° C. for 80 min, then allowed to cool to room temperature. The reaction mixture was filtered through a disposable fritted funnel and the filter cake washed with $CH_2Cl_2$. The filtrate was concentrated, then further dried under high vacuum to afford the title compound (235 mg, 97%). ESI MS (M+H)$^+$=292.0.

Example 16

A reaction flask was charged with tetrakis(triphenylphosphine)palladium(0) (5.78 mg, 5.00 μmol), Preparation 9A (33.9 mg, 0.100 mmol), sodium carbonate (42.4 mg, 0.400 mmol), and Preparation 16A (30.6 mg, 0.105 mmol). The mixture was stirred at room temperature for 10 min under $N_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 16 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na₂SO₄, filtered, and concentrated to afford a residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-55% B over 25 minutes, then a 5-minute hold at 100% B; Flow: 20 mL/min. Fractions containing the desired product were combined and dried via centrifugal evaporation to afford the title compound (5.0 mg, 13%). ESI MS (M+H)⁺=377.1. HPLC Peak t$_r$=2.37 minutes. Purity=99%. HPLC Conditions: B.

Example 17

7-(4-Methylpyridin-3-yl)-3-(pyridin-2-yl)benzo[d]isoxazole

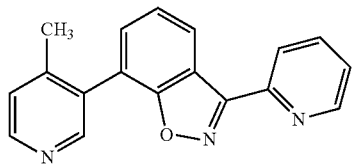
(17)

Preparation 17A:
(3-Bromo-2-fluorophenyl)(pyridin-2-yl)methanol

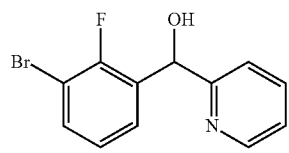
(17A)

To a solution of 3-bromo-2-fluorobenzaldehyde (0.250 g, 1.231 mmol) in THF (5.35 mL) cooled to −78° C. was added pyridin-2-ylmagnesium bromide (5.91 mL, 1.478 mmol). The reaction mixture was maintained at −78° C. for at least 1 hr, then allowed to warm to room temperature slowly over 2 hr. The reaction quenched with a saturated aqueous solution of NH₄Cl. The reaction mixture was diluted with CH₂Cl₂. Layers were separated. The aqueous phase was extracted with CH₂Cl₂ (2×). The organics were combined, dried over Na₂SO₄, filtered, and concentrated to afford a yellow residue. The crude material was dissolved in a minimal amount CH₂Cl₂ and chromatographed. Purification of the crude material by silica gel chromatography using an ISCO machine (40 g column, 40 mL/min, 1-40% EtOAc in hexanes over 25 min, t$_r$=16 min) gave the title compound (78 mg, 0.276 mmol, 22.45% yield) as a yellow residue.

Preparation 17B:
(3-Bromo-2-fluorophenyl)(pyridin-2-yl)methanone

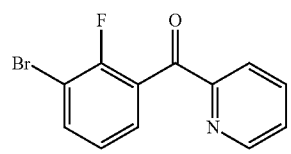
(17B)

To a solution of Preparation 17A (0.0784 g, 0.278 mmol) in wet CH₂Cl₂ (1.112 mL) was added Dess-Martin periodinane (0.248 g, 0.584 mmol) at room temperature. After 5.5 hr, the reaction was quenched with a 1:1 solution of saturated aqueous NaHCO₃: 10% (w/w) aqueous Na₂S₂O₃. The reaction mixture was diluted with additional CH₂Cl₂ and stirred until both layers became clear. The layers were separated and the organic phase washed with saturated aqueous NaHCO₃. The aqueous phase was extracted with CH₂Cl₂ (2×). The organic phases were combined, dried over Na₂SO₄, filtered, and concentrated to afford the title compound (78 mg, 0.278 mmol, 100% yield) as a pink solid.

Preparation 17C: (E)-(3-Bromo-2-fluorophenyl)(pyridin-2-yl)methanone oxime

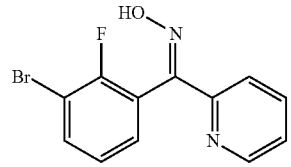
(17C)

A solution of Preparation 17B (78.7 mg, 0.281 mmol) and hydroxylamine hydrochloride (133 mg, 1.911 mmol) in pyridine (653 μL) was refluxed for 2 hr, allowed to cool to room temperature, and then concentrated in vacuo. The crude material was partitioned between EtOAc and 1N HCl. The layers were separated and the aqueous phase extracted with EtOAc (5×). The organics were combined, dried over Na₂SO₄, filtered, and concentrated to afford the title compound (80.4 mg, 0.272 mmol, 97% yield) as a yellow residue.

Preparation 17D:
7-Bromo-3-(pyridin-2-yl)benzo[d]isoxazole

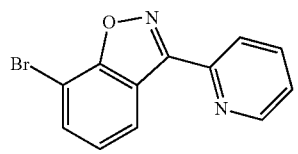
(17D)

To a suspension of sodium hydride (0.037 g, 0.927 mmol) in THF (1.403 mL) was added dropwise Preparation 17C (0.161 g, 0.546 mmol) in DMF (0.779 mL). The syringe was rinsed with additional DMF (0.779 mL) into the reaction vial. The reaction mixture was heated at 70° C. for 2 hr, and then allowed to cool to room temperature. The reaction was quenched with H$_2$O. The mixture was extracted with EtOAc (3×). The organic phases were combined, dried over Na$_2$SO$_4$, filtered, concentrated, and further dried under high vacuum to afford a brown residue. The crude material was dissolved in a minimal amount of CH$_2$Cl$_2$ to be chromatographed. Purification of the crude material by silica gel chromatography using an ISCO machine (24 g column, 35 mL/min, 0-20% EtOAc in hexanes over 15 min, t$_r$=8.5 min) gave the title compound (96 mg, 0.349 mmol, 64.0% yield) as a white solid.

Example 17

A reaction flask was charged with tetrakis(triphenylphosphine)palladium(0) (5.04 mg, 4.36 μmol), Preparation 17D (24 mg, 0.087 mmol), sodium carbonate (37.0 mg, 0.349 mmol), and 4-methylpyridin-3-ylboronic acid (12.54 mg, 0.092 mmol). The mixture was stirred at room temperature for 10 min under N$_2$, then DME (326 μL), EtOH (163 μL), and water (163 μL) were added sequentially. The resultant mixture was heated at 90° C. overnight. After 24 hr, the reaction mixture was allowed to cool to room temperature. The reaction was quenched with water. The mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (12.7 mg, 51%). ESI MS (M+H)$^+$=288.0. HPLC Peak t$_r$=2.38 minutes. Purity >99%. HPLC Conditions: A.

Example 18

7-(4-Chloropyridin-3-yl)-3-(pyridin-2-yl)benzo[d]isoxazole

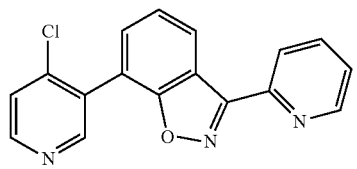

(18)

A reaction flask was charged with tetrakis(triphenylphosphine)palladium(0) (5.88 mg, 5.09 μmol), Preparation 17D (28 mg, 0.102 mmol), sodium carbonate (43.2 mg, 0.407 mmol), and 4-chloro-3-(4,4,5,5-tetramethyl-1,3,2-dioxaborolan-2-yl)pyridine (73.1 mg, 0.305 mmol). The mixture was stirred at room temperature for 10 min under N$_2$, then DME (380 μL), EtOH (190 μL), and water (190 μL) were added sequentially. The resultant mixture was heated at 90° C. overnight. After 25 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a yellow solid. The crude material was dissolved in a minimal amount of CH$_2$Cl$_2$ and chromatographed. Purification of the crude material by silica gel chromatography using an ISCO machine (12 g column, 35 mL/min, 1-30% MeOH in CH$_2$Cl$_2$ over 19 min, t$_r$=11 min) gave the title compound (5.5 mg, 0.018 mmol, 17.21% yield) as a white solid. ESI MS (M+H)$^+$=308.1. HPLC Peak t$_r$=3.315 minutes. Purity=98%. HPLC Conditions: C.

Example 19

7-(Isoquinolin-4-yl)-3-(pyridin-2-yl)benzo[d]isoxazole

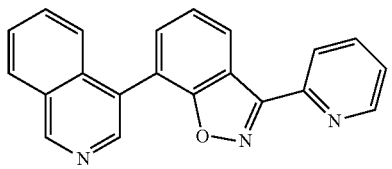

(19)

A reaction flask was charged with tetrakis(triphenylphosphine)palladium(0) (6.72 mg, 5.82 μmol), Preparation 17D (0.032 g, 0.116 mmol), sodium carbonate (0.049 g, 0.465 mmol), and 4-(4,4,5,5-tetramethyl-1,3,2-dioxaborolan-2-yl)isoquinoline (0.031 g, 0.122 mmol). The mixture was stirred at room temperature for 10 min under N$_2$, then DME (0.434 mL), EtOH (0.217 mL), and water (0.217 mL) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a dark red residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (17.7 mg, 47%). ESI MS (M+H)$^+$=324.1. HPLC Peak t$_r$=2.71 minutes. Purity >99%. HPLC Conditions: B.

Example 20

7-(4-Methylpyridin-3-yl)-3-(thiazol-2-yl)benzo[d]isoxazole

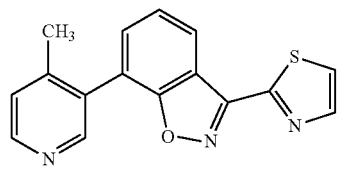

(20)

Preparation 20A: (3-Bromo-2-fluorophenyl)(thiazol-2-yl)methanol

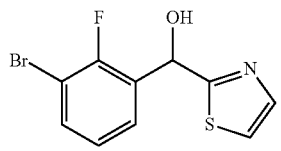

(20A)

To a solution of 2-bromothiazole (0.088 mL, 0.985 mmol) in THF (2.99 mL) cooled to 0° C. was added isopropylmagnesium chloride (0.493 mL, 0.985 mmol). After 50 min, 3-bromo-2-fluorobenzaldehyde (0.200 g, 0.985 mmol) was added. The reaction mixture was allowed to warm to room temperature overnight. After 12 hr, the reaction was quenched with saturated aqueous $NH_4Cl$. The reaction mixture was diluted with $CH_2Cl_2$. The layers were separated. The aqueous phase was extracted with $CH_2Cl_2$ (2×). The organic phases were combined, dried over $Na_2SO_4$, filtered, and concentrated to afford the title compound as a brown liquid.

Preparation 20B: (3-Bromo-2-fluorophenyl)(thiazol-2-yl)methanone

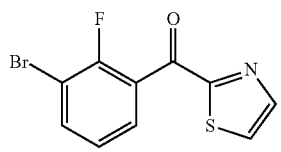

(20B)

To a solution of Preparation 20A (0.284 g, 0.986 mmol) in wet $CH_2Cl_2$ (3.94 mL) was added Dess-Martin periodinane (1.045 g, 2.464 mmol) at room temperature. After 2.5 hr, the reaction was quenched with a 1:1 solution of saturated aqueous $NaHCO_3$: 10% (w/w) aqueous $Na_2S_2O_3$. The reaction mixture was diluted with additional $CH_2Cl_2$. The mixture was stirred until both layers became clear. The layers were separated and the organic phase washed with saturated aqueous $NaHCO_3$. The aqueous phase was extracted with $CH_2Cl_2$ (2×). The organic phases were combined, dried over $Na_2SO_4$, filtered, and concentrated, and further dried under high vacuum to afford a residue. The crude material was dissolved in a minimal amount of $CH_2Cl_2$ to be chromatographed. Purification of the crude material by silica gel chromatography using an ISCO machine (40 g column, 40 mL/min, 0-15% MeOH in $CH_2Cl_2$ over 15 min, $t_r$=2.5 min) gave the title compound (158 mg, 0.552 mmol, 56.0% yield) (2 steps) as a white solid.

Preparation 20C: (E)-(3-Bromo-2-fluorophenyl)(thiazol-2-yl)methanone oxime

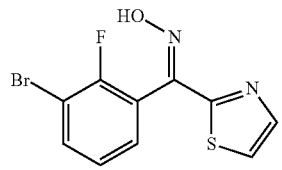

(20C)

A solution of Preparation 20B (0.141 g, 0.493 mmol) and hydroxylamine hydrochloride (0.233 g, 3.35 mmol) in pyridine (1.5 mL) was refluxed for 1.5 hr, allowed to cool to room temperature, and then concentrated in vacuo. The crude material was partitioned between EtOAc and 1N HCl. The layers were separated and the aqueous phase extracted with EtOAc (5×). The organic phases were combined, dried over $Na_2SO_4$, filtered, and concentrated to afford the title compound (148 mg, 0.491 mmol, 100% yield) as a yellow residue.

Preparation 20D: 7-Bromo-3-(thiazol-2-yl)benzo[d]isoxazole

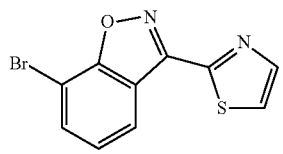

(20D)

To a suspension of sodium hydride (0.033 g, 0.830 mmol) in THF (1.255 mL) was added dropwise Preparation 20C (0.147 g, 0.488 mmol) in DMF (0.697 mL). The reaction mixture was heated at 70° C. for 2.5 hr, then allowed to cool to room temperature. The reaction was quenched with $H_2O$. The reaction mixture was extracted with EtOAc (3×). The organic phases were combined, dried over $Na_2SO_4$, filtered, concentrated, and further dried under high vacuum to afford a yellow residue. The crude material was dissolved in a minimal amount of $CH_2Cl_2$ to be chromatographed. Purification of the crude material by silica gel chromatography using an ISCO machine (24 g column, 35 mL/min, 0-50% EtOAc in hexanes over 18 min, $t_r$=6 min) gave the title compound (43 mg, 0.153 mmol, 31.3% yield) as a white solid.

Example 20

7-(4-Methylpyridin-3-yl)-3-(thiazol-2-yl)benzo[d]isoxazole

A reaction flask was charged with tetrakis(triphenylphosphine)palladium(0) (6.58 mg, 5.69 μmol), Preparation 20D (32 mg, 0.114 mmol), sodium carbonate (48.3 mg, 0.455 mmol), and 4-methylpyridin-3-ylboronic acid (16.37 mg, 0.120 mmol). The mixture was stirred at room temperature for 10 min under N$_2$, then DME (425 μL), EtOH (212 μL), and water (212 μL) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (15.8 mg, 47%). ESI MS (M+H)$^+$= 294.1. HPLC Peak t$_r$=2.36 minutes. Purity >99%. HPLC Conditions: A.

Example 21

7-(4-Chloropyridin-3-yl)-3-(pyrazin-2-yl)benzo[d]isoxazole

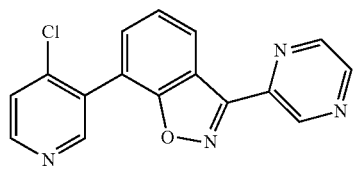

(21)

Preparation 21A:
(3-Bromo-2-fluorophenyl)(pyrazin-2-yl)methanol

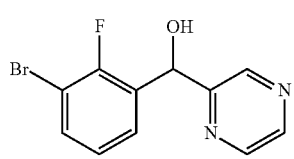

(21A)

To a stirring solution of 2-iodopyrazine (0.195 mL, 1.970 mmol) in THF (3.28 mL) at 0° C. was slowly added butyl magnesium chloride (0.985 mL, 1.970 mmol). The mixture was allowed to stir for 30 min, then 3-bromo-2-fluorobenzaldehyde (0.400 g, 1.970 mmol) was added. After 2 hr, the reaction was quenched with a saturated aqueous solution of NH$_4$Cl. The reaction mixture was diluted with CH$_2$Cl$_2$. The layers were separated. The aqueous phase was extracted with CH$_2$Cl$_2$ (2×). The organic phases were combined, dried over Na$_2$SO$_4$, filtered, and concentrated to afford a yellow residue. The crude material was dissolved in a minimal amount of CH$_2$Cl$_2$ to be chromatographed. Purification of the crude material by silica gel chromatography using an ISCO machine (40 g column, 40 mL/min, 30-70% EtOAc in hexanes over 19 min, t$_r$=12 min) gave the title compound (347 mg, 1.226 mmol, 62.2% yield) as a yellow residue.

Preparation 21B (3-Bromo-2-fluorophenyl)(pyrazin-2-yl)methanone

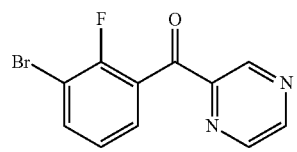

(21B)

To a solution of Preparation 21A (0.347 g, 1.226 mmol) in wet CH$_2$Cl$_2$ (4.90 mL) was added Dess-Martin periodinane (1.300 g, 3.06 mmol) at room temperature. After 2 hr, the reaction was quenched with a 1:1 solution of saturated aqueous NaHCO$_3$: 10% (w/w) aqueous Na$_2$S$_2$O$_3$. The reaction mixture was diluted with additional CH$_2$Cl$_2$. The mixture was stirred until both layers became clear. The layers were separated and the organic phase washed with saturated aqueous NaHCO$_3$. The aqueous phase was extracted with CH$_2$Cl$_2$ (2×). The organic phases were combined, dried over Na$_2$SO$_4$, filtered, and concentrated to afford the title compound (345 mg, 1.227 mmol, 100% yield) as a yellow solid.

Preparation 21C: (E)-(3-Bromo-2-fluorophenyl)(pyrazin-2-yl)methanone oxime

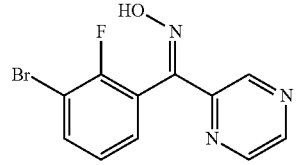

(21C)

A solution of Preparation 21B (0.606 g, 2.156 mmol) and hydroxylamine hydrochloride (1.019 g, 14.66 mmol) in pyridine (6.55 mL) was refluxed for 2 hr, allowed to cool to room temperature, and then concentrated in vacuo. The crude material was partitioned between EtOAc and 1N HCl. The layers were separated and the aqueous phase extracted with EtOAc (5×). The organics were combined, dried over Na$_2$SO$_4$, filtered, and concentrated to afford the title compound (638 mg, 2.155 mmol, 100% yield) as a yellow residue.

Preparation 21D:
7-Bromo-3-(pyrazin-2-yl)benzo[d]isoxazole

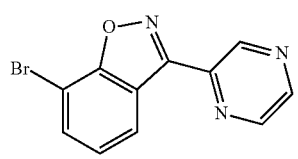

(21D)

To a suspension of sodium hydride (0.147 g, 3.66 mmol) in THF (5.54 mL) was added dropwise Preparation 21C (0.638 g, 2.155 mmol) in DMF (3.08 mL). The reaction mixture was heated at 70° C. for 2 hr, then allowed to cool to room temperature. The reaction was quenched with $H_2O$. The reaction mixture was extracted with EtOAc (3×). The organic phases were combined, dried over $Na_2SO_4$, filtered, concentrated, and further dried under high vacuum to afford a yellow residue. The crude material was dissolved in a minimal amount of $CH_2Cl_2$ to be chromatographed. Purification of the crude material by silica gel chromatography using an ISCO machine (40 g column, 40 mL/min, 0-80% EtOAc in hexanes over 25 min, $t_r$=13 min) gave the title compound (336 mg, 1.217 mmol, 56.5% yield) as a yellow solid.

Example 21

A reaction flask was charged with tetrakis(triphenylphosphine)palladium(0) (5.86 mg, 5.07 µmol), Preparation 21D (0.028 g, 0.101 mmol), sodium carbonate (0.043 g, 0.406 mmol), and 4-chloro-3-(4,4,5,5-tetramethyl-1,3,2-dioxaborolan-2-yl)pyridine (0.073 g, 0.304 mmol). The mixture was stirred at room temperature for 10 min under $N_2$, then DME (0.378 mL), EtOH (0.189 mL), and water (0.189 mL) were added sequentially. The resultant mixture was heated at 90° C. overnight. After 15 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (12.6 mg, 40%). ESI MS $(M+H)^+$=309.1. HPLC Peak $t_r$=2.22 minutes. Purity >99%. HPLC Conditions: A.

Example 22

7-(4-Methylpyridin-3-yl)-3-(pyrazin-2-yl)benzo[d]isoxazole

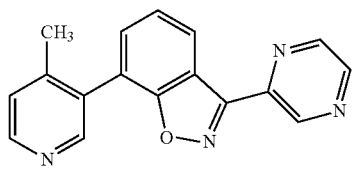

(22)

A reaction flask was charged with tetrakis(triphenylphosphine)palladium(0) (5.78 mg, 5.00 µmol), Preparation 21D (27.6 mg, 0.100 mmol), sodium carbonate (42.4 mg, 0.400 mmol), and 4-methylpyridin-3-ylboronic acid (14.38 mg, 0.105 mmol). The mixture was stirred at room temperature for 10 min under $N_2$, then DME (373 µL), EtOH (187 µL), and water (187 µL) were added sequentially. The resulting mixture was heated at 90° C. overnight. After 24 hr, the reaction mixture was allowed to cool to room temperature. Then the reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 30-100% B over 25 minutes, then a 5-minute hold at 100% B; Flow: 20 mL/min. Fractions containing the desired product were combined and dried via centrifugal evaporation to afford the title compound (11.5 mg, 40%). ESI MS $(M+H)^+$=289.1. HPLC Peak $t_r$=2.08 minutes. Purity >99%. HPLC Conditions: A.

Example 23

7-(Isoquinolin-4-yl)-3-(pyrazin-2-yl)benzo[d]isoxazole

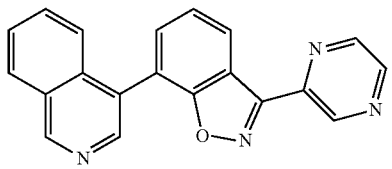

(23)

A reaction flask was charged with tetrakis(triphenylphosphine)palladium(0) (5.78 mg, 5.00 µmol), Preparation 21D (27.6 mg, 0.100 mmol), sodium carbonate (42.4 mg, 0.400 mmol), and 4-(4,4,5,5-tetramethyl-1,3,2-dioxaborolan-2-yl)isoquinoline (26.8 mg, 0.105 mmol). The mixture was stirred at room temperature for 10 min under $N_2$, then DME (373 µL), EtOH (187 µL), and water (187 µL) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a red-orange residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (19.2 mg, 59%). ESI MS $(M+H)^+$=325.1. HPLC Peak $t_r$=2.38 minutes. Purity >99%. HPLC Conditions: A.

Example 24

7-(4-Methoxypyridin-3-yl)-3-(pyrazin-2-yl)benzo[d]isoxazole

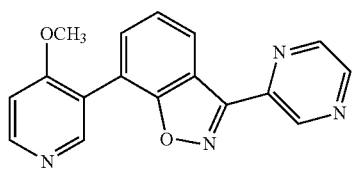

(24)

A reaction flask was charged with tetrakis(triphenylphosphine)palladium(0) (0.012 g, 9.96 μmol), Preparation 21D (0.055 g, 0.199 mmol), sodium carbonate (0.106 g, 0.996 mmol), and 4-methoxypyridin-3-ylboronic acid, HCl (0.113 g, 0.598 mmol). The mixture was stirred at room temperature for 10 min under $N_2$, then DME (0.743 mL), EtOH (0.372 mL), and water (0.372 mL) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then 10-minute hold at 100% B; Flow: 20 mL/min. Fractions containing the desired product were combined and dried via centrifugal evaporation to afford the title compound (5.2 mg, 8.6%). ESI MS $(M+H)^+$=305.1. HPLC Peak $t_r$=1.90 minutes. Purity >99%. HPLC Conditions: A.

Example 25

7-(4-Cyclopropylpyrimidin-5-yl)-3-(pyrazin-2-yl)benzo[d]isoxazole

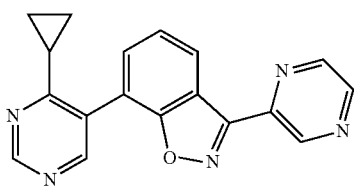

(25)

Preparation 25A: 3-(Pyrazin-2-yl)-7-(4,4,5,5-tetramethyl-1,3,2-dioxaborolan-2-yl)benzo[d]isoxazole

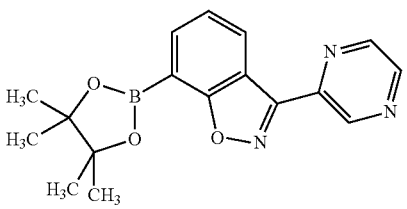

(25A)

A vial was charged with bis(acetonitrile)palladium(II) chloride (1.597 mg, 6.16 μmol), dicyclohexyl(2',6'-dimethoxybiphenyl-2-yl)phosphine (5.06 mg, 0.012 mmol), and Preparation 21D (0.085 g, 0.308 mmol). The vial was capped with a rubber septum and then evacuated and backfilled with $N_2$ (this sequence was carried out a total of 2 times). Dioxane (0.184 mL) was added via syringe, through the septum, followed by the addition of triethylamine (0.129 mL, 0.924 mmol) and 4,4,5,5-tetramethyl-1,3,2-dioxaborolane (0.067 mL, 0.462 mmol) dropwise. The septum was then replaced with a Teflon screw valve, and the vial was sealed. The reaction mixture was heated at 110° C. After 15 hr, the reaction mixture was allowed to cool to room temperature. The reaction mixture was filtered through a disposable fritted funnel and the filter cake washed with $CH_2Cl_2$. The filtrate was concentrated to the title compound as a brown residue.

Example 25

A reaction flask was charged with tetrakis(triphenylphosphine)palladium(0) (4.45 mg, 3.85 μmol), Preparation 25A (24.88 mg, 0.077 mmol), sodium carbonate (32.6 mg, 0.308 mmol), and 5-bromo-4-cyclopropylpyrimidine (16.09 mg, 0.081 mmol). The mixture was stirred at room temperature for 10 min under $N_2$, then DME (Ratio: 2.0, Volume: 287 μl), EtOH (Ratio: 1.000, Volume: 144 μl), and water (Ratio: 1.000, Volume: 144 μl) were added sequentially. The resultant mixture was heated at 90° C. overnight. After 19 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (2.2 mg, 9.0%). ESI MS $(M+H)^+$=316.1. HPLC Peak $t_r$=2.28 minutes. Purity >99%. HPLC Conditions: B.

Example 26

3-(Pyrazin-2-yl)-7-(4-(2,2,2-trifluoroethoxy)pyrimidin-5-yl)benzo[d]isoxazole

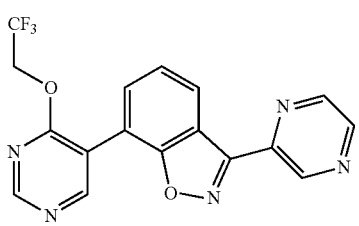

(26)

A reaction flask was charged with tetrakis(triphenylphosphine)palladium(0) (4.45 mg, 3.85 μmol), Preparation 25A (24.88 mg, 0.077 mmol), sodium carbonate (32.6 mg, 0.308 mmol), and Preparation 12A (24.58 mg, 0.081 mmol). The mixture was stirred at room temperature for 10 min under $N_2$, then DME (Ratio: 2.0, Volume: 287 μl), EtOH (Ratio: 1.000, Volume: 144 μl), and Water (Ratio: 1.000, Volume: 144 μl) were added sequentially. The resultant mixture was heated at 90° C. overnight. After 19 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (2.0 mg, 6.3%). ESI MS (M+H)$^+$=374.0. HPLC Peak $t_r$=2.45 minutes. Purity=90%. HPLC Conditions: B.

Example 27

7-(4-Methylpyrimidin-5-yl)-3-(pyrazin-2-yl)benzo[d]isoxazole

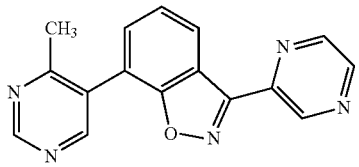

(27)

A reaction flask was charged with tetrakis(triphenylphosphine)palladium(0) (4.45 mg, 3.85 μmol), Preparation 25A (24.88 mg, 0.077 mmol), sodium carbonate (32.6 mg, 0.308 mmol), and 5-bromo-4-methylpyrimidine (13.99 mg, 0.081 mmol). The mixture was stirred at room temperature for 10 min under $N_2$, then DME (Ratio: 2.0, Volume: 287 μl), EtOH (Ratio: 1.000, Volume: 144 μl), and water (Ratio: 1.000, Volume: 144 μl) were added sequentially. The resultant mixture was heated at 90° C. overnight. After 19 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-50% B over 25 minutes, then a 5-minute hold at 100% B; Flow: 20 mL/min. Fractions containing the desired product were combined and dried via centrifugal evaporation to afford the title compound (1.4 mg, 6.2%). ESI MS (M+H)$^+$=290.0. HPLC Peak $t_r$=1.78 minutes. Purity >99%. HPLC Conditions: B.

Example 28

3-Cyclopropyl-7-(4-methylpyridin-3-yl)benzo[d]isoxazole

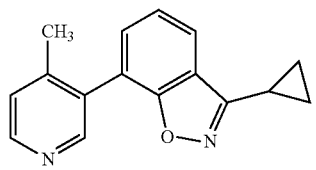

(28)

Preparation 28A:
(3-Bromo-2-fluorophenyl)(cyclopropyl)methanol

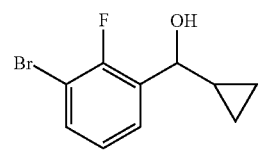

(28A)

To a solution of 3-bromo-2-fluorobenzaldehyde (0.500 g, 2.463 mmol) in THF (10.71 mL) cooled to −78° C. was added cyclopropylmagnesium bromide (5.91 mL, 2.96 mmol). The reaction mixture was maintained at −78° C. for at least 2 hr, then allowed to warm to room temperature. During this time, additional cyclopropylmagnesium bromide (5.91 mL, 2.96 mmol) was added. After 30 min, the reaction was quenched with a saturated aqueous solution of NH$_4$Cl. The reaction mixture was diluted with CH$_2$Cl$_2$. The layers were separated and the aqueous phase extracted with CH$_2$Cl$_2$ (2×). The organics were combined, dried over Na$_2$SO$_4$, filtered, and concentrated to afford the title compound (0.604 g, 2.464 mmol, 100% yield) as a yellow residue.

Preparation 28B:
(3-Bromo-2-fluorophenyl)(cyclopropyl)methanone

(28B)

To a solution of Preparation 28A (0.604 g, 2.464 mmol) in wet CH$_2$Cl$_2$ (9.86 mL) was added Dess-Martin periodinane (2.61 g, 6.16 mmol) at room temperature. After 2 hr, the reaction was quenched with a 1:1 solution of saturated aqueous NaHCO$_3$: 10% (w/w) aqueous Na$_2$S$_2$O$_3$. The reaction mixture was diluted with additional CH$_2$Cl$_2$. The mixture was stirred until both layers became clear. The layers were separated and the organic phase washed with saturated aqueous NaHCO$_3$. The aqueous phase was extracted with CH$_2$Cl$_2$ (2×). The organic phases were combined, dried over Na$_2$SO$_4$, filtered, and concentrated to afford the title compound (0.599 g, 2.464 mmol, 100% yield) as a yellow solid.

Preparation 28C:
(Z)-(3-Bromo-2-fluorophenyl)(cyclopropyl)methanone oxime

(28C)

A solution of Preparation 28B (0.599 g, 2.464 mmol) and hydroxylamine hydrochloride (1.164 g, 16.76 mmol) in pyridine (7.49 mL) was refluxed for 2.5 hr, allowed to cool to room temperature, and then concentrated in vacuo. The crude material was partitioned between EtOAc and 1N HCl. The layers were separated and the aqueous phase extracted with EtOAc (5×). Organics combined, dried over Na$_2$SO$_4$, filtered, and concentrated to afford the title compound (0.636 g, 2.464 mmol, 100% yield) as a yellow residue.

Preparation 28D:
7-Bromo-3-cyclopropylbenzo[d]isoxazole

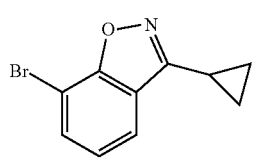
(28D)

To a suspension of sodium hydride (0.168 g, 4.19 mmol) in THF (6.34 mL) was added dropwise Preparation 28C (0.636 g, 2.464 mmol) in DMF (3.52 mL). The reaction mixture was heated at 70° C. for 2 hr, then allowed to cool to room temperature. The reaction was quenched with H$_2$O. The reaction mixture was extracted with EtOAc (3×). The organic phases were combined, dried over Na$_2$SO$_4$, filtered, concentrated, and further dried under high vacuum to afford an orange residue. The crude material was dissolved in a minimal amount of CH$_2$Cl$_2$ to be chromatographed. Purification of the crude material by silica gel chromatography using an ISCO machine (40 g column, 40 mL/min, 0-30% EtOAc in hexanes over 19 min, t$_r$=6 min) gave the title compound (0.198 g, 0.832 mmol, 33.7% yield) (4 steps) as an orange residue.

Example 28

A reaction flask was charged with tetrakis(triphenylphosphine)palladium(0) (6.07 mg, 5.25 μmol), Preparation 28D (0.025 g, 0.105 mmol), sodium carbonate (0.045 g, 0.420 mmol), and 4-methylpyridin-3-ylboronic acid (0.015 g, 0.110 mmol). The mixture was stirred at room temperature for 10 min under N$_2$, then DME (0.392 mL), EtOH (0.196 mL), and water (0.196 mL) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 0-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (10.1 mg, 38%). ESI MS (M+H)$^+$= 251.2. HPLC Peak t$_r$=2.20 minutes. Purity >99%. HPLC Conditions: A.

Example 29

3-Cyclopropyl-7-(4-methoxypyridin-3-yl)benzo[d]isoxazole

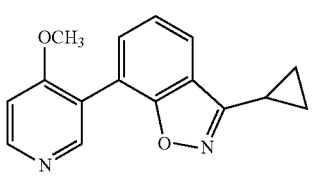
(29)

A reaction flask was charged with tetrakis(triphenylphosphine)palladium(0) (6.07 mg, 5.25 µmol), Preparation 28D (0.025 g, 0.105 mmol), sodium carbonate (0.056 g, 0.525 mmol), and 4-methoxypyridin-3-ylboronic acid, HCl (0.060 g, 0.315 mmol). The mixture was stirred at room temperature for 10 min under $N_2$, then DME (0.392 mL), EtOH (0.196 mL), and water (0.196 mL) were added sequentially. The resultant mixture was heated at 90° C. overnight. After 23 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (2.1 mg, 7.4%). ESI MS $(M+H)^+=267.2$. HPLC Peak $t_r=2.05$ minutes. Purity=98%. HPLC Conditions: A.

Example 30

7-(4-Chloropyridin-3-yl)-3-cyclopropylbenzo[d]isoxazole

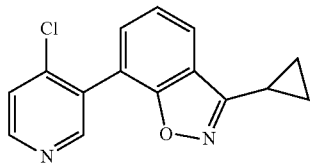

(30)

A reaction flask was charged with tetrakis(triphenylphosphine)palladium(0) (6.07 mg, 5.25 µmol), Preparation 28D (0.025 g, 0.105 mmol), sodium carbonate (0.045 g, 0.420 mmol), and 4-chloro-3-(4,4,5,5-tetramethyl-1,3,2-dioxaborolan-2-yl)pyridine (0.075 g, 0.315 mmol). The mixture was stirred at room temperature for 10 min under $N_2$, then DME (0.392 mL), EtOH (0.196 mL), and water (0.196 mL) were added sequentially. The resultant mixture was heated at 90° C. overnight. After 23 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (6.9 mg, 24%). ESI MS $(M+H)^+=271.0$. HPLC Peak $t_r=2.32$ minutes. Purity >99%. HPLC Conditions: B.

Example 31

3-Cyclopropyl-7-(4-cyclopropylpyrimidin-5-yl)benzo[d]isoxazole

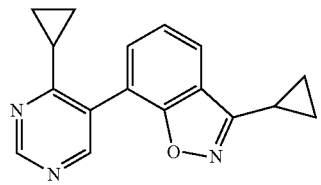

(31)

A reaction flask was charged with tetrakis(triphenylphosphine)palladium(0) (2.128 mg, 1.841 µmol), Preparation 28D (10.5 mg, 0.037 mmol), sodium carbonate (15.61 mg, 0.147 mmol), and Preparation 11A (7.70 mg, 0.039 mmol). The mixture was stirred at room temperature for 10 min under $N_2$, then DME (Ratio: 2.0, Volume: 137 µl), EtOH (Ratio: 1.000, Volume: 68.7 µl), and water (Ratio: 1.000, Volume: 68.7 µl) were added sequentially. The resultant mixture was heated at 90° C. overnight. After 15 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a yellow residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (4.0 mg, 39%). ESI MS $(M+H)^+=278.2$. HPLC Peak $t_r=2.38$ minutes. Purity >99%. HPLC Conditions: B.

Example 32

3-Cyclopropyl-7-(4-methylpyrimidin-5-yl)benzo[d]isoxazole

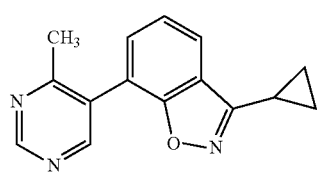

(32)

Preparation 32A: 3-Cyclopropyl-7-(4,4,5,5-tetramethyl-1,3,2-dioxaborolan-2-yl)benzo[d]isoxazole

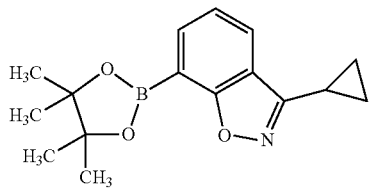

(32A)

A vial was charged with bis(acetonitrile)palladium(II) chloride (1.090 mg, 4.20 μmol), dicyclohexyl(2',6'-dimethoxybiphenyl-2-yl)phosphine (3.45 mg, 8.40 μmol), and Preparation 28D (0.050 g, 0.210 mmol). The vial was capped with a rubber septum and then evacuated and backfilled with $N_2$ (this sequence was carried out a total of 2 times). Dioxane (0.126 mL) was added via syringe, through the septum, followed by the addition of triethylamine (0.088 mL, 0.630 mmol) and 4,4,5,5-tetramethyl-1,3,2-dioxaborolane (0.046 mL, 0.315 mmol). The septum was then replaced with a Teflon screw valve, and the vial sealed. The reaction mixture was heated at 110° C. After 19 hr, the reaction mixture was allowed to cool to room temperature. The reaction mixture was filtered through a disposable fritted funnel and the filter cake washed with $CH_2Cl_2$. The filtrate was concentrated to afford the title compound as a brown residue (60 mg, 100%).

Example 32

A reaction flask was charged with tetrakis(triphenylphosphine)palladium(0) (6.08 mg, 5.26 μmol), Preparation 32A (30 mg, 0.105 mmol), sodium carbonate (44.6 mg, 0.421 mmol), and 5-bromo-4-methylpyrimidine (19.11 mg, 0.110 mmol). The mixture was stirred at room temperature for 10 min under $N_2$, then DME (Ratio: 2.0, Volume: 393 μl), EtOH (Ratio: 1.000, Volume: 196 μl), and water (Ratio: 1.000, Volume: 196 μl) were added sequentially. The resultant mixture was heated at 90° C. overnight. After 15 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a yellow residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 20 mL/min. Fractions containing the desired product were combined and dried via centrifugal evaporation to afford the title compound (6.9 mg, 26%). ESI MS (M+H)⁺=252.1. HPLC Peak $t_r$=1.88 minutes. Purity=99%. HPLC Conditions: B.

Example 33

7-(4-Methylpyridin-3-yl)-3-(pyridazin-3-yl)benzo[d]isoxazole

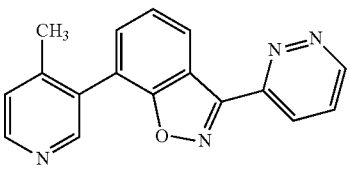

(33)

Preparation 33A:
(3-Bromo-2-fluorophenyl)(pyridazin-3-yl)methanol

(33A)

A solution of LTMP was prepared by reaction of 2,2,6,6-tetramethylpiperidine (0.151 mL, 0.896 mmol) in THF (5.6 mL) and n-butyllithium (0.358 mL, 0.896 mmol) at −30° C. and then at 0° C. for 30 min.

A solution of pyridazine (0.078 mL, 1.075 mmol) in THF (2.0 mL) and a solution of 3-bromo-2-fluorobenzaldehyde (0.200 g, 0.985 mmol) in THF (2.0 mL) were added simultaneously to a cold solution of LTMP at −78° C. The mixture was stirred at −78° C. for 4 h, followed by the addition of excess of HCl/EtOH/THF. The solution was allowed to warm to room temperature, then treated with a saturated aqueous solution of $NaHCO_3$ and extracted with $CH_2Cl_2$ (3×). The organic phases were combined, dried over $Na_2SO_4$, filtered, and concentrated to afford the title compound (0.254 g, 0.897 mmol, 100% yield) as a yellow residue.

Preparation 33B:
(3-Bromo-2-fluorophenyl)(pyridazin-3-yl)methanone

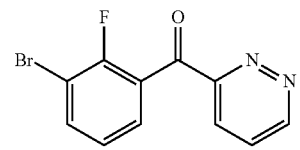

(33B)

To a solution of Preparation 33A (0.254 g, 0.897 mmol) in wet $CH_2Cl_2$ (3.59 mL) was added Dess-Martin periodinane (0.761 g, 1.794 mmol) at room temperature. After 4 hr, the reaction was quenched with a 1:1 solution of saturated aqueous $NaHCO_3$: 10% (w/w) aqueous $Na_2S_2O_3$. The reaction mixture was diluted with additional $CH_2Cl_2$ and the mixture was stirred until both layers became clear. The layers were separated and the organic phase washed with saturated aqueous NaHCO$_3$. The aqueous phase was extracted with CH$_2$Cl$_2$ (2×). The organic phases were combined, dried over Na$_2$SO$_4$, filtered, and concentrated to afford an orange residue. The crude material was dissolved in a minimal amount of CH$_2$Cl$_2$ to be chromatographed. Purification of the crude material by silica gel chromatography using an ISCO machine (40 g column, 40 mL/min, 0-85% EtOAc in hexanes over 25 min, t$_r$=18.5 min) gave the title compound (0.061 g, 0.217 mmol, 24.19% yield) (2 steps) as an orange solid.

Preparation 33C: (E)-(3-Bromo-2-fluorophenyl) (pyridazin-3-yl)methanone oxime

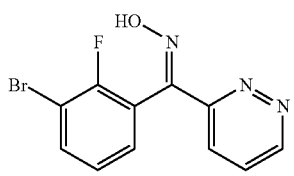

(33C)

A solution of Preparation 33B (0.061 g, 0.217 mmol) and hydroxylamine hydrochloride (0.103 g, 1.476 mmol) in pyridine (0.660 mL) was heated at 70° C. for 1.5 hr, allowed to cool to room temperature, and then concentrated in vacuo. The crude material was partitioned between EtOAc and 1N HCl. The layers were separated and the aqueous phase extracted with EtOAc (5×). The organic phases were combined, dried over Na$_2$SO$_4$, filtered, and concentrated to afford the title compound (0.043 g, 0.145 mmol, 66.9% yield) as a yellow residue.

Preparation 33D: 7-Bromo-3-(pyridazin-3-yl)benzo[d]isoxazole

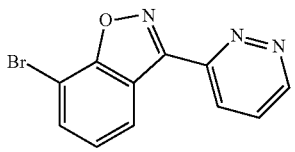

(33D)

To a suspension of sodium hydride (9.87 mg, 0.247 mmol) in THF (0.373 mL) was added dropwise Preparation 33C (0.043 g, 0.145 mmol) in DMF (0.207 mL). The syringe was rinsed with additional DMF (0.207 mL) into the reaction vial. The reaction mixture was heated at 70° C. for 2 hr, then allowed to cool to room temperature. The reaction was quenched with H$_2$O and extracted with EtOAc (3×). The organic phases were combined, dried over Na$_2$SO$_4$, filtered, concentrated, and further dried under high vacuum to afford a yellow residue. The crude material was dissolved in a minimal amount of CH$_2$Cl$_2$ to be chromatographed. Purification of the crude material by silica gel chromatography using an ISCO machine (12 g column, 30 mL/min, 20-60% EtOAc in hexanes over 16 min, t$_r$=9.5 min) gave the title compound (0.030 g, 0.109 mmol, 74.8% yield) as a white solid.

Example 33

A reaction flask was charged with tetrakis(triphenylphosphine)palladium(0) (3.14 mg, 2.72 μmol), Preparation 33D (0.015 g, 0.054 mmol), sodium carbonate (0.023 g, 0.217 mmol), and 4-methylpyridin-3-ylboronic acid (7.81 mg, 0.057 mmol). The mixture was stirred at room temperature for 10 min under N$_2$, then DME (0.203 mL), EtOH (0.101 mL), and water (0.101 mL) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-55% B over 25 minutes, then a 5-minute hold at 100% B; Flow: 20 mL/min. Fractions containing the desired product were combined and dried via centrifugal evaporation to afford the title compound (7.6 mg, 49%). ESI MS (M+H)$^+$=289.1. HPLC Peak t$_r$=1.86 minutes. Purity >99%. HPLC Conditions: B.

Example 34

7-(4-Chloropyridin-3-yl)-3-(pyridazin-3-yl)benzo[d] isoxazole

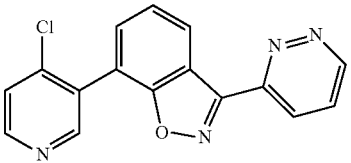

(34)

A reaction flask was charged with tetrakis(triphenylphosphine)palladium(0) (4.81 mg, 4.17 μmol), Preparation 33D (23 mg, 0.083 mmol), sodium carbonate (35.3 mg, 0.333 mmol), and 4-chloro-3-(4,4,5,5-tetramethyl-1,3,2-dioxaborolan-2-yl)pyridine (59.9 mg, 0.250 mmol). The mixture was stirred at room temperature for 10 min under N$_2$, then DME (311 μL), EtOH (155 μL), and water (155 μL) were added sequentially. The resultant mixture was heated at 90° C. overnight. After 25 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a yellow solid. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-50% B over 25 minutes, then a 15-minute hold at 100% B; Flow: 20 mL/min. Fractions containing the desired product were combined and dried via centrifugal evaporation to afford the title compound (3.1 mg, 12%). ESI MS (M+H)$^+$= 309.0. HPLC Peak $t_r$=1.99 minutes. Purity >99%. HPLC Conditions: B.

Example 35

3-(5-Fluoro-2-methoxyphenyl)-7-(4-methylpyridin-3-yl)benzo[d]isoxazole

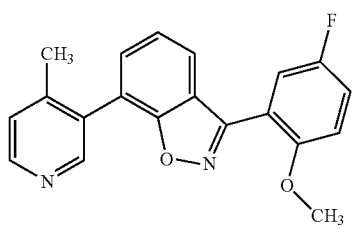
(35)

Preparation 35A: (3-bromo-2-fluorophenyl)(5-fluoro-2-methoxyphenyl)methanol

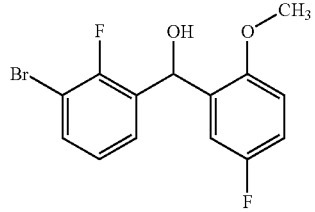
(35A)

To a solution of 3-bromo-2-fluorobenzaldehyde (1.0 g, 4.93 mmol) in THF (21.42 mL) cooled to −78° C. was added (5-fluoro-2-methoxyphenyl)magnesium bromide in THF (11.82 mL, 5.91 mmol). The reaction mixture was maintained at −78° C. for at least 1 hr, then allowed to warm to room temperature. The reaction mixture was then re-cooled to 0° C. and additional (5-fluoro-2-methoxyphenyl)magnesium bromide in THF (11.82 mL, 5.91 mmol) was added. The reaction mixture was allowed to warm to room temperature overnight. The reaction was quenched with a saturated aqueous solution of NH$_4$Cl and diluted with CH$_2$Cl$_2$. The layers were separated and the aqueous phase was extracted with CH$_2$Cl$_2$ (2×). Organics combined, dried over Na$_2$SO$_4$, filtered, and concentrated to afford a yellow residue. The crude material was dissolved in a minimal amount of CH$_2$Cl$_2$ to be chromatographed. Purification of the crude material by silica gel chromatography using an ISCO machine (80 g column, 60 mL/min, 0-30% EtOAc in hexanes over 20 min, $t_r$=17.5 min) gave the title compound (1.62 g, 4.92 mmol, 100% yield) as a colorless liquid.

Preparation 35B: (3-Bromo-2-fluorophenyl)(5-fluoro-2-methoxyphenyl)methanone

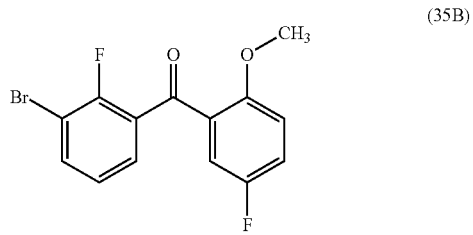 [SMILES: COc1ccc(F)cc1C(=O)c1cccc(Br)c1F]
(35B)

To a solution of Preparation 35A (1.62 g, 4.92 mmol) in wet CH$_2$Cl$_2$ (19.69 mL) was added Dess-Martin periodinane (5.22 g, 12.31 mmol) at room temperature. After 2.5 hr, the reaction was quenched with a 1:1 solution of saturated aqueous NaHCO$_3$:10% (w/w) aqueous Na$_2$S$_2$O$_3$. The reaction mixture was diluted with additional CH$_2$Cl$_2$. The mixture was stirred until both layers became clear. The layers were separated and the organic phase washed with saturated aqueous NaHCO$_3$. The aqueous phase was extracted with CH$_2$Cl$_2$ (2×). The organic phases were combined, dried over Na$_2$SO$_4$, filtered, and concentrated to afford the title compound (1.61 g, 4.92 mmol, 100% yield) as an off-white solid.

Preparation 35C: (Z)-(3-Bromo-2-fluorophenyl)(5-fluoro-2-methoxyphenyl)methanone oxime

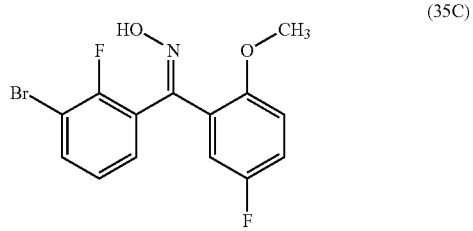 [SMILES: COc1ccc(F)cc1/C(=N/O)c1cccc(Br)c1F]
(35C)

A solution of Preparation 35B (1.46 g, 4.46 mmol) and hydroxylamine hydrochloride (2.109 g, 30.3 mmol) in pyridine (Volume: 22.32 ml) was refluxed for 1.5 hr, allowed to cool to room temperature, then concentrated in vacuo. The crude material was partitioned between EtOAc and 1N HCl. The layers were separated and the aqueous phase extracted with EtOAc (3×). Organics combined, dried over Na$_2$SO$_4$, filtered, and concentrated to afford the title compound (1.10 g, 3.18 mmol, 71.3% yield) as a yellow residue.

Preparation 35D: 7-Bromo-3-(5-fluoro-2-methoxyphenyl)benzo[d]isoxazole

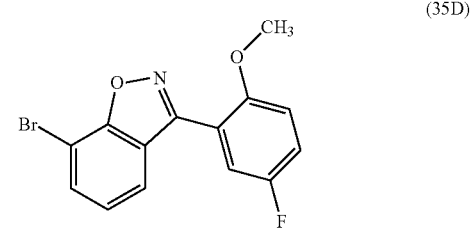 [SMILES: COc1ccc(F)cc1-c1noc2c(Br)cccc12]
(35D)

To a suspension of sodium hydride (0.219 g, 5.47 mmol) in THF (Ratio: 1.8, Volume: 41.3 ml) was added dropwise Preparation 35C (1.10 g, 3.22 mmol) in DMF (11 mL) slowly. The syringe was rinsed with additional DMF (10 mL) into the reaction vial. The reaction mixture was heated at 70° C. for 3 hr, then allowed to cool to room temperature. The reaction was quenched with H$_2$O. The reaction mixture was extracted with EtOAc (3×). The organic phases were combined, dried over Na$_2$SO$_4$, filtered, concentrated, and further dried under high vacuum to afford a yellow solid. The crude material was dissolved in a minimal amount of CH$_2$Cl$_2$ to be chromatographed. Purification of the crude material by silica gel chromatography using an ISCO machine (80 g column, 60 mL/min, 0-95% EtOAc in hexanes over 30 min, t$_r$=2, 12 min) gave an insoluble white solid. Further trituration of the product with CH$_2$Cl$_2$ at room temperature and filtration through a Buchner funnel provided the title compound (765 mg, 2.351 mmol, 73.1% yield).

Example 35

A reaction vial was charged with tetrakis(triphenylphosphine)palladium(0) (5.78 mg, 5.00 μmol), Preparation 35D (0.032 g, 0.100 mmol), sodium carbonate (42.4 mg, 0.400 mmol), and 4-methylpyridin-3-ylboronic acid (14.38 mg, 0.105 mmol). The mixture was stirred at room temperature for 10 min under N$_2$, then DME (Ratio: 2.0, Volume: 373 μl), EtOH (Ratio: 1.0, Volume: 1870, and water (Ratio: 1.000, Volume: 187 μl) were added sequentially. The resultant mixture was heated at 90° C. overnight. After 17.5 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (13 mg, 37%). ESI MS (M+H)$^+$=335.2. HPLC Peak t$_r$=2.58 minutes. Purity=99%. HPLC Conditions: D.

Example 36

3-(5-Fluoro-2-methoxyphenyl)-7-(4-morpholinopyrimidin-5-yl)benzo[d]isoxazole

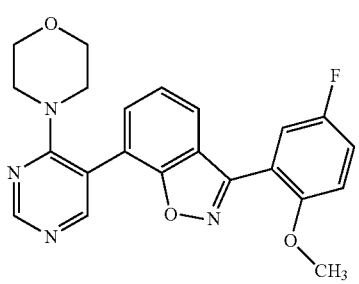

(36)

Preparation 36A: 3-(5-Fluoro-2-methoxyphenyl)-7-(4,4,5,5-tetramethyl-1,3,2-dioxaborolan-2-yl)benzo[d]isoxazole

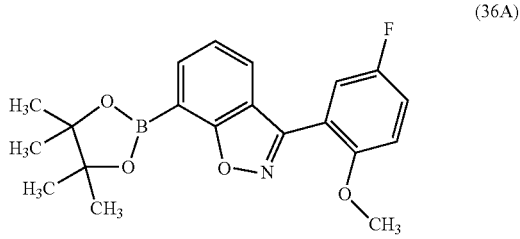 [SMILES: COc1ccc(F)cc1-c1noc2c(B3OC(C)(C)C(C)(C)O3)cccc12]

(36A)

A vial was charged with bis(acetonitrile)palladium(II) chloride (4.67 mg, 0.018 mmol), dicyclohexyl(2',6'-dimethoxybiphenyl-2-yl)phosphine (0.015 g, 0.036 mmol), and Preparation 35D (0.290 g, 0.900 mmol). The vial was capped with a rubber septum and then evacuated and backfilled with N$_2$ (this sequence was carried out a total of 2 times). Dioxane (Volume: 0.539 ml) was added via syringe through the septum, followed by the addition of triethylamine (0.376 ml, 2.70 mmol) and 4,4,5,5-tetramethyl-1,3,2-dioxaborolane (0.196 ml, 1.350 mmol). The septum was then replaced with a Teflon screw valve, and the vial sealed. The reaction mixture was heated at 110° C. After 13 hr, the reaction mixture was allowed to cool to room temperature. The reaction mixture was filtered through a disposable fritted funnel and the filter cake washed with CH$_2$Cl$_2$. The filtrate was concentrated to afford the title compound (332 mg, 100%) as a yellow-green residue.

Example 36

A reaction vial was charged with tetrakis(triphenylphosphine)palladium(0) (5.78 mg, 5.00 μmol), Preparation 16A (43.7 mg, 0.150 mmol), sodium carbonate (42.4 mg, 0.400 mmol), and Preparation 36A (0.037 g, 0.100 mmol). The mixture was stirred at room temperature for 10 min under N$_2$, then DME (Ratio: 2.0, Volume: 373 μl), EtOH (Ratio: 1.0, Volume: 187 μl), and water (Ratio: 1.000, Volume: 187 μl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 20 mL/min. Fractions containing the desired product were combined and dried via centrifugal evaporation to afford the title compound (14 mg, 35%). ESI MS (M+H)$^+$=407.2. HPLC Peak t$_r$=2.29 minutes. Purity=98%. HPLC Conditions: D.

Example 37

3-(5-Fluoro-2-methoxyphenyl)-7-(4-methylpyrimidin-5-yl)benzo[d]isoxazole

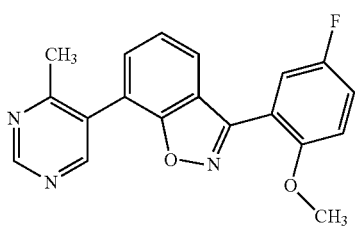

(37)

A reaction vial was charged with tetrakis(triphenylphosphine)palladium(0) (5.78 mg, 5.00 μmol), Preparation 36A (0.037 g, 0.100 mmol), sodium carbonate (42.4 mg, 0.400 mmol), and 5-bromo-4-methylpyrimidine (26.0 mg, 0.150 mmol). The mixture was stirred at room temperature for 10 min under $N_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (12.7 mg, 37%). ESI MS (M+H)$^+$=336.1. HPLC Peak $t_r$=2.32 minutes. Purity=97%. HPLC Conditions: D.

Example 38

7-(4-Chloropyridin-3-yl)-3-(5-fluoro-2-methoxyphenyl)benzo[d]isoxazole

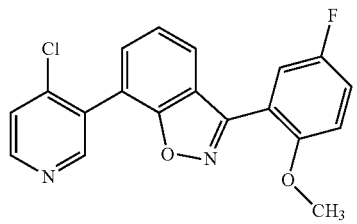

(38)

A reaction vial was charged with tetrakis(triphenylphosphine)palladium(0) (5.78 mg, 5.00 μmol), Preparation 35D (0.032 g, 0.100 mmol), sodium carbonate (0.042 g, 0.400 mmol), and 4-chloro-3-(4,4,5,5-tetramethyl-1,3,2-dioxaborolan-2-yl)pyridine (0.072 g, 0.300 mmol). The mixture was stirred at room temperature for 10 min under $N_2$, then DME (Ratio: 2.0, Volume: 0.373 ml), EtOH (Ratio: 1.0, Volume: 187 μl), and water (Ratio: 1.000, Volume: 187 μl) were added sequentially. The resultant mixture was heated at 90° C. overnight. After 17.5 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-70% B over 25 minutes, then a 5-minute hold at 100% B; Flow: 20 mL/min. Fractions containing the desired product were combined and dried via centrifugal evaporation to afford the title compound (1.7 mg, 4.7%). ESI MS (M+H)$^+$=355.0. HPLC Peak $t_r$=2.76 minutes. Purity=99%. HPLC Conditions: B.

Example 39

7-(4-Cyclopropylpyrimidin-5-yl)-3-(5-fluoro-2-methoxyphenyl)benzo[d]isoxazole

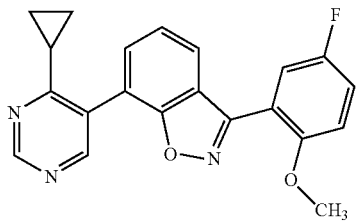

(39)

A reaction vial was charged with tetrakis(triphenylphosphine)palladium(0) (5.78 mg, 5.00 μmol), Preparation 36A (0.037 g, 0.100 mmol), sodium carbonate (42.4 mg, 0.400 mmol), and Preparation 11A (29.9 mg, 0.150 mmol). The mixture was stirred at room temperature for 10 min under $N_2$, then DME (Ratio: 2.0, Volume: 373 μl), EtOH (Ratio: 1.0, Volume: 187 μl), and water (Ratio: 1.000, Volume: 187 μl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-70% B over 25 minutes, then a 5-minute hold at 100% B; Flow: 20 mL/min. Fractions containing the desired product were combined and dried via centrifugal evaporation to afford the title compound (9.4 mg, 26%). ESI MS (M+H)$^+$= 362.2. HPLC Peak t$_r$=2.81 minutes. Purity >99%. HPLC Conditions: B.

Example 40

3-(5-Fluoro-2-methoxyphenyl)-7-(4-(2,2,2-trifluoroethoxy)pyrimidin-5-yl)benzo[d]isoxazole

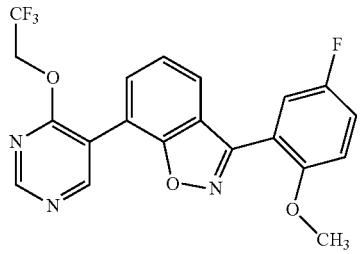

(40)

A reaction vial was charged with tetrakis(triphenylphosphine)palladium(0) (5.78 mg, 5.00 μmol), Preparation 36A (0.037 g, 0.100 mmol), sodium carbonate (42.4 mg, 0.400 mmol), and Preparation 12A (45.6 mg, 0.150 mmol). The mixture was stirred at room temperature for 10 min under N$_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 25 minutes, then a 5-minute hold at 100% B; Flow: 20 mL/min. Fractions containing the desired product were combined and dried via centrifugal evaporation to afford the title compound (9.4 mg, 22%). ESI MS (M+H)$^+$= 420.2. HPLC Peak t$_r$=2.91 minutes. Purity >99%. HPLC Conditions: B.

Example 41

3-(5-Fluoro-2-methoxyphenyl)-7-(isoquinolin-4-yl)benzo[d]isoxazole

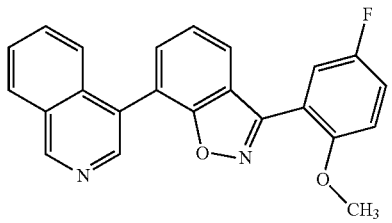

(41)

A reaction flask was charged with tetrakis(triphenylphosphine)palladium(0) (5.78 mg, 5.00 μmol), Preparation 35D (0.032 g, 0.100 mmol), sodium carbonate (42.4 mg, 0.400 mmol), and isoquinolin-4-ylboronic acid (18.16 mg, 0.105 mmol). The mixture was stirred at room temperature for 10 min under N$_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation (12 mg, 33%). ESI MS (M+H)$^+$=371.1. HPLC Peak t$_r$=2.91 minutes. Purity=99%. HPLC Conditions: B.

Example 42

5-(3-(5-Fluoro-2-methoxyphenyl)benzo[d]isoxazol-7-yl)pyrimidin-4-amine

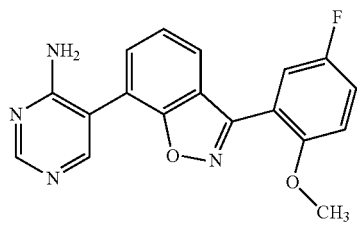

(42)

A reaction vial was charged with tetrakis(triphenylphosphine)palladium(0) (5.78 mg, 5.00 µmol), 5-iodopyrimidin-4-amine (33.1 mg, 0.150 mmol), sodium carbonate (42.4 mg, 0.400 mmol), and Preparation 36A (0.037 g, 0.100 mmol). The mixture was stirred at room temperature for 10 min under $N_2$, then DME (Ratio: 2.0, Volume: 373 µl), EtOH (Ratio: 1.0, Volume: 187 µl), and water (Ratio: 1.000, Volume: 187 µl) were added sequentially. The resultant mixture was heated at 90° C. overnight. After 17 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 20 mL/min. Fractions containing the desired product were combined and dried via centrifugal evaporation to afford the title compound (9.3 mg, 27%). ESI MS $(M+H)^+=337.1$. HPLC Peak $t_r=1.52$ minutes. Purity >99%. HPLC Conditions: E.

Example 43

3-(4-Fluoro-2-methoxyphenyl)-7-(4-methylpyridin-3-yl)benzo[d]isoxazole

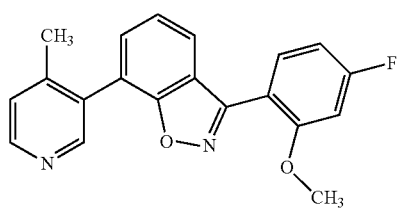

(43)

Preparation 43A: (3-Bromo-2-fluorophenyl)(4-fluoro-2-methoxyphenyl)methanol

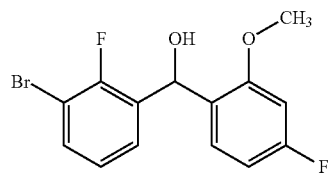

(43A)

To a solution of 3-bromo-2-fluorobenzaldehyde (1.5 g, 7.39 mmol) in THF (Volume: 32.1 ml) cooled to 0° C. was added (4-fluoro-2-methoxyphenyl)magnesium bromide (17.73 ml, 8.87 mmol). After 50 min, additional (4-fluoro-2-methoxyphenyl)magnesium bromide (17.73 ml, 8.87 mmol) was added. The reaction was quenched with a saturated aqueous solution of $NH_4Cl$. The reaction mixture was diluted with $CH_2Cl_2$. The layers were separated and the aqueous phase extracted with $CH_2Cl_2$ (2×). Organics combined, dried over $Na_2SO_4$, filtered, and concentrated to afford a yellow residue. The crude material was dissolved in a minimal amount of $CH_2Cl_2$ to be chromatographed. Purification of the crude material by silica gel chromatography using an ISCO machine (80 g column, 60 mL/min, 0-30% EtOAc in hexanes over 30 min, tr=17 min) gave the title compound (2.10 g, 6.06 mmol, 82% yield) as a colorless liquid.

Preparation 43B: (3-Bromo-2-fluorophenyl)(4-fluoro-2-methoxyphenyl)methanone

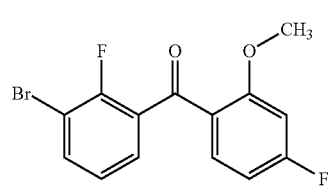

(43B)

To a solution of Preparation 43A (2.10 g, 6.38 mmol) in wet $CH_2Cl_2$ (Volume: 25.5 ml) was added Dess-Martin periodinane (6.77 g, 15.96 mmol) at room temperature. After 2 hr, the reaction was quenched with a 1:1 solution of saturated aqueous $NaHCO_3$: 10% (w/w) aqueous $Na_2S_2O_3$. The reaction mixture was diluted with additional $CH_2Cl_2$. The mixture was stirred until both layers became clear. The layers were separated and the organic phase washed with saturated aqueous $NaHCO_3$. The aqueous phase was extracted with $CH_2Cl_2$ (2×). The organic phases were combined, dried over $Na_2SO_4$, filtered, and concentrated to afford a brown residue. Purification of the crude material by silica gel chromatography using an ISCO machine (80 g column, 60 mL/min, 0-30% EtOAc in hexanes over 17 min, $t_r=11$ min) gave the title compound (1.83 g, 5.54 mmol, 87% yield) as a white solid.

Preparation 43C: (Z)-(3-Bromo-2-fluorophenyl)(4-fluoro-2-methoxyphenyl)methanone oxime

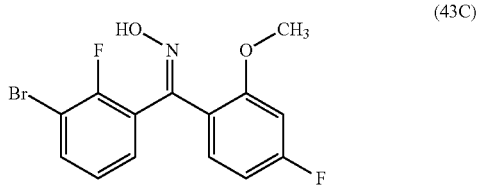 [SMILES: COc1cc(F)ccc1/C(=N/O)c1cccc(Br)c1F]

(43C)

A solution of Preparation 43B (1.83 g, 5.59 mmol) and hydroxylamine hydrochloride (2.64 g, 38.0 mmol) in pyridine (Volume: 28.0 ml) was refluxed for 1.5 hr, allowed to cool to room temperature, and then concentrated in vacuo. The crude material was partitioned between EtOAc and 1N HCl. The layers were separated and the aqueous phase extracted with EtOAc (3×). The organics were combined, dried over $Na_2SO_4$, filtered, and concentrated to afford the title compound (1.914 g, 5.59 mmol, 100% yield) as a yellow solid.

Preparation 43D: 7-Bromo-3-(4-fluoro-2-methoxyphenyl)benzo[d]isoxazole

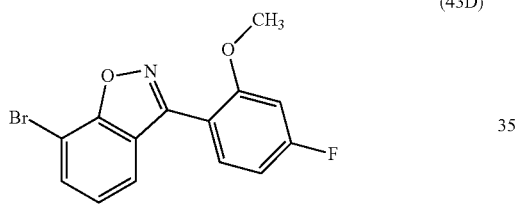

(43D)

To a suspension of sodium hydride (0.219 g, 5.47 mmol) in THF (Ratio: 1.8, Volume: 41.3 ml) was added dropwise Preparation 43C (1.10 g, 3.22 mmol) in DMF (13 mL) slowly. The syringe was rinsed with additional DMF (10 mL) into the reaction vial. The reaction mixture was heated at 70° C. for 3 hr and then allowed to cool to room temperature. The reaction was quenched with $H_2O$. The reaction mixture was extracted with EtOAc (3×). The organic phases were combined, dried over $Na_2SO_4$, filtered, concentrated, and further dried under high vacuum to afford a yellow solid. The crude material was dissolved in a minimal amount of $CH_2Cl_2$ to be chromatographed. Purification of the crude material by silica gel chromatography using an ISCO machine (80 g column, 60 mL/min, 0-50% EtOAc in hexanes over 25 min, $t_r$=12 min) gave the title compound (487 mg, 1.436 mmol, 44.7% yield) as a white solid.

Example 43

A reaction vial was charged with tetrakis(triphenylphosphine)palladium(0) (5.78 mg, 5.00 μmol), Preparation 43D (0.032 g, 0.100 mmol), sodium carbonate (42.4 mg, 0.400 mmol), and 4-methylpyridin-3-ylboronic acid (14.38 mg, 0.105 mmol). The mixture was stirred at room temperature for 10 min under $N_2$, and then DME (Ratio: 2.0, Volume: 373 μl), EtOH (Ratio: 1.0, Volume: 1870, and water (Ratio: 1.000, Volume: 187 μl) were added sequentially. The resultant mixture was heated at 90° C. overnight. After 17 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (3.6 mg, 10%).

Example 44

7-(4-Chloropyridin-3-yl)-3-(4-fluoro-2-methoxyphenyl)benzo[d]isoxazole

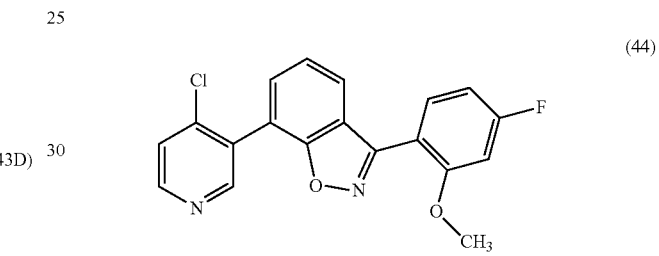

(44)

A reaction vial was charged with tetrakis(triphenylphosphine)palladium(0) (5.78 mg, 5.00 μmol), Preparation 43D (0.032 g, 0.100 mmol), sodium carbonate (42.4 mg, 0.400 mmol), and 4-chloro-3-(4,4,5,5-tetramethyl-1,3,2-dioxaborolan-2-yl)pyridine (71.9 mg, 0.300 mmol). The mixture was stirred at room temperature for 10 min under $N_2$, then DME (Ratio: 2.0, Volume: 373 μl), EtOH (Ratio: 1.0, Volume: 187 μl), and water (Ratio: 1.000, Volume: 187 μl) were added sequentially. The resultant mixture was heated at 90° C. overnight. After 17 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-70% B over 25 minutes, then a 5-minute hold at 100% B;

Flow: 20 mL/min. Fractions containing the desired product were combined and dried via centrifugal evaporation to afford the title compound (1.7 mg, 4.7%). ESI MS (M+H)$^+$= 355.0. HPLC Peak t$_r$=2.77 minutes. Purity >99%. HPLC Conditions: B.

Example 45

3-(4-Fluoro-2-methoxyphenyl)-7-(4-morpholinopyrimidin-5-yl)benzo[d]isoxazole

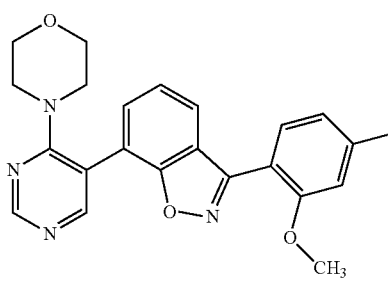

(45)

Preparation 45A: 3-(4-Fluoro-2-methoxyphenyl)-7-(4,4,5,5-tetramethyl-1,3,2-dioxaborolan-2-yl)benzo[d]isoxazole A vial was charged with bis(acetonitrile)palladium(II) chloride (3.87 mg, 0.015 mmol), dicyclohexyl(2',6'-dimethoxybiphenyl-2-yl)phosphine (0.012 g, 0.030 mmol), and Preparation 43D (0.240 g, 0.745 mmol). The vial was capped with a rubber septum and then evacuated and backfilled with N$_2$ (this sequence was carried out a total of 2 times). Dioxane (Volume: 0.446 ml) was added via syringe, through the septum, followed by the addition of triethylamine (0.312 ml, 2.235 mmol) and 4,4,5,5-tetramethyl-1,3,2-dioxaborolane (0.162 ml, 1.118 mmol). The septum was then replaced with a Teflon screw valve, and the vial sealed. The reaction mixture was heated at 110° C. After 13.5 hr, the reaction mixture was allowed to cool to room temperature. The reaction mixture was filtered through a disposable fritted funnel and the filter cake washed with CH$_2$Cl$_2$. The filtrate was concentrated to afford the title compound (275 mg, 100%) as a yellow residue.

Example 45

A reaction vial was charged with tetrakis(triphenylphosphine)palladium(0) (5.78 mg, 5.00 μmol), Preparation 16A (37.8 mg, 0.130 mmol), sodium carbonate (42.4 mg, 0.400 mmol), and Preparation 45A (0.037 g, 0.100 mmol). The mixture was stirred at room temperature for 10 min under N$_2$, then DME (Ratio: 2.0, Volume: 373 μl), EtOH (Ratio: 1.000, Volume: 187 μl), and Water (Ratio: 1.000, Volume: 187 μl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (12 mg, 30%). ESI MS (M+H)$^+$=407.2. HPLC Peak t$_r$=2.34 minutes. Purity >99%. HPLC Conditions: B.

Example 46

3-(4-Fluoro-2-methoxyphenyl)-7-(4-(2,2,2-trifluoroethoxy)pyrimidin-5-yl)benzo[d]isoxazole

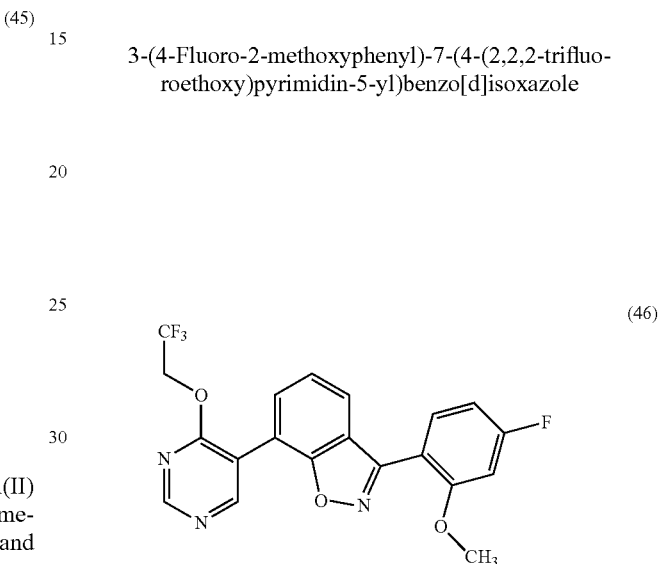

(46)

A reaction vial was charged with tetrakis(triphenylphosphine)palladium(0) (5.78 mg, 5.00 μmol), Preparation 45A (0.037 g, 0.100 mmol), sodium carbonate (42.4 mg, 0.400 mmol), and Preparation 12A (39.5 mg, 0.130 mmol). The mixture was stirred at room temperature for 10 min under N$_2$, then DME (Ratio: 2.0, Volume: 373 μl), EtOH (Ratio: 1.0, Volume: 187 μl), and Water (Ratio: 1.000, Volume: 187 μl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (14 mg, 32%). ESI MS (M+H)$^+$=420.1. HPLC Peak t$_r$=2.92 minutes. Purity=97%. HPLC Conditions: B.

Example 47

3-(4-Fluoro-2-methoxyphenyl)-7-(4-methylpyrimidin-5-yl)benzo[d]isoxazole

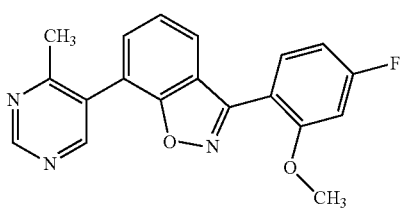

(47)

A reaction vial was charged with tetrakis(triphenylphosphine)palladium(0) (57.8 mg, 0.050 mmol), Preparation 45A (0.037 g, 0.100 mmol), sodium carbonate (42.4 mg, 0.400 mmol), and 5-bromo-4-methylpyrimidine (39.8 mg, 0.230 mmol). The mixture was stirred at room temperature for 10 min under $N_2$, then DME (Ratio: 2.0, Volume: 373 µl), EtOH (Ratio: 1.0, Volume: 187 µl), and water (Ratio: 1.000, Volume: 187 µl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (6.0 mg, 18%). ESI MS $(M+H)^+=336.1$. HPLC Peak $t_r=2.37$ minutes. Purity >99%. HPLC Conditions: B.

Example 48

7-(4-Cyclopropylpyrimidin-5-yl)-3-(4-fluoro-2-methoxyphenyl)benzo[d]isoxazole

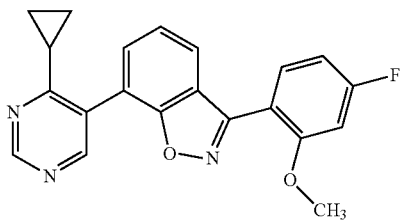

(48)

A reaction vial was charged with tetrakis(triphenylphosphine)palladium(0) (5.78 mg, 5.00 µmol), Preparation 45A (0.037 g, 0.100 mmol), sodium carbonate (42.4 mg, 0.400 mmol), and Preparation 11A (25.9 mg, 0.130 mmol). The mixture was stirred at room temperature for 10 min under $N_2$, then DME (Ratio: 2.0, Volume: 373 µl), EtOH (Ratio: 1.0, Volume: 187 µl), and water (Ratio: 1.0, Volume: 187 µl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (10 mg, 28%). ESI MS $(M+H)^+=362.2$. HPLC Peak $t_r=2.13$ minutes. Purity=99%. HPLC Conditions: E.

Example 49

3-(4-Fluoro-2-methoxyphenyl)-7-(isoquinolin-4-yl)benzo[d]isoxazole

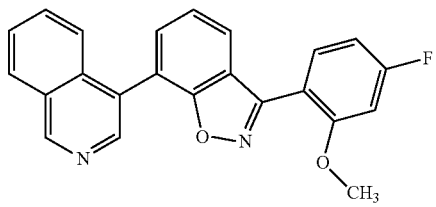

(49)

A reaction flask was charged with tetrakis(triphenylphosphine)palladium(0) (5.78 mg, 5.00 µmol), Preparation 43D (0.032 g, 0.100 mmol), sodium carbonate (42.4 mg, 0.400 mmol), and isoquinolin-4-ylboronic acid (18.16 mg, 0.105 mmol). The mixture was stirred at room temperature for 10 min under $N_2$, then DME (Ratio: 2.0, Volume: 373 µl), EtOH (Ratio: 1.000, Volume: 187 µl), and water (Ratio: 1.000, Volume: 187 µl) were added sequentially. The resultant mixture was heated at 90° C. overnight. After 24 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (7.9 mg, 21%). ESI MS $(M+H)^+=371.1$. HPLC Peak $t_r=2.21$ minutes. Purity >99%. HPLC Conditions: E.

Example 50

3-Chloro-7-(4-methylpyridin-3-yl)benzo[d]isoxazole

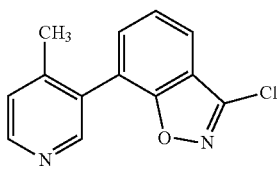
(50)

Preparation 50A:
2-Fluoro-3-(4-methylpyridin-3-yl)benzonitrile

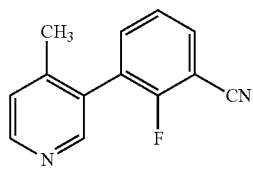
(50A)

A reaction flask was charged with tetrakis(triphenylphosphine)palladium(0) (1.040 g, 0.900 mmol), 3-bromo-2-fluorobenzonitrile (3.6 g, 18.00 mmol), sodium carbonate (7.63 g, 72.0 mmol), and 4-methylpyridin-3-ylboronic acid (2.59 g, 18.90 mmol). The mixture was stirred at room temperature for 10 min under $N_2$, then DME (67.2 mL), EtOH (33.6 mL), and water (33.6 mL) were added sequentially. The resultant mixture was heated at 90° C. overnight. After 17 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was dissolved in a minimal amount of $CH_2Cl_2$ to be chromatographed. Purification of the crude material by silica gel chromatography using an ISCO machine (120 g column, 85 mL/min, 0-70% EtOAc in hexanes over 25 min, $t_r$=15 min) gave the title compound (2.80 g, 13.19 mmol, 73.3% yield) as a purple residue. ESI MS $(M+H)^+$=213.1. HPLC Peak $t_r$=1.01 minutes. Purity >99%. HPLC Conditions: C.

Preparation 50B:
7-(4-Methylpyridin-3-yl)benzo[d]isoxazol-3-amine

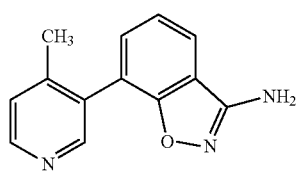
(50B)

A mixture of Preparation 50A (2.80 g, 13.19 mmol), N-hydroxyacetamide (2.97 g, 39.6 mmol), and potassium carbonate (10.94 g, 79 mmol) in DMF (57.7 mL) and Water (8.25 mL) was heated at 80° C. for 3 hr. The reaction mixture was filtered through a fritted funnel and the filter cake was washed with EtOAc. The layers in the filtrate were separated. The aqueous phase was extracted with EtOAc (3×). The organic phases were combined, washed with water (2×), brine (2×), dried over $Na_2SO_4$, filtered, concentrated, and further dried under high vacuum to afford a brown residue. The crude material was dissolved in a minimal amount of $CH_2Cl_2$ to be chromatographed. Purification of the crude material by silica gel chromatography using an ISCO machine (120 g column, 85 mL/min, 0-100% EtOAc in hexanes over 40 min, $t_r$=32 min) gave the title compound (2.07 g, 9.19 mmol, 69.7% yield) as a white solid. ESI MS $(M+H)^+$=226.1. HPLC Peak $t_r$=0.82 minutes. Purity=96%. HPLC Conditions: C.

Example 50

3-Chloro-7-(4-methylpyridin-3-yl)benzo[d]isoxazole

To a solution of Preparation 50B (1.1 g, 4.88 mmol) in concentrated hydrochloric Acid, 37% (50.9 mL) cooled to 0° C. was added sodium nitrite (0.354 g, 5.13 mmol). The reaction mixture was stirred at 0° C. for 1 hr and then allowed to stir at room temperature for 2 hr. The mixture was poured into a solution of saturated aqueous $NH_4Cl$ (50 mL). A yellow solid precipitated. The suspension was allowed to stir at room temperature overnight, then neutralized with solid $NaHCO_3$ (52 g+5 g) and diluted with $CH_2Cl_2$. The layers were separated, and the aqueous phase was extracted with $CH_2Cl_2$ (5×). The organic phases were combined, dried over $Na_2SO_4$, filtered, and concentrated to afford a yellow residue. The crude material was dissolved in a minimal amount of $CH_2Cl_2$ to be chromatographed. Purification of the crude material by silica gel chromatography using an ISCO machine (80 g column, 60 mL/min, 50-70% EtOAc in hexanes over 25 min, $t_r$=12 min) gave the title compound (1.08 g, 4.41 mmol, 90% yield) as a white solid. ESI MS $(M+H)^+$=245.1. HPLC Peak $t_r$=1.47 minutes. Purity >99%. HPLC Conditions: C.

Example 51

7-(4-(1H-Pyrazol-1-yl)pyrimidin-5-yl)-3-(2-chlorophenyl)benzo[d]isoxazole

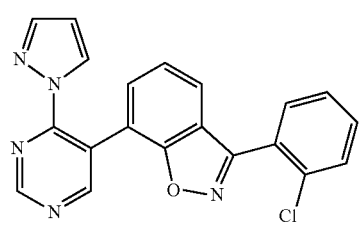
(51)

Preparation 51A:
(3-Bromo-2-fluorophenyl)(2-chlorophenyl)methanol

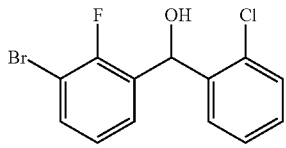
(51A)

To a stirring solution of 1-chloro-2-iodobenzene (7.05 g, 29.6 mmol) in tetrahydrofuran (Volume: 15 mL) at −15° C. was added isopropylmagnesium chloride (17.24 mL, 34.5 mmol). The mixture was allowed to stir for 30 minutes, at which time 3-bromo-2-fluorobenzaldehyde (5 g, 24.63 mmol) was added. The reaction mixture was stirred overnight. The reaction was quenched with saturated aqueous NH$_4$Cl. The reaction mixture was extracted with EtOAc (3×). The organics were combined, rinsed with brine, dried over Na$_2$SO$_4$, filtered, and concentrated to afford the title compound (7.5 g, 96%).

Preparation 51B:
(3-Bromo-2-fluorophenyl)(2-chlorophenyl)methanone

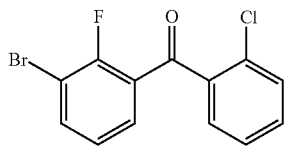
(51B)

To a stirring solution of Preparation 51A (7.5 g, 23.77 mmol) in DCM (Volume: 300 mL) at room temperature was added Dess-Martin Periodinane (11.09 g, 26.1 mmol). The mixture was allowed to stir until judged complete by HPLC. The reaction was quenched by addition of 10% Na$_2$S$_2$O$_3$ with stirring followed by addition of saturated aqueous NaHCO$_3$. The solution was extracted DCM (2×). The combined organics were dried over Na$_2$SO$_4$, filtered, and concentrated to afford the title compound (7.5 g, 100%).

Preparation 51C: (E)-(3-Bromo-2-fluorophenyl)(2-chlorophenyl)methanone oxime

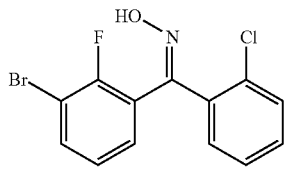
(51C)

A solution of Preparation 51B (7.21 g, 23 mmol) and hydroxylamine hydrochloride (10.87 g, 156 mmol) in pyridine (Volume: 115 ml) was refluxed for 40 min, allowed to cool to room temperature, and then concentrated in vacuo. The crude material was partitioned between EtOAc and 1N HCl. The layers were separated and the aqueous phase extracted with EtOAc (3×). Organics combined, dried over Na$_2$SO$_4$, filtered, and concentrated to afford the title compound (7.56 g, 23.00 mmol, 100% yield) as a yellow residue.

Preparation 51D:
7-Bromo-3-(2-chlorophenyl)benzo[d]isoxazole

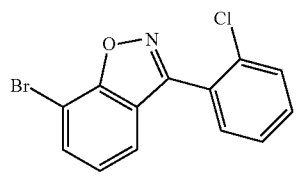
(51D)

To a suspension of sodium hydride (1.564 g, 39.1 mmol) in THF (Ratio: 1.8, Volume: 148 ml) was added dropwise Preparation 51C (7.56 g, 23 mmol) in DMF (4 mL). The syringe was rinsed with additional DMF (3.7 mL) into the reaction vial. The reaction mixture was heated at room temperature for 3 hr and then allowed to cool to room temperature. Additional NaH (102 mg, 2.55 mmol) was added. The reaction was quenched with H$_2$O. The reaction mixture was extracted with EtOAc (3×). The organic phases were combined, dried over Na$_2$SO$_4$, filtered, concentrated, and further dried under high vacuum to afford a yellow solid. The crude material was dissolved in a minimal amount of CH$_2$Cl$_2$ to be chromatographed. Purification of the crude material by silica gel chromatography using an ISCO machine (80 g column, 60 mL/min, 0-40% EtOAc in hexanes over 20 min, t$_r$=13 min) gave the title compound (3.0 g, 9.72 mmol, 42.3% yield) as a white solid.

Preparation 51E: 3-(2-Chlorophenyl)-7-(4,4,5,5-tetramethyl-1,3,2-dioxaborolan-2-yl)benzo[d]isoxazole

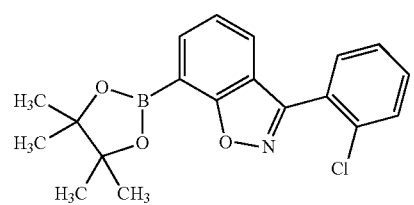
(51E)

A vial was charged with bis(acetonitrile)palladium(II) chloride (7.78 mg, 0.030 mmol), dicyclohexyl(2',6'-dimethoxybiphenyl-2-yl)phosphine (0.025 g, 0.060 mmol), and Preparation 51D (0.463 g, 1.5 mmol). The vial was capped with a rubber septum and then evacuated and backfilled with N$_2$ (this sequence was carried out a total of 2 times). Dioxane (Volume: 0.898 ml) was added via syringe, through the septum, followed by the addition of triethylamine (0.627 ml, 4.50 mmol) and 4,4,5,5-tetramethyl-1,3,2-dioxaborolane (0.326 ml, 2.250 mmol). The septum was then replaced with a Teflon screw valve, and the vial sealed. The reaction mixture was heated at 110° C. After 17 hr, the reaction mixture was allowed to cool to room temperature. The reaction mixture was filtered through a disposable fritted funnel and the filter cake washed with CH$_2$Cl$_2$. The filtrate was concentrated to afford the title compound (533 mg, 100%) as a yellow solid.

Example 51

A reaction vial was charged with tetrakis(triphenylphosphine)palladium(0) (5.78 mg, 5.00 µmol), Preparation 51E (0.037 g, 0.100 mmol), sodium carbonate (42.4 mg, 0.400 mmol), and 5-iodo-4-(1H-pyrazol-1-yl)pyrimidine (40.8 mg, 0.150 mmol). The mixture was stirred at room temperature for 10 min under $N_2$, then DME (Ratio: 2.0, Volume: 373 µl), EtOH (Ratio: 1.000, Volume: 187 µl), and water (Ratio: 1.000, Volume: 187 µl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 0.05% TFA; Mobile Phase B: 95:5 acetonitrile:water with 0.05% TFA; Gradient: 25-85% B over 25 minutes, then a 10-minute hold at 100% B; Flow: 20 mL/min. Fractions containing the desired product were combined and dried via centrifugal evaporation to afford the title compound (4.0 mg, 10%). ESI MS (M+H)+= 374.0. HPLC Peak $t_r$=2.63 minutes. Purity=97%. HPLC Conditions: C.

Example 52

7-(4-(1H-1,2,4-Triazol-1-yl)pyrimidin-5-yl)-3-(2-chlorophenyl)benzo[d]isoxazole

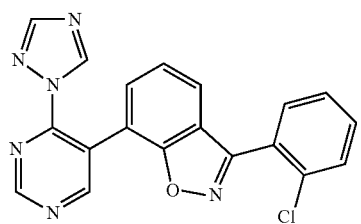

(52)

Preparation 52A:
5-Iodo-4-(1H-1,2,4-triazol-1-yl)pyrimidine

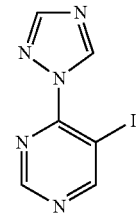

(52A)

To a solution of 1H-1,2,4-triazole (0.158 g, 2.288 mmol) in THF (Volume: 6.03 ml) cooled to 0° C. was added NaH (0.100 g, 2.496 mmol). The reaction mixture was stirred for 30 min at this temperature and then 4-chloro-5-iodopyrimidine (0.500 g, 2.080 mmol) was added. The reaction mixture was allowed to warm to room temperature. After 16 hr, reaction quenched with saturated aqueous $NH_4Cl$ and diluted with EtOAc. The aqueous and organic layers were separated. Aqueous phase was extracted with EtOAc (3×). The organics layers were combined, dried over $Na_2SO_4$, filtered, and concentrated to afford an orange residue. The crude material was dissolved in a minimal amount of $CH_2Cl_2$ to be chromatographed. Purification of the crude material by silica gel chromatography using an ISCO machine (40 g column, 40 mL/min, 20-80% EtOAc in hexanes over 20 min, $t_r$=13 min) gave 5-iodo-4-(1H-pyrazol-1-yl)pyrimidine (113 mg, 20%) as a white solid.

Example 52

A reaction vial was charged with tetrakis(triphenylphosphine)palladium(0) (5.78 mg, 5.00 µmol), Preparation 51E (0.036 g, 0.100 mmol), sodium carbonate (42.4 mg, 0.400 mmol), and Preparation 52A (41.0 mg, 0.150 mmol). The mixture was stirred at room temperature for 10 min under $N_2$, then DME (Ratio: 2.0, Volume: 373 µl), EtOH (Ratio: 1.000, Volume: 187 µl), and water (Ratio: 1.000, Volume: 187 µl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 15-minute hold at 60% B;

Flow: 20 mL/min. Fractions containing the desired product were combined and dried via centrifugal evaporation to afford the title compound (3.4 mg, 9.0%). ESI MS (M+H)$^+$= 375.1. HPLC Peak t$_r$=2.22 minutes. Purity >99%. HPLC Conditions: C.

Example 53

(R)-1-(5-(3-(2-Chlorophenyl)benzo[d]isoxazol-7-yl)pyrimidin-4-yl)-3-methylpyrrolidin-3-ol

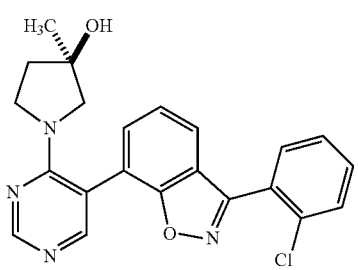

(53)

Preparation 53A: (R)-1-(5-Iodopyrimidin-4-yl)-3-methylpyrrolidin-3-ol

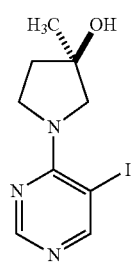

(53A)

To a solution of (R)-3-methylpyrrolidin-3-ol, HCl (0.126 g, 0.915 mmol) in THF (Volume: 2.411 ml) cooled to 0° C. was added NaH (0.080 g, 1.996 mmol). The reaction mixture was stirred for 30 min, then 4-chloro-5-iodopyrimidine (0.200 g, 0.832 mmol) was added. After 16 hr, the reaction was quenched with a saturated aqueous NH$_4$Cl. The reaction mixture was diluted with EtOAc. The aqueous and organic layers were separated. The aqueous phase was extracted with EtOAc (3×). The organics layers were combined, dried over Na$_2$SO$_4$, filtered, and concentrated to afford an orange residue. The crude material was dissolved in a minimal amount of CH$_2$Cl$_2$ to be chromatographed. Purification of the crude material by silica gel chromatography using an ISCO machine (24 g column, 35 mL/min, 40-95% EtOAc in hexanes over 25 min, t$_r$=17 min) gave the title compound (214 mg, 83%) as a yellow residue, which crystallized to a yellow solid upon standing.

Example 53

A reaction vial was charged with tetrakis(triphenylphosphine)palladium(0) (5.78 mg, 5.00 μmol), Preparation 51E (0.037 g, 0.100 mmol), sodium carbonate (42.4 mg, 0.400 mmol), and Preparation 53A (45.8 mg, 0.150 mmol). The mixture was stirred at room temperature for 10 min under N$_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 15-minute hold at 55% B; Flow: 20 mL/min. Fractions containing the desired product were combined and dried via centrifugal evaporation to afford the title compound (8.6 mg, 20%). ESI MS (M+H)$^+$= 407.1. HPLC Peak t$_r$=2.11 minutes. Purity=93%. HPLC Conditions: C.

Example 54

5-(3-(2-Chlorophenyl)benzo[d]isoxazol-7-yl)-N-cyclopropylpyrimidin-4-amine

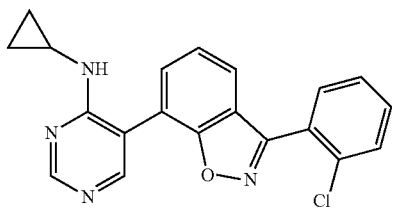

(54)

Preparation 54A: N-Cyclopropyl-5-iodopyrimidin-4-amine

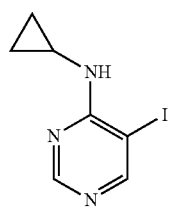

(54A)

To a vial containing a solution of 4-chloro-5-iodopyrimidine (0.400 g, 1.664 mmol) in DMF (Volume: 2.67 ml) was added cyclopropanamine (0.461 ml, 6.65 mmol) followed by cesium carbonate (1.084 g, 3.33 mmol). The vial was sealed with a Teflon cap and heated at 90° C. for 3 hr, then allowed to cool to room temperature. The reaction mixture was filtered through a disposable fritted funnel and the filter cake washed with EtOAc. The filtrate was diluted with H$_2$O and the layers were separated. The organic phase was washed with H$_2$O (2×). The combined aqueous phases were back-extracted with EtOAc (3×). All organics were combined, dried over Na$_2$SO$_4$, filtered, and concentrated to afford an orange residue. The crude material was dissolved in a minimal amount of CH$_2$Cl$_2$ to be chromatographed. Purification of the crude material by silica gel chromatography using an ISCO machine (40 g column, 40 mL/min, 20-70% EtOAc in hexanes over 19 min, t$_r$=13.5 min) gave the title compound (348 mg, 1.320 mmol, 79% yield) as a yellow solid. ESI MS (M+H)$^+$=262.0.

Example 54

A reaction vial was charged with tetrakis(triphenylphosphine)palladium(0) (5.78 mg, 5.00 μmol), Preparation 51E (0.037 g, 0.100 mmol), sodium carbonate (42.4 mg, 0.400 mmol), and Preparation 54A (39.2 mg, 0.150 mmol). The mixture was stirred at room temperature for 10 min under N$_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 14 hr, the reaction mixture was allowed to cool to room temperature. The reaction was quenched with water. The reaction mixture was diluted with EtOAc. The layers were separated and the aqueous phase was extracted with EtOAc (3×). The organic phases were combined, dried over Na$_2$SO$_4$, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (14 mg, 38%). ESI MS (M+H)$^+$=363.1. HPLC Peak t$_r$=2.35 minutes. Purity=98%. HPLC Conditions: C.

Example 55

3-(2-Chlorophenyl)-7-(4-methylpyrimidin-5-yl)benzo[d]isoxazole (55)

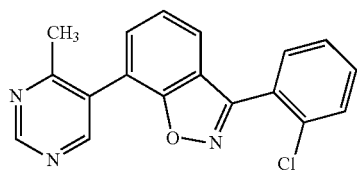

To a pressure tube were added Preparation 51E (35.6 mg, 0.100 mmol), 5-bromo-4-methylpyrimidine (26.0 mg, 0.150 mmol), and sodium carbonate (53.0 mg, 0.500 mmol) in water (Ratio: 1.000, Volume: 0.750 mL), DME (Ratio: 2, Volume: 1.5 mL) and EtOH (Ratio: 1.000, Volume: 0.750 mL) at room temperature. To this slurry was added tetrakis(triphenylphosphine)palladium(0) (5.78 mg, 5.00 μmol) and the system was purged with nitrogen and sealed. The vessel was heated to 90° C. for 12 h and then allowed to cool to room temperature. The reaction mixture was diluted with MeOH, filtered, and concentrated. The remaining oil was diluted with DMF and purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 15-minute hold at 60% B; Flow: 20 mL/min. Fractions containing the desired product were combined and dried via centrifugal evaporation to afford the title compound (1.7 mg, 4.9%). ESI MS (M+H)$^+$=322.1. HPLC Peak t$_r$=2.44 minutes. Purity=92%. HPLC Conditions: C. $^1$H NMR (500 MHz, MeOD) δ ppm 9.11 (1 hr, s), 8.74 (1 hr, s), 7.78 (1 hr, dd, J=7.91, 1.25 Hz), 7.59-7.66 (2 hr, m), 7.46-7.55 (1 hr, m), 2.55 (2 hr, s).

Example 56

3-(2-Chlorophenyl)-7-(4-ethoxypyrimidin-5-yl)benzo[d]isoxazole (56)

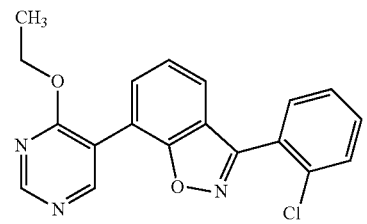

To a pressure tube were added Preparation 51E (35.6 mg, 0.100 mmol), 4-ethoxy-5-iodopyrimidine (37.5 mg, 0.150 mmol), and sodium carbonate (53.0 mg, 0.500 mmol) in DME (Ratio: 2, Volume: 1.5 mL), water (Ratio: 1.000, Volume: 0.750 mL) and EtOH (Ratio: 1.000, Volume: 0.750 mL) at room temperature. To this slurry was added tetrakis(triphenylphosphine)palladium(0) (5.78 mg, 5.00 μmol) and the system was purged with nitrogen and sealed. The vessel was heated to 90° C. for 12 hr, then allowed to cool to room temperature. The reaction mixture was diluted with MeOH, filtered and concentrated. The remaining oil was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-60% B over 25 minutes, then a 15-minute hold at 60% B; Flow: 20 mL/min. Fractions containing the desired product were combined and dried via centrifugal evaporation to afford the title compound (1.8 mg, 4.9%). ESI MS (M+H)$^+$= 352.1. HPLC Peak t$_r$=2.89 minutes. Purity=95%. HPLC Conditions: C. $^1$H NMR (500 MHz, MeOD) δ ppm 8.77 (1 hr, s), 8.75 (1 hr, s), 7.79-7.82 (1 hr, m), 7.70 (1 hr, dd, J=8.05, 1.11 Hz), 7.62 (1 hr, td, J=7.91, 1.39 Hz), 7.52-7.55 (1 hr, m), 7.48 (1 hr, t, J=7.77 Hz), 4.53-4.59 (3 hr, m), 1.38 (2 hr, t, J=7.07 Hz).

Example 57

7-(4-(2H-1,2,3-Triazol-2-yl)pyrimidin-5-yl)-3-(2-chlorophenyl)benzo[d]isoxazole

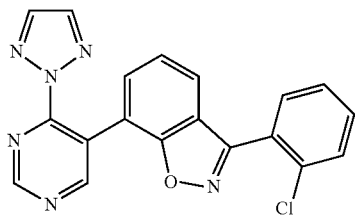

(57)

Preparation 57A:
5-Iodo-4-(2H-1,2,3-triazol-2-yl)pyrimidine

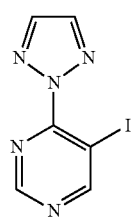

(57A)

To a solution of 1H-1,2,3-triazole (63.2 mg, 0.915 mmol) in THF (Volume: 2411 µl), was added portion wise at 0° C., NaH (39.9 mg, 0.998 mmol). The reaction mixture was stirred at that temperature for 30 min, then 4-chloro-5-iodopyrimidine (200 mg, 0.832 mmol) was added. The reaction mixture was allowed to warm to room temperature. To this solution was added saturated aqueous NH$_4$Cl and the mixture was allowed to stir for 5 min at which time it was diluted with ethyl acetate and extracted 2×. The combined organics were washed with brine 1×. The organics were dried over Na$_2$SO$_4$, filtered and concentrated in vacuo to afford the title compound (90 mg, 40%).

Example 57

To a pressure tube were added Preparation 51E (35.6 mg, 0.100 mmol), Preparation 57A (41.0 mg, 0.150 mmol), and sodium carbonate (53.0 mg, 0.500 mmol) in DME (Ratio: 2, Volume: 1.5 mL), water (Ratio: 1.000, Volume: 0.750 mL) and EtOH (Ratio: 1.000, Volume: 0.750 mL) at room temperature. To this slurry was added tetrakis(triphenylphosphine)palladium(0) (5.78 mg, 5.00 µmol) and the system was purged with nitrogen and sealed. The vessel was heated to 90° C. for 12 hr, and then allowed to cool to room temperature. The reaction mixture was diluted with MeOH, filtered, and concentrated. The remaining oil was diluted with DMF and the crude material was purified via preparative LC/MS with the following conditions: Column: Waters XBridge C18, 19×250 mm, 5-µm provided to SCP for purification. particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-60% B over 25 minutes, then a 15-minute hold at 60% B; Flow: 20 mL/min. Fractions containing the desired product were combined and dried via centrifugal evaporation to afford the title compound (4.1 mg, 11%). ESI MS (M+H)$^+$=375.0. HPLC Peak t$_r$=2.31 minutes. Purity=91%. HPLC Conditions: C.

Example 58

3-(2-Chlorophenyl)-7-(4-methylpyridin-3-yl)benzo[d]isoxazole

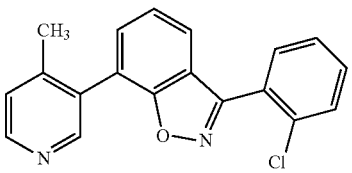

(85)

A pressure vessel was charged with Preparation 51D (31 mg, 0.100 mmol), 4-methylpyridin-3-ylboronic acid (16.51 mg, 0.121 mmol), and sodium carbonate (53.2 mg, 0.502 mmol). To the vessel was then added DME (Ratio: 2, Volume: 1.5 mL), EtOH (Ratio: 1.000, Volume: 0.750 mL), and water (Ratio: 1.000, Volume: 0.750 mL) at room temperature. To this slurry was added tetrakis(triphenylphosphine)palladium(0) (58.0 mg, 0.050 mmol) and the system was purged with nitrogen and sealed. The vessel was heated to 90° C. for 12 hr. The reaction mixture was diluted with MeOH, filtered, and concentrated. The remaining oil was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 5-100% B over 25 minutes, then a 5-minute hold at 100% B; Flow: 20 mL/min. Fractions containing the desired product were combined and dried via centrifugal evaporation to afford the title compound (1.4 mg, 4%). ESI MS (M+H)$^+$=321.0. HPLC Peak $t_r$=2.71 minutes. Purity=99%. HPLC Conditions: B. $^1$H NMR (500 MHz, MeOD) δ ppm 8.56 (2 hr, br. s.), 7.74-7.80 (1 hr, m), 7.68-7.73 (1 hr, m), 7.65-7.68 (2 hr, m), 7.62 (1 hr, td, J=7.77, 1.94 Hz), 7.52-7.59 (3 hr, m), 2.36 (3 hr, s).

Example 59

3-(2-Chlorophenyl)-7-(isoquinolin-4-yl)benzo[d]isoxazole

(59)

A pressure vessel was charged with Preparation 51D (31 mg, 0.100 mmol), isoquinolin-4-ylboronic acid (20.85 mg, 0.121 mmol), and sodium carbonate (53.2 mg, 0.502 mmol). To the vessel was then added DME (Ratio: 2, Volume: 1.5 mL), EtOH (Ratio: 1.000, Volume: 0.750 mL), and water (Ratio: 1.000, Volume: 0.750 mL) at room temperature. To this slurry was added tetrakis(triphenylphosphine)palladium (0) (58.0 mg, 0.050 mmol) and the system was purged with nitrogen and sealed. The vessel was heated to 90° C. for 12 hr. The reaction mixture was diluted with MeOH, filtered, and concentrated. The remaining oil was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 25-70% B over 25 minutes, then a 15-minute hold at 70% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 20-60% B over 25 minutes, then a 15-minute hold at 60% B; Flow: 20 mL/min. Fractions containing the desired product were combined and dried via centrifugal evaporation to afford the title compound (2.3 mg, 5.5%). ESI MS (M+H)$^+$=357.0. HPLC Peak $t_r$=2.98 minutes. Purity=86%. HPLC Conditions: B. $^1$H NMR (500 MHz, MeOD) δ ppm 9.48 (1 hr, s), 8.64 (1 hr, s), 8.34 (1 hr, d, J=7.49 Hz), 7.82-7.91 (4 hr, m), 7.78 (1 hr, d, J=8.32 Hz), 7.71 (2 hr, ddd, J=11.65, 7.77, 1.39 Hz), 7.61-7.67 (2 hr, m), 7.54-7.60 (1 hr, m).

Example 60

7-(4-(1H-Imidazol-1-yl)pyrimidin-5-yl)-3-(2-chlorophenyl)benzo[d]isoxazole

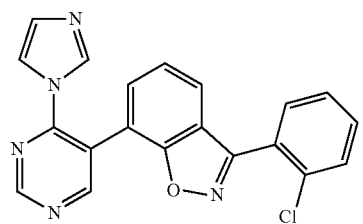

(60)

Preparation 60A: 4-(1H-Imidazol-1-yl)-5-iodopyrimidine

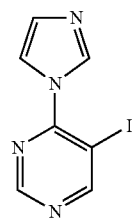

(60A)

To a solution of 1H-imidazole (0.085 g, 1.248 mmol) in THF (Volume: 10 mL) was added sodium hydride (0.062 g, 1.560 mmol). After 15 minutes at room temperature, 4-chloro-5-iodopyrimidine (0.25 g, 1.040 mmol) was added as a solution in THF (5 mL). After 2 h at room temperature, the reaction was quenched with water. The reaction mixture was extracted with EtOAc (3×). The combined organics were dried over MgSO$_4$, filtered and concentrated to give the title compound (0.155 g, 0.541 mmol, 52.1% yield) as a pale yellow solid. ESI MS (M+H)$^+$=273.0.

Example 60

To a solution of Preparation 60A (40.8 mg, 0.150 mmol) and Preparation 51E (35.6 mg, 0.1 mmol) in a mixture of DME (1 mL), ethanol (0.5 mL) and water (0.5 mL) was added Na₂CO₃ (42.4 mg, 0.400 mmol). This suspension was degassed with a stream of N₂ for 10 minutes and then tetrakis(triphenylphosphine)palladium(0) (5.78 mg, 5.00 µmol) was added followed by degassing for 10 minutes. The tube was then sealed and heated at 90° C. for 6 hours. The reaction mixture was cooled to room temperature and diluted with MeOH. The mixture was then filtered and concentrated to a brown oil. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (5.0 mg, 13%). ESI MS (M+H)⁺=374.0. HPLC Peak $t_r$=2.15 minutes. Purity=97%. HPLC Conditions: B.

Example 61

7-(Isoquinolin-4-yl)-3-(2,2,2-trifluoroethoxy)benzo[d]isoxazole

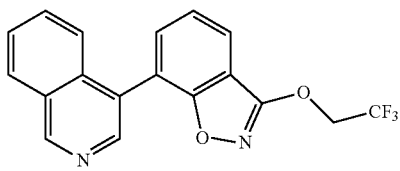

(61)

Preparation 61A:
2-Fluoro-3-(4-methylpyridin-3-yl)benzonitrile

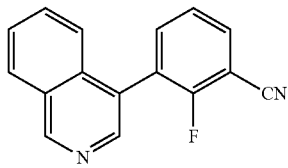

(61A)

To a solution of 3-bromo-2-fluorobenzonitrile (2.0 g, 10.00 mmol) and 4-(4,4,5,5-tetramethyl-1,3,2-dioxaborolan-2-yl)isoquinoline (2.81 g, 11.00 mmol) in a mixture of DME (30 mL), ethanol (15 mL), and water (15 mL) was added Na₂CO₃ (4.24 g, 40.0 mmol). This suspension was degassed with a stream of N₂ for 10 minutes and then tetrakis(triphenylphosphine)palladium(0) (0.578 g, 0.500 mmol) was added followed by degassing with nitrogen for 10 minutes. The tube was then sealed and heated to 90° C. for 14 hours. The vessel was cooled to room temperature and diluted with EtOAc and water. The mixture was further diluted with brine and extracted three times with EtOAc. The combined organics were dried over MgSO₄, filtered, and concentrated to give the crude product as a brown oil. The crude material was purified by flash chromatography on silica using an ISCO machine (80 g SiO₂ column, 60 mL/min, 0-20% acetone in CH₂Cl₂ over 20 minutes, $t_r$=8 minutes) to give the title compound (2.18 g, 8.69 mmol, 87% yield) as a pale yellow solid. ESI MS (M+H)⁺=249.1.

Preparation 61B:
7-(Isoquinolin-4-yl)benzo[d]isoxazol-3-amine

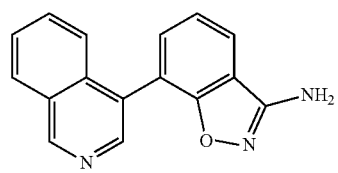

(61B)

To a solution of Preparation 61A (1.5 g, 6.04 mmol) in a mixture of DMF (Ratio: 6.00, Volume: 18 mL) and water (Ratio: 1.000, Volume: 3.00 mL) was added potassium carbonate (5.01 g, 36.3 mmol) followed by N-hydroxyacetamide (1.361 g, 18.13 mmol). The mixture was heated at 80° C. for 3 h and then cooled to room temperature. The mixture was diluted with EtOAc and washed twice with water, once with brine, and the organics were dried over MgSO₄. Filtration and concentration gave the crude product. The crude material was purified by flash chromatography on silica using an ISCO machine (40 g column, 60 mL/min, 0-15% acetone in CH₂Cl₂ over 15 minutes, $t_r$=13 minutes) to give the title compound (1.39 g, 5.27 mmol, 87% yield) as a white solid. ESI MS (M+H)⁺=262.1.

Preparation 61C:
3-Chloro-7-(isoquinolin-4-yl)benzo[d]isoxazole

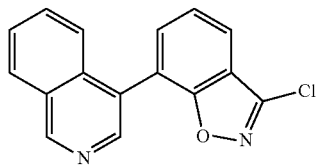

(61C)

To a solution of Preparation 61B (0.5 g, 1.914 mmol) in 12N hydrogen chloride (10 mL, 120 mmol) at 0° C. was added sodium nitrite (0.158 g, 2.296 mmol). After 30 minutes at 0° C., the mixture was warmed to room temperature and 3 mL of saturated aqueous NH₄Cl was added. The mixture stirred at room temperature overnight. Water was then added and the reaction mixture was neutralized by the addition of a slight excess of solid NaHCO₃. The mixture was extracted thrice with CH₂Cl₂ and the organics were combined and dried over Na₂SO₄. Filtration and concentration gave the title compound (0.4 g, 1.354 mmol, 70.7% yield) as a white solid. ESI MS (M+H, M+2)⁺=281, 283.

Example 61

To a stirring solution of 2,2,2-trifluoroethanol (19.96 mg, 0.199 mmol) in DMF (1 mL) at room temperature was added Preparation 61C (28 mg, 0.100 mmol). The reaction mixture was heated to 60° C. for 3 hr, then diluted with MeOH, filtered, and concentrated. The residue was diluted with DMF and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (5.8 mg, 16%). ESI MS (M+H)$^+$=345.1. HPLC Peak $t_r$=2.83 minutes. Purity=95%. HPLC Conditions: B. $^1$H NMR (500 MHz, MeOD) δ ppm 9.28 (1 hr, s), 8.50 (1 hr, s), 8.10-8.20 (1 hr, m), 7.83-7.91 (1 hr, m), 7.71-7.77 (3 hr, m), 7.64-7.69 (1 hr, m), 7.49-7.56 (2 hr, m), 4.89 (2 hr, q, J=8.05 Hz).

Example 62

7-(4-Methylpyridin-3-yl)-3-(2,2,2-trifluoroethoxy)benzo[d]isoxazole

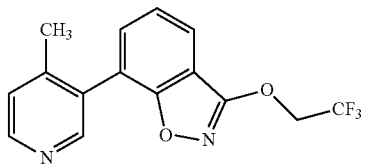

(62)

To a stirring solution of 2,2,2-trifluoroethanol (16.35 mg, 0.163 mmol) in DMF (Volume: 1 mL) at room temperature was added sodium hydride (3.92 mg, 0.163 mmol). After 3 minutes, Example 50 (20 mg, 0.082 mmol) was added. After 1 h, additional sodium hydride was added. The mixture was subsequently quenched by the addition of 3 drops of water. The resulting suspension was filtered and rinsed with MeOH, filtered and concentrated. The residue was diluted with DMF and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (13.6 mg, 54%). ESI MS (M+H)$^+$=309.0. HPLC Peak $t_r$=2.51 minutes. Purity=100%. HPLC Conditions: B. $^1$H NMR (400 MHz, MeOD) δ ppm 8.44 (1 hr, d, J=5.27 Hz), 8.42 (1 hr, s), 7.79 (1 hr, dd, J=7.78, 1.25 Hz), 7.51-7.55 (1 hr, m), 7.47 (1 hr, t, J=7.53 Hz), 7.37 (1 hr, d, J=5.27 Hz), 4.88 (3 hr, q, J=8.03 Hz), 2.27 (4 hr, s).

Example 63

3-Isopropoxy-7-(isoquinolin-4-yl)benzo[d]isoxazole

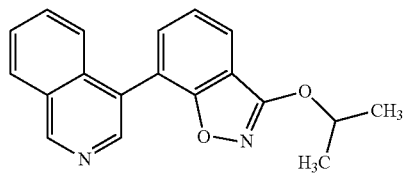

(63)

To a stirring solution of propan-2-ol (7.71 mg, 0.128 mmol) in DMF (Volume: 1 mL) at room temperature was added sodium hydride (3.08 mg, 0.128 mmol). After 3 minutes, Preparation 61C (18 mg, 0.064 mmol) was added. The mixture was allowed to stir until judged complete by HPLC. The reaction mixture was diluted with MeOH, filtered, and concentrated. The residue was diluted with DMF and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (3.3 mg, 17%). ESI MS (M+H)$^+$=305.1. HPLC Peak $t_r$=2.84 minutes. Purity=100%. HPLC Conditions: B. $^1$H NMR (500 MHz, MeOD) δ ppm 9.27 (1 hr, s), 8.50 (1 hr, s), 8.11-8.16 (1 hr, m), 7.78 (1 hr, dd, J=7.91, 1.25 Hz), 7.67-7.76 (3 hr, m), 7.65 (1 hr, dd, J=7.21, 1.11 Hz), 7.44-7.50 (1 hr, m), 5.10 (1 hr, dt, J=12.28, 6.21 Hz), 1.49 (6 hr, d, J=6.38 Hz).

Example 64

3-Isobutoxy-7-(isoquinolin-4-yl)benzo[d]isoxazole

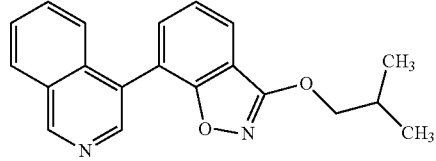

(64)

To a stirring solution of 2-methylpropan-1-ol (7.92 mg, 0.107 mmol) in DMF (Volume: 1 mL) at room temperature was added sodium hydride (2.56 mg, 0.107 mmol). After 3 minutes, Preparation 61C (15 mg, 0.053 mmol) was added. The mixture was allowed to stir until judged complete by HPLC. The reaction mixture was diluted with MeOH, filtered, and concentrated. The residue was diluted with DMF and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (8.4 mg, 49%). ESI MS (M+H)$^+$=319.0. HPLC Peak t$_r$=3.15 minutes. Purity >99%. HPLC Conditions: B. $^1$H NMR (500 MHz, MeOD) δ ppm 9.26 (1 hr, s), 8.49 (1 hr, s), 8.10-8.15 (1 hr, m), 7.80 (1 hr, dd, J=8.05, 1.11 Hz), 7.63-7.73 (4 hr, m), 7.48 (1 hr, t, J=7.49 Hz), 4.20 (2 hr, d, J=6.38 Hz), 2.16-2.28 (1 hr, m), 1.07 (6 hr, d, J=6.94 Hz).

Example 65

7-(Isoquinolin-4-yl)-3-(2,2,2-trifluoroethylthio)benzo[d]isoxazole

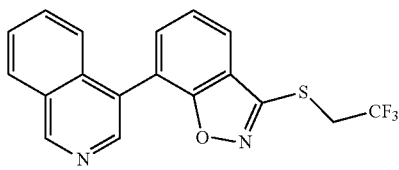

(65)

To a stirring solution of 2,2,2-trifluoroethanethiol (12.41 mg, 0.107 mmol) in DMF (Volume: 1 mL) at room temperature was added sodium hydride (2.56 mg, 0.107 mmol). After 3 minutes, Preparation 61C (15 mg, 0.053 mmol) was added. The mixture was allowed to stir until judged complete by HPLC. The reaction mixture was diluted with MeOH, filtered, and concentrated. The residue was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (8.6 mg, 45%). ESI MS (M+H)$^+$=361.0. HPLC Peak t$_r$=2.82 minutes. Purity >99%. HPLC Conditions: B. $^1$H NMR (500 MHz, MeOD) δ ppm 9.29 (1 hr, s), 8.51 (1 hr, s), 8.12-8.19 (1 hr, m), 7.78-7.82 (1 hr, m), 7.70-7.76 (3 hr, m), 7.63-7.67 (1 hr, m), 7.58 (1 hr, d, J=8.05 Hz), 4.06 (2 hr, q, J=9.52 Hz).

Example 66

7-(Isoquinolin-4-yl)-3-(2,2,2-trifluoroethylthio)benzo[d]isoxazole

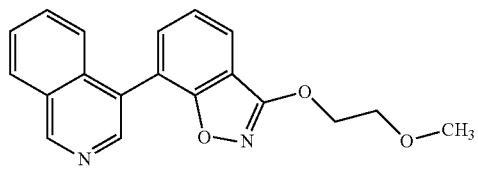

(66)

To a stirring solution of 2-methoxyethanol (8.13 mg, 0.107 mmol) in DMF (Volume: 1 mL) at room temperature was added sodium hydride (2.56 mg, 0.107 mmol). After 3 minutes, Preparation 61C (15 mg, 0.053 mmol) was added. The mixture was allowed to stir until judged complete by HPLC. The reaction mixture was diluted with MeOH, filtered, and concentrated. The residue was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (6.0 mg, 35%). ESI MS (M+H)$^+$=321.1. HPLC Peak t$_r$=2.29 minutes. Purity >99%. HPLC Conditions: B. $^1$H NMR (500 MHz, MeOD) δ ppm 9.27 (1 hr, s), 8.50 (1 hr, s), 8.12-8.17 (1 hr, m), 7.84 (1 hr, dd, J=8.05, 1.11 Hz), 7.69-7.75 (2 hr, m), 7.67 (2 hr, dd, J=7.49, 1.11 Hz), 7.46-7.52 (1 hr, m), 4.57-4.63 (2 hr, m), 3.84-3.88 (2 hr, m), 3.47 (3 hr, s).

Example 67

3-(2-Methoxyethoxy)-7-(4-methylpyridin-3-yl)benzo[d]isoxazole

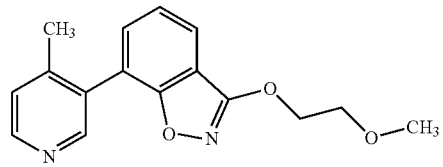

(67)

To a stirring solution of 2-methoxyethanol (12.44 mg, 0.163 mmol) in DMF (Volume: 1 mL) at room temperature was added sodium hydride (3.92 mg, 0.163 mmol). After 3 minutes, Example 50 (20 mg, 0.082 mmol) was added. The mixture was allowed to stir until judged complete by HPLC. The reaction mixture was diluted with MeOH, filtered, and concentrated. The residue was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 20 mL/min. Fractions containing the desired product were combined and dried via centrifugal evaporation to afford the title compound (13.6 mg, 59%). MS (M+H)$^+$=285.1. HPLC Peak t$_r$=1.99 minutes. Purity >99%. HPLC Conditions: B. $^1$H NMR (500 MHz, MeOD) δ ppm 8.40-8.45 (2 hr, m), 7.77 (1 hr, dd, J=7.77, 1.11 Hz), 7.46-7.50 (1 hr, m), 7.42 (1 hr, t, J=7.49 Hz), 7.36 (1 hr, d, J=5.27 Hz), 4.58 (2 hr, dd, J=4.02, 2.36 Hz), 3.83-3.88 (2 hr, m), 3.46 (3 hr, s), 2.27 (3 hr, s).

Example 68

3-(2-Methoxyethoxy)-7-(4-methylpyridin-3-yl)benzo[d]isoxazole

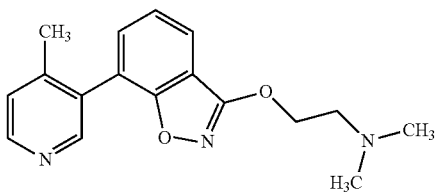

(68)

To a stirring solution of 2-(dimethylamino)ethanol (14.57 mg, 0.163 mmol) in DMF (Volume: 1 mL) at room temperature was added sodium hydride (3.92 mg, 0.163 mmol). After 3 minutes, Example 50 (20 mg, 0.082 mmol) was added. The mixture was allowed to stir until judged complete by HPLC. The reaction mixture was diluted with MeOH, filtered, and concentrated. The residue was diluted with DMF and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 20-100% B over 25 minutes, then a 5-minute hold at 100% B; Flow: 20 mL/min. Fractions containing the desired product were combined and dried via centrifugal evaporation to afford the title compound (13.2 mg, 53%). ESI MS (M+H)$^+$=298.1. HPLC Peak $t_r$=1.46 minutes. Purity=98%. HPLC Conditions: B. $^1$H NMR (500 MHz, MeOD) δ ppm 8.40-8.45 (2 hr, m), 7.77 (1 hr, dd, J=7.77, 1.11 Hz), 7.46-7.50 (1 hr, m), 7.42 (1 hr, t, J=7.49 Hz), 7.36 (1 hr, d, J=5.27 Hz), 4.58 (2 hr, dd, J=4.02, 2.36 Hz), 3.83-3.88 (2 hr, m), 3.46 (3 hr, s), 2.27 (3 hr, s).

Example 69

3-Isopropoxy-7-(4-methylpyridin-3-yl)benzo[d]isoxazole

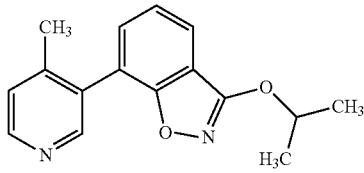

(69)

To a stirring solution of propan-2-ol (9.82 mg, 0.163 mmol) in DMF (Volume: 1 mL) at ambient temperature was added sodium hydride (3.92 mg, 0.163 mmol). After 3 minutes, Example 50 (20 mg, 0.082 mmol) was added. The mixture was allowed to stir until judged complete by HPLC. The reaction mixture was diluted with MeOH, filtered, and concentrated. The residue was diluted with DMF and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (4.8 mg, 22%). ESI MS (M+H)$^+$=269.1. HPLC Peak $t_r$=2.55 minutes. Purity >99%. HPLC Conditions: B. $^1$H NMR (500 MHz, MeOD) δ ppm 8.39-8.46 (2 hr, m), 7.72 (1 hr, dd, J=7.91, 1.25 Hz), 7.45-7.49 (1 hr, m), 7.41 (1 hr, d, J=7.49 Hz), 7.35-7.39 (1 hr, m), 5.10 (1 hr, dt, J=12.21, 6.10 Hz), 2.28 (3 hr, s), 1.49 (6 hr, d, J=6.10 Hz).

Example 70

7-(4-Methylpyridin-3-yl)-3-(2,2,2-trifluoroethylthio)benzo[d]isoxazole

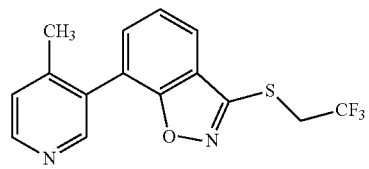

(70)

To a stirring solution of 2,2,2-trifluoroethanethiol (18.98 mg, 0.163 mmol) in DMF (Volume: 1 mL) at room temperature was added sodium hydride (3.92 mg, 0.163 mmol). After 3 minutes, Example 50 (20 mg, 0.082 mmol) was added. The mixture was allowed to stir until judged complete by HPLC. The reaction mixture was diluted with MeOH, filtered, and concentrated. The residue was diluted with DMF and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (8.2 mg, 31%). ESI MS (M+H)$^+$=325.0. HPLC Peak $t_r$=2.57 minutes. Purity >99%. HPLC Conditions: B. $^1$H NMR (500 MHz, MeOD) δ ppm 8.45 (1 hr, d, J=5.27 Hz), 8.43 (1 hr, s), 7.73 (1 hr, dd, J=7.91, 1.25 Hz), 7.54 (1 hr, d, J=1.11 Hz), 7.47-7.52 (1 hr, m), 7.38 (1 hr, d, J=4.99 Hz), 4.06 (2 hr, q, J=9.71 Hz), 2.27 (3 hr, s).

Example 71

3-Isobutoxy-7-(4-methylpyridin-3-yl)benzo[d]isoxazole

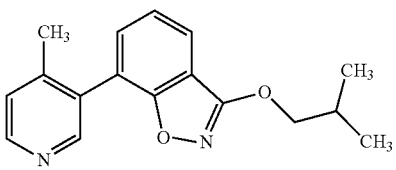

(71)

To a stirring solution of 2-methylpropan-1-ol (12.12 mg, 0.163 mmol) in DMF (Volume: 1 mL) at room temperature was added sodium hydride (3.92 mg, 0.163 mmol). After 3 minutes, Example 50 (20 mg, 0.082 mmol) was added. The reaction mixture was allowed to stir until judged complete by HPLC. The reaction mixture was diluted with MeOH, filtered, and concentrated. The residue was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 45-100% B over 25 minutes, then a 5-minute hold at 100% B; Flow: 20 mL/min. Fractions containing the desired product were combined and dried via centrifugal evaporation to afford the title compound (5.7 mg, 25%). ESI MS (M+H)$^+$=283.1. HPLC Peak $t_r$=2.88 minutes. Purity >99%. HPLC Conditions: B. $^1$H NMR (500 MHz, MeOD) δ ppm 8.39-8.47 (2 hr, m), 7.75 (1 hr, dd, J=7.91, 1.25 Hz), 7.46-7.49 (1 hr, m), 7.42 (1 hr, t, J=7.49 Hz), 7.37 (1 hr, d, J=4.99 Hz), 4.20 (2 hr, d, J=6.38 Hz), 2.28 (3 hr, s), 2.22 (1 hr, dt, J=13.32, 6.66 Hz), 1.07 (6 hr, d, J=6.66 Hz).

Example 72

3-(2-Methoxyphenyl)-7-(4-methylpyridin-3-yl)benzo[d]isoxazole

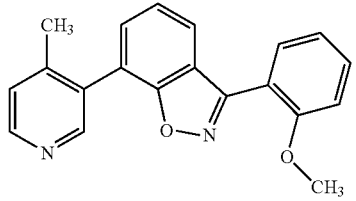

(72)

Preparation 72A:
(3-Bromo-2-fluorophenyl)(2-methoxyphenyl)methanol

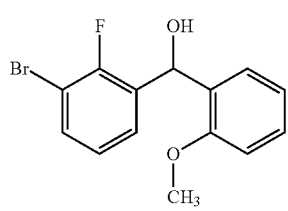

(72A)

To a solution of 3-bromo-2-fluorobenzaldehyde (1.0 g, 4.93 mmol) in THF (21.42 mL) cooled to −78° C. was added (2-methoxyphenyl)magnesium bromide in THF (5.91 mL, 5.91 mmol). The reaction mixture was maintained at −78° C. for at least 1 hr, and then allowed to warm to room temperature. The reaction mixture was cooled to 0° C. and additional (2-methoxyphenyl)magnesium bromide in THF (5.91 mL, 5.91 mmol) was added. The mixture was allowed to warm to room temperature overnight. The reaction was quenched with a saturated aqueous solution of NH$_4$Cl. The reaction mixture was diluted with DCM. The layers were separated and the aqueous phase extracted twice with DCM. The organic extracts were combined, dried over Na$_2$SO$_4$, filtered, and concentrated to afford a yellow residue. The crude material was dissolved in a minimal amount of DCM and purified via silica gel chromatography using an ISCO machine (80 g column, 60 mL/min, 0-0% EtOAc in hexanes over 27 min, $t_r$=19 min) gave the title compound (1.22 g, 3.92 mmol, 80% yield) as a pale yellow liquid. $^1$H NMR (400 MHz, CD$_3$OD) δ 7.54-7.40 (m, 2H), 7.35-7.23 (m, 2H), 7.09-6.90 (m, 3H), 6.38 (s, 1H), 4.12 (q, J=7.0 Hz, 1H), 3.76 (s, 3H).

Preparation 72B:
(3-Bromo-2-fluorophenyl)(2-methoxyphenyl)methanone

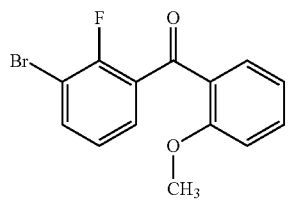

(72B)

To a solution of Preparation 72A (1.22 g, 3.92 mmol) in wet DCM (15.68 mL) was added Dess-Martin periodinane (4.16 g, 9.81 mmol) at ambient temperature. After 2.5 hr, the reaction was quenched with a 1:1 solution of saturated aqueous NaHCO$_3$: 10% (w/w) aqueous Na$_2$S$_2$O$_3$. The reaction mixture was diluted with additional DCM. The mixture was stirred until both layers became clear. The layers were separated and the organic phase washed with saturated aqueous NaHCO$_3$. The aqueous phase was extracted twice with DCM. The organic extracts were combined, dried over Na$_2$SO$_4$, filtered, and concentrated to afford the title compound (1.21 g, 3.91 mmol, 100% yield) as an orange solid. ESI MS (M, M+2)$^+$=309, 311.

Preparation 72C: (Z)-(3-Bromo-2-fluorophenyl)(2-methoxyphenyl)methanone oxime

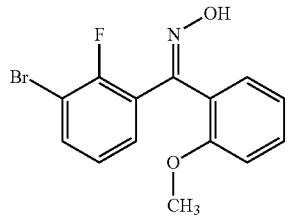

(72C)

A solution of Preparation 72B (1.2 g, 3.88 mmol) and hydroxylamine hydrochloride (1.834 g, 26.4 mmol) in pyridine (19.41 ml) was refluxed for 40 min, allowed to cool to room temperature, and then concentrated in vacuo. The crude material was partitioned between EtOAc and 1N HCl. The layers were separated and the aqueous phase extracted three times with EtOAc. The organic extracts were combined, dried over Na$_2$SO$_4$, filtered, and concentrated to afford the title compound (1.258 g, 3.88 mmol, 100% yield) as a yellow residue. ESI MS (M, M+2)⁺=324, 326.

Preparation 72D:
7-Bromo-3-(2-methoxyphenyl)benzo[d]isoxazole

(72D)

To a suspension of sodium hydride (0.264 g, 6.60 mmol) in THF (Ratio: 1.8, Volume: 49.9 ml) was added dropwise Preparation 72C (1.258 g, 3.88 mmol) in DMF (4 mL). The reaction mixture was heated at 70° C. for 3 hr, and then allowed to cool to room temperature. Additional NaH (102 mg, 2.55 mmol) was added. The reaction was quenched with H₂O. The reaction mixture was extracted three times with EtOAc. The organic extracts were combined, dried over Na₂SO₄, filtered, concentrated, and further dried under high vacuum to afford a yellow solid. The crude material was dissolved in a minimal amount of DCM and purified via silica gel chromatography using an ISCO machine (80 g column, 60 mL/min, 0-40% EtOAc in hexanes over 20 min, t$_r$=13 min) gave the title compound (1.0 g, 3.29 mmol, 85% yield) as a white solid. ESI MS (M, M+2)⁺=304, 306.

Example 72

To a stirring solution of 4-methylpyridin-3-ylboronic acid (10.81 mg, 0.079 mmol) and Preparation 72D (20 mg, 0.066 mmol) in a mixture of DME (Ratio: 2, Volume: 1.5 mL), EtOH (Ratio: 1.000, Volume: 0.750 mL), and water (Ratio: 1.000, Volume: 0.750 mL) at room temperature in a sealed tube apparatus was added tetrakis(triphenylphosphine)palladium(0) (38.0 mg, 0.033 mmol). The system was purged with nitrogen, sealed, and heated to 90° C. for 12 h. The reaction mixture was diluted with MeOH, filtered, and concentrated. The residue was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 20 mL/min. Fractions containing the desired product were combined and dried via centrifugal evaporation to afford the title compound (5.7 mg, 27%). ESI MS (M+H)⁺=317.1. HPLC Peak t$_r$=2.50 minutes. Purity=99%. HPLC Conditions: C. ¹H NMR (500 MHz, DMSO-d₆) δ ppm 8.60-8.69 (2 hr, m), 7.82 (1 hr, dd, J=8.05, 1.11 Hz), 7.70 (1 hr, d, J=6.38 Hz), 7.58-7.67 (4 hr, m), 7.52-7.57 (1 hr, m), 7.32 (1 hr, d, J=8.05 Hz), 7.12-7.22 (2 hr, m), 3.86 (4 hr, s), 2.30 (4 hr, s).

Example 73

7-(4-(Benzyloxy)pyrimidin-5-yl)-3-(2-methoxyphenyl)benzo[d]isoxazole

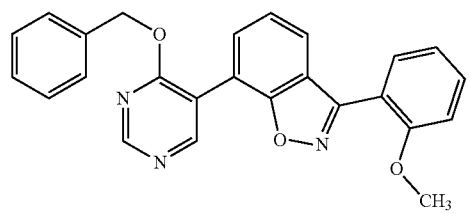

(73)

Preparation 73A: 3-(2-Methoxyphenyl)-7-(pyrimidin-5-yl)benzo[d]isoxazole

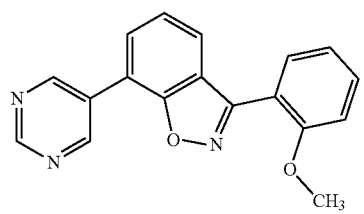

(73A)

Pyrimidin-5-ylboronic acid (433 mg, 3.49 mmol) was placed in a sealed tube apparatus. Sodium carbonate (1542 mg, 14.55 mmol) and Preparation 72D (885 mg, 2.91 mmol) in a mixture of DME (15 mL), water (7.50 mL) and EtOH (7.50 mL) were added at ambient temperature. Tetrakis(triphenylphosphine)palladium(0) (168 mg, 0.145 mmol) was then added and the system was purged with nitrogen, sealed, and heated to 90° C. for 12 h. The reaction mixture was diluted with MeOH, filtered, and concentrated. The crude material was purified twice via silica gel chromatography 0-4% MeOH/DCM to afford the title compound (90 mg, 10%). ESI MS (M+H)⁺=303.9.

Preparation 73B: 5-(3-(2-Methoxyphenyl)benzo[d]isoxazol-7-yl)pyrimidin-4-ol

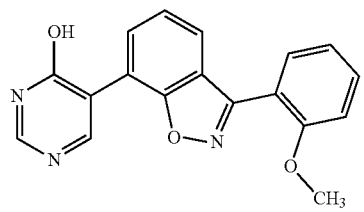

(73B)

To a stirring solution of Preparation 73A (90 mg, 0.297 mmol) in acetone (2 mL) at room temperature was added peracetic acid (0.062 mL, 0.297 mmol). The system was heated to reflux for 2 h. The reaction mixture was cooled, the pH neutralized with 1N NaOH and extracted three times with DCM. The crude product was dissolved in a small amount of CH₂Cl₂ and charged to a 4 g silica gel cartridge which was eluted with a 20 min gradient from 0% to 100% of ethyl acetate in dichloromethane to afford the title compound (95 mg, 100%). ESI MS (M+H)⁺=320.9.

Preparation 73C: 7-(4-Chloropyrimidin-5-yl)-3-(2 methoxyphenyl)benzo[d]isoxazole

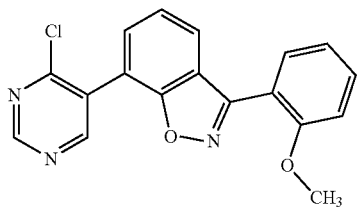

(73C)

A suspension of Preparation 73B (95 mg, 0.298 mmol) in POCl₃ (2.22 mL, 23.80 mmol) was heated to 90° C. for 1 h. The volatiles were removed in vacuo to afford the title compound (100 mg, 100%). ESI MS (M, M+2)⁺=337, 339.

Example 73

To a stirring solution of phenylmethanol (1.494 mg, 0.014 mmol) in THF (Volume: 0.5 mL) at room temperature was added sodium hydride (1.658 mg, 0.041 mmol). After 5 minutes, Preparation 73C (0.014 g, 0.041 mmol) was added and the reaction mixture was heated to 50° C. overnight. The reaction mixture was cooled and diluted with 10 drops of water, and the solvent removed with a stream of nitrogen. The remaining residue was dissolved in DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (1.6 mg, 28%). ESI MS (M+H)⁺=410.0. HPLC Peak t$_r$=3.07 minutes. Purity >99%. HPLC Conditions: B. ¹H NMR (500 MHz, MeOD) δ ppm 8.80 (1 hr, s), 8.77 (1 hr, s), 7.69-7.80 (1 hr, m), 7.52-7.57 (1 hr, m), 7.36-7.44 (1 hr, m), 7.25-7.34 (1 hr, m), 7.09-7.18 (1 hr, m), 5.56 (1 hr, s), 3.87 (1 hr, s).

Example 74

7-(4-(2-Fluoroethoxy)pyrimidin-5-yl)-3-(2-methoxyphenyl)benzo[d]isoxazole

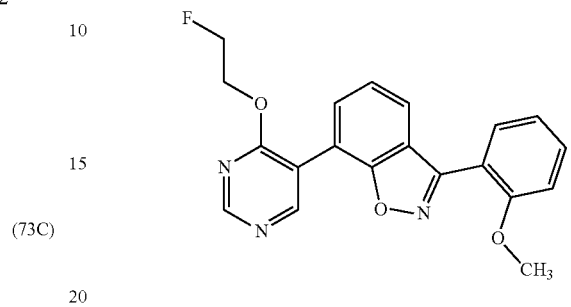

(74)

To a stirring solution of 2-fluoroethanol (0.885 mg, 0.014 mmol) in THF (Volume: 0.5 mL) at room temperature was added sodium hydride (4.97 mg, 0.124 mmol). After 5 minutes, Preparation 73C (0.014 g, 0.041 mmol) was added and the reaction mixture was heated to 50° C. overnight. The reaction mixture was cooled and diluted with 10 drops of water, and the solvent removed with a stream of nitrogen. The remaining residue was dissolved in DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (1.3 mg, 26%). ESI MS (M+H)⁺=366.0. HPLC Peak t$_r$=2.52 minutes. Purity >99%. HPLC Conditions: B. ¹H NMR (500 MHz, MeOD) δ ppm 8.82 (1 hr, s), 8.78 (1 hr, s), 7.82 (1 hr, dd, J=7.49, 1.11 Hz), 7.76 (1 hr, dd, J=8.05, 1.11 Hz), 7.60 (1 hr, dd, J=7.63, 1.80 Hz), 7.52-7.56 (1 hr, m), 7.41-7.47 (1 hr, m), 7.16 (1 hr, d, J=8.32 Hz), 7.11 (1 hr, t, J=7.49 Hz), 4.73-4.83 (3 hr, m), 3.87 (3 hr, s).

Example 75

7-(4-Isopropoxypyrimidin-5-yl)-3-(2,2,2-trifluoroethoxy)benzo[d]isoxazole

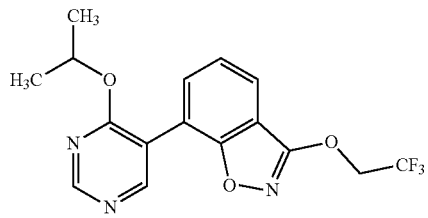

(75)

Preparation 75A:
2-Fluoro-3-(pyrimidin-5-yl)benzonitrile

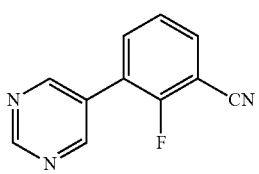

(75A)

A sealed tube apparatus was charged with a solution containing 5-bromopyrimidine (1 g, 6.29 mmol), sodium carbonate (3.33 g, 31.4 mmol), and 3-cyano-2-fluorophenylboronic acid (1.037 g, 6.29 mmol) in a mixture of DME (Ratio: 2, Volume: 31.4 ml), water (Ratio: 1.000, Volume: 15.72 ml), and EtOH (Ratio: 1.000, Volume: 15.72 ml) at ambient temperature. Tetrakis(triphenylphosphine)palladium(0) (0.363 g, 0.314 mmol) was then added and the system was purged with nitrogen, sealed, and heated to 70° C. for 12 h. The vessel was cooled to room temperature and diluted with EtOAc and water. The mixture was further diluted with brine and extracted three times with EtOAc. The combined organics were dried over MgSO$_4$, filtered, and concentrated to give the crude product. The crude material was purified by flash chromatography on silica using an ISCO machine (40 g SiO$_2$ column, 40 mL/min, 0-40% EtOAc/hexanes over 15 minutes, t$_r$=8 minutes) to afford the title compound (300 mg, 24%). ESI MS (M+H)$^+$= 200.0. $^1$H NMR (400 MHz, DMSO-d$_6$) δ ppm 9.28 (1 hr, s), 9.09 (2 hr, d, J=1.54 Hz), 8.02-8.12 (2 hr, m), 7.59 (1 hr, t, J=7.81 Hz).

Preparation 75B:
7-(Pyrimidin-5-yl)benzo[d]isoxazol-3-amine

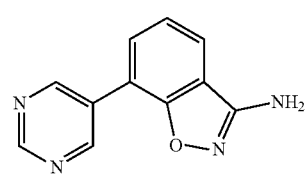

(75B)

A mixture of Preparation 75A (300 mg, 1.506 mmol), N-hydroxyacetamide (339 mg, 4.52 mmol), and potassium carbonate (1.249 g, 9.04 mmol) in DMF (6.56 mL) and water (0.94 mL) was stirred at 80° C. for 3 hr. The vessel was allowed to cool to room temperature and the mixture was filtered through a fritted funnel, and the filter cake was washed with EtOAc. The layers of the filtrate were separated, and the aqueous phase was extracted three times with EtOAc. The organic extracts were combined, washed with water and brine then dried over anhydrous sodium sulfate. The slurry was filtered, concentrated, and further dried under high vacuum to afford the title compound (240 mg, 75%) as a yellow residue. ESI MS (M+H)$^+$=213.1. $^1$H NMR (400 MHz, DMSO-d$_6$) δ ppm 9.32 (2 hr, s), 9.25 (1 hr, s), 7.98 (2 hr, ddd, J=13.31, 7.59, 1.10 Hz), 7.45 (1 hr, t, J=7.59 Hz), 6.61 (2 hr, s).

Preparation 75C:
3-Chloro-7-(pyrimidin-5-yl)benzo[d]isoxazole

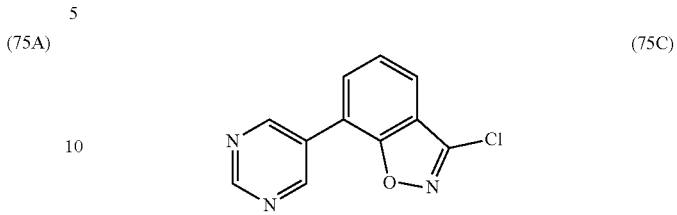

(75C)

A solution of Preparation 75B (270 mg, 1.272 mmol) in concentrated hydrochloric acid, 37% (Volume: 13.3 mL) was cooled to 0° C. was treated with sodium nitrite (92 mg, 1.336 mmol). The reaction mixture was stirred at 0° C. for 1 hr, and then at ambient temperature for 2 hr. The mixture was poured into a solution of saturated aqueous NH$_4$Cl (50 mL). A yellow solid precipitated and the suspension was allowed to stir at room temperature overnight. The reaction mixture was neutralized with solid NaHCO$_3$ (52 g+5 g), then diluted with DCM. The layers were separated and the aqueous phase was extracted with DCM five times. The organic extracts were combined, dried over Na$_2$SO$_4$, filtered, and concentrated to afford a yellow residue. The crude material was dissolved in a minimal amount of DCM and purified via silica gel chromatography using an ISCO machine (80 g column, 60 mL/min, 50-70% EtOAc in hexanes over 25 min, t$_r$=12 min) to give the title compound (50 mg, 0.216 mmol, 16.97% yield) as a white solid. ESI MS (M, M+2)$^+$=231, 233.

Preparation 75D: 7-(Pyrimidin-5-yl)-3-(2,2,2-trifluoroethoxy)benzo[d]isoxazole (75D)

To a stirring solution of 2,2,2-trifluoroethanol (43.2 mg, 0.432 mmol) in DMF (1 mL) at room temperature was added sodium hydride (10.36 mg, 0.432 mmol). After 3 minutes, Preparation 75C (50 mg, 0.216 mmol) was added. The mixture was allowed to stir until judged complete by HPLC. The reaction mixture was allowed to cool to room temperature, at which point it was diluted with water and extracted twice with EtOAc. The organics were washed twice with 10% aq. LiCl and then dried over Na$_2$SO$_4$. Filtration and concentration afforded the title compound (61 mg, 96%). ESI MS (M+H)$^+$=296.0. $^1$H NMR (400 MHz, DMSO-d$_6$) δ ppm 9.33 (2 hr, s), 9.28 (1 hr, s), 8.16 (1 hr, dd, J=7.48, 1.10 Hz), 7.90-7.98 (2 hr, m), 7.53-7.64 (1 hr, m), 5.26 (2 hr, q, J=8.66 Hz).

Preparation 75E: 5-(3-(2,2,2-Trifluoroethoxy)benzo[d]isoxazol-7-yl)pyrimidin-4-ol

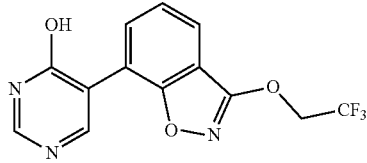

(75E)

To a stirring solution of Preparation 75D (61 mg, 0.207 mmol) in acetone (2 mL) at room temperature was added peracetic acid (0.043 mL, 0.207 mmol). The reaction mixture was heated to reflux. After 2 hours of heating at 60° C., the reaction mixture was allowed to cool to room temperature, the pH was neutralized with 1N NaOH, and extracted three times with DCM. The crude product was dissolved in a small amount of DCM and charged to a 4 g silica gel cartridge which was eluted with a 20 min gradient from 0% to 100% of ethyl acetate in DCM to afford the title compound (21 mg, 33%). ESI MS (M+H)$^+$=312.0. $^1$H NMR (400 MHz, DMSO-d$_6$) δ ppm 8.40 (1 hr, s), 8.32 (1 hr, s), 8.09 (1 hr, d, J=7.48 Hz), 7.81 (1 hr, s), 7.49 (1 hr, t, J=7.70 Hz), 5.23 (2 hr, q, J=8.66 Hz).

Preparation 75F: 7-(4-Chloropyrimidin-5-yl)-3-(2,2,2-trifluoroethoxy)benzo[d]isoxazole

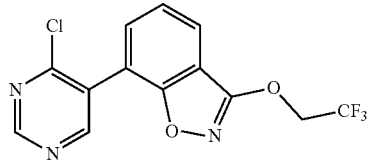

(75F)

A suspension of Preparation 75E (21 mg, 0.067 mmol) in POCl$_3$ (0.503 mL, 5.40 mmol) was heated to 90° C. for 1 h. The volatile solvents were removed in vacuo to afford the title compound (22 mg, 100%). ESI MS (M, M+2)$^+$=329.0, 331.0. $^1$H NMR (400 MHz, THF) δ ppm 9.13 (1 hr, s), 8.97 (1 hr, s), 7.92 (1 hr, dd, J=7.92, 0.88 Hz), 7.75-7.83 (1 hr, m), 7.54 (1 hr, t, J=7.59 Hz), 5.06 (2 hr, q, J=8.36 Hz).

Example 75

To a stirring solution of propan-2-ol (9.92 mg, 0.165 mmol) in THF (Volume: 0.5 mL) at room temperature was added sodium hydride (3.96 mg, 0.099 mmol). After 5 minutes, a solution of Preparation 75F (10.88 mg, 0.033 mmol) in THF (Volume: 0.5 mL) was added. The mixture was allowed to stir until judged complete by HPLC. The reaction was quenched with 5 drops of water. The reaction mixture was filtered. The filtrate was concentrated, diluted with DMF, and purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (1.3 mg, 10%). ESI MS (M+H)$^+$=354.0. HPLC Peak t$_r$=2.89 minutes. Purity=93%. HPLC Conditions: B. $^1$H NMR (400 MHz, MeOD) δ ppm 7.92 (1 hr, s), 7.82 (1 hr, s), 6.94 (2 hr, d, J=7.92 Hz), 6.75 (1 hr, s), 6.56-6.69 (1 hr, m), 4.72 (1 hr, quin, J=6.22 Hz), 4.08 (2 hr, q, J=8.14 Hz), 0.52 (5 hr, d, J=6.16 Hz).

Example 76

3-(2-Methoxyphenyl)-7-(4-(2-morpholinoethoxy)pyrimidin-5-yl)benzo[d]isoxazole

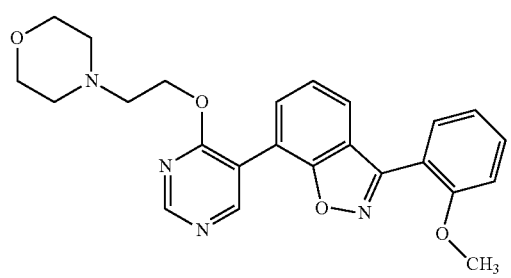

(76)

To a stirring solution of 2-morpholinoethanol (0.016 g, 0.124 mmol) in THF (Volume: 0.5 mL) at room temperature was added sodium hydride (4.97 mg, 0.124 mmol). After 5 minutes, Preparation 73C (0.014 g, 0.041 mmol) was added and the reaction mixture was heated to 50° C. overnight. The reaction mixture was diluted with 10 drops of water and concentrated. The remaining residue was dissolved in DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (0.9 mg, 5%). ESI MS (M+H)$^+$=433.3. HPLC Peak t$_r$=1.79 minutes. Purity=94%. HPLC Conditions: E. $^1$H NMR (400 MHz, MeOD) δ ppm 8.82 (1 hr, s), 8.71 (1 hr, s), 7.78 (1 hr, dd, J=8.03, 0.99 Hz), 7.71 (1 hr, dd, J=7.37, 0.99 Hz), 7.58-7.64 (1 hr, m), 7.46 (1 hr, t, J=7.70 Hz), 7.06-7.20 (2 hr, m), 4.76 (2 hr, t, J=4.84 Hz), 3.88 (3 hr, s), 3.69 (4 hr, t, J=4.18 Hz), 2.99-3.17 (2 hr, m), 2.73 (3 hr, br. s.).

Example 77

3-(2-Methoxyphenyl)-7-(4-(pyridazin-3-ylmethoxy)pyrimidin-5-yl)benzo[d]isoxazole

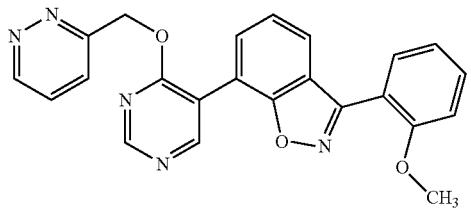

(77)

To a stirring solution of pyridazin-3-ylmethanol (0.014 g, 0.124 mmol) in THF (Volume: 0.5 mL) at room temperature was added sodium hydride (4.97 mg, 0.124 mmol). After 5 minutes, Preparation 73C (0.014 g, 0.041 mmol) was added and the reaction mixture was heated at 50° C. overnight. The reaction mixture was diluted with 10 drops of water and concentrated. The resulting residue was dissolved in DMF, filtered, and purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (1.1 mg, 6%). ESI MS (M+H)$^+$=412.0. HPLC Peak $t_r$=2.12 minutes. Purity=93%. HPLC Conditions: B. $^1$H NMR (400 MHz, MeOD) δ ppm 9.08 (1 hr, dd, J=4.95, 1.65 Hz), 8.81 (1 hr, s), 8.78 (1 hr, s), 7.73-7.80 (2 hr, m), 7.57-7.66 (2 hr, m), 7.41-7.49 (1 hr, m), 7.16 (1 hr, d, J=8.14 Hz), 7.12 (1 hr, td, J=7.54, 0.99 Hz), 5.88 (1 hr, s), 3.87 (2 hr, s).

Example 78

3-(2-Methoxyphenyl)-7-(4-(pyridazin-3-ylmethoxy)pyrimidin-5-yl)benzo[d]isoxazole

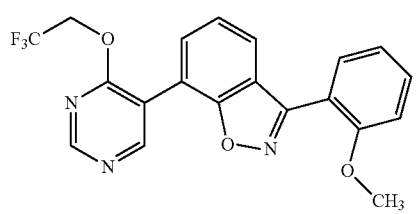

(78)

Preparation 78A: 3-(2-Methoxyphenyl)-7-(4,4,5,5-tetramethyl-1,3,2-dioxaborolan-2-yl)benzo[d]isoxazole

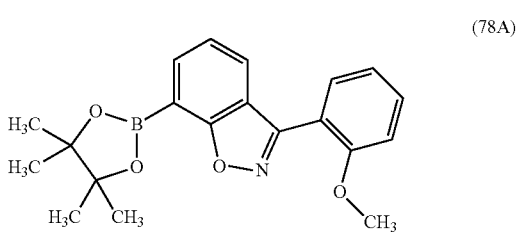 [SMILES: COc1ccccc1-c1noc2c(B3OC(C)(C)C(C)(C)O3)cccc12]

(78A)

A vial was charged with bis(acetonitrile)palladium(II) chloride (3.41 mg, 0.013 mmol), dicyclohexyl(2',6'-dimethoxybiphenyl-2-yl)phosphine (10.80 mg, 0.026 mmol), and Preparation 72D (200 mg, 0.658 mmol). The vial was capped with a rubber septum and then evacuated and backfilled with N$_2$ (this sequence was carried out a total of 2 times). Dioxane (Volume: 394 μl) was added via syringe, through the septum, followed by the addition of triethylamine (275 μl, 1.973 mmol) and 4,4,5,5-tetramethyl-1,3,2-dioxaborolane (143 μl, 0.986 mmol). The septum was then replaced with a Teflon screw valve, and the vial sealed. The reaction mixture was heated at 110° C. After 13 hr, the reaction mixture was allowed to cool to room temperature. The reaction mixture was filtered through a disposable fritted funnel and the filter cake washed with CH$_2$Cl$_2$. The filtrate was concentrated to afford the title compound as a yellow-green residue (231 mg, 100%).

Example 78

A pressure vessel was charged with Preparation 78A (0.035 g, 0.1 mmol), Preparation 12A (0.040 g, 0.130 mmol), and sodium carbonate (0.053 g, 0.500 mmol). The vessel was then charged with DME (Ratio: 2, Volume: 1.5 mL), water (Ratio: 1.000, Volume: 0.750 mL), and EtOH (Ratio: 1.000, Volume: 0.750 mL) at room temperature. To this mixture was added tetrakis(triphenylphosphine)palladium(0) (5.78 mg, 5.00 μmol) and the system was purged with nitrogen and sealed. The vessel was heated at 90° C. for 12 h. The mixture was cooled to room temperature, diluted with MeOH, filtered and concentrated. The resulting residue was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (3.9 mg, 9%). ESI MS (M+H)$^+$=402.0. HPLC Peak $t_r$=2.85 minutes. Purity=95%. HPLC Conditions: B. $^1$H NMR (400 MHz, MeOD) δ ppm 8.91 (1 hr, s), 8.84 (1 hr, s), 7.74-7.82 (2 hr, m), 7.60 (1 hr, dd, J=7.48, 1.54 Hz), 7.51-7.56 (1 hr, m), 7.40-7.49 (1 hr, m), 7.08-7.20 (2 hr, m), 4.99 (2 hr, q, J=8.51 Hz), 3.87 (3 hr, s).

Example 79

7-(4-Chloropyridin-3-yl)-3-(2-methoxyphenyl)benzo[d]isoxazole

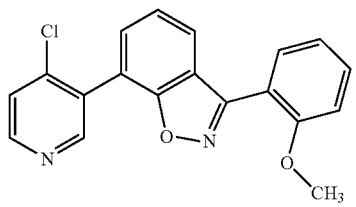

(79)

A pressure vessel was charged with 4-chloro-3-iodopyridine (31.1 mg, 0.130 mmol), Preparation 78A (35.1 mg, 0.100 mmol), and sodium carbonate (53.0 mg, 0.500 mmol). DME (Ratio: 2, Volume: 1.5 mL), water (Ratio: 1.000, Volume: 0.750 mL), and EtOH (Ratio: 1.000, Volume: 0.750 mL) were then added at room temperature. To this mixture was added tetrakis(triphenylphosphine)palladium(0) (5.78 mg, 5.00 µmol) and the system was purged with nitrogen and sealed. The vessel was heated at 90° C. for 12 hr. The reaction mixture was diluted with MeOH, filtered, and concentrated. The resulting oil was diluted with DMF and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (2.8 mg, 8%). ESI MS (M+H)$^+$=337.0. HPLC Peak $t_r$=2.69 minutes. Purity=97%. HPLC Conditions: B. $^1$H NMR (400 MHz, MeOD) δ ppm 8.67 (1 hr, s), 8.54 (1 hr, d, J=5.50 Hz), 7.81 (1 hr, dd, J=8.03, 0.99 Hz), 7.58-7.67 (3 hr, m), 7.53 (1 hr, d, J=1.76 Hz), 7.43-7.50 (1 hr, m), 7.04-7.21 (2 hr, m), 3.88 (3 hr, s).

Example 80

7-(Isoquinolin-4-yl)-3-(2-methoxyphenyl)benzo[d]isoxazole

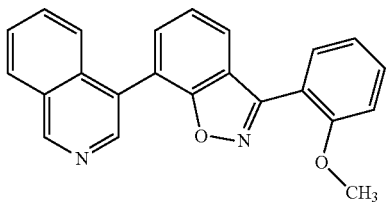

(80)

A pressure tube was charged with Preparation 72D (30 mg, 0.099 mmol), isoquinolin-4-ylboronic acid (20.47 mg, 0.118 mmol), and sodium carbonate (52.3 mg, 0.493 mmol). The vessel was then charged with water (Ratio: 1.000, Volume: 0.750 mL), DME (Ratio: 2, Volume: 1.5 mL), and EtOH (Ratio: 1.000, Volume: 0.750 mL) at room temperature. To this slurry was added tetrakis(triphenylphosphine)palladium(0) (57.0 mg, 0.049 mmol) and the system was purged with nitrogen and sealed. The vessel was heated at 90° C. for 12 hr. The reaction mixture was diluted with MeOH, filtered, and concentrated. The resulting oil was diluted with DMF and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (1.9 mg, 5%). ESI MS (M+H)$^+$=353.0. HPLC Peak $t_r$=2.80 minutes. Purity=99%. HPLC Conditions: B. $^1$H NMR (400 MHz, MeOD) δ ppm 9.30 (1 hr, s), 8.56 (1 hr, s), 8.12-8.23 (1 hr, m), 7.84 (1 hr, dd, J=8.14, 1.10 Hz), 7.73-7.78 (3 hr, m), 7.66-7.73 (2 hr, m), 7.62 (1 hr, dd, J=7.59, 1.65 Hz), 7.48-7.55 (2 hr, m), 7.18 (1 hr, d, J=8.14 Hz), 7.12 (1 hr, td, J=7.48, 0.88 Hz), 3.91 (4 hr, s).

Example 81

7-(4-(2,2-Difluoroethoxy)pyrimidin-5-yl)-3-(2-methoxyphenyl)benzo[d]isoxazole

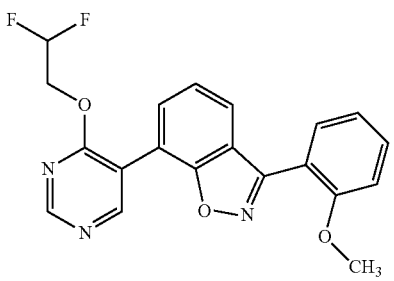

(81)

To a stirring solution of 2,2-difluoroethanol (1.134 mg, 0.014 mmol) in THF (Volume: 0.5 mL) at room temperature was added sodium hydride (4.97 mg, 0.124 mmol). After 5 minutes, Preparation 73C (0.014 g, 0.041 mmol) was added and the reaction mixture was heated at 50° C. overnight. The reaction mixture was diluted with 10 drops of water and concentrated. The resulting residue was dissolved in DMF, filtered, and the crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (0.5 mg, 8%). ESI MS (M+H)$^+$=384.0. HPLC Peak $t_r$=2.65 minutes. Purity=89%. HPLC Conditions: B.

Example 82

3-(2-Methoxyphenyl)-7-(4-methylpyrimidin-5-yl)benzo[d]isoxazole

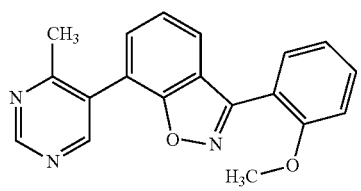

(82)

A pressure vessel was charged with Preparation 78A (35.1 mg, 0.100 mmol), 5-bromo-4-methylpyrimidine (22.49 mg, 0.130 mmol), and sodium carbonate (53.2 mg, 0.502 mmol). To this vessel was then added DME (Ratio: 2, Volume: 1.5 mL), EtOH (Ratio: 1.000, Volume: 0.750 mL), and water (Ratio: 1.000, Volume: 0.750 mL) at room temperature. To this slurry was added tetrakis(triphenylphosphine)palladium(0) (58.0 mg, 0.050 mmol) and the system was purged with nitrogen and sealed. The vessel was heated at 90° C. for 12 hr. The reaction mixture was diluted with MeOH, filtered, and concentrated. The resulting oil was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 15-55% B over 25 minutes, then a 10-minute hold at 55% B; Flow: 20 mL/min. Fractions containing the desired product were combined and dried via centrifugal evaporation to afford the title compound (4.0 mg, 12%). ESI MS (M+H)$^+$=318.1. HPLC Peak t$_r$=2.28 minutes. Purity=93%. HPLC Conditions: B. $^1$H NMR (500 MHz, MeOD) δ ppm 9.10 (1 hr, s), 8.72 (1 hr, s), 7.83 (1 hr, dd, J=7.91, 1.25 Hz), 7.61 (1 hr, dd, J=7.49, 1.66 Hz), 7.54 (1 hr, d, J=1.66 Hz), 7.45-7.52 (1 hr, m), 7.17 (1 hr, d, J=8.05 Hz), 7.12 (1 hr, t, J=7.49 Hz), 3.88 (3 hr, s), 2.55 (3 hr, s).

Example 83

3-(2-Methoxyphenyl)-7-(4-morpholinopyrimidin-5-yl)benzo[d]isoxazole

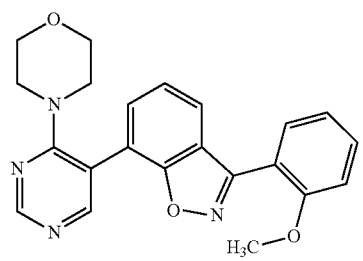

(83)

A pressure vessel was charged with Preparation 78A (35.1 mg, 0.100 mmol), Preparation 16A (37.8 mg, 0.130 mmol), and sodium carbonate (53.2 mg, 0.502 mmol). To this vessel was then added DME (Ratio: 2, Volume: 1.5 mL), EtOH (Ratio: 1.000, Volume: 0.750 mL), and water (Ratio: 1.000, Volume: 0.750 mL) at room temperature. To this slurry was added tetrakis(triphenylphosphine)palladium(0) (58.0 mg, 0.050 mmol) and the system was purged with nitrogen and sealed. The vessel was heated at 90° C. for 12 hr. The reaction mixture was diluted with MeOH, filtered, and concentrated. The resulting oil was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation to afford the title compound (4.2 mg, 11%). ESI MS (M+H)$^+$=389.1. HPLC Peak t$_r$=2.25 minutes. Purity >99%. Conditions: B. $^1$H NMR (500 MHz, DMSO-d$_6$) δ ppm 8.70 (1 hr, s), 8.42 (1 hr, s), 7.74-7.84 (2 hr, m), 7.58-7.67 (2 hr, m), 7.50-7.56 (1 hr, m), 7.32 (1 hr, d, J=8.05 Hz), 7.07-7.22 (1 hr, m), 3.85 (2 hr, s), 3.37-3.47 (3 hr, m), 3.31 (19 hr, s), 3.19-3.28 (3 hr, m).

Example 84

3-(2-Methoxyphenyl)-7-(pyrrolo[1,2-c]pyrimidin-4-yl)benzo[d]isoxazole

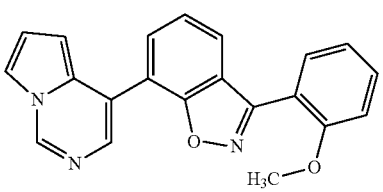

(84)

A pressure vessel was charged with Preparation 78A (35.1 mg, 0.100 mmol), Preparation 14C (19.70 mg, 0.100 mmol), and sodium carbonate (53.2 mg, 0.502 mmol). To the vessel was then added DME (Ratio: 2, Volume: 1.5 mL), EtOH (Ratio: 1.000, Volume: 0.750 mL), and water (Ratio: 1.000, Volume: 0.750 mL) at room temperature. To this slurry was added tetrakis(triphenylphosphine)palladium(0) (58.0 mg, 0.050 mmol) and the system was purged with nitrogen and sealed. The vessel was heated at 90° C. for 12 hr. The reaction mixture was diluted with MeOH, filtered, and concentrated. The resulting oil was diluted with DMF and the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 15-60% B over 25 minutes, then a 10-minute hold at 60% B; Flow: 20 mL/min. Fractions containing the desired product were combined and dried via centrifugal evaporation to afford the title compound (1.6 mg, 4.7%). ESI MS (M+H)$^+$=342.0. HPLC Peak t$_r$=2.70 minutes. Purity >99%. HPLC Conditions: B.

Example 85

7-(4-Methylpyridin-3-yl)-3-(3,3,3-trifluoropropyl)benzo[d]isoxazole

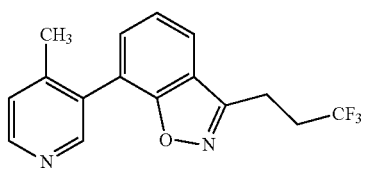

(85)

Preparation 85A: (3,3,3-Trifluoropropyl)magnesium bromide

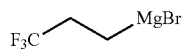

(85A)

To a 3-necked 250 mL flask was added magnesium (2.75 g, 113 mmol) and a stir bar. The magnesium was stirred vigorously under vacuum for 2 days. The flask was then placed under with N$_2$ and charged with ethyl ether (100 mL). The 3-necked flask was also equipped with a condenser and heated at 50° C. 1,2-Dibromoethane (0.1 mL) was added and followed by the addition of a small amount of 4-bromo-1,1,1-trifluorobutane in Et$_2$O. After 5-10 min, the heat source was removed and 3-bromo-1,1,1-trifluoropropane (10 g, 56.5 mmol) in 20 mL of Et$_2$O was added slowly via syringe. Upon addition of all of the 4-bromo-1,1,1-trifluorobutane, the reaction mixture was heated at 50° C. for another 30 min. The concentration was of the solution was determined to be 0.47M and the material was stored under N$_2$ at −20° C.

Preparation 85B: 1-(3-Bromo-2-fluorophenyl)-4,4,4-trifluorobutan-1-ol

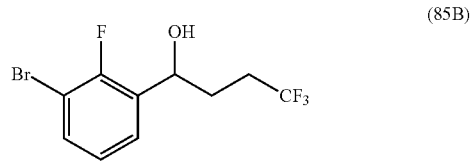 [SMILES: OC(CCC(F)(F)F)c1cccc(Br)c1F]

(85B)

To a solution of 3-bromo-2-fluorobenzaldehyde (500 mg, 2.463 mmol) in THF (10 mL) at −78° C. was added Preparation 85A (10 mL, 2.463 mmol). The reaction mixture was stirred at −78° C. for 1 h, then allowed to warm to room temperature and stirred for 6 hr. The reaction mixture was diluted with saturated aqueous NH$_4$Cl and EtOAc. The organic phase was separated and washed with brine, dried over MgSO$_4$, filtered and concentrated to give the title compound (700 mg, 1.162 mmol, 47.2% yield) as yellow liquid.

Preparation 85C: 1-(3-Bromo-2-fluorophenyl)-4,4,4-trifluorobutan-1-one

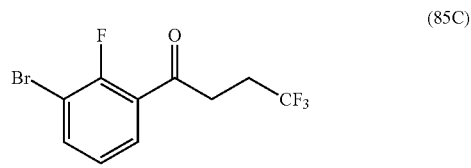 [SMILES: O=C(CCC(F)(F)F)c1cccc(Br)c1F]

(85C)

To a solution of Preparation 85B (680 mg, 2.259 mmol) in CH$_2$Cl$_2$ (10 mL) at room temperature was added Dess-Martin periodinane (1916 mg, 4.52 mmol). The suspension was stirred at room temperature overnight, then diluted with an aqueous solution of 10% Na$_2$S$_2$O$_3$ and saturated NaHCO$_3$. The mixture was stirred for 30 min until a clear solution formed. The organic phase was separated and washed with brine, dried over MgSO$_4$, filtered, and concentrated to give the title compound (650 mg, 2.130 mmol, 94% yield) as yellow liquid.

Preparation 85D: (Z)-1-(3-Bromo-2-fluorophenyl)-4,4,4-trifluorobutan-1-one oxime

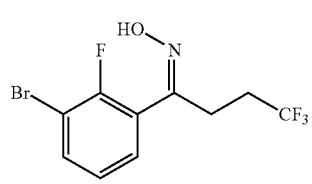

(85D)

To a solution of Preparation 85C (650 mg, 2.173 mmol) in pyridine (10 mL) at room temperature was added hydroxylamine hydrochloride (227 mg, 3.26 mmol). The reaction mixture was stirred at 70° C. for 2 h. The solvent was evaporated and the resulting residue was partitioned between EtOAc and 1N HCl. The organic phase was separated, washed with brine, dried over MgSO$_4$, filtered, and concentrated to give the title compound (680 mg, 2.057 mmol, 95% yield) as light brown liquid. ESI MS (M+H)$^+$ 314.0.

Preparation 85E:
7-Bromo-3-(3,3,3-trifluoropropyl)benzo[d]isoxazole

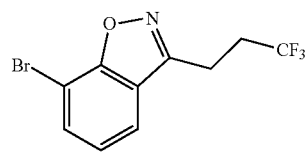

(85E)

To the suspension of NaH (35.7 mg, 0.892 mmol) in THF (4 mL) at room temperature was added Preparation 85D (200 mg, 0.446 mmol) in DMF (4.00 mL) dropwise. The reaction mixture was heated at 70° C. for 1 h. Additional NaH (35.7 mg, 0.892 mmol) was added and the reaction mixture was stirred at 70° C. for 2 h. More NaH (35.7 mg, 0.892 mmol) was added and the reaction mixture was stirred for another 30 min. The reaction mixture was cooled to room temperature and diluted with saturated NH$_4$Cl and EtOAc. The organic phase was separated and washed with brine, dried over MgSO$_4$, and concentrated. Purification of the crude material by silica gel chromatography using an ISCO machine (24 g column, 35 mL/min, 0-50% EtOAc in hexanes over 25 min) gave the title compound (22 mg, 0.074 mmol, 16.62% yield) as light brown liquid. ESI MS (M+H)$^+$= 295.9.

Example 85

To a suspension of 4-methylpyridin-3-ylboronic acid (12.29 mg, 0.090 mmol) in DME (0.5 mL), EtOH (0.250 mL) and water (0.250 mL) were added 7-bromo-3-(3,3,3-trifluoropropyl)benzo[d]isoxazole (22 mg, 0.075 mmol), followed by Na$_2$CO$_3$ (31.7 mg, 0.299 mmol). The reaction mixture was purged with N$_2$ for 10 min, then tetrakis(triphenylphosphine)palladium(0) (4.32 mg, 3.74 µmol) was added and the reaction vessel was sealed and heated at 90° C. for overnight. The reaction mixture was allowed to cool to room temperature and then filtered. The filtrate was diluted with MeOH and purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 35-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-60% B over 25 minutes, then a 15-minute hold at 60% B; Flow: 20 mL/min. Fractions containing the desired product were combined and dried via centrifugal evaporation to afford the title compound (1.5 mg, 6.8%). ESI MS (M+H)$^+$= 307.1. HPLC Peak t$_r$=2.44 minutes. Purity >99%. HPLC Conditions: B.

Example 86

3-(4-Fluorophenyl)-7-(4-methylpyridin-3-yl)isoxazolo[4,5-b]pyridine

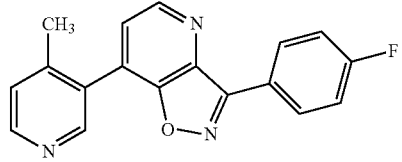

(86)

Preparation 86A: 3-Fluoro-4-iodopicolinonitrile

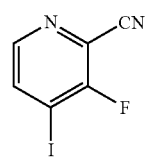

(86A)

To a solution of diisopropylamine (2.80 ml, 19.66 mmol) in THF (Volume: 201 ml) cooled to −78° C. was added n-butyllithium (7.86 ml, 19.66 mmol) dropwise. The dry ice/acetone bath was replaced with an ice water bath and reaction mixture was stirred at 0° C. for 25 min, and then re-cooled to −78° C. In a separate flask, a solution of 3-fluoropicolinonitrile (1.5 g, 12.29 mmol) in THF (50 mL) was cooled to −78° C., and then LDA (130 mL, 1.0 equiv) was added. The solution turned dark red. After 35 min, iodine (3.43 g, 13.51 mmol) was added rapidly. The reaction mixture was stirred for 45 min, then quenched with H$_2$O. Layers were separated and the aqueous phase extracted with CH$_2$Cl$_2$ (2×). Organics combined, dried over Na$_2$SO$_4$, filtered, and concentrated to afford a brown residue. The crude material was dissolved in a minimal amount of CH$_2$Cl$_2$ to be chromatographed. Purification of the crude material by silica gel chromatography using an ISCO machine (80 g column, 60 mL/min, 0-20% EtOAc in hexanes over 23 min, t$_r$=18 min) gave the title compound (1.7 g, 6.79 mmol, 55.2% yield) as a brown solid.

Preparation 86B: 3'-Fluoro-4-methyl-3,4'-bipyridine-2'-carbonitrile

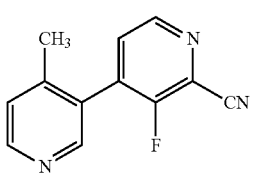

(86B)

A vial containing a mixture of 3-fluoro-4-iodopicolinonitrile (0.150 g, 0.605 mmol), 4-methylpyridin-3-ylboronic acid (0.174 g, 1.270 mmol), and cesium carbonate (0.414 g, 1.270 mmol) in dioxane (Ratio: 2.0, Volume: 1.222 ml) and water (Ratio: 1.000, Volume: 0.611 ml) was degassed with N₂ for 5 min, then PdCl₂(dppf)-CH₂Cl₂Adduct (0.026 g, 0.032 mmol) was added. The solution was heated at 85° C. for 14 hr, then allowed to cool to room temperature. The crude material was dissolved in a minimal amount of CH₂Cl₂ to be chromatographed. Purification of the crude material by silica gel chromatography using an ISCO machine (40 g column, 40 mL/min, 70-100% EtOAc in hexanes over 19 min, t$_r$=14 min) gave the title compound (24 mg, 0.111 mmol, 18.42% yield) as a purple residue. ESI MS (M+H)⁺=214.1.

Preparation 86C: (3'-Fluoro-4-methyl-3,4'-bipyridin-2'-yl)(4-fluorophenyl)methanone

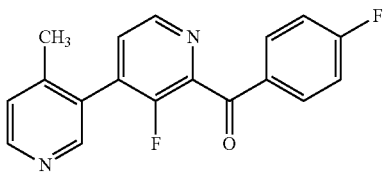

(86C)

To a solution of 3'-fluoro-4-methyl-3,4'-bipyridine-2'-carbonitrile (0.029 g, 0.136 mmol) in THF (Volume: 0.680 ml) cooled to 0° C. was added (4-fluorophenyl)magnesium bromide (0.170 ml, 0.340 mmol). The reaction mixture was allowed to stir at room temperature for 5 hr. Water and ice were carefully added, followed by acidification with 6 M HCl. After stirring for 20 min, CH₂Cl₂ was added and the pH was adjusted to 8.5 with aqueous 4 M NaOH. The layers were separated and the aqueous phase was extracted with CH₂Cl₂ (9×). The organics layers were combined, dried over Na₂SO₄, filtered, and concentrated to afford a residue. The crude material was dissolved in a minimal amount of CH₂Cl₂ to be chromatographed. Purification of the crude material by silica gel chromatography using an ISCO machine (12 g column, 30 mL/min, 70-90% EtOAc in hexanes over 14 min, tr=8 min) gave the title compound (29 mg, 0.089 mmol, 65.3% yield). ESI MS (M+H)⁺=311.1.

Preparation 86D: (Z)-(3'-Fluoro-4-methyl-3,4'-bipyridin-2'-yl)(4-fluorophenyl)methanone oxime

(86D)

A solution of (3'-fluoro-4-methyl-3,4'-bipyridin-2'-yl)(4-fluorophenyl)methanone (0.029 g, 0.093 mmol) and hydroxylamine hydrochloride (0.044 g, 0.636 mmol) in pyridine (Volume: 0.467 ml) was refluxed for 1.5 hr, allowed to cool to room temperature, and then concentrated in vacuo. The crude material was dissolved in a minimal amount of CH₂Cl₂ to be chromatographed (required a few drops of MeOH). Purification of the crude material by silica gel chromatography using an ISCO machine (4 g column, 18 mL/min, 80-100% EtOAc in hexanes over 12 min, t$_r$=2.5 min) gave the title compound (22 mg, 0.068 mmol, 72.4% yield) as a yellow solid. ESI MS (M+H)⁺=326.2.

Example 86

To a suspension of sodium hydride (4.60 mg, 0.115 mmol) in THF (Ratio: 1.8, Volume: 869 µl) was added dropwise (Z)-(3'-fluoro-4-methyl-3,4'-bipyridin-2'-yl)(4-fluorophenyl)methanone oxime (22 mg, 0.068 mmol) in DMF (Ratio: 1.0, Volume: 483 µl) slowly. The reaction mixture was heated at 70° C. for 3 hr, and then allowed to cool to room temperature. The reaction was quenched with H₂O. The reaction mixture was extracted with EtOAc (3×). The organic phases were combined, dried over Na₂SO₄, filtered, concentrated, and further dried under high vacuum to afford a yellow solid. The crude material was dissolved in a minimal amount of CH₂Cl₂ to be chromatographed. Purification of the crude material by silica gel chromatography using an ISCO machine (4 g column, 18 mL/min, 60-100% EtOAc in hexanes over 15 min, t$_r$=5 min) gave the title compound (9.6 mg, 0.030 mmol, 44.2% yield) as a white solid. ESI MS (M+H)⁺=306.1. HPLC Peak t$_r$=2.84 minutes. Purity=95%. HPLC Conditions: C.

Example 87

3-Chloro-7-(4-methylpyridin-3-yl)isoxazolo[4,5-b]pyridine

(87)

Preparation 87A: 7-(4-Methylpyridin-3-yl)isoxazolo[4,5-b]pyridin-3-amine

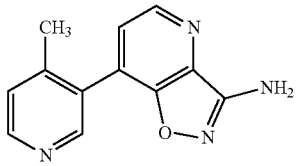

(87A)

A mixture of 3'-fluoro-4-methyl-3,4'-bipyridine-2'-carbonitrile (0.057 g, 0.267 mmol), N-hydroxyacetamide (0.060 g, 0.802 mmol), and potassium carbonate (0.222 g, 1.604 mmol) in DMF (Ratio: 7.0, Volume: 1.170 ml) and water (Ratio: 1.000, Volume: 0.167 ml) was stirred at 80° C. for 3 hr. The reaction mixture was filtered through a disposable fritted funnel. The filter cake was washed with EtOAc. Layers in the filtrate were separated and the aqueous phase was extracted with EtOAc (3×). The organic phases were combined, dried over Na$_2$SO$_4$, filtered, concentrated, and further dried under high vacuum to afford the title compound as a brown solid (49 mg, 0.206 mmol, 77% yield). ESI MS (M+H)$^+$=227.1.

Example 87

To a solution of 7-(4-methylpyridin-3-yl)isoxazolo[4,5-b]pyridin-3-amine (0.049 g, 0.217 mmol) in concentrated hydrochloric acid, 37% (Volume: 2.256 ml) cooled to 0° C. was added sodium nitrite (0.016 g, 0.227 mmol). The reaction mixture was stirred at 0° C. for 1 hr, and then allowed to stir at room temperature for 2 hr. The mixture was poured into a solution of saturated aqueous NH$_4$Cl (2.2 mL). A yellow solid precipitated, then the mixture became homogenous. The suspension was allowed to stir at room temperature overnight. The reaction mixture was neutralized with solid NaHCO$_3$ (2.3 g+222 mg), then diluted with CH$_2$Cl$_2$. Layers were separated and the aqueous phase was extracted with CH$_2$Cl$_2$ (5×). The organic phases were combined, dried over Na$_2$SO$_4$, filtered, and concentrated to afford a brown residue. The crude material was dissolved in a minimal amount of CH$_2$Cl$_2$ to be chromatographed. Purification of the crude material by silica gel chromatography using an ISCO machine (4 g column, 18 mL/min, 50-60% EtOAc in hexanes over 19 min, t$_r$=9 min) gave the title compound (16 mg, 0.064 mmol, 29.8% yield) as a white solid. ESI MS (M+H)$^+$=246.0. HPLC Peak t$_r$=1.31 minutes. Purity=99%. HPLC Conditions: C.

Example 88

7-(4-Methylpyridin-3-yl)-3-morpholinoisoxazolo[4,5-b]pyridine

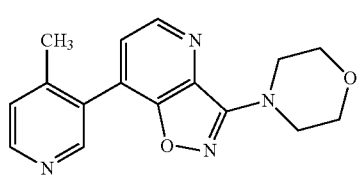

(88)

To a suspension of 3-chloro-7-(4-methylpyridin-3-yl)isoxazolo[4,5-b]pyridine (0.0069 g, 0.028 mmol) and morpholine (0.025 ml, 0.281 mmol) in DMSO (Volume: 0.100 ml) was added cesium carbonate (0.027 g, 0.084 mmol). The vial was sealed, heated at 90° C. for 4 hr, and then allowed to cool to room temperature. The reaction mixture was filtered through a disposable fritted funnel and the filter cake washed with CH$_2$Cl$_2$. The solvent was concentrated to afford a yellow liquid, which was further dried under high vacuum overnight. The crude material was dissolved in a minimal amount of CH$_2$Cl$_2$ to be chromatographed. Purification of the crude material by silica gel chromatography using an ISCO machine (4 g column, 18 mL/min, 70-100% EtOAc in hexanes over 14 min, t$_r$=4.5 min) gave 7-(4-methylpyridin-3-yl)-3-morpholinoisoxazolo[4,5-b]pyridine (6.5 mg, 0.021 mmol, 76% yield) as a white solid. ESI MS (M+H)$^+$=297.2. HPLC Peak t$_r$=1.56 minutes. Purity=97%. HPLC Conditions: C.

Example 89

7-(4-Methylpyridin-3-yl)-3-phenylisoxazolo[4,5-b]pyridine

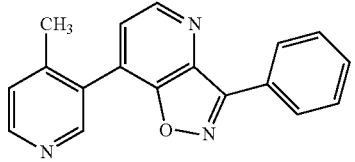

(89)

Preparation 89A: (3'-Fluoro-4-methyl-3,4'-bipyridin-2'-yl)(phenyl)methanone

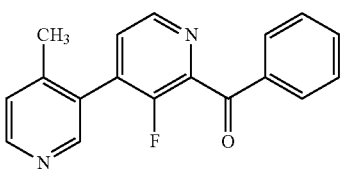

(89A)

To a solution of 3'-fluoro-4-methyl-3,4'-bipyridine-2'-carbonitrile (0.027 g, 0.127 mmol) in THF (Volume: 0.633 ml) cooled to 0° C. was added phenylmagnesium bromide (0.317 ml, 0.317 mmol). The reaction mixture was allowed to stir at room temperature overnight. Water and ice were carefully added, followed by acidification with 6 M HCl. After stirring for 1 hr, CH$_2$Cl$_2$ was added and the pH was adjusted to 8.5 with aqueous 4 M NaOH. The layers were separated and the aqueous phase was extracted with CH$_2$Cl$_2$ (5×). Organics combined, dried over Na$_2$SO$_4$, filtered, and concentrated to afford a purple residue. The crude material was dissolved in a minimal amount of CH$_2$Cl$_2$ to be chromatographed. Purification of the crude material by silica gel chromatography using an ISCO machine (4 g column, 18 mL/min, 70-100% EtOAc in hexanes over 19 min, t$_r$=6.5 min) gave the title compound (0.025 g, 0.081 mmol, 64.2% yield) as an orange residue. ESI MS (M+H)$^+$=293.1.

Preparation 89B: (Z)-(3'-Fluoro-4-methyl-3,4'-bipyridin-2'-yl)(phenyl)methanone oxime

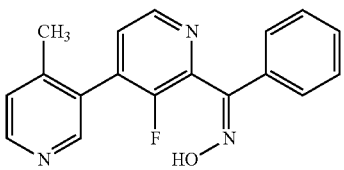

(89B)

A solution of (3'-fluoro-4-methyl-3,4'-bipyridin-2'-yl)(phenyl)methanone (0.025 g, 0.086 mmol) and hydroxylamine hydrochloride (0.040 g, 0.582 mmol) in pyridine (Volume: 0.428 ml) was refluxed for 2.5 hr, allowed to cool to room temperature, and then concentrated in vacuo. The crude material was dissolved in a minimal amount of CH$_2$Cl$_2$ to be chromatographed (required a few drops of MeOH). Purification of the crude material by silica gel chromatography using an ISCO machine (4 g column, 18 mL/min, 80-100% EtOAc in hexanes over 10 min, t$_r$=0.3, 1.5, 2 min) gave the title compound (23.7 mg, 0.076 mmol, 89% yield) as a yellow residue. ESI MS (M+H)$^+$=308.2.

Example 89

To a suspension of sodium hydride (5.24 mg, 0.131 mmol) in THF (Ratio: 1.8, Volume: 992 µl) was added dropwise (Z)-(3'-fluoro-4-methyl-3,4'-bipyridin-2'-yl)(phenyl)methanone oxime (23.7 mg, 0.077 mmol) in DMF (Ratio: 1.0, Volume: 551 µl) slowly. The reaction mixture was heated at 70° C. for 3 hr, and then allowed to cool to room temperature. The reaction was quenched with H$_2$O. The reaction mixture was extracted with EtOAc (3×). The organic phases were combined, dried over Na$_2$SO$_4$, filtered, concentrated, and further dried under high vacuum to afford a yellow residue. The crude material was re-dissolved in 1.5 mL DMF and purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-65% B over 25 minutes, then a 5-minute hold at 100% B; Flow: 20 mL/min. Fractions containing the desired product were combined and dried via centrifugal evaporation to afford the title compound (5.1 mg, 23%). ESI MS (M+H)$^+$=288.1. HPLC Peak t$_r$=2.49 minutes. Purity >99%. HPLC Conditions: B.

Example 90

3-(5-Fluoro-2-methoxyphenyl)-7-(4-methylpyridin-3-yl)isoxazolo[4,5-b]pyridine

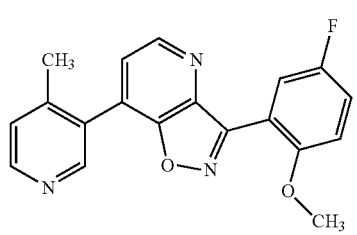

(90)

Preparation 90A: (5-Fluoro-2-methoxyphenyl)(3'-fluoro-4-methyl-3,4'-bipyridin-2'-yl)methanone

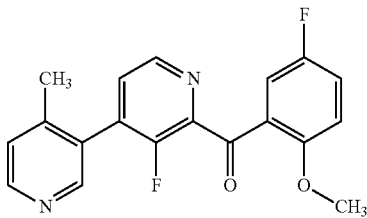

(90A)

To a solution of 3'-fluoro-4-methyl-3,4'-bipyridine-2'-carbonitrile (0.031 g, 0.145 mmol) in THF (Volume: 0.727 ml) cooled to 0° C. was added (5-fluoro-2-methoxyphenyl)magnesium bromide (0.727 ml, 0.363 mmol). The reaction mixture was allowed to stir at room temperature. Water and ice were carefully added, followed by acidification with 6 M HCl. After stirring for 1 hr, CH$_2$Cl$_2$ was added and the pH was adjusted to 8.5 with aqueous 4 M NaOH. The layers were separated. The aqueous phase was extracted with CH$_2$Cl$_2$ (5×). Organics combined, dried over Na$_2$SO$_4$, filtered, and concentrated to afford a purple residue. The crude material was dissolved in a minimal amount of CH$_2$Cl$_2$ to be chromatographed. Purification of the crude material by silica gel chromatography using an ISCO machine (4 g column, 18 mL/min, 60-100% EtOAc in hexanes over 18 min, t$_r$=9 min) gave the title compound (0.024 g, 0.070 mmol, 48.0% yield) as an orange residue. ESI MS (M+H)$^+$=340.2.

Preparation 90B: (Z)-(5-Fluoro-2-methoxyphenyl)(3'-fluoro-4-methyl-3,4'-bipyridin-2'-yl)methanone oxime

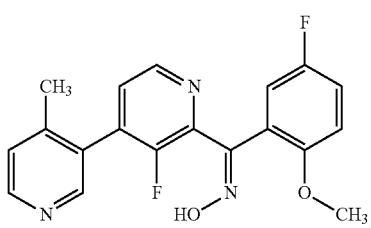

(90B)

A solution of (5-fluoro-2-methoxyphenyl)(3'-fluoro-4-methyl-3,4'-bipyridin-2'-yl)methanone (0.024 g, 0.071 mmol) and hydroxylamine hydrochloride (0.033 g, 0.480 mmol) in pyridine (Volume: 0.353 ml) was refluxed for 3 hr, allowed to cool to room temperature, and then concentrated in vacuo. The crude material was dissolved in a minimal amount of CH$_2$Cl$_2$ to be chromatographed (required a few drops of MeOH). Purification of the crude material by silica gel chromatography using an ISCO machine (4 g column, 18 mL/min, 0-95% EtOAc in hexanes over 15 min, t$_r$=0.5, 1.5. 2.5 min) gave the title compound (22 mg, 0.061 mmol, 87% yield) as a yellow residue. ESI MS (M+H)$^+$=356.1.

Example 90

To a suspension of sodium hydride (4.21 mg, 0.105 mmol) in THF (Ratio: 1.8, Volume: 796 µl) was added dropwise (Z)-(3'-fluoro-4-methyl-3,4'-bipyridin-2'-yl) (phenyl)methanone oxime (23.7 mg, 0.077 mmol) in DMF (Ratio: 1.0, Volume: 442 μl) slowly. The reaction mixture was heated at 70° C. for 3 hr, and then allowed to cool to room temperature. The reaction was quenched with H₂O. The reaction mixture was extracted with EtOAc (3×). The organic phases were combined, dried over Na₂SO₄, filtered, concentrated, and further dried under high vacuum to afford a yellow residue. The crude material was re-dissolved in 1.5 mL DMF and purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to afford the title compound (4.6 mg, 22%). ESI MS (M+H)⁺=336.1. HPLC Peak $t_r$=2.28 minutes. Purity=98%. HPLC Conditions: B.

Example 91

5-(3-(2-Chloro-4-fluorophenyl)isoxazolo[4,5-b]pyridin-7-yl)pyrimidin-4-amine

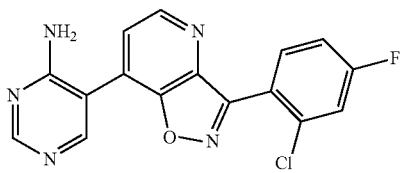
(91)

Preparation 91A:
3-Fluoro-4-(pyrimidin-5-yl)picolinonitrile

(91A)

A vial containing a mixture of 3-fluoro-4-iodopicolinonitrile (3.0 g, 12.10 mmol), pyrimidin-5-ylboronic acid (5.23 g, 42.2 mmol), and cesium carbonate (8.28 g, 25.4 mmol) in dioxane (Ratio: 2.0, Volume: 24.44 ml) and water (Ratio: 1.000, Volume: 12.22 ml) was degassed with N₂ for 5 min, then PdCl₂(dppf)-CH₂Cl₂Adduct (0.524 g, 0.641 mmol) was added. The solution was heated at 85° C. for 21 hr, and then allowed to cool to room temperature. The reaction was quenched with water. The reaction mixture was diluted with EtOAc. The layers were separated and the aqueous phase was extracted with EtOAc (3×). The organic phases were combined, dried over Na₂SO₄, filtered, and concentrated to afford a brown residue. The crude material was dissolved in a minimal amount of CH₂Cl₂ to be chromatographed. Purification of the crude material by silica gel chromatography using an ISCO machine (120 g column, 85 mL/min, 50-90% EtOAc in hexanes over 25 min, $t_r$=10 min) gave the title compound (1.089 g, 5.39 mmol, 44.5% yield) as an orange solid.

Preparation 91B: (2-Chloro-4-fluorophenyl)(3-fluoro-4-(pyrimidin-5-yl)pyridin-2-yl)methanone

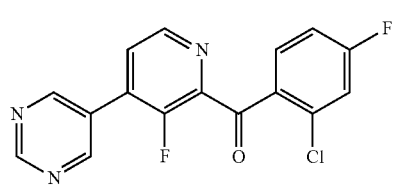
(91B)

To a solution of 2-chloro-4-fluoro-1-iodobenzene (0.307 g, 1.199 mmol) in THF (Volume: 1.622 ml) cooled to −10° C. was added isopropylmagnesium chloride, 2M in THF (0.699 ml, 1.399 mmol) in one portion. After 30 min, 3-fluoro-4-(pyrimidin-5-yl)picolinonitrile (0.200 g, 0.999 mmol) was added. The reaction mixture was stirred at −10° C. for 30 min, then allowed to warm to room temperature and stirred overnight. Water and ice were carefully added, followed by acidification with 6 M HCl. After stirring for 1 hr, CH₂Cl₂ was added and the pH was adjusted to 8.5 with aqueous 4 M NaOH. The layers were separated. The aqueous phase was extracted with CH₂Cl₂ (5×). Organics combined, dried over Na₂SO₄, filtered, and concentrated to afford an orange residue. The crude material was dissolved in a minimal amount of CH₂Cl₂ to be chromatographed. Purification of the crude material by silica gel chromatography using an ISCO machine (24 g column, 35 mL/min, 60-100% EtOAc in hexanes over 23 min, $t_r$=9 min) gave the title compound (0.029 g, 0.074 mmol, 7.44% yield) as an orange solid.

Preparation 91C: (Z)-(2-Chloro-4-fluorophenyl)(3-fluoro-4-(pyrimidin-5-yl)pyridin-2-yl)methanone oxime

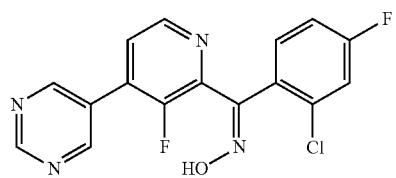
(91C)

A solution of (2-chloro-4-fluorophenyl)(3-fluoro-4-(pyrimidin-5-yl)pyridin-2-yl)methanone (0.030 g, 0.090 mmol) and hydroxylamine hydrochloride (0.043 g, 0.615 mmol) in pyridine (Volume: 0.452 ml) was refluxed for 3 hr, allowed to cool to room temperature, and then concentrated in vacuo. The crude material was dissolved in a minimal amount of CH₂Cl₂ to be chromatographed (required a few drops of MeOH). Purification of the crude material by silica gel chromatography using an ISCO machine (4 g column, 18 mL/min, 0-100% EtOAc in hexanes over 11 min, $t_r$=0.4, 2 min) gave the title compound (29 mg, 0.079 mmol, 88% yield) as a yellow residue. ESI MS (M+H)⁺=347.0.

Preparation 91D: 3-(2-Chloro-4-fluorophenyl)-7-(pyrimidin-5-yl)isoxazolo[4,5-b]pyridine

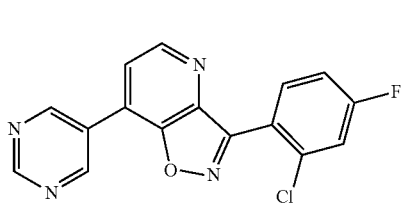
(91D)

To a suspension of sodium hydride (5.69 mg, 0.142 mmol) in THF (Ratio: 1.8, Volume: 1.075 ml) was added dropwise (Z)-(2-chloro-4-fluorophenyl)(3-fluoro-4-(pyrimidin-5-yl)pyridin-2-yl)methanone oxime (0.029 g, 0.084 mmol) in DMF (Ratio: 1.0, Volume: 0.597 ml) slowly. The reaction mixture was heated at 70° C. for 3 hr, and then allowed to cool to room temperature. The reaction was quenched with H$_2$O. The reaction mixture was extracted with EtOAc (3×). The organic phases were combined, dried over Na$_2$SO$_4$, filtered, concentrated, and further dried under high vacuum to afford a brown residue. The crude material was dissolved in a minimal amount of CH$_2$Cl$_2$ to be chromatographed. Purification of the crude material by silica gel chromatography using an ISCO machine (4 g column, 18 mL/min, 0-80% EtOAc in hexanes over 15 min, t$_r$=3 min) gave the title compound (10.3 mg, 0.028 mmol, 33.9% yield) as a yellow solid. ESI MS (M+H)$^+$=327.0.

Preparation 91E: 5-(3-(2-Chloro-4-fluorophenyl-isoxazolo[4,5-b]pyridin-7-yl)pyrimidin-4-ol

(91E)

To a vial charged with 3-(2-chloro-4-fluorophenyl)-7-(pyrimidin-5-yl)isoxazolo[4,5-b]pyridine (4.8 mg, 0.015 mmol) in acetone (Volume: 100 µl) were added peroxyacetic acid (6.18 µl, 0.029 mmol) and sulfuric acid (1.632 µl, 0.029 mmol). The reaction mixture was refluxed for 75 min, and then allowed to cool to room temperature. The reaction mixture was neutralized with 4 M NaOH and extracted with CH$_2$Cl$_2$ (5×). The organic phases were combined, dried over Na$_2$SO$_4$, filtered, and concentrated to afford the title compound as a yellow residue (5.0 mg, 99%). ESI MS (M+H)$^+$=343.0.

Preparation 91F: 3-(2-Chloro-4-fluorophenyl)-7-(4-chloropyrimidin-5-yl)isoxazolo[4,5-b]pyridine

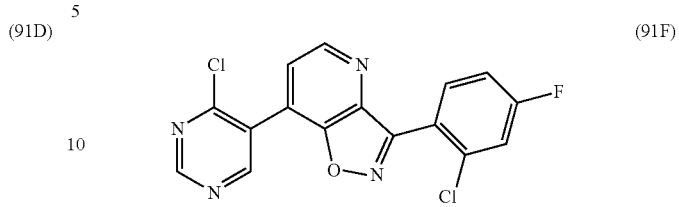
(91F)

A suspension of 5-(3-(2-chloro-4-fluorophenyl)isoxazolo[4,5-b]pyridin-7-yl)pyrimidin-4-ol (5.0 mg, 0.015 mmol) in phosphorus oxychloride (100 µl, 1.073 mmol) was heated at 90° C. for 1 h, then allowed to cool to room temperature. The solvent was evaporated to give the title compound (5.3 mg, 100%).

Example 91

A vial was charged with 4-chloro-5-iodopyrimidine (10 mg, 0.042 mmol) and freshly prepared saturated NH$_3$/MeOH (300 µL, 0.015 mmol). The reaction mixture was sealed with a Teflon lined screw cap and heated at 90° C. for 2 hr, then allowed to cool to room temperature. The solvent was evaporated. The crude material was re-dissolved in 1.5 mL DMF and purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 methanol:water with 10-mM ammonium acetate; Mobile Phase B: 95:5 methanol:water with 10-mM ammonium acetate; Gradient: 25-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-40% B over 25 minutes, then a 15-minute hold at 40% B; Flow: 20 mL/min. Fractions containing the desired product were combined and dried via centrifugal evaporation to afford the title compound (0.9 mg, 18%). ESI MS (M+H)$^+$= 342.1. HPLC Peak t$_r$=1.44 minutes. Purity=98%. HPLC Conditions: E.

Example 92

5-(3-(4-Fluorophenyl)isoxazolo[4,5-b]pyridin-7-yl)pyrimidin-4-amine

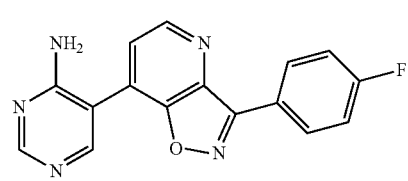
(92)

Preparation 92A: 3-Fluoro-4-(pyrimidin-5-yl)picolinonitrile

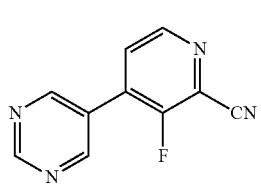

(92A)

A vial containing a mixture of 3-fluoro-4-iodopicolinonitrile (1.25 g, 5.04 mmol), pyrimidin-5-ylboronic acid (1.249 g, 10.08 mmol), and cesium carbonate (3.45 g, 10.58 mmol) in dioxane (Ratio: 2.0, Volume: 10.18 ml) and water (Ratio: 1.000, Volume: 5.09 ml) was degassed with $N_2$ for 5 min, then $PdCl_2$(dppf)-$CH_2Cl_2$Adduct (0.218 g, 0.267 mmol) was added. The solution was heated at 85° C. for 17 hr, and then allowed to cool to room temperature. The reaction was quenched with water. The reaction mixture was diluted with EtOAc. The layers were separated and the aqueous phase was extracted with EtOAc (3×). The organic phases were combined, dried over $Na_2SO_4$, filtered, and concentrated to afford a brown residue. The crude material was purified by MPLC (80 g column, 60 mL/min, 30-100% EtOAc in hexanes) to give the title compound (695 mg, 3.44 mmol, 68.2% yield) as a pink solid. ESI MS $(M+H)^+$=201.1.

Preparation 92B: 3-Fluoro-4-(4-hydroxypyrimidin-5-yl)picolinonitrile

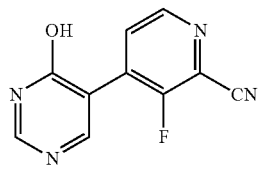

(92B)

To a vial charged with 3-fluoro-4-(pyrimidin-5-yl)picolinonitrile (0.400 g, 1.998 mmol) in acetone (Volume: 11.89 ml) were added peroxyacetic acid (0.841 ml, 4.00 mmol) and sulfuric acid (0.222 ml, 4.00 mmol). The reaction mixture was refluxed for 1 h, and then allowed to cool to room temperature. The reaction mixture was neutralized with 4 M NaOH and extracted with $CH_2Cl_2$ (5×). The organic phases were combined, dried over $Na_2SO_4$, filtered, and concentrated to afford a yellow residue. The crude material was dissolved in a minimal amount of $CH_2Cl_2$ to be chromatographed. Purification of the crude material by silica gel chromatography using an ISCO machine (40 g column, 40 mL/min, 0-25% MeOH in $CH_2Cl_2$ over 25 min, $t_r$=16 min) gave the title compound (263 mg, 1.204 mmol, 60.3% yield) as a yellow solid. ESI MS $(M+H)^+$=217.1.

Preparation 92C: (3-Fluoro-4-(4-hydroxypyrimidin-5-yl)pyridin-2-yl)(4-fluorophenyl)methanone

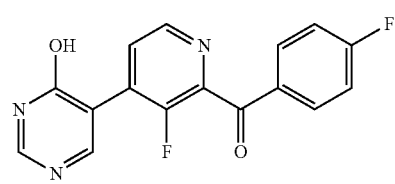

(92C)

To a solution of 3-fluoro-4-(4-hydroxypyrimidin-5-yl)picolinonitrile (0.152 g, 0.703 mmol) in tetrahydrofuran (Volume: 2.344 ml) cooled to 0° C. was added (4-fluorophenyl)magnesium bromide (1.055 ml, 2.109 mmol). The reaction mixture was allowed to stir at room temperature overnight. Water and ice were carefully added, followed by acidification with 6 M HCl. After stirring for 1 hr, $CH_2Cl_2$ was added and the pH was adjusted to 8.5 with aqueous 4 M NaOH. The layers were separated. The aqueous phase was extracted with $CH_2Cl_2$ (5×). Organics combined, dried over $Na_2SO_4$, filtered, and concentrated to afford an orange residue. The crude material was dissolved in a minimal amount of $CH_2Cl_2$ to be chromatographed. Purification of the crude material by silica gel chromatography using an ISCO machine (40 g column, 40 mL/min, 0-20% MeOH in $CH_2Cl_2$ over 25 min, $t_r$=13 min) gave the title compound (162 mg, 0.517 mmol, 73.5% yield) as a yellow residue. ESI MS $(M+H)^+$=314.1.

Preparation 92D: (Z)-(3-Fluoro-4-(4-hydroxypyrimidin-5-yl)pyridin-2-yl)(4-fluorophenyl)methanone oxime

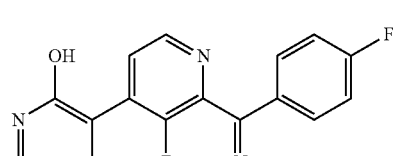

(92D)

A solution of (3-fluoro-4-(4-hydroxypyrimidin-5-yl)pyridin-2-yl)(4-fluorophenyl)methanone (0.168 g, 0.536 mmol) and hydroxylamine hydrochloride (0.039 g, 0.563 mmol) in Pyridine (Volume: 2.68 ml) was refluxed for 1.5 hr, allowed to cool to room temperature, and then concentrated in vacuo. Solvent was evaporated. The crude material was dissolved in a minimal amount of $CH_2Cl_2$ to be chromatographed (required a few drops of MeOH). Purification of the crude material by silica gel chromatography using an ISCO machine (24 g column, 35 mL/min, 1-25% MeOH in $CH_2Cl_2$ over 19 min, $t_r$=12 min) gave the title compound (0.123 g, 0.371 mmol, 69.2% yield) as a tan solid. ESI MS $(M+H)^+$=329.1.

Preparation 92E: 5-(3-(4-Fluorophenyl)isoxazolo[4,5-b]pyridin-7-yl)pyrimidin-4-ol

(92E)

To a suspension of sodium hydride (0.030 g, 0.742 mmol) in THF (Ratio: 1.8, Volume: 2.272 ml) was added dropwise (Z)-(3-fluoro-4-(4-hydroxypyrimidin-5-yl)pyridin-2-yl)(4-fluorophenyl)methanone oxime (0.116 g, 0.353 mmol) in DMF (Ratio: 1.0, Volume: 1.262 ml) slowly. The reaction mixture was heated at 70° C. for 3.5 hr. Additional NaH (12 mg) was added. The reaction mixture was heated at 70° C. for 2.5 hr, and then allowed to cool to room temperature. The solvent was evaporated, and the mixture was further concentrated in vacuo to afford a brown residue. The crude material was dissolved in a minimal amount of $CH_2Cl_2$ to be chromatographed (required a few drops of MeOH). Purification of the crude material by silica gel chromatography using an ISCO machine (24 g column, 35 mL/min, 0-30% MeOH in $CH_2Cl_2$ over 25 min, $t_r$=9 min) gave the title compound (53.4 mg, 0.173 mmol, 49.0% yield) as a yellow solid. ESI MS $(M+H)^+$=309.1.

Preparation 92F: 7-(4-Chloropyrimidin-5-yl)-3-(4-fluorophenyl)isoxazolo[4,5-b]pyridine

(92F)

A suspension of 5-(3-(4-fluorophenyl)isoxazolo[4,5-b]pyridin-7-yl)pyrimidin-4-ol (45 mg, 0.146 mmol) in phosphorus oxychloride (503 µl, 5.40 mmol) was heated at 90° C. for 1 h, then allowed to cool to room temperature. The solvent was evaporated to afford the title compound (48 mg, 100%).

Example 92

A vial was charged with 4-chloro-5-iodopyrimidine (10 mg, 0.042 mmol) and freshly prepared saturated $NH_3$/MeOH (0.147 mmol). The reaction mixture was sealed with a Teflon lined screw cap and heated at 90° C. for 2 hr, and then allowed to cool to room temperature. Upon cooling the reaction to room temperature, a solid precipitated and was filtered. The solid was washed with MeOH, $CH_2Cl_2$, $CH_3CN$, and THF to give the title compound (4.7 mg, 10%) as a light brown solid. ESI MS $(M+H)^+$=308.1. HPLC Peak $t_r$=1.98 minutes. Purity=98%. HPLC Conditions: C.

Example 93

7-(4-Methylpyridin-3-yl)-3-(pyridin-2-yl)thieno[3,2-b]pyridine

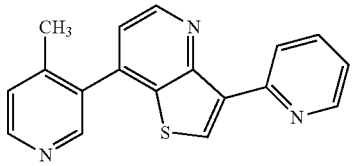

(93)

Preparation 93A: 7-Chlorothieno[3,2-b]pyridine

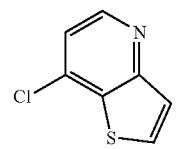

(93A)

A suspension of thieno[3,2-b]pyridin-7-ol (4.6 g, 30.4 mmol) in $POCl_3$ (15 mL, 30.4 mmol) was refluxed at 105° C. for 4 hr. The solvent was evaporated to afford a dark brown oil that was cooled in an ice bath and diluted with cold water. The aqueous layer was adjusted to a basic pH (~8) by adding an $NH_4OH$ solution. The aqueous mixture was extracted with EtOAc and DCM. The combined organic layers were washed with brine, dried over $Na_2SO_4$, filtered, and concentrated to afford an oil. Purification of the crude material by silica gel chromatography using a BIOTAGE® machine (hexanes:ethyl acetate 75:25) afforded the title compound as a pale buff solid (4.7 g, 91%). ESI MS $(M+H)^+$=170.0.

Preparation 93B: 7-(4-Methylpyridin-3-yl)thieno[3,2-b]pyridine

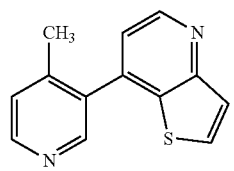

(93B)

A vessel capable of sealing was charged with a mixture of Preparation 93A (0.82 g, 4.83 mmol), 4-methylpyridin-3-ylboronic acid (0.993 g, 7.25 mmol), $Pd(Ph_3P)_4$ (279 mg, 0.242 mmol), dioxane (15 mL), and a 2.0 M aqueous solution of $K_3PO_4$ (7.2 mL, 14.5 mmol) and was purged with nitrogen for 10 min. The vessel was sealed and heated at 90° C. for 16 hours. Upon cooling, the reaction mixture was diluted with water and extracted with $CH_2Cl_2$. The combined organics were washed with brine, dried over anhydrous $Na_2SO_4$ and concentrated under reduced pressure. The crude material was purified by BIOTAGE® eluting with 30%-100% EtOAc/CH$_2$Cl$_2$ at 30 mL/min. Concentration of appropriate fractions provided the title compound (540 mg, 49% yield). LC/MS: Example 93B @ 0.40 min (RT) (Condition G). MS (ES): m/z=227.06 [M+H]$^+$. $^1$H NMR (400 MHz, CDCl$_3$) δ ppm 8.81 (1 hr, d, J=4.53 Hz), 8.62 (1 hr, d, J=5.29 Hz), 8.57 (1 hr, s), 7.81 (1 hr, d, J=5.54 Hz), 7.68 (1 hr, d, J=5.54 Hz), 7.34 (1 hr, d, J=5.04 Hz), 7.18 (1 hr, d, J=4.78 Hz), 2.25 (3 hr, s).

Preparation 93C: 3-Bromo-7-(4-methylpyridin-3-yl)thieno[3,2-b]pyridine

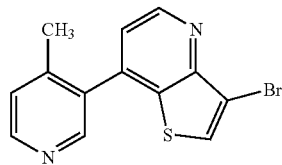

(93C)

To a stirring solution of Preparation 93B (540 mg, 2.386 mmol) in methylene chloride (15 mL) was added Br$_2$ (0.25 mL, 4.77 mmol) in methylene chloride (2 mL). The reaction mixture was stirred at room temperature for 16 hours. The reaction mixture was quenched with saturated NaHCO$_3$ and extracted with CH$_2$Cl$_2$. The combined organics were washed with brine, dried over anhydrous Na$_2$SO$_4$ and concentrated under reduced pressure. The crude material was purified by BIOTAGE® eluting with 40%-80% EtOAc/CH$_2$Cl$_2$ at 30 mL/min. Concentration of appropriate fractions provided the title compound (560 mg, 77% yield). LC/MS: Example 93C @ 1.25 min (RT) (Condition G). MS (ES): m/z=304.92; [M+H]$^+$. $^1$H NMR (400 MHz, CDCl$_3$) δ ppm 8.92 (1 hr, d, J=4.53 Hz), 8.60 (1 hr, d, J=5.04 Hz), 8.52 (1 hr, s), 7.83 (1 hr, s), 7.32 (1 hr, d, J=5.04 Hz), 7.25 (1 hr, d, J=4.78 Hz), 2.20 (3 hr, s).

Example 93

A vessel capable of sealing was charged with a mixture of Preparation 93C (40 mg, 0.131 mmol), 2-(tributylstannyl)pyridine (72.4 mg, 0.197 mmol), Pd(Ph$_3$P)$_4$ (7.57 mg, 6.55 µmol), and dioxane (3 mL) and was purged with nitrogen for 10 min. The vessel was sealed and heated at 100° C. for 16 hours. Upon cooling, the reaction mixture was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white powder (27.2 mg, 64.3% yield). LC/MS: Example 93 @ 0.83 min (RT) (Condition G). MS (ES): m/z=304.07 [M+H]$^+$. $^1$H NMR (400 MHz, CDCl$_3$) δ ppm 9.05 (1 hr, br. s.), 8.94 (1 hr, d, J=4.78 Hz), 8.78 (1 hr, d, J=5.04 Hz), 8.65 (1 hr, d, J=5.04 Hz), 8.60 (1 hr, s), 8.03 (1 hr, br. s.), 7.42 (1 hr, br. s.), 7.37 (1 hr, d, J=5.54 Hz), 7.20-7.32 (2 hr, m), 2.26 (3 hr, s).

Example 94

7-(4-Methylpyridin-3-yl)-3-(thiazol-2-yl)thieno[3,2-b]pyridine

(94)

A vessel capable of sealing was charged with a mixture of Preparation 93B (30 mg, 0.098 mmol), 2-(tributylstannyl)thiazole (73.6 mg, 0.197 mmol), Pd(Ph$_3$P)$_4$ (7.57 mg, 6.55 µmol), and dioxane (3 mL) and was purged with nitrogen for 10 min. The vessel was sealed and heated at 100° C. for 16 hours. Upon cooling, the reaction mixture was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white powder (26.7 mg, 86% yield). LC/MS: Example 94 @ 1.67 min (RT) (Condition G). MS (ES): m/z=310.00 [M+H]$^+$. $^1$H NMR (400 MHz, MeOD) δ ppm 9.02 (1 hr, d, J=4.53 Hz), 8.94 (1 hr, s), 8.85 (1 hr, d, J=6.04 Hz), 8.81 (1 hr, s), 8.11 (1 hr, d, J=6.04 Hz), 7.99 (1 hr, d, J=3.27 Hz), 7.76 (1 hr, d, J=3.52 Hz), 7.56 (1 hr, d, J=4.78 Hz), 2.49 (3 hr, s).

Example 95

7-(4-Methylpyridin-3-yl)-3-(pyrazin-2-yl)thieno[3,2-b]pyridine

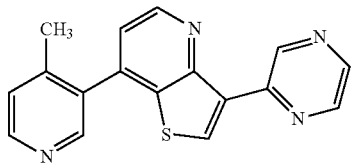

(95)

A vessel capable of sealing was charged with a mixture of Preparation 93B (40 mg, 0.131 mmol), 2-(tributylstannyl)pyrazine (72.6 mg, 0.197 mmol), Pd(Ph$_3$P)$_4$ (7.57 mg, 6.55 µmol), and dioxane (3 mL) and was purged with nitrogen for 10 min. The vessel was sealed and heated at 100° C. for 16 hours. Upon cooling, the reaction mixture was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as clear viscous oil (17 mg, 52.3% yield). LC/MS: Example 95 @ 0.1.23 min (RT) (Condition G). MS (ES): m/z=305.07 [M+H]$^+$. $^1$H NMR (400 MHz, MeOD) δ ppm 10.00 (1 hr, d, J=1.51 Hz), 9.04 (1 hr, d, J=4.78 Hz), 8.95 (2 hr, d, J=10.83 Hz), 8.86 (1 hr, d, J=5.79 Hz), 8.75 (1 hr, dd, J=2.52, 1.51 Hz), 8.61 (1 hr, d, J=2.52 Hz), 8.10 (1 hr, d, J=6.04 Hz), 7.61 (1 hr, d, J=5.04 Hz), 2.49 (3 hr, s).

Example 96

3-(4-Fluorophenyl)-7-(4-methylpyridin-3-yl)thieno[3,2-b]pyridine

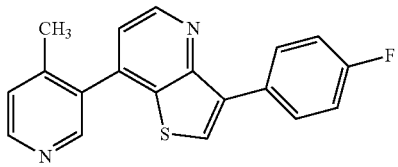

(96)

A vessel capable of sealing was charged with a mixture of Preparation 93B (40 mg, 0.131 mmol), 4-fluorophenylboronic acid (27.5 mg, 0.197 mmol), PdCl$_2$(dppf)-CH$_2$Cl$_2$ adduct (5.4 mg, 6.55 μmol), dioxane (2 mL), and a 2.0 M aqueous solution of K$_3$PO$_4$ (0.2 mL, 0.393 mmol) and was purged with nitrogen for 10 min. The vessel was sealed and heated at 90° C. for 16 hours. Upon cooling, the reaction mixture was diluted with CH$_2$Cl$_2$ (10 mL) and filtered with CH$_2$Cl$_2$/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white powder (24.9 mg, 58.7% yield). LC/MS: Example 96 @ 2.20 min (RT) (Condition G). MS (ES): m/z=321.07, [M+H]$^+$. $^1$H NMR (400 MHz, CDCl$_3$) δ ppm 8.91 (1 hr, d, J=4.53 Hz), 8.66 (1 hr, d, J=5.29 Hz), 8.62 (1 hr, s), 7.90-8.06 (2 hr, m), 7.84 (1 hr, s), 7.45 (1 hr, t, J=6.30 Hz), 7.13-7.36 (3 hr, m), 2.32 (3 hr, d, J=3.27 Hz).

Example 97

7-(4-Methylpyridin-3-yl)-3-phenylthieno[3,2-b]pyridine

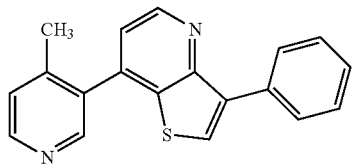

(97)

A vessel capable of sealing was charged with a mixture of Preparation 93B (30 mg, 0.0.098 mmol), phenylboronic acid (18 mg, 0.147 mmol), PdCl$_2$(dppf)-CH$_2$Cl$_2$ adduct (8 mg, 9.8 μmol), dioxane (2 mL), and a 2.0 M aqueous solution of K$_3$PO$_4$ (0.15 mL, 0.295 mmol) and was purged with nitrogen for 10 min. The vessel was sealed and heated at 90° C. for 16 hours. Upon cooling, the reaction mixture was diluted with CH$_2$Cl$_2$ (10 mL) and filtered with CH$_2$Cl$_2$/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white powder (20.1 mg, 67% yield). LC/MS: Example 97 @ 2.08 min (RT) (Condition G). MS (ES): m/z=303.06, [M+H]$^+$. $^1$H NMR (400 MHz, CDCl$_3$) δ ppm 8.95 (1 hr, d, J=4.53 Hz), 8.70 (1 hr, d, J=5.54 Hz), 8.66 (1 hr, s), 7.95-8.06 (2 hr, m), 7.90 (1 hr, s), 7.51-7.65 (3 hr, m), 7.38-7.51 (1 hr, m), 7.24 (1 hr, d, J=4.53 Hz), 2.41 (3 hr, s).

Example 98

3-(4-Fluorophenyl)-7-(4-methylpyrimidin-5-yl)thieno[3,2-b]pyridine

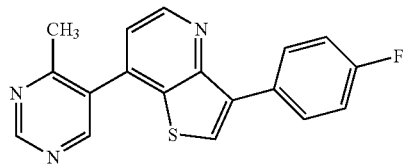

(98)

Preparation 98A:
7-Chloro-3-(4-fluorophenyl)thieno[3,2-b]pyridine

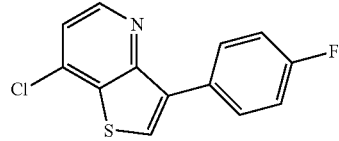

(98A)

A vessel capable of sealing was charged with a mixture of 3-bromo-7-chlorothieno[3,2-b]pyridine (500 mg, 2.012 mmol), 4-fluorophenylboronic acid (310 mg, 2.213 mmol), PdCl$_2$(dppf)-CH$_2$Cl$_2$ adduct (82 mg, 0.101 mmol), dioxane (8 mL), and a 2.0 M aqueous solution of K$_3$PO$_4$ (3 mL, 6.04 mmol) and was purged with nitrogen for 10 min. The vessel was sealed and heated at 90° C. for 1 h. Upon cooling, the reaction mixture was diluted with water and extracted with CH$_2$Cl$_2$. The combined organics were washed with brine, dried over anhydrous Na$_2$SO$_4$ and concentrated under reduced pressure. The crude material was purified by BIOTAGE® eluting with 40%-80% EtOAc/CH$_2$Cl$_2$ at 30 mL/min. Concentration of appropriate fractions provided the title compound (450 mg, 49% yield) as a white powder. LC/MS: Example 98A @ 3.62 min (RT) (Condition G). MS (ES): m/z=263.03, [M+H]$^+$.

Example 98

A vessel capable of sealing was charged with a mixture of Preparation 98A (65 mg, 0.246 mmol), 4-methylpyrimidin-5-ylboronic acid (51.0 mg, 0.370 mmol), Pd(Ph$_3$P)$_4$ (14.24 mg, 0.012 mmol), dioxane (4 mL), and a 2.0 M aqueous solution of K$_3$PO$_4$ (0.4 mL, 0.739 mmol) and was purged with nitrogen for 10 min. The vessel was sealed and heated at 90° C. for 3 hours. Upon cooling, the reaction mixture was diluted with CH₂Cl₂ (10 mL) and filtered with CH₂Cl₂/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as yellow oil (80 mg, 85.1% yield). LC/MS: Example 98 @ 3.19 min (RT) (Condition G). MS (ES): m/z=322.08, [M+H]⁺. ¹H NRM (400 MHz, MeOD) δ ppm 9.21 (1 hr, s), 8.88 (1 hr, d, J=5.02 Hz), 8.79 (1 hr, s), 8.18 (1 hr, s), 7.98 (2 hr, dd, J=9.03, 5.52 Hz), 7.51 (1 hr, d, J=4.77 Hz), 7.25 (2 hr, t, J=8.91 Hz), 2.48 (3 hr, s).

Example 99

7-(4-Cyclopropylpyrimidin-5-yl)-3-(4-fluorophenyl)thieno[3,2-b]pyridine

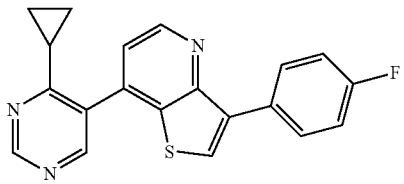

(99)

Preparation 99A:
4-Cyclopropylpyrimidin-5-ylboronic acid

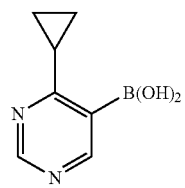

(99A)

A vessel capable of sealing was charged with a mixture of Preparation 11A (140 mg, 0.703 mmol), 4,4,4',4',5,5,5',5'-octamethyl-2,2'-bi(1,3,2-dioxaborolane) (268 mg, 1.055 mmol), potassium acetate (207 mg, 2.110 mmol), PdCl₂(dppf)-CH₂Cl₂adduct (28.7 mg, 0.035 mmol), and dioxane (6 mL) and was purged with nitrogen for 10 min. The vessel was sealed and heated to 90° C. for 3 hours. Upon cooling, the reaction mixture was diluted with EtOAc (20 mL) and filtered with EtOAc. The filtrate was concentrated under reduced pressure. LC/MS: Example 99A @ 0.52 min (RT) (Condition G). MS (ES): m/z=164.17, [M+H]⁺.

Example 99

A vessel capable of sealing was charged with a mixture of Preparation 98A (65 mg, 0.246 mmol), Preparation 99A (60.6 mg, 0.370 mmol), Pd(Ph₃P)₄ (14.24 mg, 0.012 mmol), dioxane (4 mL), and a 2.0 M aqueous solution of K₃PO₄ (0.4 mL, 0.739 mmol) and was purged with nitrogen for 10 min. The vessel was sealed and heated at 90° C. for 3 hours. Upon cooling, the reaction mixture was diluted with CH₂Cl₂ (10 mL) and filtered with CH₂Cl₂/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white solid (50.8 mg, 44.5% yield). HPLC/MS: Example 99 @ 3.57 min (RT) (Condition G). MS (ES): m/z=348.09, [M+H]⁺. ¹H NMR (400 MHz, MeOD) δ ppm 9.09 (1 hr, s), 8.88 (1 hr, d, J=4.77 Hz), 8.65 (1 hr, s), 8.15 (1 hr, s), 7.93-8.08 (2 hr, m), 7.52 (1 hr, d, J=4.77 Hz), 7.16-7.39 (2 hr, m), 1.74-1.98 (1 hr, m), 1.35 (2 hr, quin, J=3.70 Hz), 0.99-1.22 (2 hr, m).

Example 100

5-(3-(4-Fluorophenyl)thieno[3,2-b]pyridin-7-yl)pyrimidin-4-amine

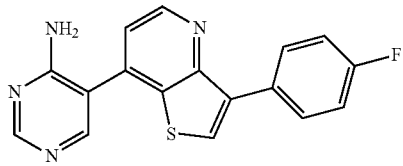

(100)

A vessel capable of sealing was charged with a mixture of Preparation 98A (120 mg, 0.455 mmol), 4-aminopyrimidin-5-ylboronic acid (126 mg, 0.910 mmol), Pd(Ph₃P)₄ (26.3 mg, 0.023 mmol), dioxane (10 mL), and a 2.0 M aqueous solution of K₃PO₄ (0.68 mL, 1.365 mmol) and was purged with nitrogen for 10 min. The vessel was sealed and heated at 90° C. for 6 hours. Upon cooling, the reaction mixture was diluted with CH₂Cl₂ (10 mL) and filtered with CH₂Cl₂/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white powder (45 mg, 30.7% yield). LC/MS: Example 100 @ 2.13 min (RT) (Condition G). MS (ES): m/z=357.08, [M+H]⁺. ¹H NMR (400 MHz, MeOD) δ ppm 8.90 (1 hr, d, J=4.77 Hz), 8.80 (1 hr, d, J=1.51 Hz), 8.47 (1 hr, d, J=1.25 Hz), 8.20 (1 hr, s), 8.04 (2 hr, dd, J=8.91, 5.40 Hz), 7.54 (1 hr, d, J=4.77 Hz), 7.26 (2 hr, t, J=8.91 Hz).

Example 101

5-(3-(4-Fluoro-2-(trifluoromethyl)phenyl)thieno[3,2-b]pyridin-7-yl)pyrimidin-4-amine

(101)

Preparation 101A: 7-Chloro-3-(4-fluoro-2-(trifluoromethyl)phenyl)thieno[3,2-b]pyridine

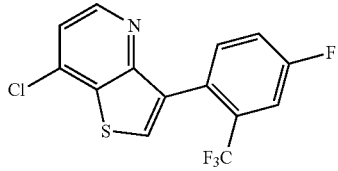
(101A)

A vessel capable of sealing was charged with a mixture of 3-bromo-7-chlorothieno[3,2-b]pyridine (123 mg, 0.495 mmol), 4-fluoro-2-(trifluoromethyl) phenylboronic acid (123 mg, 0.594 mmol), $PdCl_2$(dppf)-$CH_2Cl_2$ adduct (20.21 mg, 0.0.025 mmol), dioxane (6 mL), and a 2.0 M aqueous solution of $K_3PO_4$ (0.74 mL, 1.485 mmol) and was purged with nitrogen for 10 min. The vessel was sealed and heated at 90° C. for 3 hours. Upon cooling, the reaction mixture was diluted with $CH_2Cl_2$ and filtered with $CH_2Cl_2$/MeOH washing. The filtrate was concentrated under reduced pressure. The residue was dissolved in $CH_2Cl_2$ and washed with water, brine, dried over anhydrous $Na_2SO_4$ and concentrated under reduced pressure. The crude material was purified by BIOTAGE® eluting with 40%-60% $CH_2Cl_2$/hexanes at 30 mL/min. Concentration of appropriate fractions provided the title compound (150 mg, 91% yield) as a white solid. LC/MS: Example 101A @ 3.94 min (RT) (Condition G). MS (ES): m/z=331.94, $[M+H]^+$.

Example 101

A vessel capable of sealing was charged with a mixture of Preparation 101A (80 mg, 0.241 mmol), 4-aminopyrimidin-5-ylboronic acid (67.0 mg, 0.482 mmol), $Pd(Ph_3P)_4$ (13.9 mg, 0.012 mmol), dioxane (4 mL), and a 2.0 M aqueous solution of $K_3PO_4$ (0.36 mL, 0.724 mmol) and was purged with nitrogen for 10 min. The vessel was sealed and heated at 90° C. for 6 hours. Upon cooling, the reaction mixture was diluted with $CH_2Cl_2$ (10 mL) and filtered with $CH_2Cl_2$/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white powder (20.8 mg, 21.6% yield). LC/MS: Example 101 @ 2.13 min (RT) (Condition G). MS (ES): m/z=357.08, $[M+H]^+$. $^1$H NMR (400 MHz, MeOD) δ ppm 8.96 (1 hr, d, J=4.77 Hz), 8.81 (1 hr, d, J=1.51 Hz), 8.53 (1 hr, dd, J=6.78, 2.01 Hz), 8.48 (1 hr, d, J=1.51 Hz), 8.39 (1 hr, s), 8.21-8.38 (1 hr, m), 7.57 (1 hr, d, J=4.77 Hz), 7.40-7.54 (1 hr, m).

Example 102

5-(3-(2,4-Difluorophenyl)thieno[3,2-b]pyridin-7-yl)pyrimidin-4-amine

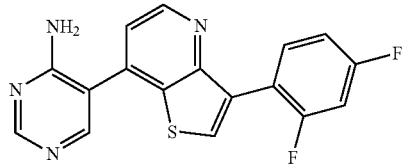
(102)

Preparation 102A: 7-Chloro-3-(2,4-difluorophenyl)thieno[3,2-b]pyridine

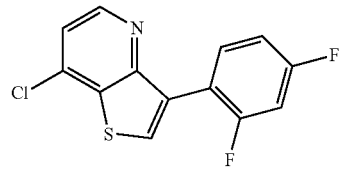
(102A)

A vessel capable of sealing was charged with a mixture of 3-bromo-7-chlorothieno[3,2-b]pyridine (110 mg, 0.443 mmol), 2,4-difluorophenylboronic acid (84 mg, 0.531 mmol), $PdCl_2$(dppf)-$CH_2Cl_2$ adduct (18.1 mg, 0.022 mmol), dioxane (3 mL), and a 2.0 M aqueous solution of $K_3PO_4$ (0.66 mL, 1.328 mmol) and was purged with nitrogen for 10 min. The vessel was sealed and heated at 90° C. for 3 hours. Upon cooling, the reaction mixture was diluted with water and extracted with $CH_2Cl_2$. The combined organics were washed with brine, dried over anhydrous $Na_2SO_4$ and concentrated under reduced pressure. The crude material was purified by BIOTAGE® eluting with 30%-60% $CH_2Cl_2$/hexanes at 30 mL/min. Concentration of appropriate fractions provided the title compound (450 mg, 49% yield) as a white powder. LC/MS: Example 102A @ 3.60 min (RT) (Condition G). MS (ES): m/z=282.02/284.02, $[M+H]^+$.

Example 102

A vessel capable of sealing was charged with a mixture of Preparation 102A (90 mg, 0.319 mmol), 4-aminopyrimidin-5-ylboronic acid (89 mg, 0.639 mmol), $Pd(Ph_3P)_4$ (18.5 mg, 0.016 mmol), dioxane (6 mL), and a 2.0 M aqueous solution of $K_3PO_4$ (0.48 mL, 0.958 mmol) and was purged with nitrogen for 10 min. The vessel was sealed and heated at 90° C. for 6 hours. Upon cooling, the reaction mixture was diluted with $CH_2Cl_2$ (10 mL) and filtered with $CH_2Cl_2$/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white powder (6.6 mg, 5.8% yield). LC/MS: Example 102 @ 2.25 min (RT) (Condition G). MS (ES): m/z=341.08, $[M+H]^+$. $^1$H NMR (400 MHz, MeOD) δ ppm 8.87 (1 hr, d, J=4.77 Hz), 8.81 (1 hr, d, J=1.51 Hz), 8.48 (1 hr, d, J=1.26 Hz), 8.24 (1 hr, d, J=1.00 Hz), 7.93 (1 hr, td, J=8.66, 6.53 Hz), 7.56 (1 hr, d, J=4.77 Hz), 7.08-7.24 (2 hr, m).

Example 103

5-(3-(2-Chloro-4-fluorophenyl)thieno[3,2-b]pyridin-7-yl)pyrimidin-4-amine

(103)

Preparation 103A: 7-Chloro-3-(2-chloro-4-fluorophenyl)thieno[3,2-b]pyridine

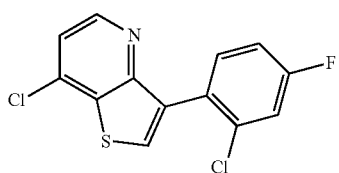

(103A)

A vessel capable of sealing was charged with a mixture of 3-bromo-7-chlorothieno[3,2-b]pyridine (260 mg, 1.046 mmol), 2-chloro-4-fluorophenylboronic acid (274 mg, 1.569 mmol), PdCl$_2$(dppf)-CH$_2$Cl$_2$ adduct (42.7 mg, 0.0052 mmol), dioxane (8 mL), and a 2.0 M aqueous solution of K$_3$PO$_4$ (1.6 mL, 3.14 mmol) and was purged with nitrogen for 10 min. The vessel was sealed and heated at 90° C. for 3 h. Upon cooling, the reaction mixture was diluted with water and extracted with CH$_2$Cl$_2$. The combined organics were washed with brine, dried over anhydrous Na$_2$SO$_4$ and concentrated under reduced pressure. The crude material was purified by BIOTAGE® eluting with 60%-100% CH$_2$Cl$_2$/hexanes at 30 mL/min. Concentration of appropriate fractions provided the title compound (250 mg, 80% yield) as a white solid. LC/MS: Example 103A @ 3.58 min (RT) (Condition G). MS (ES): m/z=297.89, [M+H]+.

Preparation 103B: 3-(2-Chloro-4-fluorophenyl)-7-iodothieno[3,2-b]pyridine

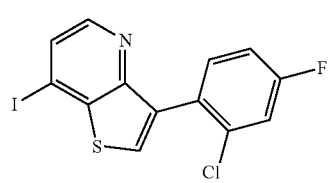

(103B)

A mixture of Preparation 103A (180 mg, 0.604 mmol) and HI (5 mL, 47% water solution, excess) was heated at 100° C. overnight. The reaction mixture was cooled to room temperature, carefully quenched with NaHCO$_3$, and extracted with CH$_2$Cl$_2$. The combined organics were washed with brine, dried over anhydrous Na$_2$SO$_4$ and concentrated under reduced pressure. The crude material was used for the next step without purification. LC/MS: Example 103B @ 3.04 min (RT) (Condition G). MS (ES): m/z=298.01, [M+H]$^+$.

Example 103

A vessel capable of sealing was charged with a mixture of Preparation 103B (130 mg, 0.334 mmol), 4-aminopyrimidin-5-ylboronic acid (69.5 mg, 0.500 mmol), PdCl$_2$(dppf)-CH$_2$Cl$_2$ adduct (13.62 mg, 0.017 mmol), dioxane (2 mL), and a 2.0 M aqueous solution of K$_3$PO$_4$ (0.5 mL, 1.00 mmol) and was purged with nitrogen for 10 min. The vessel was sealed and heated at 80° C. for 2 hours. Upon cooling, the reaction mixture was diluted with CH$_2$Cl$_2$ (10 mL) and filtered with CH$_2$Cl$_2$/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white powder (50.8 mg, 44.5% yield). LC/MS: Example 103 @ 2.13 min (RT) (Condition G). MS (ES): m/z=357.08, [M+H]$^+$. $^1$H NMR (400 MHz, DMSO-d$_6$) δ ppm 8.75 (1 hr, d, J=4.77 Hz), 8.52 (1 hr, s), 8.29 (2 hr, d, J=17.07 Hz), 7.65 (2 hr, dd, J=8.41, 2.13 Hz), 7.46 (1 hr, d, J=4.77 Hz), 7.39 (1 hr, td, J=8.53, 2.76 Hz).

Example 104

N-(3-Amino-7-(4-methylpyridin-3-yl)benzo[d]isoxazol-4-yl)methanesulfonamide

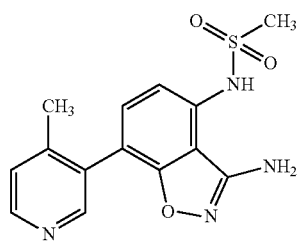

(104)

Preparation 104A:
6-Amino-2-fluoro-3-iodobenzonitrile

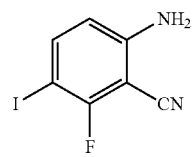

(104A)

To a solution of 2-amino-6-fluorobenzonitrile (3 g, 0.022 mol) in CH$_2$Cl$_2$ (200 mL) and MeOH (50 mL) was added sodium bicarbonate (3.7 g, 0.044 mmol) and ICl (3.75 g, 0.023 mol) in CH$_2$Cl$_2$ (20 mL). The suspension was stirred at room temperature for 2 h. The reaction mixture was concentrated and the residue was partitioned between CH$_2$Cl$_2$ and water. The organic layer was washed with Na$_2$S$_2$O$_3$, water, and brine. The organic layer was dried over Na$_2$SO$_4$ and concentrated under reduced pressure. The crude material was triturated with ether. Filtration gave the title compound as a brown solid (2.5 g, 43% yield). LC/MS: Example 104A @ 2.86 min (RT) (Condition G). MS (ES): m/z=262.93, [M+H]$^+$. $^1$H NMR (400 MHz, CDCl$_3$) δ ppm 7.60 (1 hr, dd, J=8.78, 7.03 Hz), 6.39 (1 hr, d, J=8 Hz).

Preparation 104B: N-(2-Cyano-3-fluoro-4-iodophenyl)methanesulfonamide

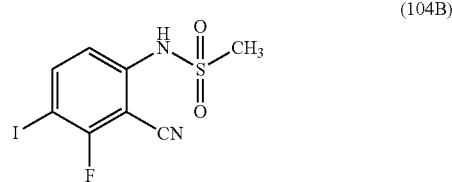

(104B)

To a solution of Preparation 104A (2.2 g, 8.40 mmol) in pyridine (15 mL) was added methanesulfonyl chloride (1.010 g, 8.82 mmol). The reaction mixture was heated at 80° C. for 5 hours. After 5 hours, methanesulfonyl chloride (200 mg) was added to the reaction mixture. The reaction mixture was heated at 80° C. for another 2 hours. Upon cooling, the reaction mixture was diluted with water and extracted with CH$_2$Cl$_2$. The combined organics were washed with brine, dried over anhydrous Na$_2$SO$_4$ and concentrated under reduced pressure. The crude material was purified by BIOTAGE® eluting with 10%-50% EtOAc/CH$_2$Cl$_2$ at 30 mL/min. Concentration of appropriate fractions provided the title compound (830 mg, 29% yield) as a white powder. LC/MS: Example 104B @ 2.44 min (RT) (Condition G). MS (ES): m/z=340.92, [M+H]$^+$. $^1$H NMR (400 MHz, MeOD) δ ppm 8.08 (1 hr, dd, J=8.78, 7.03 Hz), 7.26 (1 hr, dd, J=8.78, 1.00 Hz), 3.16 (3 hr, s).

Preparation 104C: N-(3-Amino-7-iodobenzo[d]isoxazol-4-yl)methanesulfonamide

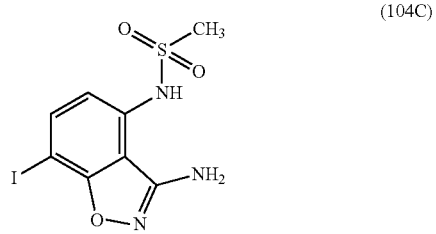 [SMILES: CS(=O)(=O)Nc1ccc(I)c2onc(N)c12]

(104C)

To a solution of Preparation 104B (800 mg, 2.352 mmol) in DMF/water (1:1, 14 mL) were added N-hydroxyacetamide (706 mg, 9.41 mmol) and potassium carbonate (1.63 g, 11.76 mmol). The reaction mixture was heated to 80° C. overnight. Upon cooling, the reaction mixture was diluted with water (30 mL) and extracted with 20% MeOH/CHCl$_3$. The combined organics were washed with brine, dried over anhydrous Na$_2$SO$_4$ and concentrated under reduced pressure. The crude material was purified by BIOTAGE® eluting with 10%-40% EtOAc/CH$_2$Cl$_2$ at 30 mL/min. Concentration of appropriate fractions provided the title compound (350 mg, 42.1% yield) as a white solid. LC/MS: Example 104C @ 2.18 min (RT) (Condition G). MS (ES): m/z=353.95, [M+H]$^+$.

Example 104

A vessel capable of sealing was charged with a mixture of Preparation 104C 2 TFA (36 mg, 0.062 mmol), 4-methylpyridin-3-ylboronic acid (16.97 mg, 0.124 mmol), mmol), Pd(Ph$_3$P)$_4$ (7.16 mg, 6.19 μmol), dioxane (2 mL), and a 2.0 M aqueous solution of K$_3$PO$_4$ (0.12 mL, 0.310 mmol) and was purged with nitrogen for 10 min. The vessel was sealed and heated at 80° C. for 12 hours. Upon cooling, the reaction mixture was diluted with CH$_2$Cl$_2$ (10 mL) and filtered with CH$_2$Cl$_2$/MeOH washing. The filtrate was concentrated under reduced pressure. The crude material was purified by preparative HPLC. The HPLC fractions that contained the product were concentrated with SPEEDVAC® and applied onto a MCX. The material was washed with methanol and the product was eluted with 2N solution of ammonia in methanol. Concentration provided the title compound as a white powder (10.6 mg, 51.6% yield). LC/MS: Example 104 @ 3.32 min (RT) (Condition G). MS (ES): m/z=355.98 [M+H]$^+$. $^1$H NMR (400 MHz, MeOD) δ ppm 8.85 (1 hr, s), 8.77 (1 hr, d, J=6.02 Hz), 8.06 (1 hr, d, J=6.02 Hz), 7.67 (1 hr, d, J=8.03 Hz), 7.43 (1 hr, d, J=7.78 Hz), 3.15 (3 hr, s).

Example 105

N-(7-(4-Methylpyridin-3-yl)benzo[b]thiophen-4-yl)methanesulfonamide

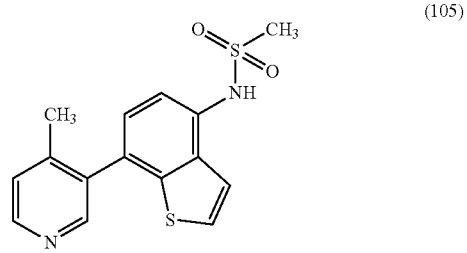 [SMILES: Cc1ccncc1-c1ccc(NS(C)(=O)=O)c2ccsc12]

(105)

Preparation 105A:
N-(Benzo[b]thiophen-4-yl)methanesulfonamide

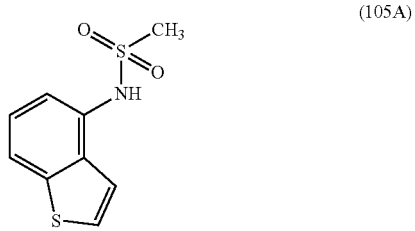

(105A)

To a stirred solution of benzo[b]thiophen-4-amine (1 g, 6.70 mmol) and pyridine (1.355 mL, 16.75 mmol) in CH$_2$Cl$_2$ (15 mL) was added dropwise methanesulfonyl chloride (0.574 mL, 7.37 mmol) at 0° C. under nitrogen atmosphere. The reaction mixture was then allowed to warm to room temperature while stirring overnight. The reaction mixture was washed with saturated sodium bicarbonate solution, water, brine and dried over sodium sulfate. Evaporation of the solvent furnished a crude residue, which was subjected to BIOTAGE® (100% methylene chloride) to give the title compound as a white solid (1.2 g, 79%). LC/MS: Example 105A @ 2.88 min (RT) (Condition H). MS (ES): m/z=226.0, [M+H]$^+$. $^1$H NMR (400 MHz, MeOD) δ ppm 7.77 (1 hr, d, J=7.81 Hz), 7.59 (2 hr, d, J=1.26 Hz), 7.25-7.42 (2 hr, m), 2.94 (3 hr, s).

Preparation 105B:
N-(7-Iodobenzo[b]thiophen-4-yl)methanesulfonamide

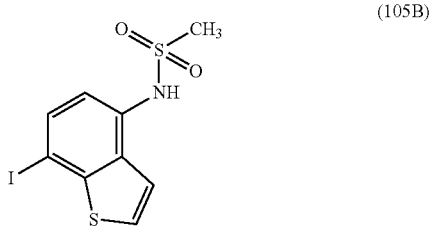

(105B)

To a stirred solution of Preparation 105A (1.13 g, 4.97 mmol) in pyridine (10 mL) was added iodine (1.514 g, 5.97 mmol), and the mixture was stirred at room temperature for 14 h. The reaction mixture was diluted with ether, washed with saturated sodium thiosulfate solution, water, brine and dried. Evaporation of the solvent furnished a crude residue, which was chromatographed (100% CH$_2$Cl$_2$) to furnish the title compound, which was used without further purification. LC/MS: Example 105B @ 3.47 min (RT) (Condition H). MS (ES): m/z=352.0, [M−H]$^+$.

Example 105

A vessel capable of sealing was charged with a mixture of Preparation 105B (300 mg, 0.849 mmol), 4-methylpyridin-3-ylboronic acid (157 mg, 1.274 mmol), PdCl$_2$(dppf)-CH$_2$Cl$_2$ adduct (69.4 mg, 0.085 mmol), dioxane (4 mL), and a 2.0 M aqueous solution of K$_3$PO$_4$ (1.3 mL, 2.55 mmol) and was purged with nitrogen for 10 min. The vessel was sealed and heated at 90° C. for 16 hours. Upon cooling, the solvent was evaporated to dryness and the residue was suspended in ethyl acetate, washed with water, brine and dried over sodium sulfate. Evaporation of the solvent furnished a crude residue, which was chromatographed using BIOTAGE® (20% EtOAc/CH$_2$Cl$_2$). Concentration provided the title compound as a white powder (60 mg, 22% yield). LC/MS: Example 105 @ 3.12 min (RT) (Condition H). MS (ES): m/z=317.1, [M+H]$^+$. $^1$H NMR (400 MHz, MeOD) δ ppm 8.46 (1 hr, d, J=5.29 Hz), 8.39 (1 hr, s), 7.71 (1 hr, d, J=5.79 Hz), 7.63 (1 hr, d, J=5.79 Hz), 7.54 (1 hr, d, J=7.81 Hz), 7.44 (1 hr, d, J=5.29 Hz), 7.25 (1 hr, d, J=7.81 Hz), 3.03 (3 hr, s), 2.19 (3 hr, s).

Example 106

N-(7-(4-Cyclopropylpyrimidin-5-yl)benzo[b]thiophen-4-yl)methanesulfonamide

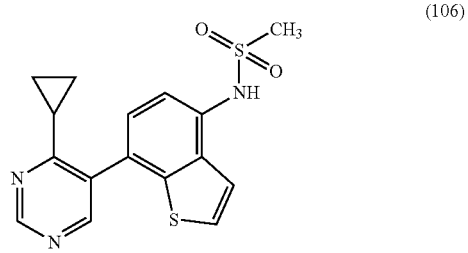 [SMILES: CS(=O)(=O)Nc1ccc(-c2cncnc2C2CC2)c2sccc12]

(106)

A vessel capable of sealing was charged with a mixture of Preparation 105B (287 mg, 0.813 mmol), Preparation 99A (200 mg, 1.220 mmol), PdCl$_2$(dppf)-CH$_2$Cl$_2$ adduct (66.4 mg, 0.81 mmol), dioxane (6 mL), and a 2.0 M aqueous solution of K$_3$PO$_4$ (1.2 mL, 2.439 mmol) and was purged with nitrogen for 10 min. The vessel was sealed and heated at 90° C. for 2 hours. Upon cooling, the reaction mixture was diluted with CH$_2$Cl$_2$ (10 mL) and filtered with CH$_2$Cl$_2$/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as an off white solid (45 mg, 16% yield). LC/MS: Example 106 @ 3.3 min (RT) (Condition H). MS (ES): m/z=344.2/391.91, [M+H]$^+$. $^1$H NMR (500 MHz, MeOD) δ ppm 9.00-9.09 (1 hr, m), 8.53-8.65 (1 hr, m), 7.76 (1 hr, t, J=6.10 Hz), 7.69 (1 hr, t, J=5.80 Hz), 7.61 (1 hr, t, J=7.17 Hz), 7.35-7.51 (1 hr, m), 2.99-3.11 (3 hr, m), 1.79-1.93 (1 hr, m), 1.30 (2 hr, br. s.), 0.94-1.12 (2 hr, m).

Example 107

N-(7-(4-Cyclopropylpyridin-3-yl)benzo[b]thiophen-4-yl)methanesulfonamide

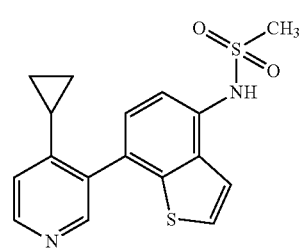

(107)

A microwave vial was charged with a mixture of 4-cyclopropylpyridin-3-ylboronic acid (180 mg, 1.104 mmol), Preparation 105B (260 mg, 0.736 mmol), PdCl$_2$(dppf)-CH$_2$Cl$_2$ adduct (60.1 mg, 0.074 mmol), dioxane (6 mL), and a 2.0 M aqueous solution of K$_3$PO$_4$ (1.1 mL, 2.209 mmol) and was purged with nitrogen for 10 min. The vial was sealed and heated at 90° C. for 2 hours in the microwave. Upon cooling, the reaction mixture was diluted with CH$_2$Cl$_2$ (10 mL) and filtered with CH₂Cl₂/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as an off white solid (45 mg, 16% yield). LC/MS: Example 107 @ 3.31 min (RT) (Condition H). MS (ES): m/z=345.2, [M+H]⁺. ¹H NMR (500 MHz, MeOD) δ ppm 8.74 (1 hr, d, J=11.29 Hz), 8.71 (1 hr, br. s.), 7.77-7.85 (1 hr, m), 7.73 (1 hr, d, J=5.49 Hz), 7.66 (1 hr, d, J=7.63 Hz), 7.58 (1 hr, d, J=6.41 Hz), 7.48 (1 hr, d, J=7.93 Hz), 3.10 (3 hr, s), 1.81-2.01 (1 hr, m), 1.33 (2 hr, br. s.), 1.24 (2 hr, br. s.).

Example 108

5-(3-(4-Fluorophenyl)benzo[b]thiophen-7-yl)-4-methylpyrimidine

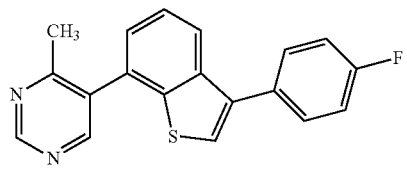

(108)

Preparation 108A:
5-(Benzo[b]thiophen-7-yl)-4-methylpyrimidine

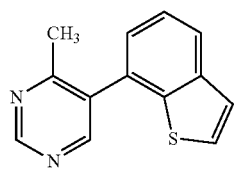

(108A)

A vessel capable of sealing was charged with a mixture of 7-bromobenzo[b]thiophene (100 mg, 0.467 mmol), 4-methylpyrimidin-5-ylboronic acid (97 mg, 0.70 mmol), PdCl₂(dppf)-CH₂Cl₂ adduct (19.2 mg, 0.023 mmol), dioxane (3 mL), and a 2.0 M water solution of K₃PO₄ (0.7 mL, 1.41 mmol) and was purged with nitrogen for 10 min. The vessel was sealed and heated at 100° C. for 16 hours. Upon cooling, the reaction mixture was diluted with CH₂Cl₂ and filtered with CH₂Cl₂/MeOH washing. The filtrate was concentrated under reduced pressure. The residue was dissolved in CH₂Cl₂ and washed with water, brine, dried over anhydrous Na₂SO₄ and concentrated under reduced pressure. The crude material was purified by BIOTAGE® eluting with 0%-15% EtOAc/CH₂Cl₂ at 30 mL/min. Concentration of appropriate fractions provided the title compound (32 mg, 30% yield). LC/MS: Example 108A @ 2.49 min (RT) (Condition G). MS (ES): m/z=227.07.1 [M+H]⁺. ¹H NMR (400 MHz, CDCl₃) δ ppm 9.19 (1 hr, s), 8.68 (1 hr, s), 7.92 (1 hr, d, J=8.06 Hz), 7.38-7.52 (3 hr, m), 7.23 (1 hr, d, J=7.05 Hz), 2.44 (3 hr, s).

Preparation 108B: 5-(3-Bromobenzo[b]thiophen-7-yl)-4-methylpyrimidine

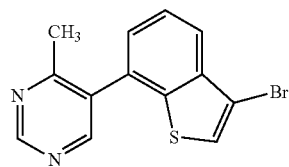

(108B)

To a stirring solution of Preparation 108B (32 mg, 0.141 mmol) in methylene chloride (5 mL) was added Br₂ (45.2 mg, 0.283 mmol) in methylene chloride (2 mL). The reaction mixture was stirred at room temperature for 2 hours. The reaction was quenched with saturated NaHCO₃. The reaction mixture and extracted with CH₂Cl₂. The combined organics were washed with brine, dried over anhydrous Na₂SO₄ and concentrated under reduced pressure. The crude material was used for next step without purification. LC/MS: Example 108B @ 3.04 min (RT) (Condition G). MS (ES): m/z=304.89; [M+H]⁺.

Example 108

A vessel capable of sealing was charged with a mixture of Preparation 108B (30 mg, 0.098 mmol), 4-fluorophenylboronic acid (20.63 mg, 0.147 mmol), PdCl₂(dppf)-CH₂Cl₂ adduct (8.03 mg, 9.83 µmol), dioxane (2 mL), and a 2.0 M aqueous solution of K₃PO₄ (0.15 mL, 0.295 mmol) and was purged with nitrogen for 10 min. The vessel was sealed and heated at 90° C. for 16 hours. Upon cooling, the reaction mixture was diluted with CH₂Cl₂ (10 mL) and filtered with CH₂Cl₂/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as brown oil (2.9 mg, 6.2% yield). LC/MS: Example 108 @ 3.34 min (RT) (Condition G). MS (ES): m/z=321.01 [M+H]⁺. ¹H NMR (400 MHz, MeOD) δ ppm 9.12 (1 hr, s), 8.69 (1 hr, s), 7.90-8.01 (1 hr, m), 7.57-7.69 (5 hr, m), 7.36 (1 hr, d, J=7.05 Hz), 7.25 (2 hr, t, J=8.81 Hz), 2.40 (3 hr, s).

Example 109

4-(3-(4-Fluorophenyl)benzo[b]thiophen-7-yl)isoquinoline

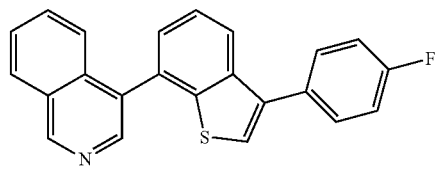

(109)

Preparation 109A:
4-(Benzo[b]thiophen-7-yl)isoquinoline

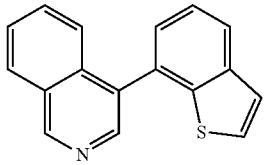

(109A)

A vessel capable of sealing was charged with a mixture of 7-bromobenzo[b]thiophene (430 mg, 2.018 mmol), isoquinolin-4-ylboronic acid (419 mg, 2.421 mmol), PdCl$_2$(dppf)-CH$_2$Cl$_2$ adduct (82 mg, 0.101 mmol), dioxane (6 mL), and a 2.0 M aqueous solution of K$_3$PO$_4$ (3 mL, 1.41 mmol) and was purged with nitrogen for 10 min. The vessel was sealed and heated at 90° C. for 16 hours. Upon cooling, the reaction mixture was diluted with CH$_2$Cl$_2$ and filtered with CH$_2$Cl$_2$/MeOH washing. The filtrate was concentrated under reduced pressure. The residue was dissolved in CH$_2$Cl$_2$ and washed with water, brine, dried over anhydrous Na$_2$SO$_4$ and concentrated under reduced pressure. The crude material was purified by BIOTAGE® eluting with 0%-15% EtOAc/CH$_2$Cl$_2$ at 30 mL/min. Concentration of appropriate fractions provided the title compound (32 mg, 30% yield). LC/MS: Example 109A @ 2.49 min (RT) (Condition G). MS (ES): m/z=262.42 [M+H]$^+$. $^1$H NMR (400 MHz, CDCl$_3$) δ ppm 9.38 (1 hr, s), 8.71 (1 hr, s), 8.08-8.15 (1 hr, m), 7.96 (1 hr, dd, J=8.06, 1.01 Hz), 7.51-7.71 (4 hr, m), 7.39-7.51 (3 hr, m).

Preparation 109B:
4-(3-Bromobenzo[b]thiophen-7-yl)isoquinoline

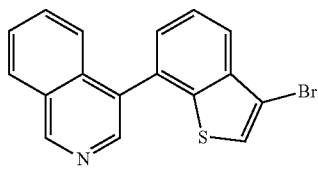

(109B)

To a stirring solution of Preparation 109A (150 mg, 0.574 mmol) in methylene chloride (10 mL) was added Br$_2$ (183 mg, 1.148 mmol) in methylene chloride (2 mL). The reaction mixture was stirred at room temperature for 16 hours. The reaction mixture was quenched with saturated NaHCO$_3$ and extracted with CH$_2$Cl$_2$. The combined organics were washed with brine, dried over anhydrous Na$_2$SO$_4$ and concentrated under reduced pressure. The crude material was purified by BIOTAGE® eluting with 0%-10% EtOAc/CH$_2$Cl$_2$ at 30 mL/min. Concentration of appropriate fractions provided the title compound (86 mg, 44% yield). LC/MS: Example 109B @ 3.06 min (RT) (Condition G). MS (ES): m/z=339.90; [M+H]$^+$.

Example 109

A vessel capable of sealing was charged with a mixture of Preparation 109B (40 mg, 0.118 mmol), 4-fluorophenylboronic acid (19.74 mg, 0.141 mmol), PdCl$_2$(dppf)-CH$_2$Cl$_2$ adduct (4.8 mg, 5.88 μmol), dioxane (2 mL), and a 2.0 M aqueous solution of K$_3$PO$_4$ (0.18 mL, 0.353 mmol) and was purged with nitrogen for 10 min. The vessel was sealed and heated at 90° C. for 16 hours. Upon cooling, the reaction mixture was diluted with CH$_2$Cl$_2$ (10 mL) and filtered with CH$_2$Cl$_2$/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a white powder (16.5 mg, 39.1% yield). LC/MS: Example 109 @ 3.32 min (RT) (Condition G). MS (ES): m/z=355.98 [M+H]$^+$. $^1$H NMR (400 MHz, MeOD) δ ppm 8.78 (1 hr, s), 8.64 (1 hr, d, J=8.24 Hz), 8.04-8.21 (3 hr, m), 7.90 (1 hr, d, J=8.24 Hz), 7.56-7.75 (5 hr, m), 7.22-7.38 (2 hr, m).

Example 110

4-(3-(2-Chloro-4-fluorophenyl)benzo[b]thiophen-7-yl)isoquinoline

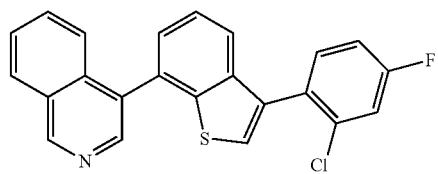

(110)

A vessel capable of sealing was charged with a mixture of Preparation 109B (40 mg, 0.118 mmol), 2-chloro-4-fluorophenylboronic acid (24.60 mg, 0.141 mmol), PdCl$_2$(dppf)-CH$_2$Cl$_2$ adduct (4.8 mg, 5.88 μmol), dioxane (2 mL), and a 2.0 M aqueous solution of K$_3$PO$_4$ (0.18 mL, 0.353 mmol) and was purged with nitrogen for 10 min. The vessel was sealed and heated at 90° C. for 16 hours. Upon cooling, the reaction mixture was diluted with CH$_2$Cl$_2$ (10 mL) and filtered with CH$_2$Cl$_2$/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as a gray powder (18.3 mg, 36.7% yield). LC/MS: Example 110 @ 3.42 min (RT) (Condition G). MS (ES): m/z=389.91, [M+H]$^+$. $^1$H NMR (400 MHz, MeOD) δ ppm 9.90 (1 hr, s), 8.80 (1 hr, s), 8.66 (1 hr, d, J=8.24 Hz), 8.06-8.24 (2 hr, m), 7.93 (1 hr, d, J=8.24 Hz), 7.44-7.77 (6 hr, m), 7.28 (1 hr, td, J=8.32, 2.59 Hz).

Example 111

3-(3-(4-Fluorophenyl)benzo[b]thiophen-7-yl)-4-methylpyridine

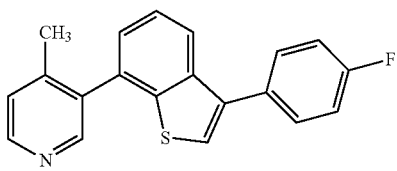

(111)

Preparation 111A:
3-(Benzo[b]thiophen-7-yl)-4-methylpyridine (111A)

A vessel capable of sealing was charged with a mixture of 7-bromobenzo[b]thiophene (370 mg, 1.736 mmol), 4-methylpyridin-3-ylboronic acid HCl (361 mg, 2.084 mmol), PdCl$_2$(dppf)-CH$_2$Cl$_2$ adduct (70.9 mg, 0.087 mmol), dioxane (8 mL), and a 2.0 M aqueous solution of K$_3$PO$_4$ (3.47 mL, 6.95 mmol) and was purged with nitrogen for 10 min. The vessel was sealed and heated at 90° C. for 10 hours. Upon cooling, the reaction mixture was diluted with CH$_2$Cl$_2$ and filtered with CH$_2$Cl$_2$/MeOH washing. The filtrate was concentrated under reduced pressure. The residue was dissolved in CH$_2$Cl$_2$ and washed with water, brine, dried over anhydrous Na$_2$SO$_4$ and concentrated under reduced pressure. The crude material was purified by BIOTAGE® eluting with 10%-40% EtOAc/CH$_2$Cl$_2$ at 30 mL/min. Concentration of appropriate fractions provided the title compound (350 mg, 89% yield). LC/MS: Example 111A @ 1.50 min (RT) (Condition G). MS (ES): m/z=226.12.1 [M+H]$^+$. $^1$H NMR (400 MHz, CDCl$_3$) δ ppm 8.50-8.64 (2 hr, m), 7.89 (1 hr, dd, J=7.93, 1.13 Hz), 7.40-7.55 (3 hr, m), 7.25-7.33 (1 hr, m), 7.22 (1 hr, d, J=6.30 Hz), 2.21 (3 hr, s).

Preparation 111B:
3-(3-Bromobenzo[b]thiophen-7-yl)-4-methylpyridine

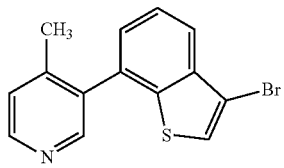

(111B)

To a stirring solution of Preparation 111A (70 mg, 0.311 mmol) in methylene chloride (10 mL) was added Br$_2$ (0.016 mL, 0.311 mmol) in methylene chloride (0.4 mL). The reaction mixture was stirred at room temperature for 30 min. The reaction was quenched with saturated NaHCO$_3$ and extracted with CH$_2$Cl$_2$. The combined organics were washed with brine, dried over anhydrous Na$_2$SO$_4$ and concentrated under reduced pressure. The crude material was purified by BIOTAGE® eluting with 10%-40% EtOAc/CH$_2$Cl$_2$ at 30 mL/min. Concentration of appropriate fractions provided the title compound as brown oil (73 mg, 83% yield). LC/MS: Example 111B @ 2.20 min (RT) (Condition G). MS (ES): m/z=303.94; [M+H]$^+$. $^1$H NMR (400 MHz, CDCl$_3$) δ ppm 8.58 (1 hr, d, J=5.04 Hz), 8.54 (1 hr, s), 7.87-7.98 (1 hr, m), 7.55-7.66 (1 hr, m), 7.49 (1 hr, s), 7.25-7.36 (2 hr, m), 2.19 (3 hr, s).

Example 111

A vessel capable of sealing was charged with a mixture of Preparation 111B (40 mg, 0.131 mmol), 4-fluorophenylboronic acid (27.6 mg, 0.197 mmol), PdCl$_2$(dppf)-CH$_2$Cl$_2$ adduct (5.37 mg, 6.57 μmol), dioxane (3 mL), and a 2.0 M aqueous solution of K$_3$PO$_4$ 1 (0.2 mL, 0.394 mmol) and was purged with nitrogen for 10 min. The vessel was sealed and heated at 90° C. for 16 hours. Upon cooling, the reaction mixture was diluted with CH$_2$Cl$_2$ (10 mL) and filtered with CH$_2$Cl$_2$/MeOH washing. The filtrate was concentrated under reduced pressure. The crude material was purified by preparative HPLC. The HPLC fractions that contained the product were concentrated with SPEEDVAC® and applied onto a MCX cartridge. The material was washed with methanol and the product was eluted with 2N solution of ammonia in methanol. Concentration provided the title compound as clear viscous oil (21.4 mg, 49% yield). LC/MS: Example 111 @ 2.64 min (RT) (Condition G). MS (ES): m/z=320.07 [M+H]$^+$. $^1$H NMR (400 MHz, MeOD) δ ppm 8.82 (1 hr, s), 8.78 (1 hr, d, J=6.04 Hz), 8.06 (1 hr, d, J=5.79 Hz), 8.00 (1 hr, d, J=8.06 Hz), 7.52-7.72 (4 hr, m), 7.42 (1 hr, d, J=7.05 Hz), 7.25 (2 hr, t, J=8.69 Hz), 2.46 (3 hr, s).

Examples 112 to 114

The following compounds were synthesized from Example 50 and a variety of alcohols using the following procedure:

TABLE 1

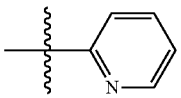 [SMILES: *c1ccccn1]

| Ex. | R | Compound Name | LC/MS* ret. T (min.) | [M + H]+ |
|---|---|---|---|---|
| 112 | 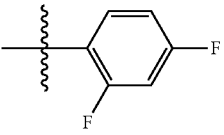 [SMILES: *c1ccc(F)cc1F] | 4-methyl-3-(3-(pyridin-2-yl)benzo[b]thiophen-7-yl)pyridine | 1.15 | 303.00 |
| 113 | 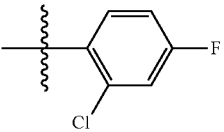 | 3-(3-(2,4-difluorophenyl)benzo[b]thiophen-7-yl)-4-methylpyridine | 2.63 | 338.02 |
| 114 | 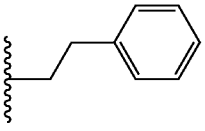 | 3-(3-(2-chloro-4-fluorophenyl)benzo[b]thiophen-7-yl)-4-methylpyridine | 2.80 | 353.97 |

*LC/MS retention times for Compounds 112-114 were obtained using HPLC condition G: PHENOMENEX®-Luna 4.6 x 30 mm S10, 4 minute gradient time, flow rate: 4.0 mL/min, Solvent A: 10% MeOH/90% water/0.1% TFA; Solvent B: 90% MeOH/10% water/0.1% TFA, wavelength 220 nm.

Examples 115 to 134

The following compounds were synthesized from Example 50 and a variety of alcohols using the following procedure: 3-chloro-7-(4-methylpyridin-3-yl)benzo[d]isoxazole (0.024 g, 0.1 mmol) was dissolved in 12 mL of THF in a 20 mL scintillation vial. To each 16×100 mm Wheaton tube containing alcohol was added 0.5 mL of this THF solution (for total overall concentration of 0.1M) followed by sodium hydride (4.80 mg, 0.200 mmol). The reaction mixtures were agitated at 400 rpm on an INNOVA® platform shaker at room temperature for 10 min. Then to each vial was added 0.50 mL of the core solution and reaction mixtures were agitated at 400 rpm on an INNOVA® platform shaker at room temperature for 12 h. Reactions were quenched with MeOH. The reaction mixtures were placed in the SPEEDVAC® to dry for 3 hours at 40° C. The crude materials were then re-dissolved in 1.5 mL of DMF and purified on HPLC. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 MeOH:water with 0.05% TFA; Mobile Phase B: 95:5 MeOH:water with 0.05% TFA; Gradient adjusted accordingly to isolate product; Flow: 20 mL/min. Fractions containing the desired product were combined and dried via centrifugal evaporation. All compounds were analyzed using the following HPLC conditions: Column: Waters XBridge C18, 4.6×50 mm, 5-μm particles; Mobile Phase A: 5:95 acetonitrile:water with 10 mM NH4OAc; Mobile Phase B: 95:5 acetonitrile:water with 10 mM NH4OAc; Temperature: 23° C.; Gradient: 0-100% B over 4 minutes, then a 1-minute hold at 100% B; Flow: 4 mL/min.

TABLE 2

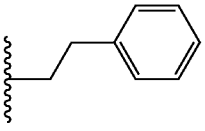

| Ex. | R | Name | [M + H]+ | Ret time | Purity |
|---|---|---|---|---|---|
| 115 |  | 7-(4-methylpyridin-3-yl)-3-phenethoxybenzo[d]isoxazole | 331 | 3.1 | 100 |

TABLE 2-continued

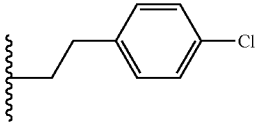 [SMILES: *CCc1ccc(Cl)cc1]

| Ex. | R | Name | [M + H]+ | Ret time | Purity |
|---|---|---|---|---|---|
| 116 | 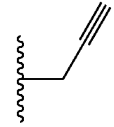 [SMILES: *CC#C] | 3-(4-chlorophenethoxy)-7-(4-methylpyridin-3-yl)benzo[d]isoxazole | 365.2 | 2.38 | 100 |
| 117 | 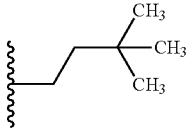 [SMILES: *CCC(C)(C)C] | 7-(4-methylpyridin-3-yl)-3-(prop-2-ynyloxy)benzo[d]isoxazole | 265.12 | 2.41 | 100 |
| 118 | 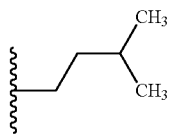 [SMILES: *CCC(C)C] | 3-(3,3-dimethylbutoxy)-7-(4-methylpyridin-3-yl)benzo[d]isoxazole | 311.27 | 2.47 | 100 |
| 119 | 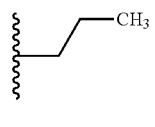 | 3-(isopentyloxy)-7-(4-methylpyridin-3-yl)benzo[d]isoxazole | 297.24 | 2.35 | 100 |
| 120 | 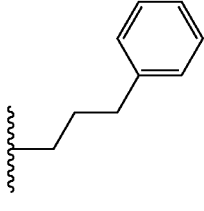 [SMILES: *CCCc1ccccc1] | 7-(4-methylpyridin-3-yl)-3-propoxybenzo[d]isoxazole | 269.2 | 2.02 | 100 |
| 121 | 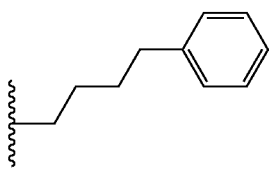 [SMILES: *CCCCc1ccccc1] | 7-(4-methylpyridin-3-yl)-3-(3-phenylpropoxy)benzo[d]isoxazole | 345.25 | 2.37 | 100 |
| 122 | 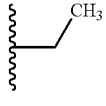 | 7-(4-methylpyridin-3-yl)-3-(4-phenylbutoxy)benzo[d]isoxazole | 359.26 | 2.05 | 87 |
| 123 | 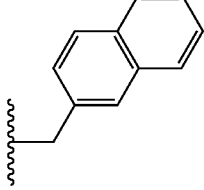 | 3-ethoxy-7-(4-methylpyridin-3-yl)benzo[d]isoxazole | 255.17 | 1.82 | 100 |
| 124 | | 7-(4-methylpyridin-3-yl)-3-(naphthalen-2-ylmethoxy)benzo[d]isoxazole | 367.24 | 2.41 | 100 |

TABLE 2-continued

| Ex. | R | Name | [M + H]⁺ | Ret time | Purity |
|---|---|---|---|---|---|
| 125 | -C(CH₃)₃ | 3-tert-butoxy-7-(4-methylpyridin-3-yl)benzo[d]isoxazole | 283.21 | 2.15 | 95 |
| 126 | -CH₃ | 3-methoxy-7-(4-methylpyridin-3-yl)benzo[d]isoxazole | 241.16 | 1.61 | 100 |
| 127 | -CH₂-phenyl | 3-(benzyloxy)-7-(4-methylpyridin-3-yl)benzo[d]isoxazole | 317.19 | 2.15 | 100 |
| 128 | -CH₂-(4-chlorophenyl) | 3-(4-chlorobenzyloxy)-7-(4-methylpyridin-3-yl)benzo[d]isoxazole | 351.17 | 2.32 | 100 |
| 129 | -CH₂-(4-methoxyphenyl) | 3-(4-methoxybenzyloxy)-7-(4-methylpyridin-3-yl)benzo[d]isoxazole | 347.21 | 2.12 | 100 |
| 130 | 1-methylpiperidin-4-yl | 3-(1-methylpiperidin-4-yloxy)-7-(4-methylpyridin-3-yl)benzo[d]isoxazole | 324.23 | 1.16 | 100 |
| 131 | -CH(CH₃)₂ | 3-isopropoxy-7-(4-methylpyridin-3-yl)benzo[d]isoxazole | 269.19 | 1.99 | 100 |
| 132 | -CH₂CH₂-(1H-imidazol-1-yl) | 3-(2-(1H-imidazol-1-yl)ethoxy)-7-(4-methylpyridin-3-yl)benzo[d]isoxazole | 321.05 | 1.87 | 100 |
| 133 | -CH₂-(pyrazin-2-yl) | 7-(4-methylpyridin-3-yl)-3-(pyrazin-2-ylmethoxy)benzo[d]isoxazole | 319.18 | 1.51 | 92 |

TABLE 2-continued

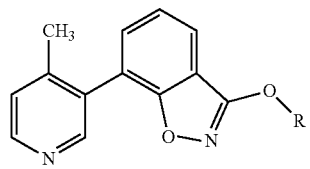

| Ex. | R | Name | [M + H]+ | Ret time | Purity |
|---|---|---|---|---|---|
| 134 | (thiazol-2-ylmethyl) | 7-(4-methylpyridin-3-yl)-3-(thiazol-2-ylmethoxy)benzo[d]isoxazole | 324.13 | 1.7 | 100 |

BIOLOGICAL ASSAYS

The pharmacological properties of the compounds of this invention may be confirmed by a number of biological assays. The exemplified biological assays, which follow, have been carried out with compounds of the invention and/or salts thereof.

CYP17 Total SPA Assay

The assays were performed in U-bottom 384-well opti-plates. The final assay volume was 15 µl prepared from 7.5 µl additions of microsomes (prepared as a high-speed pellet from homogenized HEK2 cells stably transfected with CYP17), substrates (3H-Pregnenolone and NADPH) and test compounds in assay buffer (50 mM Potassium phosphate pH 7.2, 10% glycerol). The reaction was initiated by the combination of the microsomes and substrates in wells containing compound. The reaction was incubated at room temperature for 45 minutes and terminated by adding 7.5 µl of 0.2N HCl to each well. Following an incubation period of 10 minutes, anti-DHEA-coated SPA beads were added to the terminated reaction. The plate was sealed and incubated overnight with shaking at 4° C. The beads were allowed to settle in the plate for 1 hour and the plate read on a TOPCOUNT® (Perkin-Elmer) plate reader.

Inhibition data were calculated by comparison to no enzyme control reactions for 100% inhibition and vehicle-only reactions for 0% inhibition. The final concentration of reagents in the assays are NADPH, 2 mM; 3H-Pregnenolone, 1 uM; microsomes, 1.25 ug/ml; Anti-DHEA-SPA beads (0.125 mg/well) in 0.5% Triton X-100 and DMSO, 0.05%. Dose response curves were generated to determine the concentration required inhibiting 50% of enzyme activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Table 5 below lists the 1050 values for the following examples of this invention measured in the Total CYP17 SPA Assay hereinabove. The compounds of the present invention, as exemplified by the following examples, showed Human CYP17 SPA $IC_{50}$ values of less than 1 µM.

TABLE 5

Human CYP17 Inhibition

| Example No. 1 | Human CYP17 SPA $IC_{50}$ Value (nM) |
|---|---|
| 1 | 1.1 |
| 4 | 357 |
| 6 | 3.2 |
| 14 | 192 |
| 26 | 65 |
| 30 | 48 |
| 52 | 42 |
| 57 | 524 |
| 68 | 524 |
| 86 | 3.9 |
| 94 | 76 |
| 98 | 8.0 |
| 99 | 4.0 |
| 103 | 4.0 |
| 109 | 56 |
| 124 | 611 |
| 128 | 251 |
| 129 | 79 |

CYP17 Lyase Assay

Human CYP17 was expressed in HEK293 cells and microsomal preparations were made and subsequently used as the source of enzyme in the lyase assay. The reaction consists of 200 nM [3H]-Hydroxypregnenolone (ARC), 200 nM 17-Hydroxypregnenolone (Sigma), 2 mM NADPH (CalBiochem), and CYP17-HEK293 microsomes which were incubated in the presence of DMSO or test compounds for 20 minutes at room temperature. Compounds were dissolved in DMSO and serially diluted. The reaction was stopped by the addition of 0.2 N HCl and the product was captured using anti-mouse YSi SPA beads (GE) conjugated to an anti-DHEA monoclonal antibody (Abcam). Signal intensity determined by a Packard Top Count was used to calculate percent inhibition and $IC_{50}$ values.

CYP17 Hydroxylase Assay

E. coli was transformed to express active human CYP17 and membranes prepared from the transformed E. coli were used as the source of enzyme. The reaction was carried out in a 50 uL final volume containing 200 nM hCYP17 membranes, 2504 Pregnenolone (Sigma), 7 mM NADPH (CalBiochem), 1 µM cytochrome P450 reductase (Invitrogen), and 50 mM sodium phosphate buffer, pH 7.3. The $IC_{50}$ determination of compounds dissolved in 100% DMSO was done by serial dilution into the assay buffer to a final concentration of 0.2% DMSO. The reaction was incubated at 37° C. for 120 minutes and stopped by the addition of 200 uL of 0.02N HCl in acetonitrile. Samples were then spun at 750000 g and 200 uL of the supernatant was transferred to a clean tube for analysis. The product of the reaction, 17 alpha pregnenolone, was measured via LC/MS.

What is claimed is:
1. A compound of Formula (I)

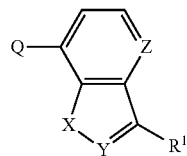

or a pharmaceutically acceptable salt thereof, wherein:
X is O and Y is N;
Z is N;
Q is:

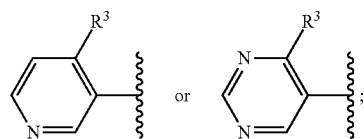

$R^1$ is:
(i) H, halo, $C_{1-4}$fluoroalkyl, $C_{1-6}$alkoxy, $C_{1-4}$fluoroalkoxy, —S($C_{1-4}$fluoroalkyl), —O($C_{1-4}$alkylenyl)O($C_{1-3}$alkyl), —O($CH_2$)$_{1-4}$N($C_{1-3}$alkyl)$_2$, —O($C_{3-6}$alkynyl), or —O(methylpiperidinyl);
(ii) phenyl substituted with zero to 2 substituents independently selected from F, Cl, —$CF_3$, and/or —$OCH_3$;
(iii) $C_{3-6}$ cycloalkyl, morpholinyl, thiazolyl, pyridinyl, pyridazinyl, or pyrazinyl; or
(iv) —O($CH_2$)$_{1-4}$$R^x$ wherein $R^x$ is imidazolyl, thiazolyl, phenyl, fluorophenyl, chlorophenyl, methoxyphenyl, naphthalenyl, or pyrazinyl;
and
$R^3$ is:
(i) F, Cl, $C_{1-4}$alkyl, $C_{1-4}$alkoxy, or $C_{1-4}$fluoroalkoxy;
(ii) $C_{3-6}$cyclopropyl, morpholinyl, pyrazolyl, imidazolyl, or triazolyl;
(iii) —O($CH_2$)$_{1-4}$$R^y$ wherein $R^y$ is phenyl, morpholinyl, or pyridazinyl;
(iv) pyrrolidinyl substituted with zero to 2 substituents independently selected from —$CH_3$ and/or —OH; or
(v) —$NH_2$, —NH($C_{1-4}$alkyl), —NH($C_{2-3}$fluoroalkyl), or —NH($C_{3-6}$cycloalkyl).

2. The compound according to claim 1 or a pharmaceutically acceptable salt thereof, wherein:
Q is

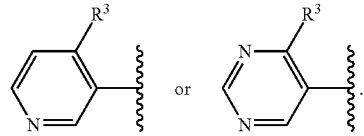

3. The compound according to claim 1 or a pharmaceutically acceptable salt thereof, wherein:

$R^1$ is:
(i) H, Cl, —$NH_2$, —$CH_2CH_2CF_3$, $C_{1-6}$alkoxy, fluoroethoxy, —$SCH_2CF_3$, —$OCH_2CH_2OCH_3$, —$OCH_2CH_2N(CH_3)_2$, —O($CH_2C\equiv CH$), or —O(methylpiperidinyl);
(ii) phenyl substituted with zero to 2 substituents independently selected from F, Cl, —$CF_3$, and/or —$OCH_3$;
(iii) cyclopropyl, morpholinyl, thiazolyl, pyridinyl, pyridazinyl, or pyrazinyl; or
(iv) —O($CH_2$)$_{1-4}$$R^x$ wherein $R^x$ is imidazolyl, thiazolyl, phenyl, chlorophenyl, methoxyphenyl, naphthalenyl, or pyrazinyl;
and
$R^3$ is:
(i) Cl, —$CH_3$, $C_{1-3}$alkoxy, or fluoroethoxy;
(ii) cyclopropyl, morpholinyl, pyrazolyl, imidazolyl, or triazolyl;
(iii) —O($CH_2$)$_{1-2}$$R^y$ wherein $R^y$ is phenyl, morpholinyl, or pyridazinyl;
(iv) pyrrolidinyl substituted with —$CH_3$ and —OH; or
(v) —$NH_2$, —NH($CH_2CF_3$), or —NH(cyclopropyl).

4. The compound according to claim 1 or a pharmaceutically acceptable salt thereof, wherein:
$R^1$ is:
(i) Cl, —$NH_2$, —$CH_2CH_2CF_3$, $C_{1-6}$alkoxy, fluoroethoxy, —$SCH_2CF_3$, —$OCH_2CH_2OCH_3$, —$OCH_2CH_2N(CH_3)_2$, —O($CH_2C\equiv CH$), or —O(methylpiperidinyl);
(ii) phenyl substituted with zero to 2 substituents independently selected from F, Cl, and/or —$OCH_3$;
(iii) cyclopropyl, thiazolyl, pyridinyl, pyridazinyl, or pyrazinyl; or
(iv) —O($CH_2$)$_{1-4}$$R^x$ wherein $R^x$ is imidazolyl, thiazolyl, phenyl, chlorophenyl, methoxyphenyl, naphthalenyl, or pyrazinyl;
and
$R^3$ is:
(i) Cl, —$CH_3$, $C_{1-3}$alkoxy, or fluoroethoxy;
(ii) cyclopropyl, morpholinyl, pyrazolyl, imidazolyl, or triazolyl;
(iii) —O($CH_2$)$_{1-2}$$R^y$ wherein $R^y$ is phenyl, morpholinyl, or pyridazinyl;
(iv) pyrrolidinyl substituted with —$CH_3$ and —OH; or
(v) —$NH_2$, —NH($CH_2CF_3$), or —NH(cyclopropyl).

5. The compound according to claim 1 or a pharmaceutically acceptable salt thereof, wherein:
$R^1$ is Cl, morpholinyl, or phenyl substituted with zero to 2 substituents independently selected from F, Cl, and/or —$OCH_3$; and
$R^3$ is —$CH_3$ or —$NH_2$.

6. The compound according to claim 1 or a pharmaceutically acceptable salt thereof, wherein:
Q is

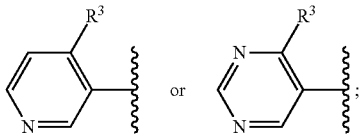

$R^1$ is H, pyridinyl, or phenyl substituted with 1 to 2 substituents independently selected from F and/or Cl; and
$R^3$ is —$CH_3$ or cyclopropyl.

7. The compound according to claim 1 or a pharmaceutically acceptable salt thereof, wherein:

R¹ is thiazolyl, pyridinyl, pyrazinyl, or phenyl substituted with zero to 2 substituents independently selected from F, Cl, and/or —CF₃; and R³ is —CH₃, cyclopropyl, or —NH₂.

8. The compound according to claim 1 or a pharmaceutically acceptable salt thereof, wherein said compound is:
- 3-(4-Fluorophenyl)-7-(4-methylpyridin-3-yl)isoxazolo[4,5-b]pyridine (86);
- 3-Chloro-7-(4-methylpyridin-3-yl)isoxazolo[4,5-b]pyridine (87);
- 7-(4-Methylpyridin-3-yl)-3-morpholinoisoxazolo[4,5-b]pyridine (88);
- 7-(4-Methylpyridin-3-yl)-3-phenylisoxazolo[4,5-b]pyridine (89);
- 3-(5-Fluoro-2-methoxyphenyl)-7-(4-methylpyridin-3-yl)isoxazolo[4,5-b]pyridine (90);
- 5-(3-(2-Chloro-4-fluorophenyl)isoxazolo[4,5-b]pyridin-7-yl)pyrimidin-4-amine (91); or
- 5-(3-(4-Fluorophenyl)isoxazolo[4,5-b]pyridin-7-yl)pyrimidin-4-amine (92).

\* \* \* \* \*